(12) United States Patent
Hoarty et al.

(10) Patent No.: US 12,239,684 B2
(45) Date of Patent: *Mar. 4, 2025

(54) MODULATORS OF COMPLEMENT ACTIVITY

(71) Applicant: Ra Pharmaceuticals, Inc., Cambridge, MA (US)

(72) Inventors: Michelle Denise Hoarty, Billerica, MA (US); Ketki Ashok Dhamnaskar, Foster City, CA (US); Daniel Elbaum, Newton, MA (US); Kristopher Josephson, San Carlos, CA (US); Kelley Cronin Larson, Quincy, MA (US); Zhong Ma, Lexington, MA (US); Nathan Ezekiel Nims, Winchester, MA (US); Alonso Ricardo, Winchester, MA (US); Kathleen Seyb, Wakefield, MA (US); Guo-Qing Tang, Acton, MA (US); Douglas A. Treco, Arlington, MA (US); Zhaolin Wang, Wellesley, MA (US); Ping Ye, Lexington, MA (US); Hong Zheng, New York, NY (US); Sarah Jacqueline Perlmutter, Urbana, IL (US)

(73) Assignee: RA PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,907

(22) Filed: Jun. 1, 2023

(65) Prior Publication Data

US 2024/0156896 A1 May 16, 2024

Related U.S. Application Data

(63) Continuation of application No. 17/143,232, filed on Jan. 7, 2021, now Pat. No. 11,707,503, which is a continuation of application No. 16/776,551, filed on Jan. 30, 2020, now Pat. No. 10,918,691, which is a continuation of application No. 16/393,393, filed on Apr. 24, 2019, now Pat. No. 10,588,936, which is a continuation of application No. 15/905,158, filed on Feb. 26, 2018, now Pat. No. 10,328,115, which is a continuation of application No. 15/547,085, filed as application No. PCT/US2016/015412 on Jan. 28, 2016, now Pat. No. 9,937,222.

(60) Provisional application No. 62/185,298, filed on Jun. 26, 2015, provisional application No. 62/108,772, filed on Jan. 28, 2015.

(30) Foreign Application Priority Data

Jun. 12, 2015 (WO) ................ PCT/US2015/035473

(51) Int. Cl.
| | |
|---|---|
| *A61K 38/00* | (2006.01) |
| *A61K 38/10* | (2006.01) |
| *A61K 39/00* | (2006.01) |
| *C07K 16/36* | (2006.01) |

(52) U.S. Cl.
CPC .............. *A61K 38/10* (2013.01); *A61K 39/00* (2013.01); *C07K 16/36* (2013.01); *C07K 2317/76* (2013.01)

(58) Field of Classification Search
CPC ........ A61K 38/10; A61K 39/00; C07K 16/36; C07K 2317/76
See application file for complete search history.

(56) References Cited

U.S. PATENT DOCUMENTS

| | | | |
|---|---|---|---|
| 4,033,940 A | 7/1977 | Hughes et al. | |
| 4,179,337 A | 12/1979 | Davis et al. | |
| 4,216,141 A | 8/1980 | Rivier et al. | |
| 4,271,068 A | 6/1981 | Kamber et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,270,170 A | 12/1993 | Schatz et al. | |
| 5,338,665 A | 8/1994 | Schatz et al. | |
| 5,371,109 A | 12/1994 | Engstrom et al. | |
| 5,427,908 A | 6/1995 | Dower et al. | |
| 5,580,717 A | 12/1996 | Dower et al. | |
| 5,585,353 A | 12/1996 | Merrifield et al. | |
| 5,591,828 A | 1/1997 | Bosslet et al. | |
| 5,596,078 A | 1/1997 | Andersson et al. | |
| 5,618,676 A | 4/1997 | Hitzeman et al. | |
| 5,643,768 A | 7/1997 | Kawasaki | |
| 5,658,754 A | 8/1997 | Kawasaki | |
| 5,726,287 A | 3/1998 | Andersson et al. | |
| 5,750,344 A | 5/1998 | Doyle | |

(Continued)

FOREIGN PATENT DOCUMENTS

| | | |
|---|---|---|
| CN | 101668541 A | 3/2010 |
| EP | 3154561 A2 | 4/2017 |

(Continued)

OTHER PUBLICATIONS

Abuchowski, A. et al, (1977) Effect of covalent attachment of polyethylene glycol on immunogenicity and circulating life of bovine liver catalase, J. Biol. Chem., 252, 3582.

(Continued)

*Primary Examiner* — Jeanette M Lieb
(74) *Attorney, Agent, or Firm* — Glenn J. Foulds; Fenwick & West LLP

(57) ABSTRACT

The present invention provides polypeptide modulators of complement activity, including cyclic polypeptide modulators. Also provided are methods of utilizing such modulators as therapeutics.

13 Claims, 17 Drawing Sheets

Specification includes a Sequence Listing.

(56) References Cited

U.S. PATENT DOCUMENTS

| | | |
|---|---|---|
| 5,766,897 A | 6/1998 | Braxton |
| 5,824,784 A | 10/1998 | Kinstler et al. |
| 5,834,318 A | 11/1998 | Buettner |
| 5,837,500 A | 11/1998 | Ladner et al. |
| 5,843,701 A | 12/1998 | Gold et al. |
| 5,854,018 A | 12/1998 | Hitzeman et al. |
| 5,856,123 A | 1/1999 | Hitzeman et al. |
| 5,919,651 A | 7/1999 | Hitzeman et al. |
| 5,922,680 A | 7/1999 | Paulsen et al. |
| 5,990,237 A | 11/1999 | Bentley et al. |
| 5,990,273 A | 11/1999 | Andersson et al. |
| 6,086,918 A | 7/2000 | Stern et al. |
| 6,194,550 B1 | 2/2001 | Gold et al. |
| 6,242,565 B1 | 6/2001 | Kishida et al. |
| 6,258,558 B1 | 7/2001 | Szostak et al. |
| 6,261,804 B1 | 7/2001 | Szostak et al. |
| 6,268,343 B1 | 7/2001 | Knudsen et al. |
| 6,309,669 B1 | 10/2001 | Setterstrom et al. |
| 6,348,584 B1 | 2/2002 | Hodgson et al. |
| 6,355,245 B1 | 3/2002 | Evans et al. |
| 6,361,943 B1 | 3/2002 | Yanagawa et al. |
| 6,673,901 B2 | 1/2004 | Koide |
| 6,716,973 B2 | 4/2004 | Baskerville et al. |
| 6,720,472 B2 | 4/2004 | Chada et al. |
| 6,844,010 B1 | 1/2005 | Setterstrom et al. |
| 6,962,781 B1 | 11/2005 | Williams |
| 7,348,401 B2 | 3/2008 | Johnson et al. |
| 7,744,910 B2 | 6/2010 | Gschneidner et al. |
| 8,101,586 B2 | 1/2012 | Rock et al. |
| 8,329,169 B2 | 12/2012 | Fung et al. |
| 8,377,437 B2 | 2/2013 | Van Lookeren Campagne |
| 8,652,477 B2 | 2/2014 | Schwaeble et al. |
| 8,703,136 B2 | 4/2014 | Baas et al. |
| 8,753,625 B2 | 6/2014 | Fung et al. |
| 8,911,733 B2 | 12/2014 | Holers et al. |
| 9,937,222 B2 | 4/2018 | Hoarty et al. |
| 10,106,579 B2 | 10/2018 | Hoarty et al. |
| 10,208,089 B2 | 2/2019 | Hoarty et al. |
| 10,328,115 B2 | 6/2019 | Hoarty et al. |
| 10,435,438 B2 | 10/2019 | Hoarty et al. |
| 10,588,936 B2 | 3/2020 | Hoarty et al. |
| 10,835,574 B2 | 11/2020 | DeMarco et al. |
| 10,918,691 B2 | 2/2021 | Hoarty et al. |
| 11,014,965 B2 | 5/2021 | Hoarty et al. |
| 11,123,399 B2 | 9/2021 | Ricardo et al. |
| 2003/0040472 A1 | 2/2003 | Larsen et al. |
| 2005/0090448 A1 | 4/2005 | Johnson et al. |
| 2005/0191343 A1 | 9/2005 | Liang |
| 2006/0027059 A1 | 2/2006 | Hsien |
| 2006/0270590 A1 | 11/2006 | Lockwood et al. |
| 2008/0146490 A1 | 6/2008 | Joabsson et al. |
| 2008/0269318 A1 | 10/2008 | Romano |
| 2008/0313749 A1 | 12/2008 | Timmerman et al. |
| 2009/0054623 A1 | 2/2009 | DeFrees |
| 2010/0015139 A1 | 1/2010 | Bansal |
| 2010/0092493 A1 | 4/2010 | Cao |
| 2010/0093624 A1 | 4/2010 | Low et al. |
| 2010/0099113 A1 | 4/2010 | Knör et al. |
| 2010/0143344 A1 | 6/2010 | Baas et al. |
| 2010/0166748 A1 | 7/2010 | Guild et al. |
| 2011/0172126 A1 | 7/2011 | Brust |
| 2011/0190221 A1 | 8/2011 | Francois et al. |
| 2011/0269807 A1 | 11/2011 | Baciu |
| 2012/0225056 A1 | 9/2012 | Rother et al. |
| 2013/0029912 A1 | 1/2013 | Holers et al. |
| 2013/0053302 A1 | 2/2013 | Lambris et al. |
| 2013/0053311 A1 | 2/2013 | Kalthoff et al. |
| 2013/0246083 A1 | 9/2013 | Bell |
| 2013/0273052 A1 | 10/2013 | Gies et al. |
| 2013/0344082 A1 | 12/2013 | Lambris et al. |
| 2013/0345257 A1 | 12/2013 | Hahn et al. |
| 2014/0234275 A1 | 8/2014 | Williams |
| 2015/0011474 A1 | 1/2015 | Berghard et al. |
| 2015/0057342 A1 | 2/2015 | Koren et al. |
| 2015/0166606 A1 | 6/2015 | Wang et al. |
| 2015/0359900 A1 | 12/2015 | Wang et al. |
| 2016/0206580 A1 | 7/2016 | Los et al. |
| 2016/0376355 A1 | 12/2016 | Bell et al. |
| 2017/0137468 A1 | 5/2017 | Arata et al. |
| 2018/0280530 A1 | 10/2018 | Guo et al. |

FOREIGN PATENT DOCUMENTS

| | | |
|---|---|---|
| JP | 2013-543380 A | 12/2013 |
| RU | 2406507 C2 | 12/2010 |
| RU | 2505311 C2 | 1/2014 |
| RU | 2014137303 A | 4/2016 |
| WO | WO 1993/011161 A1 | 6/1993 |
| WO | WO 1998/032427 A1 | 7/1998 |
| WO | WO 2000/021559 A2 | 4/2000 |
| WO | WO 2005/023866 A2 | 3/2005 |
| WO | WO 2006/088888 A2 | 8/2006 |
| WO | WO 2008/109742 A1 | 9/2008 |
| WO | WO 2008/113834 A2 | 9/2008 |
| WO | WO 2009/014633 A1 | 1/2009 |
| WO | WO 2009/046198 A2 | 4/2009 |
| WO | WO 2009/067191 A2 | 5/2009 |
| WO | WO 2011/057158 A1 | 5/2011 |
| WO | WO 2012/044893 A1 | 4/2012 |
| WO | WO 2012/139081 A3 | 11/2012 |
| WO | WO 2012/162215 A1 | 11/2012 |
| WO | WO 2012/174055 A1 | 12/2012 |
| WO | WO 2013/037267 A1 | 3/2013 |
| WO | WO 2013/052736 A2 | 4/2013 |
| WO | WO 2013/126006 A1 | 8/2013 |
| WO | WO 2013/172954 A1 | 11/2013 |
| WO | WO 2014/078622 A1 | 5/2014 |
| WO | WO 2015/140304 A1 | 9/2015 |
| WO | WO 2015/191951 A2 | 12/2015 |
| WO | WO 2016/094834 A2 | 6/2016 |
| WO | WO 2016/123371 A1 | 8/2016 |
| WO | WO 2017/035362 A1 | 3/2017 |
| WO | WO 2017/105939 A1 | 6/2017 |
| WO | WO 2018/106859 A1 | 6/2018 |
| WO | WO 2019/051436 A1 | 3/2019 |
| WO | WO 2019/112984 A1 | 6/2019 |
| WO | WO 2020/185541 A2 | 9/2020 |
| WO | WO 2020/219822 A1 | 10/2020 |

OTHER PUBLICATIONS

Altschul et al., (1997) Gapped Blast and PSI-Blast: a new generation of protein database search programs, Nucleic Acids Res. 25(17):3389-3402.

Amara, et al., (2008) "Interaction Between the Coagulation and Complement System" in Current Topics in Complemen II, J.D. Lambris (ed.), pp. 71-79 (Adv Exp Med Biol. 2008;632:71-9).

Amara, et al., (2010) Molecular intercommunication between the complement and coagulation systems. J. Immunol. 185:5628-5636.

Anonymous: "History of Changes for Study: NCT04382755" May 8, 2020, XP055809235, Retrieved from the Internet: URL:https://www.clinicaltrials.gov/ct2/history/NCT04382755?V_I=View#StudyPage Top [retrieved on May 31, 2021] the whole document.

Anonymous: "NCT04436497: Healey ALS Platform Trial—Regimen A Zilucoplan" Jun. 17, 2020.

ARIPO Form 18 Office Action for corresponding ARIPO Application No. AP/P/2016/009612 entitled "Modulation of Complement Activity" dated Feb. 19, 2019.

Australian Examination Report for corresponding Australian Application No. 2015274482, dated Nov. 24, 2017.

Baggio, R. et al. (2002) Identification of epitope-like consensus motifs using mRNA display, J. Mol. Recog. 15:126-134.

Ballanti et al., (2013) Complement and autoimmunity. Immunol Res 56:477-491.

Banks, P. et al., (2000) Impact of a red-shifted dye label for high throughput fluorescence polarization assays of G protein-coupled receptors. J Biomol Screen. 5(5):329-34.

Baskerville, S. and Bartel, D.P. (2002) A ribozyme that ligates RNA to protein, Proc. Natl. Acad. Sci. USA 99:9154-9159.

(56) References Cited

OTHER PUBLICATIONS

Beauchamp C. O. et al., (1983) A new procedure for the synthesis of polyethylene glycol-protein adducts; effects on function, receptor recognition, and clearance of superoxide dismutase, lactoferrin, and alpha 2-macroglobulin, Anal. Biochem., 131, 25.
Bergseth, G. et al., (2013) An international serum standard for application in assays to detect human complement activation products. Mol Immunol. 56:232-9.
Berman, H.M. et al., (2000) The Protein Data Bank, Nucleic Acids Research, 28: 235-242.
Blackwell, H. E. and Grubbs, R. H. (1998) Highly Efficient Synthesis of Covalently Cross-Linked Peptide Helices by Ring-Closing Metathesis, Angew. Chem., Int. Ed. 37, 3281-3284.
Bracken, et al.(1994) Synthesis and Nuclear Magnetic Resonance Structure Determination of an .alpha.-Helical, Bicyclic, Lactam-Bridged Hexapeptide, J. Am. Chem. Soc., 116, 6431-6432.
Brodsky (2014) Paroxysmal nocturnal hemoglobinuria. Blood 2014;124:2804-2811.
Canadian Examination Report for corresponding Canadian Application No. 2949985, dated Oct. 26, 2017.
Cantel et al. (2008) Synthesis and conformational analysis of a cyclic peptide obtained via i to i+4 intramolecular side-chain to side-chain azide-alkyne 1,3-dipolar cycloaddition, J. Org. Chem., 73 (15), 5663-5674.
Cazander G., et al., (2012) Complement activation and inhibition in wound healing. Clin Dev Immunol, 2012:534291.
Chang, Kyeong-Ok Characterization and inhibition of norovirus proteases of genogroups I and II using a fluorescence resonance energy transfer assay. Virology, 2012, 423(2), 125-133.
Cheng et al. Chromatographic separtion and Tandem MS identification of active peptides in potato protein hydrolysate that inhibit autoxidation of soybean oil-in-water emulsions. Journal of Agricultural and Food Chemistry 2010, 58(15):8825-8832; Abstract.
Chinese Office Action for corresponding Chinese Application No. 2015800313418 dated Dec. 21, 2018.
Cichewicz et al. Cutaneous delivery of alpha-tocopherol and lipoic acid using microemulsions: influence of composition and charge J Pharm Pharmacol. Jun. 2013, vol. 65, No. 6, pp. 817-826.
Coin, I et al. (2007) Solid-phase peptide synthesis: from standard procedures to the synthesis of difficult sequences, Nature Protcols 2(12):3247-56.
Coto, Y. et al. (2008) Reprogramming the translation initiation for the synthesis of physiologically stable cyclic peptides, ACS Chem. Biol. 3:120-129.
Cwirla, S.E. et al. (1990) Peptides on phage: a vast library of peptides for identifying ligands, Proc. Natl. Acad. Sci. U.S.A. 87:6378-6382.
De Boer J.P., et al., (1993) Activation patterns of coagulation and fibrinolysis in baboons following infusion with lethal or sublethal dose of *Escherichia coli*. Circulatory shock. 39, 59-67.
Deangelis RA., et al., (2012) Targeted complement inhibition as a promising strategy for preventing inflammatory complications in hemodialysis.,Immunobiology, 217(11): 1097-1105.
Declercq et al: "Zilucoplan in patients with acute hypoxic respiratory failure due to COVID-19 (Zilucov): a structured summary of a study protocol for a randomised controlled trial", Trials, vol. 21, No. 1, Dec. 1, 2020.
Dedkova, L. et al. (2003) Enhanced D-amino acid incorporation into protein by modified ribosomes, J. Am. Chem. Soc. 125: 6616-6617.
Dennis et al. (2002) Albumin binding as a general strategy for improving the pharmokinetics of proteins. J Biol Chem. 277(38):35035-43.
Devlin, J.J., et. al., (1990). Random peptide libraries: a source of specific protein binding molecules, Science 249, 404-406.
Diurno et al: "Eculizumab treatment in patients with COVID-19: preliminary results from real life ASL Napoli 2 Nord experience", Apr. 1, 2020 (Apr. 1, 2020).
Engelhardt, et al., (2002) Severe cold hemagglutinin disease (CHD) successfully treated with rituximab., Blood, 100(5):1922-23.

Examination Report for corresponding New Zealand Application No. 727420 dated May 25, 2018.
Extended European Search Report for corresponding European Application No. 15807069.8 dated Mar. 19, 2018.
Extended European Search Report for corresponding European Application No. 16744125.2 dated Dec. 21, 2018.
Extended European Search Report for corresponding European Application No. 18788604.9 dated Apr. 15, 2021.
Extended European Search Report for corresponding European Application No. 19194070.9 dated Mar. 2, 2020.
Extended European Search Report for corresponding European Application No. 20157916.6 entitled "Modulators of Complement Activity" dated May 13, 2020.
First Examination Report dated May 22, 2017 in New Zealand Application No. 727420 entitled "Modulation of Complement Activity".
First Examination Report for corresponding India Application No. 201617040921 entitled "Modulation of Complement Activity" dated Dec. 9, 2019.
Forster, A.C. et al. (2003) Programming peptidomimetic syntheses by translating genetic codes designed de novo, Proc. Natl. Acad. Sci. USA 100: 6353-6357.
Fourth Examination Report for corresponding Australian Application No. 2015274482 dated Sep. 13, 2018.
Frankel, A. et al., (2003) Encodamers: unnatural peptide oligomers encoded in RNA, Chem. Biol. 10:1043-1050.
Fredslund, F. et al. (2008). Structure of and influence of a tick complement inhibitor on human complement component 6, Nature. 9:753-760.
Freskgard, Per-Ola et al. "Antibody therapies in CNS diseases", Neuropharmacology, Pergamon Press, Oxford, GB, vol. 120, Mar. 10, 2016.
Garbuzova-Davis and Sanberg "Blood-CNS Barrier Impairment in ALS patients versus an animal model" Frontiers in Cellular Neuroscience, vol. 8, Jan. 1, 2014.
Garland Donita L. et al: "Abstract", Scientific Reports, vol. 11, No. 1, Jan. 1, 2021, Retrieved from the Internet: URL:https://www.nature.com/articles/s41598-021-89978-8.pdf.
Genbank Accession No. EKQ53330.1, hypothetical protein B655 1297 [*Methanobacterium* sp. Maddingley MBC34] Sep. 26, 2013 [online]. Retrieved from the Internet <URL: http:www.ncbi.nlm.nih.gov/protein/EKQ53330.1>.
Goto, Y. et al. (2008) Reprogramming the translation initiation for the synthesis of physiologically stable cyclic peptides, ACS Chem. Biol. 3:120-129.
Hadders, M.A. et al. (2012). Assembly and regulation of the membrane attack complex based on structures of C5b6 and sC5b9, Cell Reports. 1:200-207.
Haeger M., et al., (1992) Complement, neutrophil, and macrophage activation in women with severe preeclampsia and the syndrome of hemolysis, elevated liver enzymes, and low platelet count in Obstetrics & Gynecology, 79(1):19-26.
Hajishengallis G. (2010) Complement and periodontitis. Biochem Pharmacol. 15; 80(12): 1.
Hammer, R.P., "Harnessing mRNS-display for the Discovery of Macrocyclic Peptide Drugs" BPS Peptide Showcase East, Mar. 14, 2016.
Hartman et al., (2006) Enzymatic aminoacylation of tRNA with unnatural amino acids, Proc. Natl. Acad. Sci. USA 103:4356-4361.
Hartman, M.C.T. et al. (2007) An expanded set of amino acid analogs for the ribosomal translation of unnatural peptides, PLoS ONE 2:e972.
He, M and Taussig, M (2002). Briefs in Functional Genomics and Proteomics. 1(2): 204-212.
Heinis, C. et al., (2009) Phage-encoded combinatorial chemical libraries based on bicyclic peptides. Nat Chem Biol. 5(7):502-7.
Hill et al., (2006) The incidence and prevalence of paroxysmal nocturnal hemoglobinuria (PNH) and survival of patients in Yorkshire. Blood 2006;108:Abstract 985.
Hillmen et al., (2013) Long-term safety and efficacy of sustained eculizumab treatment in patients with paroxysmal nocturnal haemoglobinuria. Br J Haematol 2013;162:62-73.

(56) References Cited

OTHER PUBLICATIONS

Hillmen, P. et al. (2006) "The Complement Inhibitor Eculizumab in Paroxysmal Nocturnal Hemoglobinuria" The New England Journal of Medicine, 355(12):1233-1243.

Hollinger, P. et al., "Diabodies":Small bivalent and bispecific antibody fragments. PNAS. 1993. 90:6444-8.

Howard et al: "Clinical Effects of the Self-administered Subcutaneous Complement Inhibitor Zilucoplan in Patients With Moderate to Severe Generalized Myasthenia Gravis: Results of a Phase 2 Randomized, Double-Blind, Placebo-Controlled, Multicenter Clinical Trial", JAMA Neurology, vol. 77. No. 5. Feb. 17, 2020.

Howard, James F. et al: "Safety and efficacy of eculizumab in anti-acetylcholine receptor antibody-positive refractory generalised myasthenia gravis (Regain): a phase 3, randomised, double-blind, placebo-controlled, multicentre study", Lancet Neurology, vol. 16, No. 12, 2017, pp. 976-986, XP085267220.

Huber-Lang, et al., (2006) Generation of C5a in the absence of C3: a new complement activation pathway. Nature Med. 12(6):682-687.

International Search Report and Written Opinion dated Apr. 22, 2016 in application No. PCT/US2016/015412, entitled: Modulators of Complement Activity.

International Search Report and Written Opinion dated Apr. 24, 2018 in application No. PCT/US2017/065005, entitled: Modulators of Complement Activity.

International Search Report and Written Opinion dated Dec. 4, 2015 in Application No. PCT/US2015/035473, entitled: Modulation of Complement Activity.

International Search Report and Written Opinion dated Mar. 1, 2019 in application No. PCT/US2018/063719 entitled "Modulators of Complement Activity".

International Search Report and Written Opinion dated Mar. 17, 2017 in Application No. PCT/US2016/065228, entitled: Modulators of Complement Activity.

International Search Report and Written Opinion dated Nov. 15, 2018 in applicaiton No. PCT/US2018/050317 entitled: Formulations for Compound Delivery.

International Search Report and Written Opinion dated Sep. 3, 2020 in PCT Application No. PCT/US2020/021330 entitled "Modulators of Complement Activity".

International Search Report and Written Opinion in application No. PCT/US2019/057316 entitled "Neurological Disease Treatment With Complement Inhibitors" dated Apr. 2, 2020.

Israel Office Action for corresponding Israel application No. 259762 entitled "Modulators of Complement Activity" dated Jun. 30, 2019.

Jackson, R.J., et al., (2001) Development of a tRNA-dependent in vitro translation system, RNA 7:765-773.

Janke et al. The arginine mimicking [beta]-amino acid [beta]3hPhe(3-H2N—CH) as S1 ligand in cyclotheonamide-based [beta]-tryptase inhibitors. Bioorg Med Chem. 2011, 19(23):7236-43;p. 7237, col. 1, Scheme 2.

Japanese Office Action for corresponding Japanese Application No. 2017-517219 dated Jun. 5, 2018.

Japanese Office Action for corresponding Japanese Application No. 2017-517219, dated Nov. 21, 2017.

Jennette et al., (2013) Complement in ANCA-associated vasculitis., Semin Nephrol. 33(6): 557-64.

Jha P., et al., (2007) The role of complement system in ocular diseases including uveitis and macular degeneration., Mol Immunol. 44(16): 3901-3908.

Jiang et al: "Blockade of the C5a-C5aR axis alleviates lung damage in hDPP4-transgenic mice infected with MERS-CoV", Emerging Microbes & Infections, vol. 7, No. 1, Apr. 24, 2018.

Johnston, J. "A Phase 1 Multiple-Dose Clinical Study of RA101495, a Subcutaneously Admin1stered Synthetic Macrocyclic Peptide Inhibitor of Complement C5 for Treatment of Paroxysmal Nocturnal Hemoglobinuria" Library of the European Hematology Association, 2016, XP055661443.

Johnston, Jeffrey et al. "A Phase 1 Single-Ascending-Dose Clinical Study of RA101495, a Subcutaneously Administered Synthetic Macrocyclic Peptide Inhibitor of Complement C5 for Treatment of Paroxysmal Nocturnal Hemoglobinuria" 2016, XP055697141, Retrieved from the Internet: URL:https://rapharma.com/wp-content/upload s/2018/12/9-Ra-Pharma-EHA-2016-RA101495-SAD-Poster.pdf.

Josephson, K. et al., (2005) Ribosomal synthesis of unnatural peptides, J. Am. Chem. Soc. 127: 11727-11735.

Josephson, K. et al., (2013) "mRNA display: from basic principles to macrocycle drug discovery" Drug Discovery Today, vol. 00, No. 00.

Kairemo E et al., (2010) A nationwide survey of paroxysmal nocturnal haemoglobinuria in Finland. Haematologica 2010;95[suppl. 2]:303:Abstract 0727.

Kay, B.K. et al. (2001) Screening phage-displayed combinatorial peptide libraries, Methods. 24:240-246.

Keefe, A.D. and Szostak, J.W. (2001) Functional proteins from a random-sequence library, Nature 15:715-718.

Keshari et al 2014 (Dec. 2014 ASH abstract) A Novel C5 Complement Inhibitor Protects Against Sepsis-Induced Activation of Complement, Coagulation and Inflammation and Provides Survival Benefit in E. coli Sepsis.

Keshari et al 2015 (ASH abstract—Blood 2015 126(765)) Complement C5 Inhibition Blocks the Cytokine Storm and Consumptive Coagulopathy by Decreasing Lipopolysaccharide (LPS) Release in E. coli Sepsis.

Korean Office Action for corresponding Korean Application No. 10-2016-7034788 dated Jun. 5, 2018.

Korean Office Action for corresponding Korean Application No. 10-2019-7014115 dated Aug. 14, 2020.

Kourtzelis I., et al., (2010) Complement anaphylatoxin C5a contributes to hemodialysis-associated thrombosis., Blood, 116(4):631-639.

Krisinger, et al., (2014) Thrombin generates previously unidentified C5 products that support the terminal complement activation pathway. Blood. 120(8):1717-1725.

Langenheim, J.F. et al., (2009) Improving the pharmacokinetics/pharmacodynamics of prolactin, GH, and their antagonists by fusion to a synthetic albumin-binding peptide. J Endocrinol. 203(3):375-87.

Law, S.K., et al. (1997). The internal thioester and the covalent binding properties of the complement proteins C3 and C4. Protein Science. 6:263-274.

Lea, W.A. et al., (2011) Fluorescence polarization assays in small molecule screening. Expert Opin Drug Discov. Jan;6(1)17-32.

Lee et al. "Pharmacological inhibition of complement C5a-C5a1 receptor signalling ameliorates disease pathology in the hSOD1G93A mouse model of amyotrophic lateral sclerosis" British Journal of Pharmacology, vol. 174, No. 8, Mar. 3, 2017.

Legendre, C.M. et al. (2013) "Terminal Complement Inhibitor Eculizumab in Atypical Hemolytic-Uremic Syndrome" The New England Journal of Medicine, 368(23):2169-2181.

Levengood, M.R. and Van der Donk, W.A., (2008) Use of lantibiotic synthetases for the preparation of bioactive constrained peptides, Bioorg. and Med. Chem. Lett. 18:3025-3028.

Levi, M. et al., (2013) Sepsis and thrombosis. Seminars in thrombosis and hemostasis 39, 559-66.

Liu, R. et al. (2000). Optimized synthesis of RNA-protein fusions for in vitro protein selection, Methods Enzymol. 318:268-293.

Mackworth-Young, (2004) Antiphospholipid syndrome: multiple mechanisms., Clin Exp Immunol 136:393-401.

Markiewski, et al., (2007) The role of complement in inflammatory diseases from behind the scenes into the spotlight . Am J Pathol. 171: 715-27.

Meri S., (2013) Complement activation in diseases presenting with thrombotic microangiopathy., European Journal of Internal Medicine, 24: 496-502.

Mexican Office Action for corresponding Mexican Application No. Mx/a/2016/016449 dated Jul. 20, 2020.

Milletti, F., 2012 Cell-penetrating peptides: classes, origin, and current landscape. Drug Discov Today. Aug;17(15-16):850-60.

Millward, S.W. et al., (2005) A general route for post-translational cyclization of mRNA display libraries, J. Am. Chem. Soc. 127:14142-14143.

(56) References Cited

OTHER PUBLICATIONS

Mollnes, T. E. et al., (2002) Essential role of the C5a receptor in *E coli*-induced oxidative burst and phagocytosis revealed by a novel lepirudin-based human whole blood model of inflammation. Blood 100, 1869-1877.

Morgan, Paul et al. "Complement, a target for therapy in inflammatory and degenerative diseases" Nature Reviews Drug Discovery 14:857-877. (Year: 2015).

Murakami, H. et al. (2006) A highly flexible tRNA acylation method for non-natural polypeptide synthesis, Nat. Methods 3:357-359.

Nakayama H et al., (2016) Eculizumab dosing intervals longer than 17 days may be associated with greater risk of breakthrough hemolysis in patients with paroxysmal nocturnal hemoglobinuria. Biol Pharm Bull.

Nemoto, H. et al., (1997) In vitro virus: bonding of mRNA bearing puromycin at the 3'-terminal end to the C-terminal end of its encoded protein on the ribosome in vitro, FEBS Lett. 414:405-408.

Nguyen A. et al., (2006) The pharmacokinetics of an albumin-binding Fab (AB.Fab) can be modulated as a function of affinity for albumin. Protein Eng Des Sel. 19:291-7.

Nishimura et al. (2012) A rare genetic polymorphism in C5 confers poor response to the anti-C5 monoclonal antibody eculizumab by nine Japanese patients with PNH Blood (ASH Annual Meeting Abstracts) 120: Abstract 3197.

Nishimura J-I et al., (2004) Clinical course and flow cytometric analysis of paroxysmal nocturnal hemoglobinuria in the United States and Japan. Medicine 2004;83:193-207.

Nishimura, J. et al., (2014) Genetic variants in C5 and poor response to eculizumab. N Engl J Med. 370: 632-9.

Oliva, B. et al., (1997) An automated classification of the structure of protein loops, J Mol Biol. Mar. 7;266(4):814-30.

Park, Brian "Zilucoplan for Myasthenia Gravis Gets Orphan Drug Designation" Neurology Advisor, Sep. 9, 2019.

Parker, C. et al., (2005) Diagnosis and management of paroxysmal nocturnal hemoglobinuria. Blood. 106: 3699-709.

Parker, C.J., (2007) the pathophysiology of paroxysmal nocturnal hemoglobinuria. Exp Hematol. 35: 523-33.

Parker, C.J., (2012) Paroxysmal nocturnal hemoglobinuria. Curr Opin Hematol. 19: 141-8.

Parker, G.J. et al., (2000) Development of high throughput screening assays using fluorescence polarization: nuclear receptor-ligand-binding and kinase/phosphatase assays. J Biomol Screen. Apr. 2000;5(2):77-88.

Prystay, L. et al., (2001) Determination of equilibrium dissociation constants in fluorescence polarization. J Biomol Screen. Jun;6(3):141-50.

Pu, J.J. et al., (2011) Paroxysmal nocturnal hemoglobinuria from bench to bedside. Clin Transl Sci. Jun;4(3):219-24.

Quigg RJ., (2003) Complement and the kidney., J Immunol 171:3319-24.

RA Pharmaceuticals, Inc., Protocol, RA101495-01.201: A Phase 2 Multicenter, Open-Label, Uncontrolled Study to Evaluate the Safety, Tolerability, Efficacy, Pharmacokinetics, and Pharmacodynamics of RA101495 in Subjects With Paroxysmal Nocturnal Hemoglobinuria.

RA Pharmaceuticals, Inc., Statistical Analysis Plan, RA101495-01.201: A Phase 2 Multicenter, Open-Label, Uncontrolled Study to Evaluate the Safety, Tolerability, Efficacy, Pharmacokinetics, and Pharmacodynamics of RA101495 in Subjects With Paroxysmal Nocturnal Hemoglobinuria.

RAPharma: "Zilucoplan in Generalized Myasthenia Gravis", dated Dec. 10, 2018 URL:https://rapharma.com/wp-content/upload s/2018/12/Zilucoplan-in-Generalized-Myasthenia-Gravis-1.pdf.

Ricardo A. et al. 939 Preclinical evaluation of RA101495, a potent cyclic peptide inhibitor of C5 for the treatment of paroxysmal nocturnal hemoglobinuria. 57th Annual Meeting and Exposition. Orlando, FL. Dec. 5-8, 2015.

Ricardo et al 2014 (Dec. 2014 ASH abstract) Development of RA101348, a Potent Cyclic Peptide Inhibitor of C5 for Complement-Mediated Diseases.

Ricardo et al 2015 (Dec. 2015 ASH abstract) Preclinical Evaluation of RA101495, a Potent Cyclic Peptide Inhibitor of C5 for the Treatment of Paroxysmal Nocturnal Hemoglobinuria.

Ricardo et al. "Preclinical Evaluation of RA101495, a Potent Cyclic Peptide Inhibitor of C5 for the Treatment of Paroxysmal Nocturnal Hemoglobinuria", ASH Meeting 2015, Abstract #939. Dec. 5, 2015.

Ricardo et al., "Development of RA101348, a Potent Cyclic Peptide Inhibitor of C5 for Complement-Mediated Diseases", Dec. 17, 2014 56th ASH Annual Meeting and Exposition, (last updated Dec. 17, 2014) Abstract retrieved from website <URL https://ash.confex.com/ash/2014/webprogram/Paper74528.html>.

Ricklin, Daniel et al. "Complement in Immune and Inflammatory Disorders: Pathophysiological Mechanisms" J. Immunol. 190: 3831-3838. (Year: 2013).

Ripka, A.S. et al., (1998) Synthesis of novel cyclic protease inhibitors using grubbs olefin metathesis. Bioorg Med Chem Lett. 8(4):357-60.

Risitano et al., (2012) The complement receptor 2/factor H fusion protein TT30 protects paroxysmal nocturnal hemoglobinuria erythrocytes from complement-mediated hemolysis and C3 fragment. Blood 119(6): 6307-16.

Risseeuw, M.D.P., (2009) Alkylated and bicyclic sugar amino acids: synthesis and applications. Doctoral Thesis, Leiden University. Chapter 1, p. 9-26.

Rittirsch D., et al., (2008) Harmful molecular mechanisms in sepsis. Nature Reviews Immunology 8, 776-87.

Rittirsch, et al., (2012) Role of complement in multiorgan failure. Clin Dev Immunol, 2012:962927.

Roberts, R.W., and Szostak, J.W. (1997) RNA-peptide fusions for the in vitro selection of peptides and proteins, Proc. Natl. Acad. Sci. USA 94, 12297-12302.

Rock, et al., (2010) The sterile inflammatory response. Annu Rev Immunol. 28:321-342.

Roth et al., (2009) Long-term efficacy of the complement inhibitor eculizumab in cold agglutinin disease.,Blood, 113:3885-86.

Rothe, A. et al. (2006) In vitro display technologies reveal novel biopharmaceutics, The FASEB Journal. 20(10)1599-1610.

Rubartelli, et al., (2013) Mechanisms of sterile inflammation. Frontiers in Immunology 4:398-99.

Russian Office Action for corresponding Russian Application No. 2016147080 dated May 30, 2018.

Russian Office Action for corresponding Russian Application No. 2016147080, dated Dec. 20, 2017.

Russian Office Action for corresponding Russian Application No. 2018121615 entitled "Modulators of Complement Activity" dated Mar. 16, 2020.

Salmon, et al., (2002) Complement activation as a mediator of antiphospholipid antibody induced pregnancy loss and thrombosis. Ann Rheum Dis 2002;61 (Suppl II):ii46-ii50.

Sando, S. et al., (2007) Unexpected preference of the *E. coli* translation system for the ester bond during incorporation of backbone-elongated substrates, J. Am. Chem. Soc. 129:6180-6186.

Schafmeister and Verdine (2000) An All-Hydrocarbon Cross-Linking System for Enhancing the Helicity and Metabolic Stability of Peptides, J. Am. Chem. Soc., 122 (24), 5891-5892.

Schlippe, et al. (2012) In vitro selection of highly modified cyclic peptides that act as tight binding inhibitors. J Am Chem. 134:10469-77.

Schrezenmeier, H. et al., (2014) Baseline characteristics and disease burden in patients in the International Paroxysmal Nocturnal Hemoglobinuria Registry. Haematologica. 99: 922-9.

Scott et al. (1999) Production of cyclic peptides and proteins in vivo, PNAS. vol. 96 No. 24 p. 13638-13643.

Second Examination Report for corresponding Australian Application No. 2015274482 dated May 10, 2018.

Seebeck, F.P. and Szostak, J.W. (2006) Ribosomal synthesis of dehydroalanine-containing peptides J. Am. Chem. Soc. Jun. 7;128(22):7150-1.

Sergeeva, A. et al. (2006). Display technologies: application for the discovery of drug and gene delivery agents, Adv. Drug Deliv. Rev. 58:1622-1654.

Shimizu, Y. et al. (2001) Cell-free translation reconstituted with purified components, Nat. Biotech. 19:751-755.

(56) References Cited

OTHER PUBLICATIONS

Singapore Written Opinion for corresponding Singapore Application No. 11201610222U, dated Dec. 28, 2017.
Sjoberg A.T., et al., (2009) Complement activation and inhibition: a delicate balance. Trends in Immunology. 30(2):83-90.
Smith, A. B. 3rd, et al. (1994) De Novo Design, Synthesis, and X-ray Crystal Structures of Pyrrolinone-Based .beta.-Strand Peptidomimetics, J. Am. Chem. Soc. 116:9947-9962.
Smith, G.P. and Petrenko, V.A., (1997) Phage Display, Chem. Rev. 97:391-410.
Socie' G et al., (1996) Paroxysmal nocturnal haemoglobinura: long-term follow-up and prognostic factors. Lancet 1996;348:573-577.
Sorbera et al: "Taking aim at a fast-moving target: targets to watch for SARS-CoV-2 and COVID-19", Drugs of the Future, vol. 45, No. 4, Jan. 1, 2020.
Soto, Y. et al. (2008) Reprogramming the translation initiation for the synthesis of physiologically stable cyclic peptides, ACS Chem. Biol. 3:120-129.
Stahel et al., (1998) The role of the complement system in traumatic brain injury.Brain Research Reviews, 27: 243-56.
Subtelny et al., (2008) Ribosomal synthesis of N-methyl peptides, J. Am. Chem. Soc. 130: 6131-6136.
Sun et al: Treatment With Anti -C5a Antibody Improves the Outcome of H7N9 Virus Infection in African Green Monkeys11 , Clinical Infectious Diseases, vol. 60, No. 4, Nov. 27, 2014.
Takashashi, T.T et al. (2003) mRNA display: ligand discovery, interaction analysis and beyond, Trends in Biochem. Sci. 28(3):159-165.
Third Examination Report for corresponding Australian Application No. 2015274482 dated Aug. 28, 2018.
Thomas et al., (1996) Inhibition of complement activity by humanized anti-C5 antibody and single-chain Fv. Molecular Immunology. 33(17-18):1389-401.
Tian, W. et al., (2012) Development of novel fluorescence polarization-based assay for studying the β-catenin/Tcf4 Interaction. J Biomol Screen. Apr;17(4):530-4.
Timmerman, P. et al., (2005) Rapid and quantitative cyclization of multiple peptide loops onto synthetic scaffolds for structural mimicry of protein surfaces, ChemBioChem 6:821-824.
US National Library of Medicine: "Phase 2 Safety and Efficacy Study of RA101495 to Treat PNH Patients", Mar. 8, 2017 (Mar. 8, 2017), XP055661467.
Van De Goot F., et al., (2009) Acute inflammation is persistent locally in burn wounds: a pivotal role for complement and C-reactive protein . J Burn Care Res 2009, 30:274-280.
Van De Walle Inge et al: "ARGX-117, a therapeutic complement inhibiting antibody targeting C2", Journal of Allergy and Clinical Immunology, Elsevier, Amsterdam, NL, vol. 147, No. 4, Sep. 11, 2020, p. 1420.
Van Den Elsen, J.M.H., (2002) X-ray crystal structure of the C4d fragment of human complement component C4, J. Mol. Biol. 322:1103-1115.
Vogt, (1999) Cleavage of the fifth component of complement and generation of a functionally active C5b6-like complex by human leukocyte elastase. Immunobiology. 201:470-477.
Yamagishi, Y. et al., (2011) Natural product-like macrocyclic N-methyl peptide inhibitors against a ubiquitin ligase uncovered from a ribosome-expressed de novo library. Chemistry & Biology 18:1562-70.
Girrbach, M. et al., "A fluorescence polarization assay for the experimental validation of an in silica model of the chemokine CXCL8 binding to receptor-derived peptides," Phys. Chem. Chem. Phys., vol. 16, Mar. 2014, pp. 8036-8043.

SEQUENCE LISTING

```
Sequence total quantity: 211
SEQ ID NO: 1                    moltype = AA  length = 13
FEATURE                         Location/Qualifiers
REGION                          1..13
                                note = Description of Artificial Sequence: Synthetic peptide
SITE                            1
                                note = N-term Ac
MOD_RES                         1
                                note = Nva
MOD_RES                         8
                                note = 7-azatryptophan
MOD_RES                         12
                                note = Tert-butylglycine
SITE                            13
                                note = C-term NH2
source                          1..13
                                mol_type = protein
                                organism = synthetic construct
SEQUENCE: 1
VCYKNYHWEY PGY                                                                  13

SEQ ID NO: 2                    moltype = AA  length = 13
FEATURE                         Location/Qualifiers
REGION                          1..13
                                note = Description of Artificial Sequence: Synthetic peptide
SITE                            1
                                note = N-term Ac
MOD_RES                         1
                                note = Nva
MOD_RES                         6
                                note = Tert-butylglycine
MOD_RES                         8
                                note = 7-azatryptophan
MOD_RES                         11
                                note = MeGly
MOD_RES                         12
                                note = Nva
MOD_RES                         13
                                note = N-methyl-Serine
SITE                            13
                                note = C-term NH2
source                          1..13
                                mol_type = protein
                                organism = synthetic construct
SEQUENCE: 2
VCYENGYWEY GVS                                                                  13

SEQ ID NO: 3                    moltype = AA  length = 13
FEATURE                         Location/Qualifiers
REGION                          1..13
                                note = Description of Artificial Sequence: Synthetic peptide
SITE                            1
                                note = N-term Ac
MOD_RES                         1
                                note = Nva
MOD_RES                         6
                                note = Tert-butylglycine
MOD_RES                         8
                                note = 7-azatryptophan
MOD_RES                         12
                                note = Phenyl-glycine
MOD_RES                         13
                                note = Nva
SITE                            13
                                note = C-term NH2
source                          1..13
                                mol_type = protein
                                organism = synthetic construct
SEQUENCE: 3
VCYENGYWEY PGV                                                                  13

SEQ ID NO: 4                    moltype = AA  length = 13
FEATURE                         Location/Qualifiers
REGION                          1..13
                                note = Description of Artificial Sequence: Synthetic peptide
SITE                            1
                                note = N-term Ac
MOD_RES                         1
```

```
                        note = Nva
MOD_RES                 6
                        note = Tert-butylglycine
MOD_RES                 8
                        note = 7-azatryptophan
MOD_RES                 12
                        note = Phenyl-glycine
SITE                    13
                        note = C-term NH2
source                  1..13
                        mol_type = protein
                        organism = synthetic construct
SEQUENCE: 4
VCYENGYWEY PGP                                                              13

SEQ ID NO: 5            moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Phenyl-glycine
MOD_RES                 13
                        note = Tert-butylglycine
SITE                    13
                        note = C-term NH2
source                  1..13
                        mol_type = protein
                        organism = synthetic construct
SEQUENCE: 5
VCYNNGEWEY PGG                                                              13

SEQ ID NO: 6            moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 4
                        note = 7-azatryptophan
MOD_RES                 5
                        note = MeGly
MOD_RES                 6
                        note = Tert-butylglycine
MOD_RES                 7
                        note = Nva
MOD_RES                 8
                        note = 7-azatryptophan
MOD_RES                 12
                        note = Phenyl-glycine
SITE                    13
                        note = C-term NH2
source                  1..13
                        mol_type = protein
                        organism = synthetic construct
SEQUENCE: 6
VCYWGGVWEY PGP                                                              13

SEQ ID NO: 7            moltype = AA   length = 11
FEATURE                 Location/Qualifiers
REGION                  1..11
                        note = Description of Artificial Sequence: Synthetic peptide
SITE                    1
                        note = N-term Ac
MOD_RES                 4
                        note = Tert-butylglycine
MOD_RES                 6
                        note = 7-azatryptophan
MOD_RES                 9
                        note = MeGly
```

```
MOD_RES              10
                     note = Nva
MOD_RES              11
                     note = N-methyl-Serine
SITE                 11
                     note = C-term NH2
source               1..11
                     mol_type = protein
                     organism = synthetic construct
SEQUENCE: 7
YENGYWEYGV S                                                              11

SEQ ID NO: 8         moltype = AA  length = 13
FEATURE              Location/Qualifiers
REGION               1..13
                     note = Description of Artificial Sequence: Synthetic peptide
SITE                 1
                     note = N-term Ac
MOD_RES              1
                     note = Nva
REGION               2..7
                     note = Bridging moiety between residues
MOD_RES              5
                     note = Phenyl-glycine
MOD_RES              8
                     note = N-methyl-Serine
MOD_RES              9
                     note = Tert-butylglycine
MOD_RES              11
                     note = 7-azatryptophan
SITE                 13
                     note = C-term NH2
source               1..13
                     mol_type = protein
                     organism = synthetic construct
SEQUENCE: 8
VCKEGYCSGK WEY                                                            13

SEQ ID NO: 9         moltype = AA  length = 13
FEATURE              Location/Qualifiers
REGION               1..13
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              8
                     note = N-methyl-Serine
MOD_RES              11
                     note = Nva
MOD_RES              13
                     note = Nva
SITE                 13
                     note = C-term NH2
source               1..13
                     mol_type = protein
                     organism = synthetic construct
SEQUENCE: 9
VCGTWEYSHC VPV                                                            13

SEQ ID NO: 10        moltype = AA  length = 13
FEATURE              Location/Qualifiers
REGION               1..13
                     note = Description of Artificial Sequence: Synthetic peptide
REGION               2..7
                     note = Bridging moiety between residues
SITE                 13
                     note = C-term NH2
source               1..13
                     mol_type = protein
                     organism = synthetic construct
SEQUENCE: 10
MCSERYCEVR WEY                                                            13
```

```
SEQ ID NO: 11           moltype = AA   length = 13
FEATURE                 Location/Qualifiers
REGION                  1..13
                        note = Description of Artificial Sequence: Synthetic peptide
REGION                  2..7
                        note = Bridging moiety between residues
SITE                    13
                        note = C-term NH2
source                  1..13
                        mol_type = protein
                        organism = synthetic construct
SEQUENCE: 11
MCVERFCDVY WEF                                                              13

SEQ ID NO: 12           moltype = AA   length = 13
FEATURE                 Location/Qualifiers
REGION                  1..13
                        note = Description of Artificial Sequence: Synthetic peptide
MOD_RES                 1..2
                        note = Nva
MOD_RES                 6
                        note = Tert-butylglycine
MOD_RES                 8
                        note = 7-azatryptophan
MOD_RES                 12
                        note = Phenyl-glycine
MOD_RES                 13
                        note = Nva
SITE                    13
                        note = C-term NH2
source                  1..13
                        mol_type = protein
                        organism = synthetic construct
SEQUENCE: 12
VVYENGYWEY PGV                                                              13

SEQ ID NO: 13           moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Phenyl-glycine
MOD_RES                 13
                        note = Nva
SITE                    13
                        note = C-term NH2
source                  1..13
                        mol_type = protein
                        organism = synthetic construct
SEQUENCE: 13
VSYENGYWEY PGV                                                              13

SEQ ID NO: 14           moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1..2
                        note = Nva
MOD_RES                 5
                        note = N-methyl-Asparagine
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
```

-continued

```
SITE                    13
                        note = C-term NH2
source                  1..13
                        mol_type = protein
                        organism = synthetic construct
SEQUENCE: 14
VVYENGYWEY PGV                                                                     13

SEQ ID NO: 15           moltype = AA  length = 16
FEATURE                 Location/Qualifiers
REGION                  1..16
                        note = Description of Artificial Sequence: Synthetic peptide
REGION                  2..7
                        note = Bridging moiety between residues
MOD_RES                 9
                        note = Tert-butylglycine
MOD_RES                 11
                        note = 7-azatryptophan
MOD_RES                 15
                        note = Phenyl-glycine
MOD_RES                 16
                        note = Nva
SITE                    16
                        note = C-term NH2
source                  1..16
                        mol_type = protein
                        organism = synthetic construct
SEQUENCE: 15
MCVERFCDGY WEYPGV                                                                  16

SEQ ID NO: 16           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1..2
                        note = Nva
MOD_RES                 6
                        note = Tert-butylglycine
MOD_RES                 8
                        note = 7-azatryptophan
MOD_RES                 12
                        note = Phenyl-glycine
MOD_RES                 13
                        note = Nva
SITE                    13
                        note = C-term NH2
source                  1..13
                        mol_type = protein
                        organism = synthetic construct
SEQUENCE: 16
VVYENGYWEY PGV                                                                     13

SEQ ID NO: 17           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 17
VCYENGYWEY PGV                                                                     13

SEQ ID NO: 18           moltype = AA  length = 12
```

| FEATURE | Location/Qualifiers |
|---|---|
| REGION | 1..12 |
| | note = Description of Artificial Sequence: Synthetic peptide |
| SITE | 1 |
| | note = N-term Ac |
| MOD_RES | 1 |
| | note = Nva |
| MOD_RES | 6 |
| | note = Tert-butylglycine |
| MOD_RES | 8 |
| | note = 7-azatryptophan |
| MOD_RES | 12 |
| | note = Phenyl-glycine |
| SITE | 12 |
| | note = C-term NH2 |
| source | 1..12 |
| | mol_type = protein |
| | organism = synthetic construct |

SEQUENCE: 18
VCYENGYWEY PG                                                                    12

| SEQ ID NO: 19 | moltype = AA  length = 12 |
|---|---|
| FEATURE | Location/Qualifiers |
| REGION | 1..12 |
| | note = Description of Artificial Sequence: Synthetic peptide |
| SITE | 1 |
| | note = N-term Ac |
| REGION | 1..6 |
| | note = Bridging moiety between residues |
| SITE | 12 |
| | note = C-term NH2 |
| source | 1..12 |
| | mol_type = protein |
| | organism = synthetic construct |

SEQUENCE: 19
CVERFCDVYW EF                                                                    12

| SEQ ID NO: 20 | moltype = AA  length = 14 |
|---|---|
| FEATURE | Location/Qualifiers |
| REGION | 1..14 |
| | note = Description of Artificial Sequence: Synthetic peptide |
| SITE | 1 |
| | note = N-term Ac |
| MOD_RES | 1..2 |
| | note = Nva |
| MOD_RES | 6 |
| | note = Tert-butylglycine |
| MOD_RES | 8 |
| | note = 7-azatryptophan |
| MOD_RES | 12 |
| | note = Cyclohexylglycine |
| MOD_RES | 13 |
| | note = Nva |
| SITE | 14 |
| | note = C-term NH2 |
| source | 1..14 |
| | mol_type = protein |
| | organism = synthetic construct |

SEQUENCE: 20
VVYENGYWEY PGVK                                                                  14

| SEQ ID NO: 21 | moltype = AA  length = 12 |
|---|---|
| FEATURE | Location/Qualifiers |
| REGION | 1..12 |
| | note = Description of Artificial Sequence: Synthetic peptide |
| SITE | 1 |
| | note = N-term Ac |
| MOD_RES | 5 |
| | note = Tert-butylglycine |
| MOD_RES | 7 |
| | note = 7-azatryptophan |
| MOD_RES | 11 |
| | note = Phenyl-glycine |
| MOD_RES | 12 |
| | note = Nva |
| SITE | 12 |
| | note = C-term NH2 |
| source | 1..12 |
| | mol_type = protein |

```
                        organism = synthetic construct
SEQUENCE: 21
CYENGYWEYP GV                                                                  12

SEQ ID NO: 22           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1..2
                        note = Nva
MOD_RES                 3
                        note = N-methyl-Tyrosine
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 22
VVYENGYWEY PGV                                                                 13

SEQ ID NO: 23           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 23
VCGTWEYSHC V                                                                   11

SEQ ID NO: 24           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 4
                        note = Tert-butylglycine
MOD_RES                 6
                        note = 7-azatryptophan
MOD_RES                 10
                        note = Phenyl-glycine
MOD_RES                 11
                        note = Nva
SITE                    11
                        note = C-term NH2
source                  1..11
                        mol_type = protein
                        organism = synthetic construct
SEQUENCE: 24
YENGYWEYPG V                                                                   11

SEQ ID NO: 25           moltype = AA  length = 13
```

```
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 25
VSYEAGYWEY PGV                                                                      13

SEQ ID NO: 26           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 4
                        note = Tert-butylglycine
MOD_RES                 10
                        note = Phenyl-glycine
MOD_RES                 11
                        note = Nva
SITE                    11
                        note = C-term NH2
source                  1..11
                        mol_type = protein
                        organism = synthetic construct
SEQUENCE: 26
YENGYWEYPG V                                                                        11

SEQ ID NO: 27           moltype = AA  length = 14
FEATURE                 Location/Qualifiers
REGION                  1..14
                        note = Description of Artificial Sequence: Synthetic peptide
SITE                    1
                        note = N-term Ac
MOD_RES                 1..2
                        note = Nva
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    14
                        note = C-term (PEG2000)NH2
source                  1..14
                        mol_type = protein
                        organism = synthetic construct
SEQUENCE: 27
VVYENGYWEY PGVK                                                                     14

SEQ ID NO: 28           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
```

```
SITE                    11
                        note = C-term NH2
source                  1..11
                        mol_type = protein
                        organism = synthetic construct
SEQUENCE: 28
VCYENGYWEY P                                                                    11

SEQ ID NO: 29           moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 29
VSYENAYWEY PGV                                                                  13

SEQ ID NO: 30           moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 30
VSYENGAWEY PGV                                                                  13

SEQ ID NO: 31           moltype = AA   length = 12
FEATURE                 Location/Qualifiers
REGION                  1..12
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 11
                        note = Nva
SITE                    12
                        note = C-term NH2
source                  1..12
                        mol_type = protein
                        organism = synthetic construct
SEQUENCE: 31
VCGTWEYSHC VP                                                                   12
```

```
SEQ ID NO: 32            moltype = AA  length = 13
FEATURE                  Location/Qualifiers
REGION                   1..13
                         note = Description of Artificial Sequence: Synthetic peptide
SITE                     1
                         note = N-term Ac
MOD_RES                  1
                         note = Nva
MOD_RES                  6
                         note = Tert-butylglycine
MOD_RES                  8
                         note = 7-azatryptophan
MOD_RES                  12
                         note = Cyclohexylglycine
MOD_RES                  13
                         note = Nva
SITE                     13
                         note = C-term NH2
source                   1..13
                         mol_type = protein
                         organism = synthetic construct
SEQUENCE: 32
VSYENGYWEY AGV                                                             13

SEQ ID NO: 33            moltype = AA  length = 13
FEATURE                  Location/Qualifiers
REGION                   1..13
                         note = Description of Artificial Sequence: Synthetic peptide
SITE                     1
                         note = N-term Ac
MOD_RES                  1
                         note = Nva
MOD_RES                  6
                         note = Tert-butylglycine
MOD_RES                  8
                         note = 7-azatryptophan
MOD_RES                  13
                         note = Nva
SITE                     13
                         note = C-term NH2
source                   1..13
                         mol_type = protein
                         organism = synthetic construct
SEQUENCE: 33
VSYENGYWEY PAV                                                             13

SEQ ID NO: 34            moltype = AA  length = 11
FEATURE                  Location/Qualifiers
REGION                   1..11
                         note = Description of Artificial Sequence: Synthetic peptide
SITE                     1
                         note = N-term Ac
MOD_RES                  1
                         note = Nva
REGION                   2..10
                         note = Bridging moiety between residues
MOD_RES                  3
                         note = Phenyl-glycine
MOD_RES                  5
                         note = 7-azatryptophan
MOD_RES                  8
                         note = N-methyl-Serine
MOD_RES                  11
                         note = Nva
SITE                     11
                         note = C-term NH2
source                   1..11
                         mol_type = protein
                         organism = synthetic construct
SEQUENCE: 34
VCGAWEYSHC V                                                               11

SEQ ID NO: 35            moltype = AA  length = 11
FEATURE                  Location/Qualifiers
REGION                   1..11
                         note = Description of Artificial Sequence: Synthetic peptide
SITE                     1
                         note = N-term Ac
```

```
MOD_RES          1
                 note = Nva
REGION           2..10
                 note = Bridging moiety between residues
MOD_RES          3
                 note = Phenyl-glycine
MOD_RES          5
                 note = 7-azatryptophan
MOD_RES          8
                 note = N-methyl-Serine
MOD_RES          11
                 note = Nva
SITE             11
                 note = C-term NH2
source           1..11
                 mol_type = protein
                 organism = synthetic construct
SEQUENCE: 35
VCGTWEYSAC V                                                             11

SEQ ID NO: 36    moltype = AA   length = 11
FEATURE          Location/Qualifiers
REGION           1..11
                 note = Description of Artificial Sequence: Synthetic peptide
SITE             1
                 note = N-term Ac
MOD_RES          1
                 note = Nva
REGION           2..10
                 note = Bridging moiety between residues
MOD_RES          3
                 note = Phenyl-glycine
MOD_RES          5
                 note = 7-azatryptophan
MOD_RES          8
                 note = N-methyl-Serine
MOD_RES          11
                 note = Nva
SITE             11
                 note = C-term NH2
source           1..11
                 mol_type = protein
                 organism = synthetic construct
SEQUENCE: 36
VCGTWEYSHC V                                                             11

SEQ ID NO: 37    moltype = AA   length = 13
FEATURE          Location/Qualifiers
REGION           1..13
                 note = Description of Artificial Sequence: Synthetic peptide
SITE             1
                 note = N-term Ac
MOD_RES          1
                 note = Nva
MOD_RES          6
                 note = Tert-butylglycine
MOD_RES          8
                 note = 7-azatryptophan
MOD_RES          12
                 note = Cyclohexylglycine
MOD_RES          13
                 note = Nva
SITE             13
                 note = C-term NH2
source           1..13
                 mol_type = protein
                 organism = synthetic construct
SEQUENCE: 37
VSYANGYWEY PGV                                                           13

SEQ ID NO: 38    moltype = AA   length = 11
FEATURE          Location/Qualifiers
REGION           1..11
                 note = Description of Artificial Sequence: Synthetic peptide
SITE             1
                 note = N-term Ac
MOD_RES          1
                 note = Nva
REGION           2..10
```

```
                            note = Bridging moiety between residues
MOD_RES                     3
                            note = Phenyl-glycine
MOD_RES                     5
                            note = 7-azatryptophan
MOD_RES                     8
                            note = N-methyl-Serine
SITE                        11
                            note = C-term NH2
source                      1..11
                            mol_type = protein
                            organism = synthetic construct
SEQUENCE: 38
VCGTWEYSHC A                                                              11

SEQ ID NO: 39               moltype = AA  length = 11
FEATURE                     Location/Qualifiers
REGION                      1..11
                            note = Description of Artificial Sequence: Synthetic peptide
SITE                        1
                            note = N-term Ac
MOD_RES                     1
                            note = Nva
REGION                      2..10
                            note = Bridging moiety between residues
MOD_RES                     3
                            note = Phenyl-glycine
MOD_RES                     5
                            note = 7-azatryptophan
MOD_RES                     8
                            note = N-methyl-alanine
MOD_RES                     11
                            note = Nva
SITE                        11
                            note = C-term NH2
source                      1..11
                            mol_type = protein
                            organism = synthetic construct
SEQUENCE: 39
VCGTWEYAHC V                                                              11

SEQ ID NO: 40               moltype = AA  length = 14
FEATURE                     Location/Qualifiers
REGION                      1..14
                            note = Description of Artificial Sequence: Synthetic peptide
SITE                        1
                            note = N-term Ac
MOD_RES                     1..2
                            note = Nva
MOD_RES                     6
                            note = Tert-butylglycine
MOD_RES                     8
                            note = 7-azatryptophan
MOD_RES                     12
                            note = Cyclohexylglycine
MOD_RES                     13
                            note = Nva
SITE                        14
                            note = C-term (BODIPY-TMR-X)NH2
source                      1..14
                            mol_type = protein
                            organism = synthetic construct
SEQUENCE: 40
VVYENGYWEY PGVK                                                           14

SEQ ID NO: 41               moltype = AA  length = 11
FEATURE                     Location/Qualifiers
REGION                      1..11
                            note = Description of Artificial Sequence: Synthetic peptide
SITE                        1
                            note = N-term Ac
MOD_RES                     1
                            note = Nva
REGION                      2..10
                            note = Bridging moiety between residues
MOD_RES                     3
                            note = Phenyl-glycine
MOD_RES                     5
                            note = 7-azatryptophan
```

| | | |
|---|---|---|
| MOD_RES | 7 | |
| | note = O-methyl tyrosine | |
| MOD_RES | 8 | |
| | note = N-methyl-Serine | |
| MOD_RES | 11 | |
| | note = Nva | |
| SITE | 11 | |
| | note = C-term NH2 | |
| source | 1..11 | |
| | mol_type = protein | |
| | organism = synthetic construct | |
| SEQUENCE: 41 | | |
| VCGTWEYSHC V | | 11 |
| | | |
| SEQ ID NO: 42 | moltype = AA  length = 10 | |
| FEATURE | Location/Qualifiers | |
| REGION | 1..10 | |
| | note = Description of Artificial Sequence: Synthetic peptide | |
| SITE | 1 | |
| | note = N-term Ac | |
| MOD_RES | 1 | |
| | note = Nva | |
| REGION | 2..10 | |
| | note = Bridging moiety between residues | |
| MOD_RES | 3 | |
| | note = Phenyl-glycine | |
| MOD_RES | 5 | |
| | note = 7-azatryptophan | |
| MOD_RES | 8 | |
| | note = N-methyl-Serine | |
| SITE | 10 | |
| | note = C-term NH2 | |
| source | 1..10 | |
| | mol_type = protein | |
| | organism = synthetic construct | |
| SEQUENCE: 42 | | |
| VCGTWEYSHC | | 10 |
| | | |
| SEQ ID NO: 43 | moltype = AA  length = 11 | |
| FEATURE | Location/Qualifiers | |
| REGION | 1..11 | |
| | note = Description of Artificial Sequence: Synthetic peptide | |
| SITE | 1 | |
| | note = N-term Ac | |
| MOD_RES | 1 | |
| | note = Nva | |
| REGION | 2..10 | |
| | note = Bridging moiety between residues | |
| MOD_RES | 3 | |
| | note = Phenyl-glycine | |
| MOD_RES | 5 | |
| | note = 7-azatryptophan | |
| MOD_RES | 11 | |
| | note = Nva | |
| SITE | 11 | |
| | note = C-term NH2 | |
| source | 1..11 | |
| | mol_type = protein | |
| | organism = synthetic construct | |
| SEQUENCE: 43 | | |
| VCGTWEYPHC V | | 11 |
| | | |
| SEQ ID NO: 44 | moltype = AA  length = 11 | |
| FEATURE | Location/Qualifiers | |
| REGION | 1..11 | |
| | note = Description of Artificial Sequence: Synthetic peptide | |
| SITE | 1 | |
| | note = N-term Ac | |
| MOD_RES | 1 | |
| | note = Nva | |
| REGION | 2..10 | |
| | note = Bridging moiety between residues | |
| MOD_RES | 3 | |
| | note = Phenyl-glycine | |
| MOD_RES | 5 | |
| | note = 7-azatryptophan | |
| MOD_RES | 7 | |
| | note = 4-fluorophenylalanine | |
| MOD_RES | 8 | |

```
                        note = N-methyl-Serine
MOD_RES                 11
                        note = Nva
SITE                    11
                        note = C-term NH2
source                  1..11
                        mol_type = protein
                        organism = synthetic construct
SEQUENCE: 44
VCGTWEFSHC V                                                           11

SEQ ID NO: 45           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1..2
                        note = Nva
MOD_RES                 6
                        note = Tert-butylglycine
MOD_RES                 8
                        note = N-methyl-Tryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 45
VVYENGYWEY PGV                                                         13

SEQ ID NO: 46           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Phenyl-glycine
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 46
VCGTWEYSAC V                                                           11

SEQ ID NO: 47           moltype = AA  length = 13
FEATURE                 Location/Qualifiers
REGION                  1..13
                        note = Description of Artificial Sequence: Synthetic peptide
SITE                    1
                        note = N-term PEG2000
MOD_RES                 1..2
                        note = Nva
MOD_RES                 6
                        note = Tert-butylglycine
MOD_RES                 8
                        note = 7-azatryptophan
MOD_RES                 12
                        note = Phenyl-glycine
MOD_RES                 13
                        note = Nva
SITE                    13
                        note = C-term NH2
source                  1..13
                        mol_type = protein
```

```
                          organism = synthetic construct
SEQUENCE: 47
VVYENGYWEY PGV                                                          13

SEQ ID NO: 48             moltype = AA  length = 11
FEATURE                   Location/Qualifiers
REGION                    1..11
                          note = Description of Artificial Sequence: Synthetic peptide
SITE                      1
                          note = N-term Ac
MOD_RES                   1
                          note = Nva
REGION                    2..10
                          note = Bridging moiety between residues
MOD_RES                   3
                          note = Phenyl-glycine
MOD_RES                   5
                          note = 7-azatryptophan
MOD_RES                   8
                          note = N-methyl-Serine
MOD_RES                   11
                          note = Nva
SITE                      11
                          note = C-term NH2
source                    1..11
                          mol_type = protein
                          organism = synthetic construct
SEQUENCE: 48
VCGTWEFSAC V                                                            11

SEQ ID NO: 49             moltype = AA  length = 13
FEATURE                   Location/Qualifiers
REGION                    1..13
                          note = Description of Artificial Sequence: Synthetic peptide
SITE                      1
                          note = N-term Ac
MOD_RES                   1..2
                          note = Nva
MOD_RES                   6
                          note = Tert-butylglycine
MOD_RES                   8
                          note = 7-azatryptophan
MOD_RES                   12
                          note = N-methyl-phenyl-glycine
MOD_RES                   13
                          note = Nva
SITE                      13
                          note = C-term NH2
source                    1..13
                          mol_type = protein
                          organism = synthetic construct
SEQUENCE: 49
VVYENGYWEY PGV                                                          13

SEQ ID NO: 50             moltype = AA  length = 12
FEATURE                   Location/Qualifiers
REGION                    1..12
                          note = Description of Artificial Sequence: Synthetic peptide
REGION                    2..7
                          note = Bridging moiety between residues
SITE                      12
                          note = C-term NH2
source                    1..12
                          mol_type = protein
                          organism = synthetic construct
SEQUENCE: 50
MCVERFCDVY WE                                                           12

SEQ ID NO: 51             moltype = AA  length = 11
FEATURE                   Location/Qualifiers
REGION                    1..11
                          note = Description of Artificial Sequence: Synthetic peptide
SITE                      1
                          note = N-term Ac
MOD_RES                   1
                          note = Nva
REGION                    2..10
                          note = Bridging moiety between residues
MOD_RES                   3
```

```
                        note = Phenyl-glycine
MOD_RES                 5
                        note = 7-azatryptophan
MOD_RES                 11
                        note = Nva
SITE                    11
                        note = C-term NH2
source                  1..11
                        mol_type = protein
                        organism = synthetic construct
SEQUENCE: 51
VCGTWEYPHC V                                                               11

SEQ ID NO: 52           moltype = AA  length = 10
FEATURE                 Location/Qualifiers
REGION                  1..10
                        note = Description of Artificial Sequence: Synthetic peptide
SITE                    1
                        note = N-term Ac
MOD_RES                 3
                        note = Tert-butylglycine
MOD_RES                 5
                        note = 7-azatryptophan
MOD_RES                 9
                        note = Phenyl-glycine
MOD_RES                 10
                        note = Nva
SITE                    10
                        note = C-term NH2
source                  1..10
                        mol_type = protein
                        organism = synthetic construct
SEQUENCE: 52
ENGYWEYPGV                                                                 10

SEQ ID NO: 53           moltype = AA  length = 11
FEATURE                 Location/Qualifiers
REGION                  1..11
                        note = Description of Artificial Sequence: Synthetic peptide
SITE                    1
                        note = N-term Ac
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 53
ACGTWEYSHC V                                                               11

SEQ ID NO: 54           moltype = AA  length = 14
FEATURE                 Location/Qualifiers
REGION                  1..14
                        note = Description of Artificial Sequence: Synthetic peptide
SITE                    1
                        note = N-term Ac
MOD_RES                 1
                        note = Nva
REGION                  2..14
                        note = Bridging moiety between residues
MOD_RES                 6
                        note = Tert-butylglycine
MOD_RES                 8
                        note = 7-azatryptophan
MOD_RES                 12
                        note = Phenyl-glycine
MOD_RES                 13
                        note = Nva
SITE                    14
                        note = C-term NH2
```

```
source                  1..14
                        mol_type = protein
                        organism = synthetic construct
SEQUENCE: 54
VCYENGYWEY PGVC                                                              14

SEQ ID NO: 55           moltype = AA  length = 12
FEATURE                 Location/Qualifiers
REGION                  1..12
                        note = Description of Artificial Sequence: Synthetic peptide
SITE                    1
                        note = N-term Ac
REGION                  1..9
                        note = Bridging moiety between residues
MOD_RES                 2
                        note = Phenyl-glycine
MOD_RES                 4
                        note = 7-azatryptophan
MOD_RES                 7
                        note = N-methyl-Serine
MOD_RES                 10
                        note = Nva
MOD_RES                 12
                        note = Nva
SITE                    12
                        note = C-term NH2
source                  1..12
                        mol_type = protein
                        organism = synthetic construct
SEQUENCE: 55
CGTWEYSHCV PV                                                                12

SEQ ID NO: 56           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 2
                        note = Homocysteine
MOD_RES                 3
                        note = Phenyl-glycine
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 56
VCGTWEYSHC V                                                                 11

SEQ ID NO: 57           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
```

```
                        mol_type = protein
                        organism = synthetic construct
SEQUENCE: 57
VSAENGYWEY PGV                                                          13

SEQ ID NO: 58           moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1..2
                        note = Nva
MOD_RES                 4
                        note = N-methyl-Glutamic Acid
MOD_RES                 6
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 58
VVYENGYWEY PGV                                                          13

SEQ ID NO: 59           moltype = AA   length = 11
FEATURE                 Location/Qualifiers
REGION                  1..11
                        note = Description of Artificial Sequence: Synthetic peptide
SITE                    1
                        note = N-term Ac
MOD_RES                 4
                        note = Tert-butylglycine
MOD_RES                 6
                        note = 1-methyltryptophan
MOD_RES                 10
                        note = Phenyl-glycine
MOD_RES                 11
                        note = Nva
SITE                    11
                        note = C-term NH2
source                  1..11
                        mol_type = protein
                        organism = synthetic construct
SEQUENCE: 59
YENGYWEYPG V                                                            11

SEQ ID NO: 60           moltype = AA   length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 8
                        note = 7-azatryptophan
MOD_RES                 12
                        note = Phenyl-glycine
MOD_RES                 13
                        note = Tert-butylglycine
SITE                    13
                        note = C-term NH2
source                  1..13
                        mol_type = protein
                        organism = synthetic construct
SEQUENCE: 60
VCYNNGEWEC PGG                                                          13

SEQ ID NO: 61           moltype = AA   length = 11
FEATURE                 Location/Qualifiers
```

```
                          -continued

REGION                    1..11
                          note = Description of Artificial Sequence: Synthetic peptide
SITE                      1
                          note = N-term Ac
MOD_RES                   1
                          note = Nva
REGION                    2..10
                          note = Bridging moiety between residues
MOD_RES                   3
                          note = Phenyl-glycine
MOD_RES                   5
                          note = 7-azatryptophan
MOD_RES                   8
                          note = N-methyl-Serine
MOD_RES                   11
                          note = Nva
SITE                      11
                          note = C-term NH2
source                    1..11
                          mol_type = protein
                          organism = synthetic construct
SEQUENCE: 61
VCGTWEYSHC V                                                                        11

SEQ ID NO: 62             moltype = AA  length = 13
FEATURE                   Location/Qualifiers
REGION                    1..13
                          note = Description of Artificial Sequence: Synthetic peptide
SITE                      1
                          note = N-term Ac
MOD_RES                   1
                          note = Nva
MOD_RES                   6
                          note = Tert-butylglycine
MOD_RES                   8
                          note = 7-azatryptophan
MOD_RES                   12
                          note = Cyclohexylglycine
MOD_RES                   13
                          note = Nva
SITE                      13
                          note = C-term NH2
source                    1..13
                          mol_type = protein
                          organism = synthetic construct
SEQUENCE: 62
VSYENGYWEA PGV                                                                      13

SEQ ID NO: 63             moltype = AA  length = 9
FEATURE                   Location/Qualifiers
REGION                    1..9
                          note = Description of Artificial Sequence: Synthetic peptide
SITE                      1
                          note = N-term Ac
REGION                    1..9
                          note = Bridging moiety between residues
MOD_RES                   2
                          note = Phenyl-glycine
MOD_RES                   4
                          note = 7-azatryptophan
MOD_RES                   7
                          note = N-methyl-Serine
SITE                      9
                          note = C-term NH2
source                    1..9
                          mol_type = protein
                          organism = synthetic construct
SEQUENCE: 63
CGTWEYSHC                                                                            9

SEQ ID NO: 64             moltype = AA  length = 13
FEATURE                   Location/Qualifiers
REGION                    1..13
                          note = Description of Artificial Sequence: Synthetic peptide
SITE                      1
                          note = N-term Ac
MOD_RES                   1
                          note = Nva
MOD_RES                   6
```

```
                        note = Tert-butylglycine
MOD_RES                 8
                        note = 7-azatryptophan
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 64
VSYENGYWAY PGV                                                                          13

SEQ ID NO: 65           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 10
                        note = Homocysteine
MOD_RES                 11
                        note = Nva
SITE                    11
                        note = C-term NH2
source                  1..11
                        mol_type = protein
                        organism = synthetic construct
SEQUENCE: 65
VCGTWEYSHC V                                                                            11

SEQ ID NO: 66           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 10
                        note = Homocysteine
MOD_RES                 11
                        note = Nva
SITE                    11
                        note = C-term NH2
source                  1..11
                        mol_type = protein
                        organism = synthetic construct
SEQUENCE: 66
VCGTWEYSHC V                                                                            11

SEQ ID NO: 67           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
```

```
MOD_RES            3
                   note = Phenyl-glycine
REGION             4..10
                   note = Bridging moiety between residues
MOD_RES            5
                   note = 7-azatryptophan
MOD_RES            8
                   note = N-methyl-Serine
MOD_RES            11
                   note = Nva
SITE               11
                   note = C-term NH2
source             1..11
                   mol_type = protein
                   organism = synthetic construct
SEQUENCE: 67
VTGCWEYSAC V                                                                    11

SEQ ID NO: 68      moltype = AA  length = 11
FEATURE            Location/Qualifiers
REGION             1..11
                   note = Description of Artificial Sequence: Synthetic peptide
SITE               1
                   note = N-term Ac
SITE               1
                   note = Nle
REGION             2..10
                   note = Bridging moiety between residues
MOD_RES            3
                   note = Phenyl-glycine
MOD_RES            5
                   note = 7-azatryptophan
MOD_RES            8
                   note = N-methyl-Serine
MOD_RES            11
                   note = Nva
SITE               11
                   note = C-term NH2
source             1..11
                   mol_type = protein
                   organism = synthetic construct
SEQUENCE: 68
LCGTWEYSHC V                                                                    11

SEQ ID NO: 69      moltype = AA  length = 12
FEATURE            Location/Qualifiers
REGION             1..12
                   note = Description of Artificial Sequence: Synthetic peptide
SITE               1
                   note = N-term Ac
MOD_RES            2
                   note = Nva
REGION             3..11
                   note = Bridging moiety between residues
MOD_RES            4
                   note = Phenyl-glycine
MOD_RES            6
                   note = 7-azatryptophan
MOD_RES            9
                   note = N-methyl-Serine
MOD_RES            12
                   note = Nva
SITE               12
                   note = C-term NH2
source             1..12
                   mol_type = protein
                   organism = synthetic construct
SEQUENCE: 69
YVCGTWEYSH CV                                                                   12

SEQ ID NO: 70      moltype = AA  length = 11
FEATURE            Location/Qualifiers
REGION             1..11
                   note = Description of Artificial Sequence: Synthetic peptide
SITE               1
                   note = N-term Ac
MOD_RES            1
                   note = Nva
REGION             2..10
```

```
                        note = Bridging moiety between residues
MOD_RES                 3
                        note = Phenyl-glycine
MOD_RES                 5
                        note = 7-azatryptophan
MOD_RES                 7
                        note = 3-chlorophenylalanine
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 70
VCGTWEFSAC V                                                                    11

SEQ ID NO: 71           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 6
                        note = Tert-butylglycine
MOD_RES                 8
                        note = 7-azatryptophan
MOD_RES                 12
                        note = Phenyl-glycine
MOD_RES                 13
                        note = Nva
SITE                    13
                        note = C-term NH2
source                  1..13
                        mol_type = protein
                        organism = synthetic construct
SEQUENCE: 71
VCYENGYWEC PGV                                                                  13

SEQ ID NO: 72           moltype = AA  length = 9
FEATURE                 Location/Qualifiers
REGION                  1..9
                        note = Description of Artificial Sequence: Synthetic peptide
SITE                    1
                        note = N-term Ac
MOD_RES                 2
                        note = Tert-butylglycine
MOD_RES                 4
                        note = 7-azatryptophan
MOD_RES                 8
                        note = Phenyl-glycine
MOD_RES                 9
                        note = Nva
SITE                    9
                        note = C-term NH2
source                  1..9
                        mol_type = protein
                        organism = synthetic construct
SEQUENCE: 72
NGYWEYPGV                                                                       9

SEQ ID NO: 73           moltype = AA  length = 8
FEATURE                 Location/Qualifiers
REGION                  1..8
                        note = Description of Artificial Sequence: Synthetic peptide
SITE                    1
                        note = N-term Ac
MOD_RES                 1
                        note = Tert-butylglycine
MOD_RES                 3
                        note = 7-azatryptophan
MOD_RES                 7
                        note = Phenyl-glycine
```

```
MOD_RES                 8
                        note = Nva
SITE                    8
                        note = C-term NH2
source                  1..8
                        mol_type = protein
                        organism = synthetic construct
SEQUENCE: 73
GYWEYPGV                                                                        8

SEQ ID NO: 74           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 74
VCATWEYSHC V                                                                    11

SEQ ID NO: 75           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Cyclohexylglycine
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 75
VCGTWEYSHC V                                                                    11

SEQ ID NO: 76           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
```

```
SEQUENCE: 76
VSYENGYAEY PGV                                                               13

SEQ ID NO: 77           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1..2
                        note = Nva
MOD_RES                 6
                        note = Tert-butylglycine
MOD_RES                 8
                        note = 7-azatryptophan
MOD_RES                 10
                        note = N-methyl-Tyrosine
MOD_RES                 12
                        note = Cyclohexylglycine
MOD_RES                 13
                        note = Nva
SITE                    13
                        note = C-term NH2
source                  1..13
                        mol_type = protein
                        organism = synthetic construct
SEQUENCE: 77
VVYENGYWEY PGV                                                               13

SEQ ID NO: 78           moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 3
                        note = Phenyl-glycine
MOD_RES                 5
                        note = 7-azatryptophan
MOD_RES                 8
                        note = N-methyl-Serine
MOD_RES                 11
                        note = Nva
MOD_RES                 13
                        note = Nva
SITE                    13
                        note = C-term NH2
source                  1..13
                        mol_type = protein
                        organism = synthetic construct
SEQUENCE: 78
VCGTWEYSHC VPV                                                               13

SEQ ID NO: 79           moltype = AA  length = 9
FEATURE                 Location/Qualifiers
REGION                  1..9
                        note = Description of Artificial Sequence: Synthetic peptide
SITE                    1
                        note = N-term Ac
REGION                  1..9
                        note = Bridging moiety between residues
MOD_RES                 2
                        note = Tert-butylglycine
MOD_RES                 4
                        note = 7-azatryptophan
MOD_RES                 7
                        note = N-methyl-Serine
SITE                    9
                        note = C-term NH2
source                  1..9
                        mol_type = protein
                        organism = synthetic construct
SEQUENCE: 79
CGYWEYSHC                                                                    9

SEQ ID NO: 80           moltype = AA  length = 11
FEATURE                 Location/Qualifiers
```

```
                         -continued
REGION                   1..11
                         note = Description of Artificial Sequence: Synthetic peptide
SITE                     1
                         note = N-term Ac
MOD_RES                  1
                         note = Cyclohexylglycine
REGION                   2..10
                         note = Bridging moiety between residues
MOD_RES                  3
                         note = Phenyl-glycine
MOD_RES                  5
                         note = 7-azatryptophan
MOD_RES                  8
                         note = N-methyl-Serine
MOD_RES                  11
                         note = Nva
SITE                     11
                         note = C-term NH2
source                   1..11
                         mol_type = protein
                         organism = synthetic construct
SEQUENCE: 80
GCGTWEYSAC V                                                                      11

SEQ ID NO: 81            moltype = AA  length = 11
FEATURE                  Location/Qualifiers
REGION                   1..11
                         note = Description of Artificial Sequence: Synthetic peptide
SITE                     1
                         note = N-term Ac
REGION                   2..10
                         note = Bridging moiety between residues
MOD_RES                  3
                         note = Phenyl-glycine
MOD_RES                  5
                         note = 7-azatryptophan
MOD_RES                  8
                         note = N-methyl-Serine
MOD_RES                  11
                         note = Nva
SITE                     11
                         note = C-term NH2
source                   1..11
                         mol_type = protein
                         organism = synthetic construct
SEQUENCE: 81
VCGTWEYSAC V                                                                      11

SEQ ID NO: 82            moltype = AA  length = 11
FEATURE                  Location/Qualifiers
REGION                   1..11
                         note = Description of Artificial Sequence: Synthetic peptide
SITE                     1
                         note = N-term Ac
MOD_RES                  1
                         note = Nva
REGION                   2..10
                         note = Bridging moiety between residues
MOD_RES                  3
                         note = 2-O-methylphenylglycine
MOD_RES                  5
                         note = 7-azatryptophan
MOD_RES                  8
                         note = N-methyl-Serine
MOD_RES                  11
                         note = Nva
SITE                     11
                         note = C-term NH2
source                   1..11
                         mol_type = protein
                         organism = synthetic construct
SEQUENCE: 82
VCGTWEYSHC V                                                                      11

SEQ ID NO: 83            moltype = AA  length = 11
FEATURE                  Location/Qualifiers
REGION                   1..11
                         note = Description of Artificial Sequence: Synthetic peptide
SITE                     1
```

```
                          note = N-term Ac
MOD_RES                   1
                          note = Nva
MOD_RES                   2
                          note = Homocysteine
REGION                    2..10
                          note = Bridging moiety between residues
MOD_RES                   3
                          note = Phenyl-glycine
MOD_RES                   5
                          note = 7-azatryptophan
MOD_RES                   8
                          note = N-methyl-Serine
MOD_RES                   11
                          note = Nva
SITE                      11
                          note = C-term NH2
source                    1..11
                          mol_type = protein
                          organism = synthetic construct
SEQUENCE: 83
VCGTWEYSHC V                                                                 11

SEQ ID NO: 84             moltype = AA  length = 11
FEATURE                   Location/Qualifiers
REGION                    1..11
                          note = Description of Artificial Sequence: Synthetic peptide
SITE                      1
                          note = N-term Ac
MOD_RES                   1
                          note = Nva
REGION                    2..10
                          note = Bridging moiety between residues
MOD_RES                   3
                          note = Phenyl-glycine
MOD_RES                   5
                          note = 7-azatryptophan
MOD_RES                   8
                          note = N-methyl-Serine
SITE                      9
                          note = D-Alanine
MOD_RES                   11
                          note = Nva
SITE                      11
                          note = C-term NH2
source                    1..11
                          mol_type = protein
                          organism = synthetic construct
SEQUENCE: 84
VCGTWEYSAC V                                                                 11

SEQ ID NO: 85             moltype = AA  length = 11
FEATURE                   Location/Qualifiers
REGION                    1..11
                          note = Description of Artificial Sequence: Synthetic peptide
SITE                      1
                          note = N-term Ac
MOD_RES                   1
                          note = Nva
REGION                    2..10
                          note = Bridging moiety between residues
MOD_RES                   3
                          note = Phenyl-glycine
MOD_RES                   8
                          note = N-methyl-Serine
MOD_RES                   11
                          note = Nva
SITE                      11
                          note = C-term NH2
source                    1..11
                          mol_type = protein
                          organism = synthetic construct
SEQUENCE: 85
VCGTAEYSHC V                                                                 11

SEQ ID NO: 86             moltype = AA  length = 11
FEATURE                   Location/Qualifiers
REGION                    1..11
                          note = Description of Artificial Sequence: Synthetic peptide
```

```
SITE                     1
                         note = N-term Ac
MOD_RES                  1
                         note = Nva
REGION                   2..10
                         note = Bridging moiety between residues
MOD_RES                  3
                         note = Phenyl-glycine
MOD_RES                  5
                         note = 7-azatryptophan
MOD_RES                  8
                         note = N-methyl-Serine
MOD_RES                  11
                         note = Nva
SITE                     11
                         note = C-term NH2
source                   1..11
                         mol_type = protein
                         organism = synthetic construct
SEQUENCE: 86
VCGTWAYSHC V                                                                   11

SEQ ID NO: 87            moltype = AA  length = 11
FEATURE                  Location/Qualifiers
REGION                   1..11
                         note = Description of Artificial Sequence: Synthetic peptide
SITE                     1
                         note = N-term Ac
MOD_RES                  1
                         note = Nva
REGION                   2..10
                         note = Bridging moiety between residues
MOD_RES                  3
                         note = Phenyl-glycine
MOD_RES                  5
                         note = 7-azatryptophan
MOD_RES                  8
                         note = N-methyl-Serine
MOD_RES                  11
                         note = Nva
SITE                     11
                         note = C-term NH2
source                   1..11
                         mol_type = protein
                         organism = synthetic construct
SEQUENCE: 87
VCGTWEASHC V                                                                   11

SEQ ID NO: 88            moltype = AA  length = 11
FEATURE                  Location/Qualifiers
REGION                   1..11
                         note = Description of Artificial Sequence: Synthetic peptide
REGION                   2..7
                         note = Bridging moiety between residues
SITE                     11
                         note = C-term NH2
source                   1..11
                         mol_type = protein
                         organism = synthetic construct
SEQUENCE: 88
MCVERFCDVY W                                                                   11

SEQ ID NO: 89            moltype = AA  length = 10
FEATURE                  Location/Qualifiers
REGION                   1..10
                         note = Description of Artificial Sequence: Synthetic peptide
SITE                     1
                         note = N-term Ac
MOD_RES                  1
                         note = Nva
REGION                   2..9
                         note = Bridging moiety between residues
MOD_RES                  3
                         note = Phenyl-glycine
MOD_RES                  5
                         note = 7-azatryptophan
MOD_RES                  8
                         note = N-methyl-Serine
MOD_RES                  10
```

```
                        note = Nva
SITE                    10
                        note = C-term NH2
source                  1..10
                        mol_type = protein
                        organism = synthetic construct
SEQUENCE: 89
VCGTWEYSCV                                                                        10

SEQ ID NO: 90           moltype = AA  length = 11
FEATURE                 Location/Qualifiers
REGION                  1..11
                        note = Description of Artificial Sequence: Synthetic peptide
SITE                    1
                        note = N-term heptanoyl
MOD_RES                 1
                        note = Nva
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 90
VCGTWEYSAC V                                                                      11

SEQ ID NO: 91           moltype = AA  length = 14
FEATURE                 Location/Qualifiers
REGION                  1..14
                        note = Description of Artificial Sequence: Synthetic peptide
SITE                    1
                        note = N-term Ac
MOD_RES                 1
                        note = Nva
REGION                  5..13
                        note = Bridging moiety between residues
MOD_RES                 6
                        note = Tert-butylglycine
MOD_RES                 8
                        note = 7-azatryptophan
MOD_RES                 12
                        note = Cyclohexylglycine
MOD_RES                 14
                        note = Nva
SITE                    14
                        note = C-term NH2
source                  1..14
                        mol_type = protein
                        organism = synthetic construct
SEQUENCE: 91
VSYECGYWEY PGCV                                                                   14

SEQ ID NO: 92           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 3
                        note = Phenyl-glycine
MOD_RES                 8
                        note = N-methyl-Serine
MOD_RES                 11
                        note = Nva
SITE                    11
                        note = C-term NH2
```

```
source               1..11
                     mol_type = protein
                     organism = synthetic construct
SEQUENCE: 92
VCGTFEYSAC V                                                              11

SEQ ID NO: 93        moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              7
                     note = Homophenylalanine
MOD_RES              8
                     note = N-methyl-Serine
MOD_RES              11
                     note = Nva
SITE                 11
                     note = C-term NH2
source               1..11
                     mol_type = protein
                     organism = synthetic construct
SEQUENCE: 93
VCGTWEFSAC V                                                              11

SEQ ID NO: 94        moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              4
                     note = Aib
MOD_RES              5
                     note = 7-azatryptophan
MOD_RES              8
                     note = N-methyl-Serine
MOD_RES              11
                     note = Nva
SITE                 11
                     note = C-term NH2
source               1..11
                     mol_type = protein
                     organism = synthetic construct
SEQUENCE: 94
VCGXWEYSHC V                                                              11

SEQ ID NO: 95        moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Tetrahydroisoquinoline
MOD_RES              5
                     note = 7-azatryptophan
MOD_RES              8
                     note = N-methyl-Serine
MOD_RES              11
```

```
                        note = Nva
SITE                    11
                        note = C-term NH2
source                  1..11
                        mol_type = protein
                        organism = synthetic construct
SEQUENCE: 95
VCXTWEYSHC V                                                               11

SEQ ID NO: 96           moltype = AA  length = 11
FEATURE                 Location/Qualifiers
REGION                  1..11
                        note = Description of Artificial Sequence: Synthetic peptide
MOD_RES                 1
                        note = Nva
REGION                  2..11
                        note = Bridging moiety between residues
MOD_RES                 4
                        note = N-methyl-Serine
MOD_RES                 5
                        note = Phenyl-glycine
MOD_RES                 6
                        note = 4-fluoro-N-methyl-phenylalanine
MOD_RES                 7
                        note = N-methyl-Serine
MOD_RES                 9
                        note = 4-fluoro-N-methyl-phenylalanine
SITE                    11
                        note = C-term NH2
source                  1..11
                        mol_type = protein
                        organism = synthetic construct
SEQUENCE: 96
VCYSGFSHFG C                                                               11

SEQ ID NO: 97           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
MOD_RES                 2
                        note = Homocysteine
REGION                  2..10
                        note = Bridging moiety between residues
MOD_RES                 3
                        note = Phenyl-glycine
MOD_RES                 5
                        note = 7-azatryptophan
MOD_RES                 8
                        note = N-methyl-Serine
MOD_RES                 10
                        note = Homocysteine
MOD_RES                 11
                        note = Nva
SITE                    11
                        note = C-term NH2
source                  1..11
                        mol_type = protein
                        organism = synthetic construct
SEQUENCE: 97
VCGTWEYSHC V                                                               11

SEQ ID NO: 98           moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
MOD_RES                 2
                        note = Homocysteine
REGION                  2..10
                        note = Bridging moiety between residues
MOD_RES                 3
                        note = Phenyl-glycine
```

```
MOD_RES             5
                    note = 7-azatryptophan
MOD_RES             8
                    note = N-methyl-Serine
MOD_RES             10
                    note = Homocysteine
MOD_RES             11
                    note = Nva
SITE                11
                    note = C-term NH2
source              1..11
                    mol_type = protein
                    organism = synthetic construct
SEQUENCE: 98
VCGTWEYSHC V                                                           11

SEQ ID NO: 99       moltype = AA  length = 13
FEATURE             Location/Qualifiers
REGION              1..13
                    note = Description of Artificial Sequence: Synthetic peptide
SITE                1
                    note = N-term Ac
MOD_RES             1
                    note = Nva
REGION              2..10
                    note = Bridging moiety between residues
MOD_RES             6
                    note = Tert-butylglycine
MOD_RES             8
                    note = 7-azatryptophan
MOD_RES             12
                    note = Phenyl-glycine
MOD_RES             13
                    note = Tert-butylglycine
SITE                13
                    note = C-term NH2
source              1..13
                    mol_type = protein
                    organism = synthetic construct
SEQUENCE: 99
VCYNNGEWEC PGG                                                         13

SEQ ID NO: 100      moltype = AA  length = 11
FEATURE             Location/Qualifiers
REGION              1..11
                    note = Description of Artificial Sequence: Synthetic peptide
SITE                1
                    note = N-term Ac
MOD_RES             1
                    note = Nva
REGION              2..10
                    note = Bridging moiety between residues
MOD_RES             3
                    note = Phenyl-glycine
SITE                4
                    note = D-Alanine
MOD_RES             5
                    note = 7-azatryptophan
MOD_RES             8
                    note = N-methyl-Serine
MOD_RES             11
                    note = Nva
SITE                11
                    note = C-term NH2
source              1..11
                    mol_type = protein
                    organism = synthetic construct
SEQUENCE: 100
VCGAWEYSHC V                                                           11

SEQ ID NO: 101      moltype = AA  length = 13
FEATURE             Location/Qualifiers
REGION              1..13
                    note = Description of Artificial Sequence: Synthetic peptide
SITE                1
                    note = N-term Ac
MOD_RES             1
                    note = Nva
REGION              2..10
```

```
MOD_RES                    note = Bridging moiety between residues
                           5
                           note = MeGly
MOD_RES                    6
                           note = Tert-butylglycine
MOD_RES                    8
                           note = 7-azatryptophan
MOD_RES                    11
                           note = Nva
MOD_RES                    13
                           note = Nva
SITE                       13
                           note = C-term NH2
source                     1..13
                           mol_type = protein
                           organism = synthetic construct
SEQUENCE: 101
VCYEGGYWEC VPV                                                              13

SEQ ID NO: 102             moltype = AA  length = 13
FEATURE                    Location/Qualifiers
REGION                     1..13
                           note = Description of Artificial Sequence: Synthetic peptide
SITE                       1
                           note = N-term Ac
MOD_RES                    1
                           note = Nva
REGION                     2..13
                           note = Bridging moiety between residues
MOD_RES                    5
                           note = MeGly
MOD_RES                    6
                           note = Tert-butylglycine
MOD_RES                    8
                           note = 7-azatryptophan
MOD_RES                    10..11
                           note = Nva
SITE                       13
                           note = C-term NH2
source                     1..13
                           mol_type = protein
                           organism = synthetic construct
SEQUENCE: 102
VCYEGGYWEV VPC                                                              13

SEQ ID NO: 103             moltype = AA  length = 13
FEATURE                    Location/Qualifiers
REGION                     1..13
                           note = Description of Artificial Sequence: Synthetic peptide
SITE                       1
                           note = N-term Ac
MOD_RES                    1
                           note = Nva
REGION                     2..8
                           note = Bridging moiety between residues
MOD_RES                    6
                           note = Tert-butylglycine
MOD_RES                    12
                           note = Phenyl-glycine
MOD_RES                    13
                           note = Nva
SITE                       13
                           note = C-term NH2
source                     1..13
                           mol_type = protein
                           organism = synthetic construct
SEQUENCE: 103
VCYENGYCEY PGV                                                              13

SEQ ID NO: 104             moltype = AA  length = 13
FEATURE                    Location/Qualifiers
REGION                     1..13
                           note = Description of Artificial Sequence: Synthetic peptide
SITE                       1
                           note = N-term Ac
MOD_RES                    5
                           note = Phenyl-glycine
MOD_RES                    6
                           note = 7-azatryptophan
```

```
MOD_RES              7
                     note = Tert-butylglycine
MOD_RES              9
                     note = Nva
MOD_RES              12
                     note = Nva
REGION               13
                     note = C-term NH2
source               1..13
                     mol_type = protein
                     organism = synthetic construct
SEQUENCE: 104
YPYCGWGEVN YVE                                                              13

SEQ ID NO: 105       moltype = AA  length = 13
FEATURE              Location/Qualifiers
REGION               1..13
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              8
                     note = N-methyl-Serine
MOD_RES              11
                     note = Nva
MOD_RES              13
                     note = Nva
source               1..13
                     mol_type = protein
                     organism = synthetic construct
SEQUENCE: 105
VCGTWEYSHC VPV                                                              13

SEQ ID NO: 106       moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              8
                     note = N-methyl-Serine
MOD_RES              11
                     note = Nva
REGION               11
                     note = C-term NH2
source               1..11
                     mol_type = protein
                     organism = synthetic construct
SEQUENCE: 106
VCGTWEYSHC V                                                                11

SEQ ID NO: 107       moltype = AA  length = 10
FEATURE              Location/Qualifiers
REGION               1..10
                     note = Description of Artificial Sequence: Synthetic peptide
REGION               2..7
                     note = Bridging moiety between residues
SITE                 10
                     note = C-term NH2
source               1..10
                     mol_type = protein
                     organism = synthetic construct
SEQUENCE: 107
MCVERFCDVY                                                                  10
```

```
SEQ ID NO: 108         moltype = AA   length = 9
FEATURE                Location/Qualifiers
REGION                 1..9
                       note = Description of Artificial Sequence: Synthetic peptide
REGION                 2..7
                       note = Bridging moiety between residues
SITE                   9
                       note = C-term NH2
source                 1..9
                       mol_type = protein
                       organism = synthetic construct
SEQUENCE: 108
MCVERFCDV                                                                     9

SEQ ID NO: 109         moltype = AA   length = 7
FEATURE                Location/Qualifiers
REGION                 1..7
                       note = Description of Artificial Sequence: Synthetic peptide
REGION                 2..7
                       note = Bridging moiety between residues
SITE                   7
                       note = C-term NH2
source                 1..7
                       mol_type = protein
                       organism = synthetic construct
SEQUENCE: 109
MCVERFC                                                                       7

SEQ ID NO: 110         moltype = AA   length = 11
FEATURE                Location/Qualifiers
REGION                 1..11
                       note = Description of Artificial Sequence: Synthetic peptide
MOD_RES                1
                       note = Nva
REGION                 2..11
                       note = Bridging moiety between residues
MOD_RES                4
                       note = N-methyl-Serine
MOD_RES                5
                       note = Phenyl-glycine
MOD_RES                6
                       note = 4-fluoro-N-methyl-phenylalanine
MOD_RES                7
                       note = N-methyl-Serine
MOD_RES                9
                       note = 4-fluoro-N-methyl-phenylalanine
MOD_RES                10
                       note = MeGly
SITE                   11
                       note = C-term NH2
source                 1..11
                       mol_type = protein
                       organism = synthetic construct
SEQUENCE: 110
VCYSGFSHFG C                                                                 11

SEQ ID NO: 111         moltype = AA   length = 11
FEATURE                Location/Qualifiers
REGION                 1..11
                       note = Description of Artificial Sequence: Synthetic peptide
MOD_RES                1
                       note = Nva
REGION                 2..9
                       note = Bridging moiety between residues
MOD_RES                4
                       note = Tert-butylglycine
MOD_RES                5
                       note = Phenyl-glycine
MOD_RES                7
                       note = MeGly
MOD_RES                10
                       note = Phenyl-glycine
MOD_RES                11
                       note = N-methyl-alanine
SITE                   11
                       note = C-term NH2
source                 1..11
                       mol_type = protein
```

|   |   |   |
|---|---|---|
| | organism = synthetic construct | |
| SEQUENCE: 111 | | |
| VCYGGNGLCG A | | 11 |
| | | |
| SEQ ID NO: 112 | moltype = AA   length = 11 | |
| FEATURE | Location/Qualifiers | |
| REGION | 1..11 | |
| | note = Description of Artificial Sequence: Synthetic peptide | |
| REGION | 1..11 | |
| | note = Bicyclic peptide | |
| MOD_RES | 1 | |
| | note = Nva | |
| MOD_RES | 5 | |
| | note = Tert-butylglycine | |
| MOD_RES | 6 | |
| | note = Phenyl-glycine | |
| MOD_RES | 8 | |
| | note = Tert-butylglycine | |
| MOD_RES | 9 | |
| | note = N-methyl-Serine | |
| MOD_RES | 11 | |
| | note = Tert-butylglycine | |
| SITE | 11 | |
| | note = C-term NH2 | |
| source | 1..11 | |
| | mol_type = protein | |
| | organism = synthetic construct | |
| SEQUENCE: 112 | | |
| VCCNGGCGSC G | | 11 |
| | | |
| SEQ ID NO: 113 | moltype = AA   length = 5 | |
| FEATURE | Location/Qualifiers | |
| REGION | 1..5 | |
| | note = Description of Artificial Sequence: Synthetic peptide | |
| SITE | 1 | |
| | note = N-term Ac | |
| MOD_RES | 1 | |
| | note = Tert-butylglycine | |
| MOD_RES | 3 | |
| | note = 7-azatryptophan | |
| SITE | 5 | |
| | note = C-term NH2 | |
| source | 1..5 | |
| | mol_type = protein | |
| | organism = synthetic construct | |
| SEQUENCE: 113 | | |
| GYWEY | | 5 |
| | | |
| SEQ ID NO: 114 | moltype = AA   length = 5 | |
| FEATURE | Location/Qualifiers | |
| REGION | 1..5 | |
| | note = Description of Artificial Sequence: Synthetic peptide | |
| SITE | 1 | |
| | note = N-term Ac | |
| MOD_RES | 2 | |
| | note = 7-azatryptophan | |
| SITE | 5 | |
| | note = C-term NH2 | |
| source | 1..5 | |
| | mol_type = protein | |
| | organism = synthetic construct | |
| SEQUENCE: 114 | | |
| YWEYP | | 5 |
| | | |
| SEQ ID NO: 115 | moltype = AA   length = 11 | |
| FEATURE | Location/Qualifiers | |
| REGION | 1..11 | |
| | note = Description of Artificial Sequence: Synthetic peptide | |
| SITE | 1 | |
| | note = N-term Ac | |
| MOD_RES | 4 | |
| | note = Tert-butylglycine | |
| MOD_RES | 6 | |
| | note = 7-azatryptophan | |
| MOD_RES | 7 | |
| | note = N-methyl-Glutamic Acid | |
| MOD_RES | 10 | |
| | note = Phenyl-glycine | |
| MOD_RES | 11 | |

```
                     note = Nva
SITE                 11
                     note = C-term NH2
source               1..11
                     mol_type = protein
                     organism = synthetic construct
SEQUENCE: 115
YENGYWEYPG V                                                              11

SEQ ID NO: 116       moltype = AA  length = 10
FEATURE              Location/Qualifiers
REGION               1..10
                     note = Description of Artificial Sequence: Synthetic peptide
SITE                 1
                     note = N-term heptanoyl
REGION               1..9
                     note = Bridging moiety between residues
MOD_RES              2
                     note = Phenyl-glycine
MOD_RES              4
                     note = 7-azatryptophan
MOD_RES              7
                     note = N-methyl-Serine
MOD_RES              10
                     note = Nva
SITE                 10
                     note = C-term NH2
source               1..10
                     mol_type = protein
                     organism = synthetic construct
SEQUENCE: 116
CGTWEYSACV                                                                10

SEQ ID NO: 117       moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              11
                     note = Nva
SITE                 11
                     note = C-term NH2
source               1..11
                     mol_type = protein
                     organism = synthetic construct
SEQUENCE: 117
VCGTWEYSAC V                                                              11

SEQ ID NO: 118       moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 5-fluorotryptophan
MOD_RES              8
                     note = N-methyl-Serine
MOD_RES              11
                     note = Nva
SITE                 11
                     note = C-term NH2
source               1..11
                     mol_type = protein
```

```
                        organism = synthetic construct
SEQUENCE: 118
VCGTWEYSAC V                                                                11

SEQ ID NO: 119          moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
SEQUENCE: 119
VCFTWEYSAC V                                                                11

SEQ ID NO: 120          moltype = AA  length = 11
FEATURE                 Location/Qualifiers
REGION                  1..11
                        note = Description of Artificial Sequence: Synthetic peptide
SITE                    1
                        note = N-term Ac
MOD_RES                 1
                        note = Nva
REGION                  2..10
                        note = Bridging moiety between residues
SITE                    3
                        note = D-Cyclohexylglycine
MOD_RES                 5
                        note = 7-azatryptophan
MOD_RES                 8
                        note = N-methyl-Serine
MOD_RES                 11
                        note = Nva
SITE                    11
                        note = C-term NH2
source                  1..11
                        mol_type = protein
                        organism = synthetic construct
MOD_RES                 3
                        note = D-Cyclohexylglycine
SEQUENCE: 120
VCGTWEYSAC V                                                                11

SEQ ID NO: 121          moltype = AA  length = 11
FEATURE                 Location/Qualifiers
REGION                  1..11
                        note = Description of Artificial Sequence: Synthetic peptide
SITE                    1
                        note = N-term Ac
MOD_RES                 4
                        note = Tert-butylglycine
MOD_RES                 6
                        note = 5-methyl-O-tryptophan
MOD_RES                 10
                        note = Phenyl-glycine
MOD_RES                 11
                        note = Nva
SITE                    11
                        note = C-term NH2
source                  1..11
                        mol_type = protein
                        organism = synthetic construct
SEQUENCE: 121
YENGYWEYPG V                                                                11

SEQ ID NO: 122          moltype = AA  length = 11
```

```
FEATURE              Location/Qualifiers
REGION               1..11
                     note = Description of Artificial Sequence: Synthetic peptide
REGION               1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              8
                     note = N-methyl-Serine
MOD_RES              11
                     note = Nva
SITE                 11
                     note = C-term NH2
source               1..11
                     mol_type = protein
                     organism = synthetic construct
SEQUENCE: 122
VCGTWDYSAC V                                                              11

SEQ ID NO: 123       moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              8
                     note = N-methyl-Serine
MOD_RES              11
                     note = Nva
SITE                 11
                     note = C-term NH2
source               1..11
                     mol_type = protein
                     organism = synthetic construct
SEQUENCE: 123
VCGTWQYSAC V                                                              11

SEQ ID NO: 124       moltype = AA  length = 11
FEATURE              Location/Qualifiers
REGION               1..11
                     note = Description of Artificial Sequence: Synthetic peptide
SITE                 1
                     note = N-term Ac
MOD_RES              1
                     note = Nva
REGION               2..10
                     note = Bridging moiety between residues
MOD_RES              3
                     note = Phenyl-glycine
MOD_RES              5
                     note = 7-azatryptophan
MOD_RES              8
                     note = N-methyl-Serine
MOD_RES              11
                     note = Nva
SITE                 11
                     note = C-term NH2
source               1..11
                     mol_type = protein
                     organism = synthetic construct
SEQUENCE: 124
VCGTWNYSAC V                                                              11

SEQ ID NO: 125       moltype = AA  length = 12
FEATURE              Location/Qualifiers
```

```
REGION              1..12
                    note = Description of Artificial Sequence: Synthetic peptide
SITE                1
                    note = N-term Ac
MOD_RES             1
                    note = Nva
REGION              2..10
                    note = Bridging moiety between residues
MOD_RES             3
                    note = Phenyl-glycine
MOD_RES             5
                    note = 7-azatryptophan
MOD_RES             8
                    note = N-methyl-Serine
MOD_RES             12
                    note = Nva
SITE                12
                    note = C-term NH2
source              1..12
                    mol_type = protein
                    organism = synthetic construct
SEQUENCE: 125
VCGTWEYSHG CV                                                               12

SEQ ID NO: 126      moltype = AA  length = 11
FEATURE             Location/Qualifiers
REGION              1..11
                    note = Description of Artificial Sequence: Synthetic peptide
SITE                1
                    note = N-term Ac
MOD_RES             1
                    note = Nva
REGION              2..10
                    note = Bridging moiety between residues
MOD_RES             3
                    note = Phenyl-glycine
MOD_RES             5
                    note = 1-methyl-tryptophan
MOD_RES             8
                    note = N-methyl-Serine
MOD_RES             11
                    note = Nva
SITE                11
                    note = C-term NH2
source              1..11
                    mol_type = protein
                    organism = synthetic construct
SEQUENCE: 126
VCGTWEYSAC V                                                                11

SEQ ID NO: 127      moltype = AA  length = 11
FEATURE             Location/Qualifiers
REGION              1..11
                    note = Description of Artificial Sequence: Synthetic peptide
SITE                1
                    note = N-term Ac
MOD_RES             4
                    note = Tert-butylglycine
SITE                6
                    note = D-Tryptophan
MOD_RES             10
                    note = Phenyl-glycine
MOD_RES             11
                    note = Nva
SITE                11
                    note = C-term NH2
source              1..11
                    mol_type = protein
                    organism = synthetic construct
SEQUENCE: 127
YENGYWEYPG V                                                                11

SEQ ID NO: 128      moltype = AA  length = 10
FEATURE             Location/Qualifiers
REGION              1..10
                    note = Description of Artificial Sequence: Synthetic peptide
SITE                1
                    note = N-term Ac
SITE                5
```

```
MOD_RES                 9
                        note = D-Tryptophan
MOD_RES                 10
                        note = Phenyl-glycine
SITE                    10
                        note = Nva
                        note = C-term NH2
source                  1..10
                        mol_type = protein
                        organism = synthetic construct
SEQUENCE: 128
YENYWEYPGV                                                                  10

SEQ ID NO: 129          moltype = AA  length = 11
FEATURE                 Location/Qualifiers
REGION                  1..11
                        note = Description of Artificial Sequence: Synthetic peptide
SITE                    1
                        note = N-term Ac
MOD_RES                 4
                        note = Tert-butylglycine
MOD_RES                 6
                        note = 7-azatryptophan
SITE                    7
                        note = D-Glutamic Acid
MOD_RES                 10
                        note = Phenyl-glycine
MOD_RES                 11
                        note = Nva
SITE                    11
                        note = C-term NH2
source                  1..11
                        mol_type = protein
                        organism = synthetic construct
SEQUENCE: 129
YENGYWEYPG V                                                                11

SEQ ID NO: 130          moltype = AA  length = 11
FEATURE                 Location/Qualifiers
REGION                  1..11
                        note = Description of Artificial Sequence: Synthetic peptide
SITE                    1
                        note = N-term Ac
REGION                  1..6
                        note = Bridging moiety between residues
SITE                    11
                        note = C-term NH2
source                  1..11
                        mol_type = protein
                        organism = synthetic construct
SEQUENCE: 130
CVERFCVYWE F                                                                11

SEQ ID NO: 131          moltype = AA  length = 9
FEATURE                 Location/Qualifiers
REGION                  1..9
                        note = Description of Artificial Sequence: Synthetic peptide
SITE                    1
                        note = N-term Ac
REGION                  1..6
                        note = Bridging moiety between residues
SITE                    9
                        note = C-term NH2
source                  1..9
                        mol_type = protein
                        organism = synthetic construct
SEQUENCE: 131
CVERFCWEF                                                                   9

SEQ ID NO: 132          moltype = AA  length = 13
FEATURE                 Location/Qualifiers
REGION                  1..13
                        note = Description of Artificial Sequence: Synthetic peptide
SITE                    1
                        note = N-term Ac
MOD_RES                 1
                        note = Nva
MOD_RES                 6
                        note = Tert-butylglycine
```

```
MOD_RES            12
                   note = Phenyl-glycine
MOD_RES            13
                   note = Tert-butylglycine
SITE               13
                   note = C-term NH2
source             1..13
                   mol_type = protein
                   organism = synthetic construct
SEQUENCE: 132
VCYNNGECEY PGG                                                          13

SEQ ID NO: 133     moltype = AA  length = 13
FEATURE            Location/Qualifiers
REGION             1..13
                   note = Description of Artificial Sequence: Synthetic peptide
SITE               1
                   note = N-term Ac
MOD_RES            1
                   note = Nva
REGION             2..8
                   note = Bridging moiety between residues
MOD_RES            6
                   note = Tert-butylglycine
MOD_RES            12
                   note = Phenyl-glycine
MOD_RES            13
                   note = Tert-butylglycine
SITE               13
                   note = C-term NH2
source             1..13
                   mol_type = protein
                   organism = synthetic construct
SEQUENCE: 133
VCYNNGECEY PGG                                                          13

SEQ ID NO: 134     moltype = AA  length = 13
FEATURE            Location/Qualifiers
REGION             1..13
                   note = Description of Artificial Sequence: Synthetic peptide
SITE               1
                   note = N-term Ac
MOD_RES            1..2
                   note = Nva
MOD_RES            6
                   note = Tert-butylglycine
MOD_RES            7
                   note = N-methyl-Tyrosine
MOD_RES            8
                   note = 7-azatryptophan
MOD_RES            12
                   note = Cyclohexylglycine
MOD_RES            13
                   note = Nva
SITE               13
                   note = C-term NH2
source             1..13
                   mol_type = protein
                   organism = synthetic construct
SEQUENCE: 134
VVYENGYWEY PGV                                                          13

SEQ ID NO: 135     moltype = AA  length = 11
FEATURE            Location/Qualifiers
REGION             1..11
                   note = Description of Artificial Sequence: Synthetic peptide
SITE               1
                   note = N-term Ac
MOD_RES            1
                   note = Nva
REGION             2..10
                   note = Bridging moiety between residues
MOD_RES            3
                   note = Phenyl-glycine
MOD_RES            6
                   note = (S)-2-amino-3-(1H-tetrazol-5-yl)propanoic acid
MOD_RES            8
                   note = N-methyl-Serine
MOD_RES            11
```

|   |   |
|---|---|
|  | note = Nva |
| SITE | 11 |
|  | note = C-term NH2 |
| source | 1..11 |
|  | mol_type = protein |
|  | organism = synthetic construct |

SEQUENCE: 135
VCGTWXYSHC V                                                             11

|   |   |
|---|---|
| SEQ ID NO: 136 | moltype = AA   length = 11 |
| FEATURE | Location/Qualifiers |
| REGION | 1..11 |
|  | note = Description of Artificial Sequence: Synthetic peptide |
| SITE | 1 |
|  | note = N-term Ac |
| MOD_RES | 1 |
|  | note = Nva |
| REGION | 2..10 |
|  | note = Bridging moiety between residues |
| MOD_RES | 3 |
|  | note = Phenyl-glycine |
| SITE | 5 |
|  | note = D-Tryptophan |
| MOD_RES | 8 |
|  | note = N-methyl-Serine |
| MOD_RES | 11 |
|  | note = Nva |
| SITE | 11 |
|  | note = C-term NH2 |
| source | 1..11 |
|  | mol_type = protein |
|  | organism = synthetic construct |

SEQUENCE: 136
VCGTWEYSHC V                                                             11

|   |   |
|---|---|
| SEQ ID NO: 137 | moltype = AA   length = 11 |
| FEATURE | Location/Qualifiers |
| REGION | 1..11 |
|  | note = Description of Artificial Sequence: Synthetic peptide |
| SITE | 1 |
|  | note = N-term heptanoyl |
| MOD_RES | 1 |
|  | note = Nva |
| REGION | 2..10 |
|  | note = Bridging moiety between residues |
| SITE | 3 |
|  | note = D-phenyl-glycine |
| MOD_RES | 5 |
|  | note = Azatryptophan |
| MOD_RES | 8 |
|  | note = N-methyl-Serine |
| MOD_RES | 11 |
|  | note = Nva |
| SITE | 11 |
|  | note = C-term NH2 |
| source | 1..11 |
|  | mol_type = protein |
|  | organism = synthetic construct |
| MOD_RES | 3 |
|  | note = D-phenyl-glycine |

SEQUENCE: 137
VCGTWEYSAC V                                                             11

|   |   |
|---|---|
| SEQ ID NO: 138 | moltype = AA   length = 10 |
| FEATURE | Location/Qualifiers |
| REGION | 1..10 |
|  | note = Description of Artificial Sequence: Synthetic peptide |
| SITE | 1 |
|  | note = N-term heptanoyl |
| REGION | 1..9 |
|  | note = Bridging moiety between residues |
| SITE | 2 |
|  | note = D-phenyl-glycine |
| MOD_RES | 4 |
|  | note = Azatryptophan |
| MOD_RES | 7 |
|  | note = N-methyl-Serine |
| MOD_RES | 10 |
|  | note = Nva |

```
SITE                    10
                        note = C-term NH2
source                  1..10
                        mol_type = protein
                        organism = synthetic construct
MOD_RES                 2
                        note = D-phenyl-glycine
SEQUENCE: 138
CGTWEYSACV                                                                       10

SEQ ID NO: 139          moltype = AA  length = 12
FEATURE                 Location/Qualifiers
REGION                  1..12
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
SITE                    12
                        note = C-term NH2
source                  1..12
                        mol_type = protein
                        organism = synthetic construct
SEQUENCE: 139
CVERFCDGYW EF                                                                    12

SEQ ID NO: 140          moltype = AA  length = 12
FEATURE                 Location/Qualifiers
REGION                  1..12
                        note = Description of Artificial Sequence: Synthetic peptide
SITE                    1
                        note = N-term Ac
REGION                  1..6
                        note = Bridging moiety between residues
MOD_RES                 2
                        note = Tert-butylglycine
MOD_RES                 8
                        note = Tert-butylglycine
SITE                    12
                        note = C-term NH2
source                  1..12
                        mol_type = protein
                        organism = synthetic construct
SEQUENCE: 140
CGERFCDGYW EF                                                                    12

SEQ ID NO: 141          moltype = AA  length = 13
FEATURE                 Location/Qualifiers
REGION                  1..13
                        note = Description of Artificial Sequence: Synthetic peptide
SITE                    1
                        note = N-term Ac
REGION                  1..6
                        note = Bridging moiety between residues
SITE                    13
                        note = C-term NH2
source                  1..13
                        mol_type = protein
                        organism = synthetic construct
SEQUENCE: 141
CVERFCDVYW EYP                                                                   13

SEQ ID NO: 142          moltype = AA  length = 13
FEATURE                 Location/Qualifiers
REGION                  1..13
                        note = Description of Artificial Sequence: Synthetic peptide
SITE                    1
                        note = N-term Ac
REGION                  1..6
                        note = Bridging moiety between residues
SITE                    13
                        note = C-term NH2
source                  1..13
                        mol_type = protein
                        organism = synthetic construct
SEQUENCE: 142
CVERFCDVYW EFP                                                                   13
```

```
SEQ ID NO: 143          moltype = AA  length = 13
FEATURE                 Location/Qualifiers
REGION                  1..13
                        note = Description of Artificial Sequence: Synthetic peptide
SITE                    1
                        note = N-term Ac
REGION                  1..6
                        note = Bridging moiety between residues
MOD_RES                 10
                        note = Azatryptophan
SITE                    13
                        note = C-term NH2
source                  1..13
                        mol_type = protein
                        organism = synthetic construct
SEQUENCE: 143
CVERFCDVYW EYP                                                              13

SEQ ID NO: 144          moltype = AA  length = 13
FEATURE                 Location/Qualifiers
REGION                  1..13
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
SITE                    13
                        note = C-term NH2
source                  1..13
                        mol_type = protein
                        organism = synthetic construct
SEQUENCE: 144
CVERFCDGYW EYP                                                              13

SEQ ID NO: 145          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Phenyl-glycine
MOD_RES                 15
                        note = Nva
SITE                    15
                        note = C-term NH2
source                  1..15
                        mol_type = protein
                        organism = synthetic construct
SEQUENCE: 145
CVERFCDGYW EYPGV                                                            15

SEQ ID NO: 146          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
SITE                    14
                        note = D-phenyl-glycine
MOD_RES                 15
                        note = Nva
SITE                    15
                        note = C-term NH2
```

```
source              1..15
                    mol_type = protein
                    organism = synthetic construct
MOD_RES             14
                    note = D-phenyl-glycine
SEQUENCE: 146
CVERFCDGYW EYPGV                                                              15

SEQ ID NO: 147      moltype = AA   length = 12
FEATURE             Location/Qualifiers
REGION              1..12
                    note = Description of Artificial Sequence: Synthetic peptide
SITE                1
                    note = N-term Ac
REGION              1..6
                    note = Bridging moiety between residues
MOD_RES             2
                    note = Tert-butylglycine
SITE                12
                    note = C-term NH2
source              1..12
                    mol_type = protein
                    organism = synthetic construct
SEQUENCE: 147
CGERFCDVYW EF                                                                 12

SEQ ID NO: 148      moltype = AA   length = 13
FEATURE             Location/Qualifiers
REGION              1..13
                    note = Description of Artificial Sequence: Synthetic peptide
SITE                1
                    note = N-term Ac
REGION              1..6
                    note = Bridging moiety between residues
MOD_RES             13
                    note = Propargyl-Gly
SITE                13
                    note = C-term NH2
source              1..13
                    mol_type = protein
                    organism = synthetic construct
SEQUENCE: 148
CVERFCDVYW EFG                                                                13

SEQ ID NO: 149      moltype = AA   length = 15
FEATURE             Location/Qualifiers
REGION              1..15
                    note = Description of Artificial Sequence: Synthetic peptide
SITE                1
                    note = N-term Ac
REGION              1..6
                    note = Bridging moiety between residues
MOD_RES             8
                    note = Tert-butylglycine
MOD_RES             14
                    note = Phenyl-glycine
MOD_RES             15
                    note = Nva
SITE                15
                    note = C-term NH2
source              1..15
                    mol_type = protein
                    organism = synthetic construct
SEQUENCE: 149
CAERFCDGYW EYPGV                                                              15

SEQ ID NO: 150      moltype = AA   length = 15
FEATURE             Location/Qualifiers
REGION              1..15
                    note = Description of Artificial Sequence: Synthetic peptide
SITE                1
                    note = N-term Ac
REGION              1..6
                    note = Bridging moiety between residues
MOD_RES             8
                    note = Tert-butylglycine
SITE                14
                    note = D-phenyl-glycine
MOD_RES             15
```

```
                        note = Nva
SITE                    15
                        note = C-term NH2
source                  1..15
                        mol_type = protein
                        organism = synthetic construct
MOD_RES                 14
                        note = D-phenyl-glycine
SEQUENCE: 150
CAERFCDGYW EYPGV                                                         15

SEQ ID NO: 151          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Phenyl-glycine
MOD_RES                 15
                        note = Nva
SITE                    15
                        note = C-term NH2
source                  1..15
                        mol_type = protein
                        organism = synthetic construct
SEQUENCE: 151
CVARFCDGYW EYPGV                                                         15

SEQ ID NO: 152          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
SITE                    14
                        note = D-phenyl-glycine
MOD_RES                 15
                        note = Nva
SITE                    15
                        note = C-term NH2
source                  1..15
                        mol_type = protein
                        organism = synthetic construct
MOD_RES                 14
                        note = D-phenyl-glycine
SEQUENCE: 152
CVARFCDGYW EYPGV                                                         15

SEQ ID NO: 153          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
SITE                    15
                        note = C-term NH2
```

```
source                   1..15
                         mol_type = protein
                         organism = synthetic construct
SEQUENCE: 153
CVERFCDGYW EYPGV                                                          15

SEQ ID NO: 154           moltype = AA  length = 15
FEATURE                  Location/Qualifiers
REGION                   1..15
                         note = Description of Artificial Sequence: Synthetic peptide
SITE                     1
                         note = N-term Ac
REGION                   1..6
                         note = Bridging moiety between residues
MOD_RES                  8
                         note = Tert-butylglycine
MOD_RES                  10
                         note = Azatryptophan
MOD_RES                  14
                         note = Phenyl-glycine
MOD_RES                  15
                         note = Nva
SITE                     15
                         note = C-term NH2
source                   1..15
                         mol_type = protein
                         organism = synthetic construct
SEQUENCE: 154
CVEAFCDGYW EYPGV                                                          15

SEQ ID NO: 155           moltype = AA  length = 15
FEATURE                  Location/Qualifiers
REGION                   1..15
                         note = Description of Artificial Sequence: Synthetic peptide
SITE                     1
                         note = N-term Ac
REGION                   1..6
                         note = Bridging moiety between residues
MOD_RES                  8
                         note = Tert-butylglycine
MOD_RES                  10
                         note = Azatryptophan
SITE                     14
                         note = D-phenyl-glycine
MOD_RES                  15
                         note = Nva
SITE                     15
                         note = C-term NH2
source                   1..15
                         mol_type = protein
                         organism = synthetic construct
MOD_RES                  14
                         note = D-phenyl-glycine
SEQUENCE: 155
CVEAFCDGYW EYPGV                                                          15

SEQ ID NO: 156           moltype = AA  length = 15
FEATURE                  Location/Qualifiers
REGION                   1..15
                         note = Description of Artificial Sequence: Synthetic peptide
SITE                     1
                         note = N-term Ac
REGION                   1..6
                         note = Bridging moiety between residues
MOD_RES                  8
                         note = Tert-butylglycine
MOD_RES                  10
                         note = Azatryptophan
MOD_RES                  14
                         note = Phenyl-glycine
MOD_RES                  15
                         note = Nva
SITE                     15
                         note = C-term NH2
source                   1..15
                         mol_type = protein
                         organism = synthetic construct
SEQUENCE: 156
CVERACDGYW EYPGV                                                          15
```

```
SEQ ID NO: 157        moltype = AA  length = 15
FEATURE               Location/Qualifiers
REGION                1..15
                      note = Description of Artificial Sequence: Synthetic peptide
SITE                  1
                      note = N-term Ac
REGION                1..6
                      note = Bridging moiety between residues
MOD_RES               8
                      note = Tert-butylglycine
MOD_RES               10
                      note = Azatryptophan
SITE                  14
                      note = D-phenyl-glycine
MOD_RES               15
                      note = Nva
SITE                  15
                      note = C-term NH2
source                1..15
                      mol_type = protein
                      organism = synthetic construct
MOD_RES               14
                      note = D-phenyl-glycine
SEQUENCE: 157
CVERACDGYW EYPGV                                                              15

SEQ ID NO: 158        moltype = AA  length = 15
FEATURE               Location/Qualifiers
REGION                1..15
                      note = Description of Artificial Sequence: Synthetic peptide
SITE                  1
                      note = N-term Ac
REGION                1..6
                      note = Bridging moiety between residues
MOD_RES               8
                      note = Tert-butylglycine
MOD_RES               10
                      note = Azatryptophan
MOD_RES               14
                      note = Phenyl-glycine
MOD_RES               15
                      note = Nva
SITE                  15
                      note = C-term NH2
source                1..15
                      mol_type = protein
                      organism = synthetic construct
SEQUENCE: 158
CVERFCAGYW EYPGV                                                              15

SEQ ID NO: 159        moltype = AA  length = 15
FEATURE               Location/Qualifiers
REGION                1..15
                      note = Description of Artificial Sequence: Synthetic peptide
SITE                  1
                      note = N-term Ac
REGION                1..6
                      note = Bridging moiety between residues
MOD_RES               8
                      note = Tert-butylglycine
MOD_RES               10
                      note = Azatryptophan
SITE                  14
                      note = D-phenyl-glycine
MOD_RES               15
                      note = Nva
SITE                  15
                      note = C-term NH2
source                1..15
                      mol_type = protein
                      organism = synthetic construct
MOD_RES               14
                      note = D-phenyl-glycine
SEQUENCE: 159
CVERFCAGYW EYPGV                                                              15

SEQ ID NO: 160        moltype = AA  length = 15
FEATURE               Location/Qualifiers
```

```
REGION                  1..15
                        note = Description of Artificial Sequence: Synthetic peptide
REGION                  1..6
                        note = Bridging moiety between residues
MOD_RES                 1
                        note = 3-thiopropionic acid
MOD_RES                 8
                        note = Tert-butylglycine
MOD_RES                 10
                        note = Azatryptophan
MOD_RES                 14
                        note = Phenyl-glycine
MOD_RES                 15
                        note = Nva
SITE                    15
                        note = C-term NH2
source                  1..15
                        mol_type = protein
                        organism = synthetic construct
SEQUENCE: 160
CVERFCDGYW EYPGV                                                            15

SEQ ID NO: 161          moltype = AA  length = 15
FEATURE                 Location/Qualifiers
REGION                  1..15
                        note = Description of Artificial Sequence: Synthetic peptide
REGION                  1..6
                        note = Bridging moiety between residues
MOD_RES                 1
                        note = 3-thiopropionic acid
MOD_RES                 8
                        note = Tert-butylglycine
MOD_RES                 10
                        note = Azatryptophan
SITE                    14
                        note = D-phenyl-glycine
MOD_RES                 15
                        note = Nva
SITE                    15
                        note = C-term NH2
source                  1..15
                        mol_type = protein
                        organism = synthetic construct
MOD_RES                 14
                        note = D-phenyl-glycine
SEQUENCE: 161
CVERFCDGYW EYPGV                                                            15

SEQ ID NO: 162          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Phenyl-glycine
SITE                    15
                        note = C-term NH2
source                  1..15
                        mol_type = protein
                        organism = synthetic construct
SEQUENCE: 162
CAERFCDGYW EYPGK                                                            15

SEQ ID NO: 163          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
```

```
                              note = Tert-butylglycine
MOD_RES                       10
                              note = Azatryptophan
SITE                          14
                              note = D-phenyl-glycine
SITE                          15
                              note = C-term NH2
source                        1..15
                              mol_type = protein
                              organism = synthetic construct
MOD_RES                       14
                              note = D-phenyl-glycine
SEQUENCE: 163
CAERFCDGYW EYPGK                                                            15

SEQ ID NO: 164                moltype = AA  length = 15
FEATURE                       Location/Qualifiers
REGION                        1..15
                              note = Description of Artificial Sequence: Synthetic peptide
SITE                          1
                              note = N-term Ac
REGION                        1..6
                              note = Cyclic
MOD_RES                       8
                              note = Tert-butylglycine
MOD_RES                       10
                              note = Azatryptophan
MOD_RES                       14
                              note = Phenyl-glycine
MOD_RES                       15
                              note = Nva
SITE                          15
                              note = C-term NH2
source                        1..15
                              mol_type = protein
                              organism = synthetic construct
SEQUENCE: 164
CVERFCDGYW EYPGV                                                            15

SEQ ID NO: 165                moltype = AA  length = 15
FEATURE                       Location/Qualifiers
REGION                        1..15
                              note = Description of Artificial Sequence: Synthetic peptide
SITE                          1
                              note = N-term Ac
REGION                        1..6
                              note = Bridging moiety between residues
MOD_RES                       8
                              note = Tert-butylglycine
MOD_RES                       10
                              note = Azatryptophan
MOD_RES                       14
                              note = Phenyl-glycine
MOD_RES                       15
                              note = N-e-lauryl lysine
REGION                        1..15
                              note = C-term NH2
source                        1..15
                              mol_type = protein
                              organism = synthetic construct
SEQUENCE: 165
CAERFCDGYW EYPGK                                                            15

SEQ ID NO: 166                moltype = AA  length = 15
FEATURE                       Location/Qualifiers
REGION                        1..15
                              note = Description of Artificial Sequence: Synthetic peptide
SITE                          1
                              note = N-term Ac
REGION                        1..6
                              note = Bridging moiety between residues
MOD_RES                       8
                              note = Tert-butylglycine
MOD_RES                       10
                              note = Azatryptophan
MOD_RES                       14
                              note = Phenyl-glycine
MOD_RES                       15
                              note = N-e-capryl lysine
```

```
SITE                    15
                        note = C-term NH2
source                  1..15
                        mol_type = protein
                        organism = synthetic construct
SEQUENCE: 166
CAERFCDGYW EYPGK                                                                        15

SEQ ID NO: 167          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Phenyl-glycine
MOD_RES                 15
                        note = N-e-caprylic lysine
SITE                    15
                        note = C-term NH2
source                  1..15
                        mol_type = protein
                        organism = synthetic construct
SEQUENCE: 167
CAERFCDGYW EYPGK                                                                        15

SEQ ID NO: 168          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 7
                        note = Alpha-methyl L-aspartic acid
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
SITE                    15
                        note = C-term NH2
source                  1..15
                        mol_type = protein
                        organism = synthetic construct
SEQUENCE: 168
CVERFCDGYW EYPGV                                                                        15

SEQ ID NO: 169          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 7
                        note = (S)-2-amino-3-(1H-tetrazol-5-yl)propanoic acid
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
SITE                    15
                        note = C-term NH2
source                  1..15
```

```
                         mol_type = protein
                         organism = synthetic construct
SEQUENCE: 169
CVERFCXGYW EYPGV                                                       15

SEQ ID NO: 170           moltype = AA   length = 15
FEATURE                  Location/Qualifiers
REGION                   1..15
                         note = Description of Artificial Sequence: Synthetic peptide
SITE                     1
                         note = N-term Ac
REGION                   1..6
                         note = Cyclic
MOD_RES                  8
                         note = Tert-butylglycine
MOD_RES                  10
                         note = Azatryptophan
MOD_RES                  14
                         note = Cyclohexylglycine
MOD_RES                  15
                         note = Nva
SITE                     15
                         note = C-term NH2
source                   1..15
                         mol_type = protein
                         organism = synthetic construct
SEQUENCE: 170
KVERFDDGYW EYPGV                                                       15

SEQ ID NO: 171           moltype = AA   length = 15
FEATURE                  Location/Qualifiers
REGION                   1..15
                         note = Description of Artificial Sequence: Synthetic peptide
SITE                     1
                         note = N-term Ac
REGION                   1..6
                         note = Bridging moiety between residues
MOD_RES                  8
                         note = Tert-butylglycine
MOD_RES                  10
                         note = Azatryptophan
MOD_RES                  14
                         note = Phenyl-glycine
source                   1..15
                         mol_type = protein
                         organism = synthetic construct
SEQUENCE: 171
CAERFCDGYW EYPGK                                                       15

SEQ ID NO: 172           moltype = AA   length = 15
FEATURE                  Location/Qualifiers
REGION                   1..15
                         note = Description of Artificial Sequence: Synthetic peptide
SITE                     1
                         note = N-term Ac
REGION                   1..6
                         note = Bridging moiety between residues
MOD_RES                  8
                         note = Tert-butylglycine
MOD_RES                  10
                         note = Azatryptophan
MOD_RES                  14
                         note = Phenyl-glycine
MOD_RES                  15
                         note = N-e-lauryl lysine
source                   1..15
                         mol_type = protein
                         organism = synthetic construct
SEQUENCE: 172
CAERFCDGYW EYPGK                                                       15

SEQ ID NO: 173           moltype = AA   length = 15
FEATURE                  Location/Qualifiers
REGION                   1..15
                         note = Description of Artificial Sequence: Synthetic peptide
SITE                     1
                         note = N-term Ac
REGION                   1..6
                         note = Bridging moiety between residues
```

```
MOD_RES           7
                  note = N-methyl-Aspartic Acid
MOD_RES           8
                  note = Tert-butylglycine
MOD_RES           10
                  note = Azatryptophan
MOD_RES           14
                  note = Cyclohexylglycine
MOD_RES           15
                  note = Nva
SITE              15
                  note = C-term NH2
source            1..15
                  mol_type = protein
                  organism = synthetic construct
SEQUENCE: 173
CVERFCDGYW EYPGV                                                            15

SEQ ID NO: 174    moltype = AA  length = 15
FEATURE           Location/Qualifiers
REGION            1..15
                  note = Description of Artificial Sequence: Synthetic peptide
SITE              1
                  note = N-term Ac
REGION            1..6
                  note = Cyclic
MOD_RES           8
                  note = Tert-butylglycine
MOD_RES           10
                  note = Azatryptophan
MOD_RES           14
                  note = Cyclohexylglycine
MOD_RES           15
                  note = Nva
source            1..15
                  mol_type = protein
                  organism = synthetic construct
SEQUENCE: 174
KVERFDDGYW EYPGV                                                            15

SEQ ID NO: 175    moltype = AA  length = 15
FEATURE           Location/Qualifiers
REGION            1..15
                  note = Description of Artificial Sequence: Synthetic peptide
SITE              1
                  note = N-term Ac
REGION            1..6
                  note = Cyclic
MOD_RES           7
                  note = (S)-2-amino-3-(1H-tetrazol-5-yl)propanoic acid
MOD_RES           8
                  note = Tert-butylglycine
MOD_RES           10
                  note = Azatryptophan
MOD_RES           14
                  note = Cyclohexylglycine
MOD_RES           15
                  note = Nva
source            1..15
                  mol_type = protein
                  organism = synthetic construct
SEQUENCE: 175
KVERFDXGYW EYPGV                                                            15

SEQ ID NO: 176    moltype = AA  length = 15
FEATURE           Location/Qualifiers
REGION            1..15
                  note = Description of Artificial Sequence: Synthetic peptide
SITE              1
                  note = N-term Ac
REGION            1..6
                  note = Cyclic
MOD_RES           8
                  note = Tert-butylglycine
MOD_RES           10
                  note = Azatryptophan
MOD_RES           14
                  note = Cyclohexylglycine
MOD_RES           15
```

```
                        note = N-e-(PEG2-gamma-glutamic
                         acid-N-Alpha-octadecanedioic acid) lysine or
                         (1S,28S)-1-amino-7,16,25,30-tetraoxo-9,12,18,21-tetraoxa-6,
                         15,24,29-tetraazahexatetracontane-1,28,46-tricarboxylic
                         acid
source                  1..15
                        mol_type = protein
                        organism = synthetic construct
SEQUENCE: 176
KVERFDDGYW EYPGK                                                            15

SEQ ID NO: 177          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Cyclic
MOD_RES                 7
                        note = N-methyl-Aspartic Acid
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
source                  1..15
                        mol_type = protein
                        organism = synthetic construct
SEQUENCE: 177
KVERFDDGYW EYPGV                                                            15

SEQ ID NO: 178          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
source                  1..15
                        mol_type = protein
                        organism = synthetic construct
SEQUENCE: 178
CVERFCDGYW EWPGV                                                            15

SEQ ID NO: 179          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 12
                        note = Homophenylalanine
MOD_RES                 14
                        note = Cyclohexylglycine
MOD_RES                 15
                        note = Nva
source                  1..15
                        mol_type = protein
                        organism = synthetic construct
SEQUENCE: 179
```

```
CVERFCDGYW EFPGV                                                        15

SEQ ID NO: 180          moltype = AA   length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 12
                        note = Meta-chloro homophenylalanine
MOD_RES                 14
                        note = Cyclohexylglycine
MOD_RES                 15
                        note = Nva
source                  1..15
                        mol_type = protein
                        organism = synthetic construct
SEQUENCE: 180
CVERFCDGYW EFPGV                                                        15

SEQ ID NO: 181          moltype = AA   length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 12
                        note = 2-naphthylalanine
MOD_RES                 14
                        note = Cyclohexylglycine
MOD_RES                 15
                        note = Nva
source                  1..15
                        mol_type = protein
                        organism = synthetic construct
SEQUENCE: 181
CVERFCDGYW EAPGV                                                        15

SEQ ID NO: 182          moltype = AA   length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = 3-aminomethyl-L-phenylalanine
MOD_RES                 14
                        note = Cyclohexylglycine
MOD_RES                 15
                        note = Nva
source                  1..15
                        mol_type = protein
                        organism = synthetic construct
SEQUENCE: 182
CVERFCDGYF EYPGV                                                        15

SEQ ID NO: 183          moltype = AA   length = 15
FEATURE                 Location/Qualifiers
REGION                  1..15
                        note = Description of Artificial Sequence: Synthetic peptide
SITE                    1
                        note = N-term Ac
CROSSLNK                1..6
```

```
                        note = Cyclo-triazolyl linkage between residues
MOD_RES                 1
                        note = (S)-2-amino-5-azidopentanoic acid
MOD_RES                 6
                        note = (S)-2-aminopent-4-ynoic acid
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
source                  1..15
                        mol_type = protein
                        organism = synthetic construct
SEQUENCE: 183
XVERFXDGYW EYPGV                                                     15

SEQ ID NO: 184          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Cyclic
MOD_RES                 7
                        note = N-methyl-Aspartic Acid
MOD_RES                 8
                        note = Tert-butylglycine
MOD_RES                 10
                        note = Azatryptophan
MOD_RES                 14
                        note = Cyclohexylglycine
MOD_RES                 15
                        note = N-e-palmitoyl lysine
source                  1..15
                        mol_type = protein
                        organism = synthetic construct
SEQUENCE: 184
KVERFDDGYW EYPGK                                                     15

SEQ ID NO: 185          moltype = AA  length = 14
FEATURE                 Location/Qualifiers
REGION                  1..14
                        note = Description of Artificial Sequence: Synthetic peptide
CROSSLNK                1..5
                        note = Cyclo-thioalkyl linkage between residues
MOD_RES                 7
                        note = Tert-butylglycine
MOD_RES                 9
                        note = Azatryptophan
MOD_RES                 13
                        note = Cyclohexylglycine
MOD_RES                 14
                        note = Nva
source                  1..14
                        mol_type = protein
                        organism = synthetic construct
SEQUENCE: 185
VERFCDGYWE YPGV                                                      14

SEQ ID NO: 186          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 7
                        note = Cycloleucine
MOD_RES                 8
                        note = Tert-butylglycine
MOD_RES                 10
                        note = Azatryptophan
MOD_RES                 14
                        note = Cyclohexylglycine
```

```
MOD_RES                 15
                        note = Nva
source                  1..15
                        mol_type = protein
                        organism = synthetic construct
SEQUENCE: 186
CVERFCLGYW EYPGV                                                                15

SEQ ID NO: 187          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 7
                        note = 4-amino-tetrahydro-pyran-4-carboxylic acid
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
source                  1..15
                        mol_type = protein
                        organism = synthetic construct
SEQUENCE: 187
CVERFCXGYW EYPGV                                                                15

SEQ ID NO: 188          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 12
                        note = 3-aminomethyl-L-phenylalanine
MOD_RES                 14
                        note = Cyclohexylglycine
MOD_RES                 15
                        note = Nva
source                  1..15
                        mol_type = protein
                        organism = synthetic construct
SEQUENCE: 188
CVERFCDGYW EFPGV                                                                15

SEQ ID NO: 189          moltype = AA  length = 15
FEATURE                 Location/Qualifiers
REGION                  1..15
                        note = Description of Artificial Sequence: Synthetic peptide
SITE                    1
                        note = N-term Ac
CROSSLNK                1..6
                        note = Cyclo-olefinyl linkage between residues
MOD_RES                 1
                        note = (S)-2-aminohept-6-enoic acid
MOD_RES                 6
                        note = (S)-2-aminopent-4-enoic acid
MOD_RES                 8
                        note = Tert-butylglycine
MOD_RES                 10
                        note = Azatryptophan
MOD_RES                 14
                        note = Cyclohexylglycine
MOD_RES                 15
                        note = Nva
source                  1..15
                        mol_type = protein
                        organism = synthetic construct
```

```
SEQUENCE: 189
XVERFXDGYW EYPGV                                                              15

SEQ ID NO: 190          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Bridging moiety between residues
MOD_RES                 8
                        note = Tert-butylglycine
MOD_RES                 10
                        note = Azatryptophan
MOD_RES                 14
                        note = Phenyl-glycine
MOD_RES                 15
                        note = N-e-palmitoyl lysine
source                  1..15
                        mol_type = protein
                        organism = synthetic construct
SEQUENCE: 190
CAERFCDGYW EYPGK                                                              15

SEQ ID NO: 191          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Cyclic
MOD_RES                 7
                        note = N-methyl-Aspartic Acid
MOD_RES                 8
                        note = Tert-butylglycine
MOD_RES                 10
                        note = Azatryptophan
MOD_RES                 14
                        note = Cyclohexylglycine
MOD_RES                 15
                        note = N-e-(PEG2-gamma-glutamic
                          acid-N-Alpha-octadecanedioic acid) lysine or
                          (1S,28S)-1-amino-7,16,25,30-tetraoxo-9,12,18,21-tetraoxa-6,
                          15,24,29-tetraazahexatetracontane-1,28,46-tricarboxylic
                          acid
source                  1..15
                        mol_type = protein
                        organism = synthetic construct
SEQUENCE: 191
KVERFDDGYW EYPGK                                                              15

SEQ ID NO: 192          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Cyclic
MOD_RES                 7
                        note = N-methyl-Aspartic Acid
MOD_RES                 8
                        note = Tert-butylglycine
MOD_RES                 10
                        note = Azatryptophan
MOD_RES                 14
                        note = Cyclohexylglycine
source                  1..15
                        mol_type = protein
                        organism = synthetic construct
SEQUENCE: 192
KVERFDDGYW EYPGK                                                              15

SEQ ID NO: 193          moltype = AA  length = 15
FEATURE                 Location/Qualifiers
REGION                  1..15
                        note = Description of Artificial Sequence: Synthetic peptide
```

```
SITE                     1
                         note = N-term Ac
REGION                   1..6
                         note = Cyclic
MOD_RES                  7
                         note = N-methyl-Aspartic Acid
MOD_RES                  8
                         note = Tert-butylglycine
MOD_RES                  10
                         note = Azatryptophan
MOD_RES                  14
                         note = Cyclohexylglycine
SITE                     15
                         note = C-term NH2
source                   1..15
                         mol_type = protein
                         organism = synthetic construct
SEQUENCE: 193
KVERFDDGYW EYPGK                                                         15

SEQ ID NO: 194           moltype = AA  length = 15
FEATURE                  Location/Qualifiers
REGION                   1..15
                         note = Description of Artificial Sequence: Synthetic peptide
SITE                     1
                         note = N-term Ac
REGION                   1..6
                         note = Cyclic
MOD_RES                  7
                         note = N-methyl-Aspartic Acid
MOD_RES                  8
                         note = Tert-butylglycine
MOD_RES                  10
                         note = Azatryptophan
MOD_RES                  14
                         note = Cyclohexylglycine
MOD_RES                  15
                         note = N-e-(PEG24-gamma-glutamic
                          acid-N-Alpha-hexadecanoyl)lysine
source                   1..15
                         mol_type = protein
                         organism = synthetic construct
SEQUENCE: 194
KVERFDDGYW EYPGK                                                         15

SEQ ID NO: 195           moltype = AA  length = 15
FEATURE                  Location/Qualifiers
REGION                   1..15
                         note = Description of Artificial Sequence: Synthetic peptide
SITE                     1
                         note = N-term Ac
REGION                   1..6
                         note = Cyclic
MOD_RES                  7
                         note = N-methyl-Aspartic Acid
MOD_RES                  8
                         note = Tert-butylglycine
MOD_RES                  10
                         note = Azatryptophan
MOD_RES                  14
                         note = Cyclohexylglycine
MOD_RES                  15
                         note = N-e-palmitoyl lysine
SITE                     15
                         note = C-term NH2
source                   1..15
                         mol_type = protein
                         organism = synthetic construct
SEQUENCE: 195
KVERFDDGYW EYPGK                                                         15

SEQ ID NO: 196           moltype = AA  length = 15
FEATURE                  Location/Qualifiers
REGION                   1..15
                         note = Description of Artificial Sequence: Synthetic peptide
SITE                     1
                         note = N-term Ac
REGION                   1..6
                         note = Cyclic
```

```
MOD_RES          7
                 note = N-methyl-Aspartic Acid
MOD_RES          8
                 note = Tert-butylglycine
MOD_RES          14
                 note = Cyclohexylglycine
MOD_RES          15
                 note = N-e-palmitoyl lysine
source           1..15
                 mol_type = protein
                 organism = synthetic construct
SEQUENCE: 196
KVERFDDGYW EYPGK                                                        15

SEQ ID NO: 197   moltype = AA  length = 15
FEATURE          Location/Qualifiers
REGION           1..15
                 note = Description of Artificial Sequence: Synthetic peptide
SITE             1
                 note = N-term Ac
REGION           1..6
                 note = Cyclic
MOD_RES          7
                 note = N-methyl-Aspartic Acid
MOD_RES          8
                 note = Tert-butylglycine
MOD_RES          14
                 note = Cyclohexylglycine
source           1..15
                 mol_type = protein
                 organism = synthetic construct
SEQUENCE: 197
KVERFDDGYW EYPGK                                                        15

SEQ ID NO: 198   moltype = AA  length = 15
FEATURE          Location/Qualifiers
REGION           1..15
                 note = Description of Artificial Sequence: Synthetic peptide
SITE             1
                 note = N-term Ac
REGION           1..6
                 note = Cyclic
MOD_RES          7
                 note = N-methyl-Aspartic Acid
MOD_RES          8
                 note = Tert-butylglycine
MOD_RES          14
                 note = Cyclohexylglycine
MOD_RES          15
                 note =
                 N-e-1-(4,4-dimethyl-2,6-dioxocyclohex-1-ylidene)-3-methylbu
                 tyl-L-lysine
source           1..15
                 mol_type = protein
                 organism = synthetic construct
SEQUENCE: 198
KVERFDDGYW EYPGK                                                        15

SEQ ID NO: 199   moltype = AA  length = 15
FEATURE          Location/Qualifiers
REGION           1..15
                 note = Description of Artificial Sequence: Synthetic peptide
REGION           1..6
                 note = Cyclic
MOD_RES          1
                 note = 3-thiopropionic acid
MOD_RES          7
                 note = N-methyl-Aspartic Acid
MOD_RES          8
                 note = Tert-butylglycine
MOD_RES          10
                 note = Azatryptophan
MOD_RES          14
                 note = Cyclohexylglycine
MOD_RES          15
                 note = N-e-palmitoyl lysine
source           1..15
                 mol_type = protein
                 organism = synthetic construct
```

```
SEQUENCE: 199
CVERFCDGYW EYPGK                                                                15

SEQ ID NO: 200          moltype = AA  length = 15
FEATURE                 Location/Qualifiers
REGION                  1..15
                        note = Description of Artificial Sequence: Synthetic peptide
REGION                  1..6
                        note = Cyclic
MOD_RES                 1
                        note = 3-thiopropionic acid
SITE                    2
                        note = D-Alanine
MOD_RES                 7
                        note = N-methyl-Aspartic Acid
MOD_RES                 8
                        note = Tert-butylglycine
MOD_RES                 10
                        note = Azatryptophan
MOD_RES                 14
                        note = Cyclohexylglycine
MOD_RES                 15
                        note = N-e-palmitoyl lysine
source                  1..15
                        mol_type = protein
                        organism = synthetic construct
SEQUENCE: 200
CAERFCDGYW EYPGK                                                                15

SEQ ID NO: 201          moltype = AA  length = 15
FEATURE                 Location/Qualifiers
REGION                  1..15
                        note = Description of Artificial Sequence: Synthetic peptide
SITE                    1
                        note = N-term Ac
REGION                  1..6
                        note = Cyclic
MOD_RES                 7
                        note = N-methyl-Aspartic Acid
MOD_RES                 8
                        note = Tert-butylglycine
MOD_RES                 10
                        note = Azatryptophan
MOD_RES                 14
                        note = Aib
MOD_RES                 15
                        note = N-e-palmitoyl lysine
source                  1..15
                        mol_type = protein
                        organism = synthetic construct
SEQUENCE: 201
KVERFDDGYW EYPXK                                                                15

SEQ ID NO: 202          moltype = AA  length = 19
FEATURE                 Location/Qualifiers
REGION                  1..19
                        note = Description of Artificial Sequence: Synthetic peptide
SITE                    1
                        note = N-term Ac
SITE                    19
                        note = C-term NH2
source                  1..19
                        mol_type = protein
                        organism = synthetic construct
SEQUENCE: 202
RLIEDICLIP RWGCLWEDD                                                            19

SEQ ID NO: 203          moltype = AA  length = 20
FEATURE                 Location/Qualifiers
REGION                  1..20
                        note = Description of Artificial Sequence: Synthetic peptide
SITE                    20
                        note = C-term NH2
source                  1..20
                        mol_type = protein
                        organism = synthetic construct
SEQUENCE: 203
QRLMEDICLP RWGCLWEDDF                                                           20
```

```
SEQ ID NO: 204             moltype = AA   length = 20
FEATURE                    Location/Qualifiers
REGION                     1..20
                           note = Description of Artificial Sequence: Synthetic peptide
SITE                       1
                           note = N-term Ac
SITE                       20
                           note = C-term NH2
source                     1..20
                           mol_type = protein
                           organism = synthetic construct
SEQUENCE: 204
QRLIEDICLP RWGCLWEDDF                                                    20

SEQ ID NO: 205             moltype = AA   length = 16
FEATURE                    Location/Qualifiers
REGION                     1..16
                           note = Description of Artificial Sequence: Synthetic peptide
source                     1..16
                           mol_type = protein
                           organism = synthetic construct
SEQUENCE: 205
RKKRRRESRK KRRRES                                                        16

SEQ ID NO: 206             moltype = AA   length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 206
RKKRRQRRR                                                                9

SEQ ID NO: 207             moltype = AA   length = 16
FEATURE                    Location/Qualifiers
REGION                     1..16
                           note = Description of Artificial Sequence: Synthetic peptide
source                     1..16
                           mol_type = protein
                           organism = synthetic construct
SEQUENCE: 207
RQIKIWFQNR RMKWKK                                                        16

SEQ ID NO: 208             moltype = AA   length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 208
AAVLLPVLLA AP                                                            12

SEQ ID NO: 209             moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 209
VPTLK                                                                    5

SEQ ID NO: 210             moltype = AA   length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 210
PLILLRLLRG QF                                                            12

SEQ ID NO: 211             moltype = AA   length = 15
FEATURE                    Location/Qualifiers
REGION                     1..15
                           note = Description of Artificial Sequence: Synthetic peptide
SITE                       1
```

```
                 note = N-term Ac
REGION           1..6
                 note = Bridging moiety between residues
MOD_RES          8
                 note = Tert-butylglycine
MOD_RES          10
                 note = Azatryptophan
MOD_RES          14
                 note = Cyclohexylglycine
MOD_RES          15
                 note = Nva
source           1..15
                 mol_type = protein
                 organism = synthetic construct
SEQUENCE: 211
CVERFCDGYW EYPGV                                                     15
```

MODULATORS OF COMPLEMENT ACTIVITY

CROSS REFERENCE TO RELATED APPLICATIONS

This application is a continuation of U.S. application Ser. No. 17/143,232 filed Jan. 7, 2021, entitled Modulators of Complement Activity, which is a continuation of U.S. application Ser. No. 16/776,551 filed Jan. 30, 2020, entitled Modulators of Complement Activity, which is a continuation of U.S. application Ser. No. 16/393,393 filed Apr. 24, 2019, entitled Modulators of Complement Activity, which is a continuation of U.S. application Ser. No. 15/905,158 filed Feb. 26, 2018, entitled Modulators of Complement Activity, which is a continuation of U.S. application Ser. No. 15/547,085 filed Jul. 28, 2017, entitled Modulators of Complement Activity, which is a 35 U.S.C. § 371 U.S. National Stage Entry of International Application No. PCT/US2016/015412 filed Jan. 28, 2016, entitled Modulators of Complement Activity, which claims the benefit of U.S. Provisional Patent Application No. 62/108,772 filed Jan. 28, 2015, entitled Modulation of Complement Activity, International Publication No. PCT/US2015/035473 filed Jun. 12, 2015, entitled Modulation of Complement Activity, and U.S. Provisional Patent Application No. 62/185,298 filed Jun. 26, 2015, entitled Modulation of Complement Activity, the contents of each of which are herein incorporated by reference in their entirety.

SEQUENCE LISTING

The instant application contains a Sequence Listing which has been submitted electronically in XML format and is hereby incorporated by reference in its entirety. Said XML copy, created on Jan. 22, 2024, is named 35130-55925US.xml and is 789,837 bytes in size.

FIELD OF THE INVENTION

The present invention relates to compounds, including polypeptides, which are useful as modulators of complement activity. Also provided are methods of utilizing these modulators as therapeutics.

BACKGROUND OF THE INVENTION

The vertebrate immune response is comprised of adaptive and innate immunity components. While the adaptive immune response is selective for particular pathogens and is slow to respond, components of the innate immune response recognize a broad range of pathogens and respond rapidly upon infection. One such component of the innate immune response is the complement system.

The complement system includes about 20 circulating proteins, synthesized primarily by the liver. Components of this particular immune response were first termed "complement" due to the observation that they complemented the antibody response in the destruction of bacteria. These proteins remain in an inactive form prior to activation in response to infection. Activation occurs by way of a pathway of proteolytic cleavage initiated by pathogen recognition and leading to pathogen destruction. Three such pathways are known in the complement system and are referred to as the classical pathway, the lectin pathway and the alternative pathway. The classical pathway is activated when an IgG or IgM molecule binds to the surface of a pathogen. The lectin pathway is initiated by the mannan-binding lectin protein recognizing the sugar residues of a bacterial cell wall. The alternative pathway remains active at low levels in the absence of any specific stimuli. While all three pathways differ with regard to initiating events, all three pathways converge with the cleavage of complement component C3. C3 is cleaved into two products termed C3a and C3b. Of these, C3b becomes covalently linked to the pathogen surface while C3a acts as a diffusible signal to promote inflammation and recruit circulating immune cells. Surface-associated C3b forms a complex with other components to initiate a cascade of reactions among the later components of the complement system. Due to the requirement for surface attachment, complement activity remains localized and minimizes destruction to non-target cells.

Pathogen-associated C3b facilitates pathogen destruction in two ways. In one pathway, C3b is recognized directly by phagocytic cells and leads to engulfment of the pathogen. In the second pathway, pathogen-associated C3b initiates the formation of the membrane attack complex (MAC). In the first step, C3b complexes with other complement components to form the C5-convertase complex. Depending on the initial complement activation pathway, the components of this complex may differ. C5-convertase formed as the result of the classical complement pathway comprises C4b and C2a in addition to C3b. When formed by the alternative pathway, C5-convertase comprises two subunits of C3b as well as one Bb component.

Complement component C5 is cleaved by either C5-convertase complex into C5a and C5b. C5a, much like C3a, diffuses into the circulation and promotes inflammation, acting as a chemoattractant for inflammatory cells. C5b remains attached to the cell surface where it triggers the formation of the MAC through interactions with C6, C7, C8 and C9. The MAC is a hydrophilic pore that spans the membrane and promotes the free flow of fluid into and out of the cell, thereby destroying it.

An important component of all immune activity is the ability of the immune system to distinguish between self and non-self cells. Pathology arises when the immune system is unable to make this distinction. In the case of the complement system, vertebrate cells express proteins that protect them from the effects of the complement cascade. This ensures that targets of the complement system are limited to pathogenic cells. Many complement-related disorders and diseases are associated with abnormal destruction of self cells by the complement cascade. In one example, subjects suffering from paroxysmal nocturnal hemoglobinuria (PNH) are unable to synthesize functional versions of the complement regulatory proteins CD55 and CD59 on hematopoietic stem cells. This results in complement-mediated hemolysis and a variety of downstream complications. Other complement-related disorders and diseases include, but are not limited to autoimmune diseases and disorders, neurological diseases and disorders, blood diseases and disorders and infectious diseases and disorders. Experimental evidence suggests that many complement-related disorders are alleviated through inhibition of complement activity. Therefore, there is a need for the development of compounds and methods for selectively blocking complement-mediated cell destruction and for treating related indications. The present invention meets this need by providing polypeptides described herein and related methods for their use.

SUMMARY OF THE INVENTION

In some embodiments, the present invention provides a method of reducing the cleavage of C5 in a biological system by at least 50/6 relative to cleavage of C5 in an untreated control system, comprising providing a polypeptide with the amino acid sequence of SEQ ID NO: 184 to the biological system, wherein the polypeptide is provided at a final concentration of from about 0.1 nM to about 50 nM, and wherein cleavage of C5 is reduced by at least 50% relative to cleavage of C5 in the untreated control system.

In some embodiments, the present invention provides a method of reducing hemolysis in a biological system by at least 50% relative to hemolysis in an untreated control system, comprising providing a polypeptide with the amino acid sequence of SEQ ID NO: 184 to the biological system, wherein the polypeptide is provided at a final concentration of from about 0.1 nM to about 50 nM, and wherein hemolysis is reduced by at least 50% relative to hemolysis in an untreated control system.

Also provided herein is a method of reducing hemolysis in a subject by about 50% to about 95% relative to hemolysis levels previously observed in a subject, comprising administering a polypeptide with the amino acid sequence of SEQ ID NO: 184, wherein the polypeptide is administered at a dose sufficient to achieve plasma levels of the polypeptide of from about 0.2 mg/L (0.1 µM) to about 40 mg/L (20 µM). Such subjects may be human, non-human primate, or porcine subjects. In some cases, subjects are human subjects with paroxysmal nocturnal hemoglobinuria (PNH).

In some embodiments, polypeptides with the amino acid sequence of SEQ ID NO: 184 are administered to human subjects at a dose of about 0.01 mg/kg to about 20 mg/kg. Such administration may be carried out daily or weekly.

In some embodiments, the present invention provides a method of reducing hemolysis in a subject with PNH comprising administering a polypeptide with the amino acid sequence of SEQ ID NO: 184, wherein the polypeptide is administered at a dose of from about 0.01 mg/kg to about 20 mg/kg and wherein administration is daily, weekly or monthly. In some cases, such subjects have been treated previously or are currently receiving treatment with ECULIZUMAB®.

Also provided is a method of reducing hemolysis in a subject comprising administering a polypeptide, wherein the subject has PNH, and wherein the subject is not responsive to treatment with ECULIZUMAB®.

According to some methods of the invention, hemolysis is reduced by about 50% to about 95% relative hemolysis observed previously in a subject.

DESCRIPTION OF THE FIGURES

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

Figure 8:
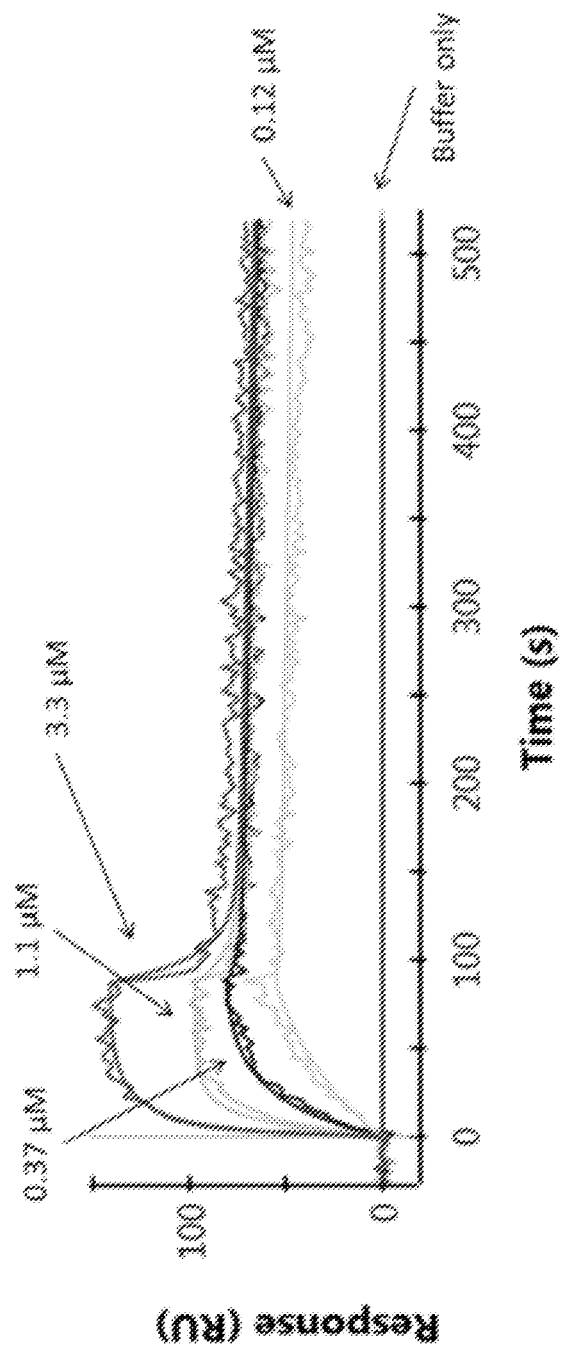

FIG. 8 is a line graph showing results from surface plasmon resonance analysis of C5 binding by R3183 (SEQ ID NO: 184).

Figure 9:
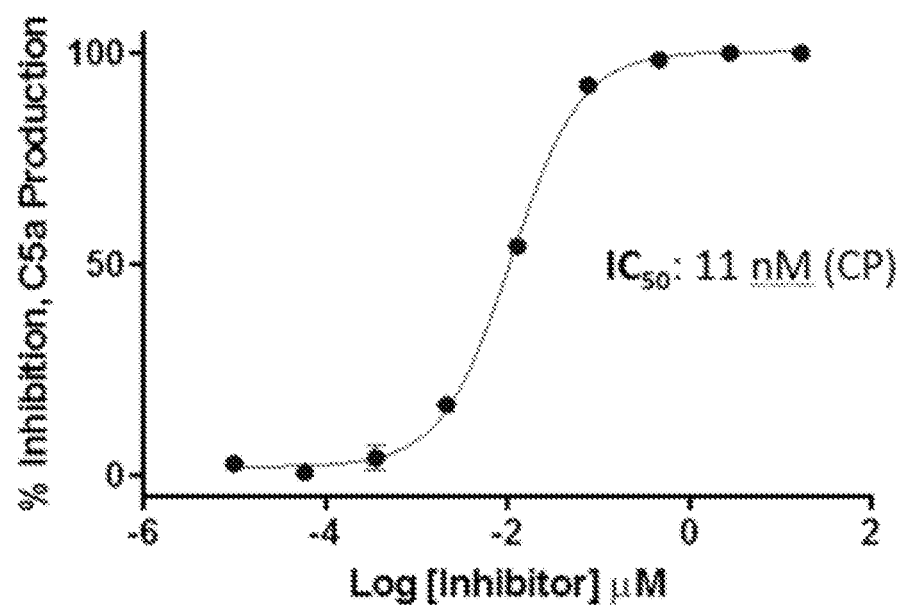

FIG. 9 is a line graph showing results of a C5a immunoassay with human red blood cell hemolysis assay supernatant.

Figure 10:
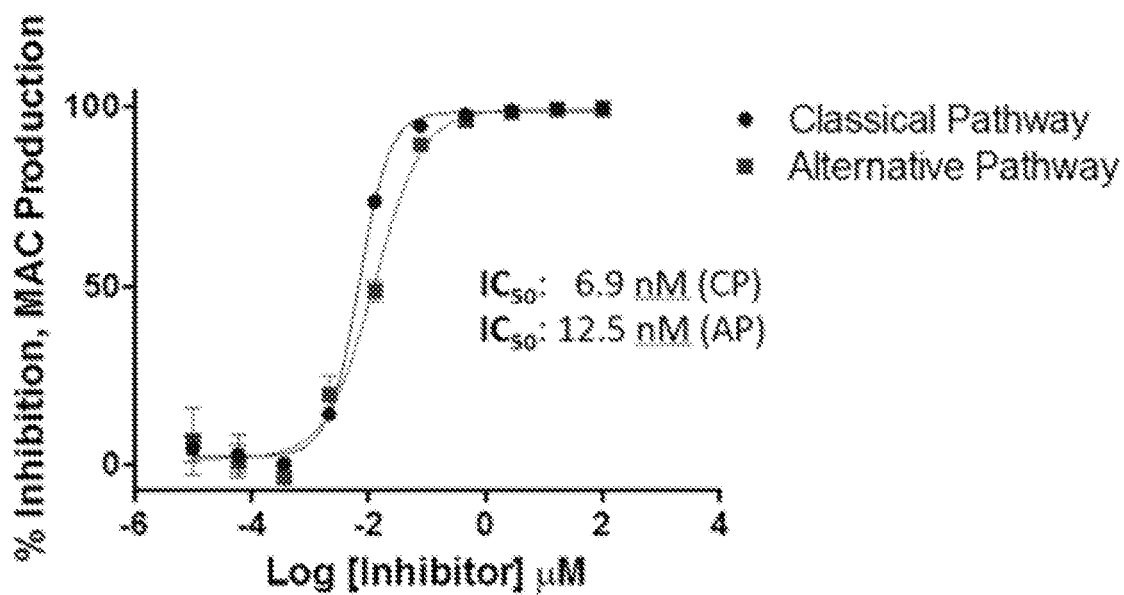

FIG. 10 is a line graph showing results of a membrane attack complex (MAC) formation immunoassay performed on supernatant from a human red blood cell hemolysis assay.

Figure 11A:
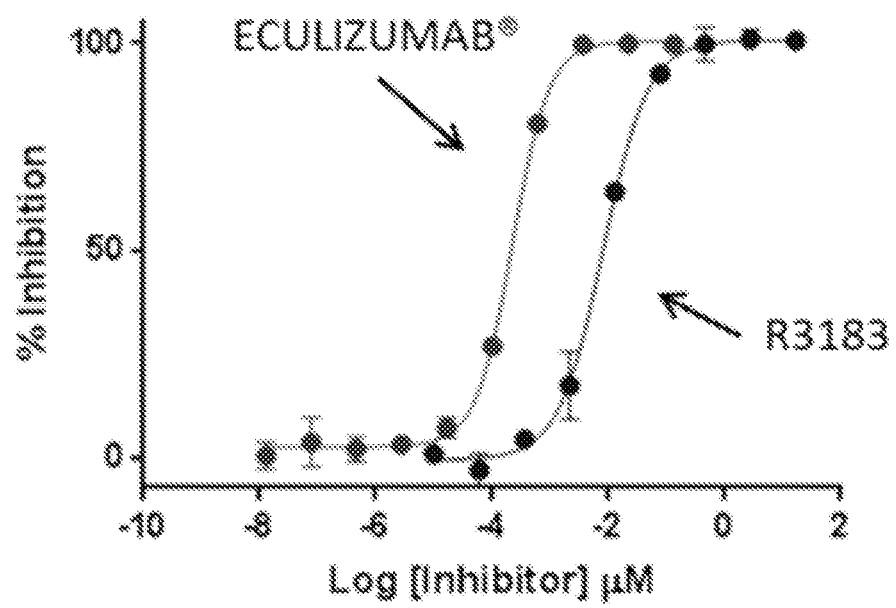
Figure 11B:
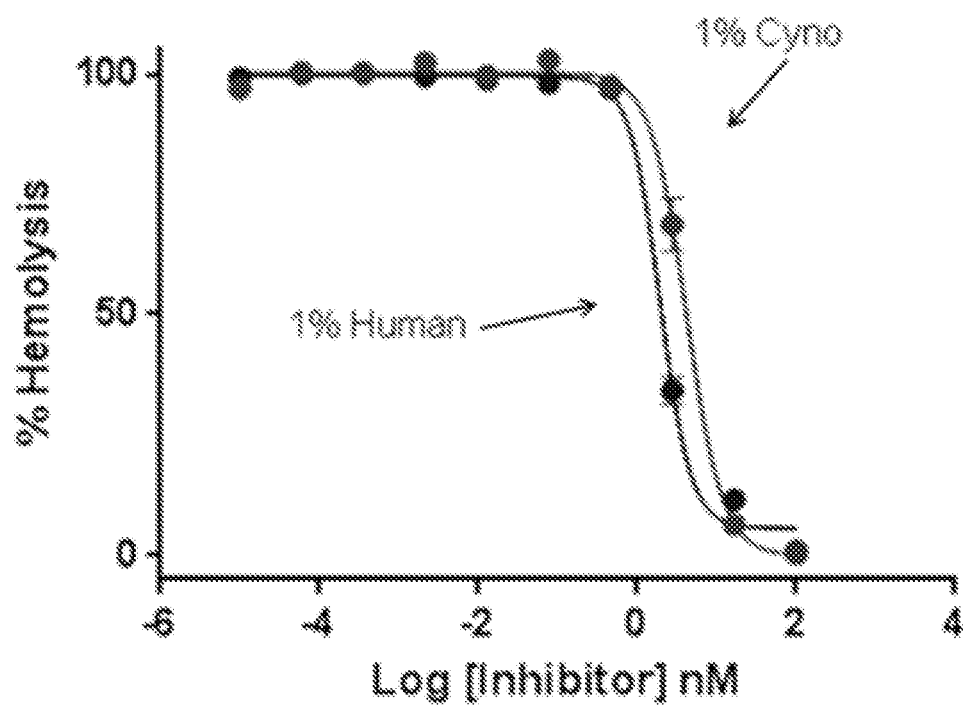

FIGS. 11A and 11B are line graphs showing results of human hemolysis assays. FIG. 11A is a line graph comparing inhibition between ECULIZUMAB® and R3183 (SEQ ID NO: 184). FIG. 11B is a line graph presenting results of a hemolysis assay with R3183 (SEQ ID NO: 184) in the presence of human or non-human primate serum.

Figure 12A:
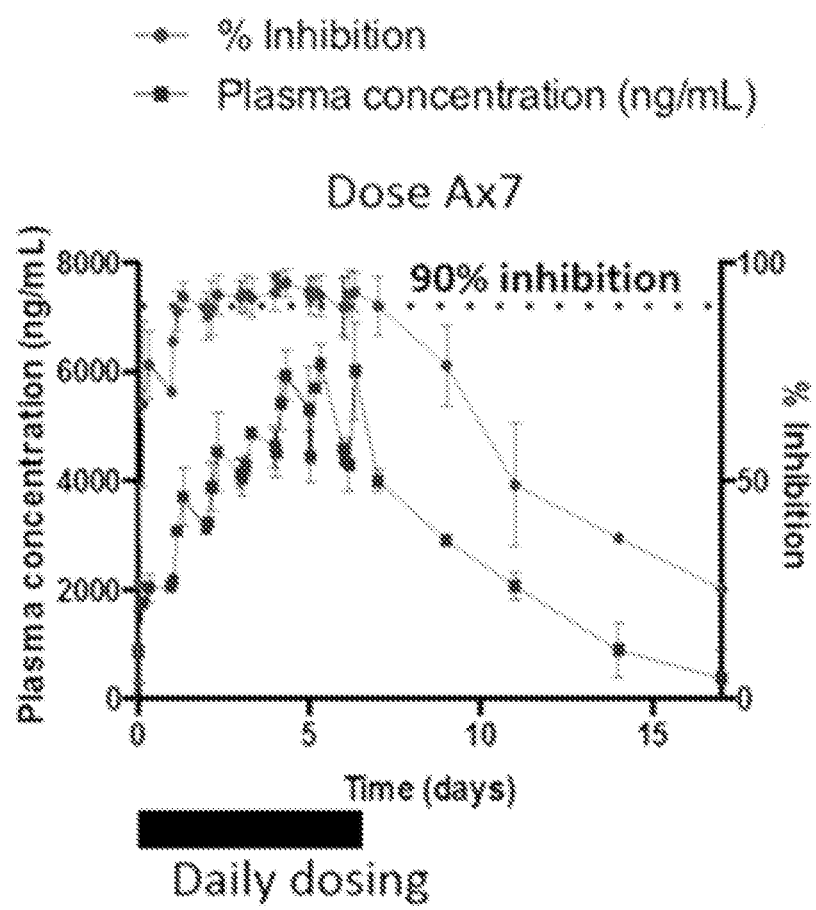
Figure 12B:
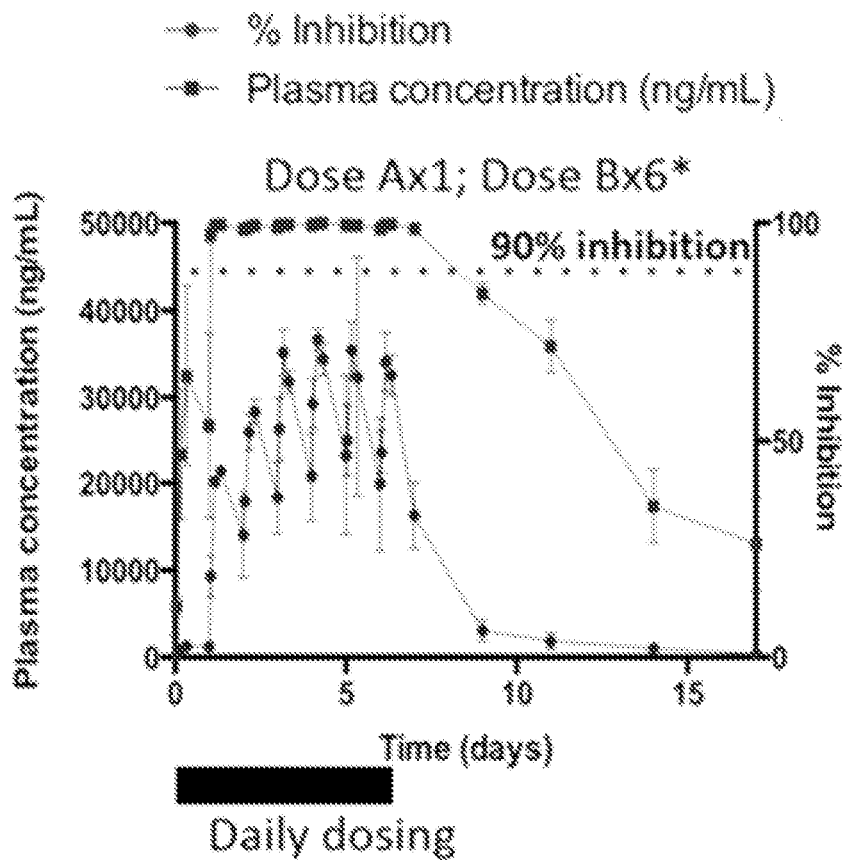

FIGS. 12A and B are line graphs showing results from compound administration in animal models. FIG. 12A is a line graph showing results of R3183 administration in an animal model. FIG. 12B is a line graph showing results of R3183 administration in an animal model.

Figure 13:
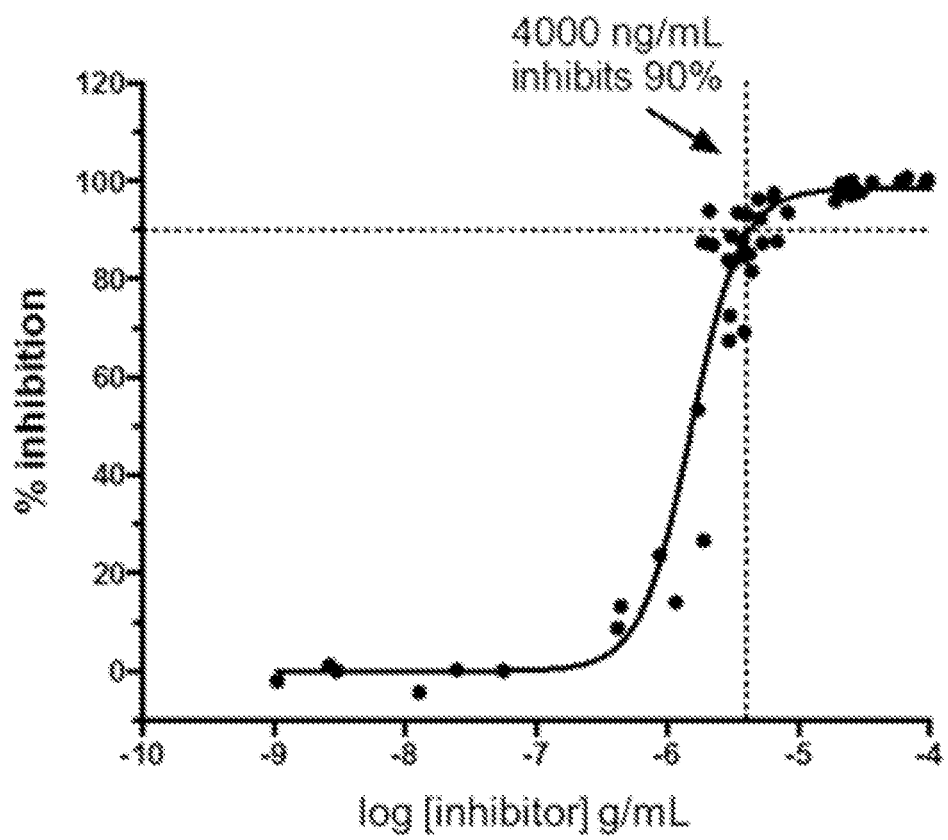

FIG. 13 is a scatter plot showing combined data from pharmacokinetic and pharmacodynamics studies.

Figure 14:
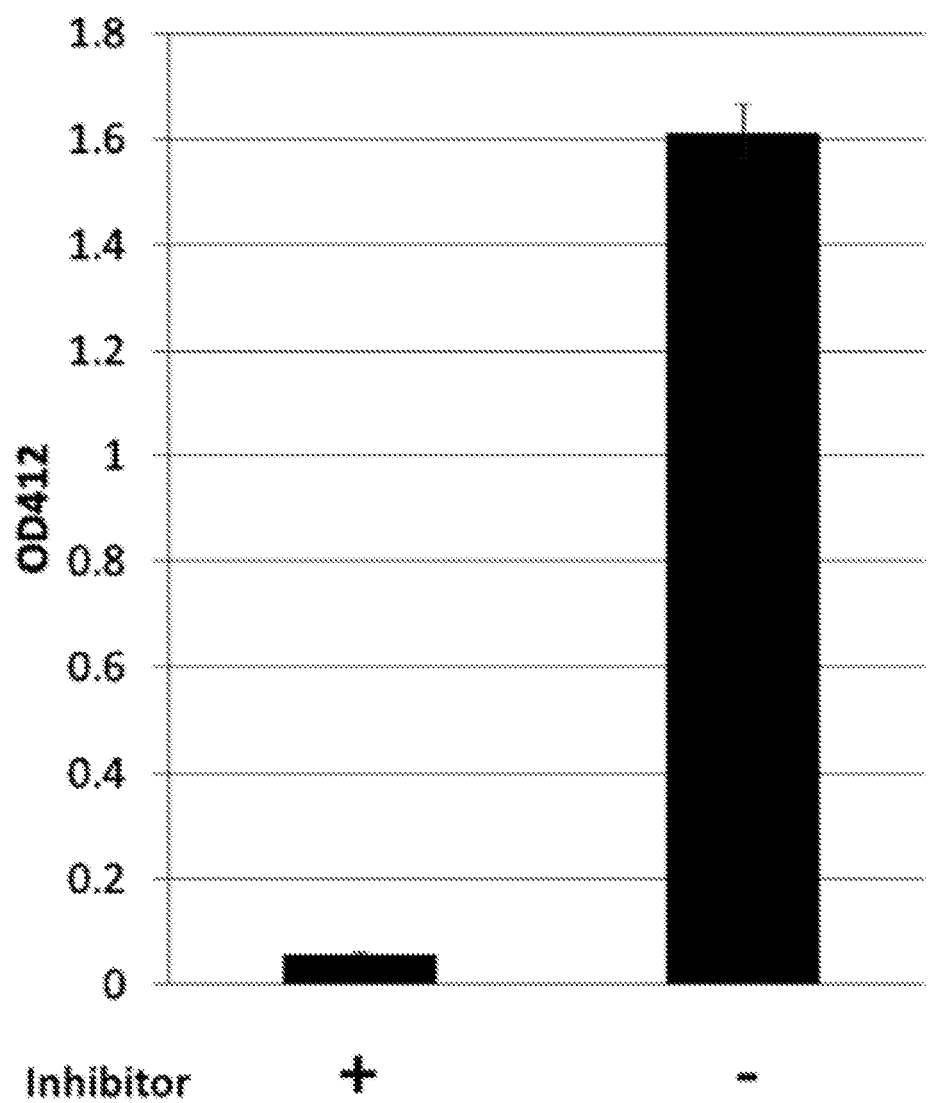

FIG. 14 is a bar graph showing results of a hemolysis assay.

DETAILED DESCRIPTION

The present invention relates to the discovery of novel C5 modulatory compounds and methods of their use. Such compounds may include, but are not limited to polypeptides (e.g. cyclic polypeptides, peptidomimetics and cyclic peptidomimetics), small molecules, antibodies, antibody fragments, and aptamers. In some cases, C5 modulatory compounds are polypeptides useful in the diagnosis and/or treatment of diseases in which the inhibition of complement activation is desirable. In some embodiments, polypeptides of the invention specifically bind complement component C5. In further embodiments, polypeptides of the invention reduce complement-mediated cell lysis (e.g., red blood cell hemolysis) by preventing cleavage of C5 into C5a and C5b fragments.

Definitions

Biological system: As used herein, the term "biological system" refers to a cell, a group of cells, a tissue, an organ, a group of organs, an organelle, a biological signaling pathway (e.g., a receptor-activated signaling pathway, a charge-activated signaling pathway, a metabolic pathway, a cellular signaling pathway, etc.), a group of proteins, a group of nucleic acids, or a group of molecules (including, but not limited to biomolecules) that carry out at least one biological function or biological task within cellular membranes, cellular compartments, cells, cell cultures, tissues, organs, organ systems, organisms, multicellular organisms, or any biological entities. In some embodiments, biological systems are cell signaling pathways comprising intracellular and/or extracellular signaling biomolecules. In some embodiments, biological systems comprise proteolytic cascades (e.g., the complement cascade).

Control system: As used herein, the term "control system" refers to a biological system that is untreated and used for comparison to a biological system that is or has been treated or otherwise manipulated.

Downstream event: As used herein, the term "downstream" or "downstream event," refers to any event occurring after and as a result of another event. In some cases, downstream events are events occurring after and as a result of C5 cleavage and/or complement activation. Such events may include, but are not limited to generation of C5 cleavage products, activation of MAC, hemolysis, and hemolysis-related disease (e.g., PNH).

Sample: As used herein, the term "sample" refers to an aliquot or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample is or comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Subject: As used herein, the term "subject" refers to any organism to which a compound in accordance with the invention may be administered, e.g., for experimental, diagnostic, prophylactic, and/or therapeutic purposes. Typical subjects include animals (e.g., mammals such as mice, rats, rabbits, porcine subjects, non-human primates, and humans.)

1. Compounds and Compositions

In some embodiments, the present invention provides compounds and compositions for modulation of complement activity. In some cases, compounds include C5 modulatory compounds. Such compounds may include, but are not limited to polypeptides (e.g. cyclic polypeptides, peptidomimetics and cyclic peptidomimetics). As used herein, a "mimetic" refers to a molecule which exhibits some of the properties or features of another molecule. A "peptidomimetic" or "polypeptide mimetic" is a mimetic in which the molecule contains structural elements that are not found in natural polypeptides (i.e., polypeptides comprised of only the 20 proteinogenic amino acids). In some embodiments, peptidomimetics are capable of recapitulating or mimicking the biological action(s) of a natural peptide. A peptidomimetic may differ in many ways from natural polypeptides, including, but not limited to changes in backbone structure and the presence of amino acids that do not occur in nature. In some cases, peptidomimetics may include amino acids with side chains that are not found among the known 20 proteinogenic amino acids, non-polypeptide-based bridging moieties used to effect cyclization between the ends or internal portions of the molecule, substitutions of the amide bond hydrogen moiety by methyl groups (N-methylation) or other alkyl groups, replacement of a peptide bond with a chemical group or bond that is resistant to chemical or enzymatic treatments, N- and C-terminal modifications, and conjugation with a non-peptidic extension (such as polyethylene glycol, lipids, carbohydrates, nucleosides, nucleotides, nucleoside bases, various small molecules, or phosphate or sulfate groups).

Some polypeptides of the invention may be cyclic. Cyclic polypeptides include any polypeptides that have as part of their structure one or more cyclic features such as a loop, bridging moiety, and/or an internal linkage. As used herein, the term "bridging moiety" refers to one or more components of a bridge formed between two adjacent or non-adjacent amino acids, unnatural amino acids or non-amino acids in a polypeptide. Bridging moieties may be of any size or composition. In some embodiments, bridging moieties may comprise one or more chemical bonds between two adjacent or non-adjacent amino acids, unnatural amino acids, non-amino acid residues or combinations thereof. In some embodiments, such chemical bonds may be between one or more functional groups on adjacent or non-adjacent amino acids, unnatural amino acids, non-amino acid residues or combinations thereof. Bridging moieties may comprise one or more features including, but not limited to an amide bond (lactam), disulfide bond, thioether bond, aromatic ring, triazole ring, and hydrocarbon chain. In some embodiments, bridging moieties comprise an amide bond between an amine functionality and a carboxylate functionality, each present in an amino acid, unnatural amino acid or non-amino acid residue side chain. In some embodiments, the amine or carboxylate functionalities are part of a non-amino acid residue or unnatural amino acid residue. In some cases, bridging moieties may comprise bonds formed between residues that may include, but are not limited to (S)-2-amino-5-azidopentanoic acid (also referred to herein as "X02"), (S)-2-aminohept-6-enoic acid (also referred to herein as "X30"), (S)-2-aminopent-4-ynoic acid (also referred to herein as "X31") and (S)-2-aminopent-4-enoic acid (also referred to herein as "X12".) Bridging moieties may be formed through cyclization reactions using olefin metathesis. In some cases, such bridging moieties may be formed between X12 and X30 residues. In some embodiments, the bridging moiety comprises a disulfide bond formed between two thiol containing residues. In some embodiments, the bridging moiety comprises one or more thioether bonds. Such thioether bonds, may include those found in cyclo-thioalkyl compounds. These bonds are formed during a chemical cyclization reaction between chloro acetic acid (also referred to herein as "X35") N-terminal modified groups and cysteine residues. In some cases, bridging moieties comprise one or more triazole ring. Such triazole rings may include, but are not limited to those formed by cyclization reaction between X02 and X31. In some embodiments, bridging moieties comprise non-protein or non-polypeptide based moieties, including, but not limited to cyclic rings (including, but not limited to aromatic ring structures (e.g. xylyls)). Such bridging moieties may be introduced by reaction with reagents containing multiple reactive halides, including, but not limited to poly(bromomethyl)benzenes, poly(bromomethyl)pyridines, poly(bromomethyl)alkylbenzenes and/or (E)-1,4-dibromobut-2-ene. In some embodiments, bridging moieties of the present invention include, but are not limited to the following structures:

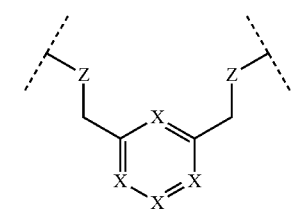
I

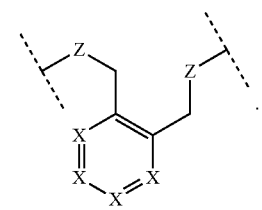
II

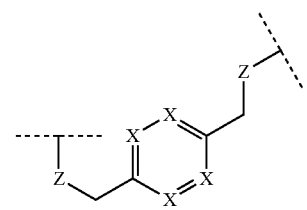
III

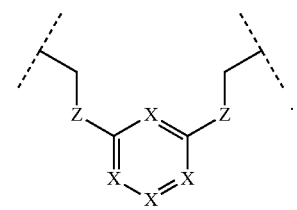
IV

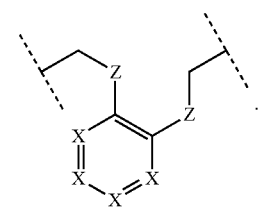
V

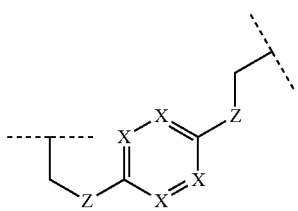
VI

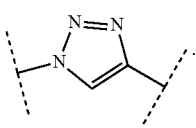
VII

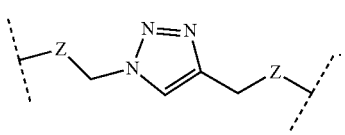
VIII

-continued

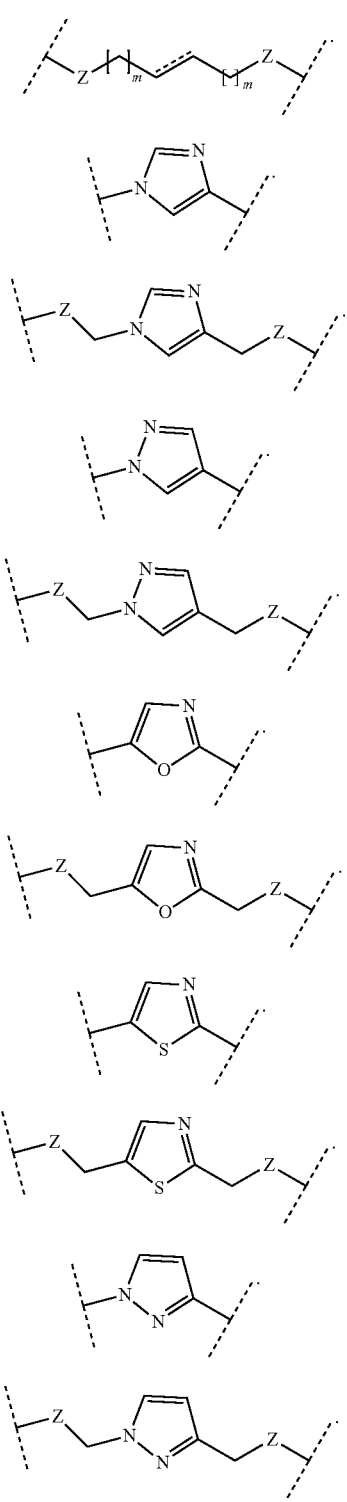

IX

X

XI

XII

XIII

XIV

XV

XVI

XVII

XVIII

XIX

In certain embodiments of this invention, polypeptides are rendered macrocyclic by formation of covalent bonds between atoms present within the linear polypeptide and atoms of a bridging moiety. This bridging moiety serves the purpose of chemically tethering two reactive sites on the linear polypeptide so as to furnish a cyclic polypeptide product. Embodiments of the present invention include polypeptides cyclized in the aforementioned manner and comprising a bridging moiety containing an aromatic, 6-membered ring. In these embodiments, atoms of the linear polypeptide that form explicit chemical bonds with the bridging moiety may be heteroatoms (including, but not limited to, nitrogen, oxygen and sulfur), or saturated or unsaturated carbon atoms. In each of these embodiments of this invention, the atoms of the polypeptide side chain may be bonded directly to a carbon atom within the aromatic ring of the bridging moiety. In alternative forms, the atoms of the polypeptide side chain may be bonded to a saturated —CH$_2$— group that is in turn directly bonded to a carbon atom within the aromatic ring of the bridging moiety. In certain cases, the aromatic, 6-membered ring within the bridging moiety is benzene, as in the following structures wherein Z may be selected from NH, S, O and (CH)$_2$:

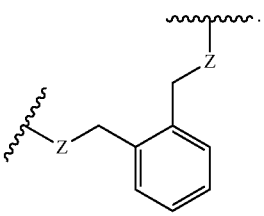

XX

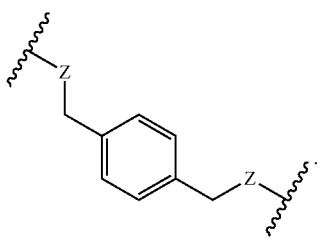

XXI

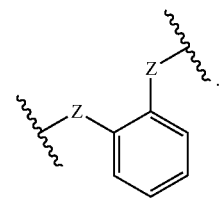

XXII

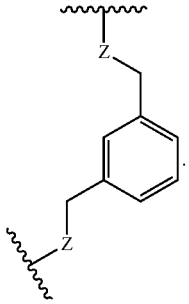

XXIII wherein each X is independently N or CH, such that no ring contains more than 2 N; each Z is independently absent or selected from a bond, NR, O, S, CH$_2$, C(O)NR, NRC(O), S(O)$_v$NR and NRS(O)$_v$; each m is independently selected from 0, 1, 2, and 3; each v is independently selected from 1 and 2; each R is independently selected from H and C1-C6, and each bridging moiety is connected to the polypeptide by an independently selected bond or C1-C6 spacer.

-continued

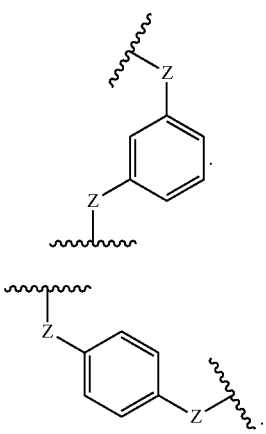
XXIV

XXV

Z = NH, S, O, CH(2)

In alternative forms of this invention, the aromatic, 6-membered ring that comprises the bridging moiety is heterocyclic and contains one or more nitrogen atoms. In these embodiments, the aromatic heterocycle may be pyridine, containing a single nitrogen atom in the aromatic ring [e.g. any of the structures below wherein Z may be selected from NH, S, O and (CH)$_2$]:

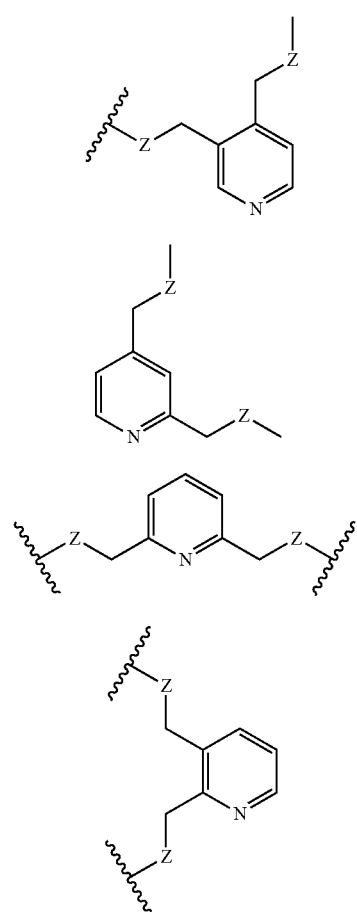

XXVI

XXVII

XXVIII

XXIX

-continued

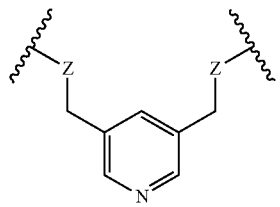
XXX

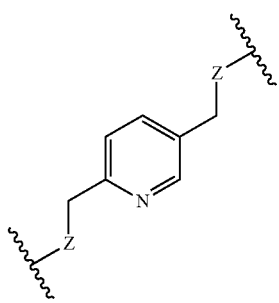
XXXI

XXXII

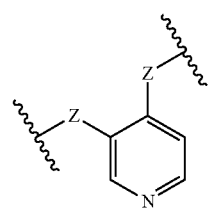
XXXIII

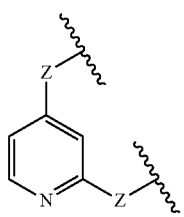
XXXIV

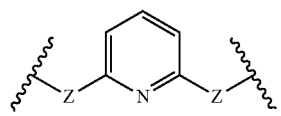
XXXV

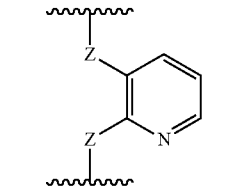
XXXVI

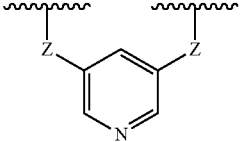

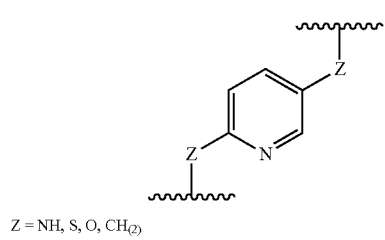

XXXVII

Z = NH, S, O, CH(2)

Aromatic heterocycles may alternatively be pyridazine, containing two adjacent nitrogen atoms in a 1,2-orientation within the aromatic ring [e.g. any of the structures below wherein Z may be selected from NH, S, O and $(CH_2)$]:

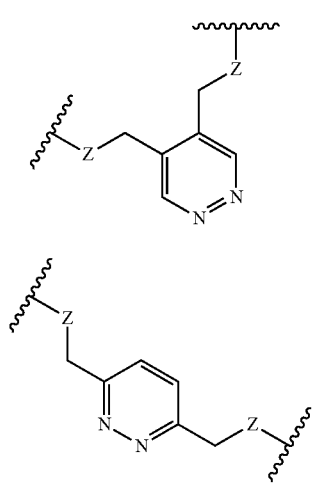

XXXVIII

XXXIX

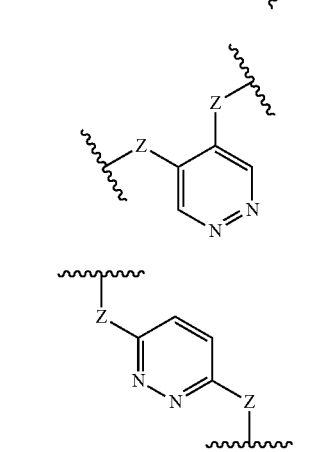

XL

XLI

XLII

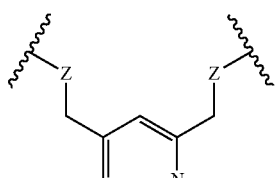

XLIII

XLIV

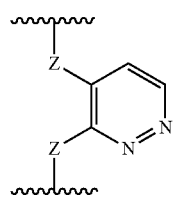

XLV

Z = NH, S, O, CH(2)

In other embodiments, the aromatic heterocycle may be pyrimidine, containing two nitrogen atoms in a 1,3-orientation within the aromatic ring [e.g. any of the structures below wherein Z may be selected from NH, S, O and $(CH_2)$]:

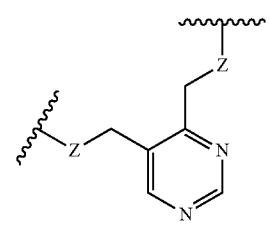

XLVI

XLVII

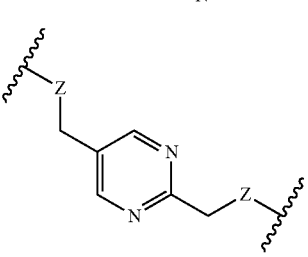

XLVIII

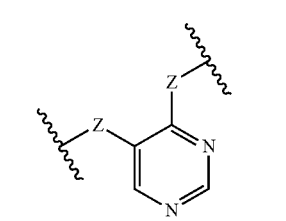

XLIX

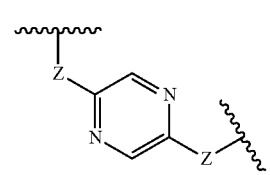

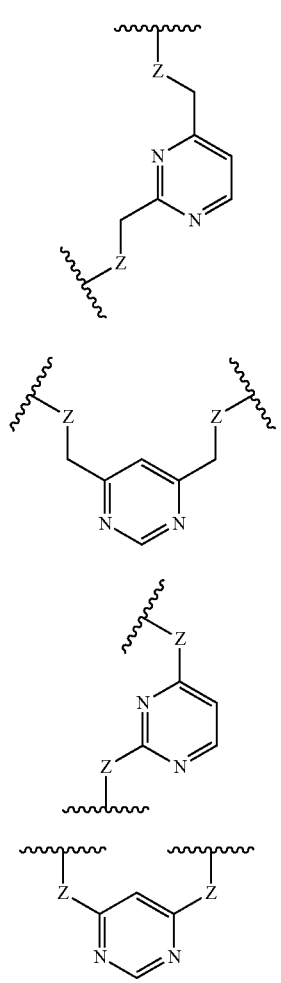

Z = NH, S, O, CH$_{(2)}$

Alternatively, the aromatic heterocycle may be pyrazine, containing two nitrogen atoms in a 1,4-orientation within the aromatic ring [e.g. any of the structures below wherein Z may be selected from NH, S, O and (CH)$_2$]:

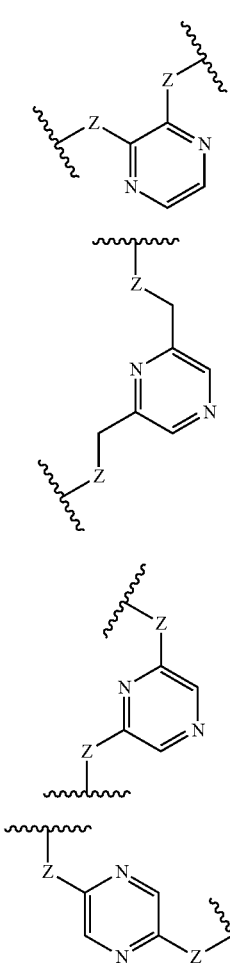

Z = NH, S, O, CH$_{(2)}$

In alternative forms of this invention, polypeptides are rendered macrocyclic as a result of the formation of covalent bonds between atoms of the linear polypeptide and atoms of a bridging moiety consisting of a heterocyclic, aromatic, 5-membered ring. In these embodiments, atoms of the linear polypeptide that form explicit chemical bonds with the bridging moiety may be heteroatoms (including, but not limited to, nitrogen, oxygen and sulfur), or saturated or unsaturated carbon atoms. In each of these embodiments of this invention, the atoms of the polypeptide side chain may be bonded directly to a carbon atom or nitrogen atom within the aromatic ring of the bridging moiety. In alternative forms, the atoms of the polypeptide side chain may be bonded to a saturated —CH$_2$— group that is in turn directly bonded to a carbon atom or nitrogen atom within the aromatic ring of the bridging moiety. In certain cases, the heterocyclic, aromatic, 5-membered ring within the bridging moiety is 1,2,3-triazole. In these embodiments, the aromatic ring may be substituted at positions 1 and 4 with chemical functionality of the linear polypeptide that are being tethered. Alternatively, the 1,2,3-triazole scaffold may be substituted at positions 1 and 4 with —CH$_2$— groups that are directly bonded to the atoms of the linear polypeptide being tethered [e.g. either of the structures below wherein Z may be selected from NH, S, O and (CH)$_2$]:

LX

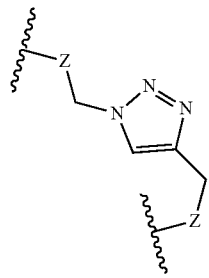

LXI

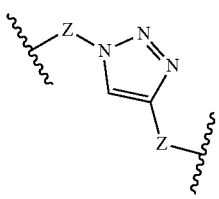

Z = NH, S, O, CH$_{(2)}$

In other embodiments of this invention, the heterocyclic, aromatic, 5-membered ring that comprises the bridging moiety is pyrazole. In these embodiments, the aromatic ring may be substituted either at positions 1 and 3 or at positions 1 and 4 with chemical functionality of the linear polypeptide that are being tethered. Alternatively, the pyrazole scaffold may be substituted either at positions 1 and 3 or at positions 1 and 4 with —CH$_2$— groups that are directly bonded to the atoms of the linear polypeptide being tethered [e.g. any of the structures below wherein Z may be selected from NH, S, O and (CH)$_2$]:

LXII

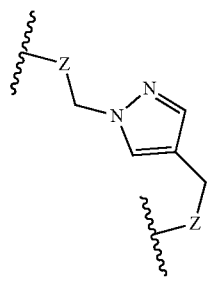

LXIII

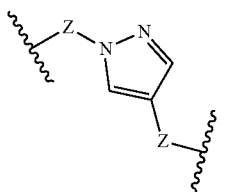

LXIV

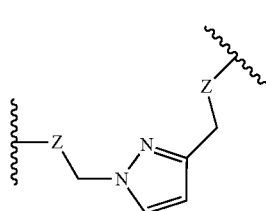

LXV

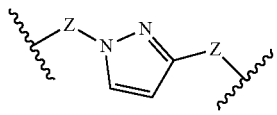

Z = NH, S, O, CH$_{(2)}$

Unless otherwise defined, all technical and scientific terms used herein have the same meaning as commonly understood by one of ordinary skill in the art to which this invention belongs. Although methods and materials similar or equivalent to those described herein can be used in the practice or testing of the cyclic polypeptides and methods featured in the invention, suitable methods and materials are described below.

Polypeptides as Drugs

By virtue of their size and complexity, polypeptides are able to form numerous, highly specific contacts with their biological targets and can show a high level of selectivity for the correct or desired target as compared to a closely related target within the same family. Off-target effects (known also as side effects) often cause highly effective drugs to fail regulatory approval due to safety concerns.

Numerous polypeptides (including, but not limited to peptidomimetics, have been developed into effective drugs. These include, but are not limited to, insulin, glucagon-like peptide 1 (GLP-1), somatostatin, vasopressin, cyclosporine A, and the like. The therapeutic polypeptide can be identical to the naturally occurring molecule (i.e. that which circulates in humans and is considered "wild-type" in the human population). In many other cases, the polypeptide is not suitable or sub-optimal for therapeutic use due to a short circulating half-life that is often due to metabolic instability in the body. In these cases a modified or a variant form of the polypeptide (peptidomimetic) is used which results in improved pharmacokinetic and pharmacodynamic behavior. In other cases a polypeptide derived from a natural source has an equivalent mechanism of action and a preferred pharmaceutical profile and can be used as a therapy. For example, exenatide, a synthetic version of exedin-4, has biological properties similar to human glucagon-like peptide-1 (GLP-1) but improved pharmacokinetics, and has been approved by the FDA for the treatment of diabetes mellitus type 2. As another example, salmon calcitonin, calcitonin extracted from the Ultimobranchial glands of salmon, resembles human calcitonin but is more active than human calcitonin and may be used to treat postmenopausal osteoporosis, hypercalcaemia, Paget's disease, bone metastases and phantom limb pain.

Polypeptides are typically limited to non-oral routes of administration. In nearly all cases, polypeptides must be delivered by injection, since even very short polypeptides (e.g., polypeptides with 4-10 amino acid residues) are incapable or poorly capable of passing through the cell membranes lining the intestinal tract. For efficient oral availability, drugs typically need to pass through both the luminal and basolateral membranes of gut epithelial cells in order to enter the systemic circulation. The poor membrane permeability and lack of oral bioavailability of polypeptides significantly limits their therapeutic use.

The effectiveness of a polypeptide as a drug may be influenced by its proteolytic stability. Within the body, polypeptides can be modified or degraded by enzymes, which can limit their effectiveness for interacting with an intended target.

Metabolic stability of polypeptides is important as it is related to their global flexibility, intramolecular fluctuations, various internal dynamic processes as well as many biologic functions. The metabolic stability of polypeptides may be critical in the development of pharmaceuticals, affecting parameters such as, but not limited to, clearance, half-life and bioavailability of the drugs.

Maintaining a given level of a therapeutic polypeptide within the body or the bloodstream may be difficult due to efflux. The rate of efflux of a polypeptide from the body may vary and should be monitored when considering the administration of therapeutic polypeptides.

There remains a significant medical need for complement activation inhibitors or inhibitors of complement activity and inhibitor formulations that are highly potent and highly specific.

Discovery of Peptidomimetics

Peptidomimetics may be identified by a variety of means. In some cases a naturally occurring peptide or a sequence found in a natural protein is used as a starting point. In these instances, the starting peptide sequence has been chosen because it is known to physically interact with a desired target molecule. A natural peptide may be chosen because it is an agonist or antagonist for a receptor, inhibits an enzyme, or modulates a channel. A sequence found in a natural protein may be chosen because it comprises a domain that participates in an interaction with another protein or some other molecule in a human or animal. In many cases, structural data on interacting proteins can be obtained from public databases (e.g. the RCSB Protein Data Bank; H. M. Berman, J. Westbrook, Z. Feng, G. Gilliland, T. N. Bhat, H. Weissig, I. N. Shindyalov, P. E. Bourne (2000) The Protein Data Bank Nucleic Acids Research, 28: 235-242) and the specific region of a protein that interacts with the desired target can be identified from crystallographic data on the protein complex. In other cases, polypeptides corresponding to various portions of a protein can be prepared and tested for binding to a target of interest. Once identified, chemical modifications are introduced to improve its stability and potency, with the resulting peptidomimetic having improved pharmacokinetic or pharmacodynamic parameters.

In other cases, a polypeptide is isolated by one of several methods for isolating polypeptide sequences from libraries of polypeptides based on their affinities to specific target proteins, nucleic acids, carbohydrates, lipids, or whole cells. Such methods include phage display, mRNA display, ribosome display, DNA display, DNA-encoded assembly, and two-hybrid screening, as well as their modifications (See, e.g., Takashashi, T. T et al. (2003). Trends in Biochem. Sci. 28(3):159-165; Kay, B. K. et al. (2001). Methods. 24:240-246: He, M and Taussig, M (2002). Briefs in Functional Genomics and Proteomics. 1(2): 204-212; Rothe, A. et al. (2006). The FASEB Journal. 20(10):1599-1610; all of which are included herein by reference in their entireties.)

Polypeptides can adopt three-dimensional structures that are capable of binding to other biological molecules with certain degrees of affinity and specificity. Some will bind with very high affinity and specificity. A library of random polypeptide sequences will be populated by molecules with a wide variety of three-dimensional structures. In order to isolate a polypeptide with a conformation that interacts with a specific target protein, individual sequences from the library can be prepared and tested or screened for their affinity to the target. However, for very large libraries (>$10^6$ members), the screening of individual sequences for binding affinity is not feasible. To overcome this limitation, a number of techniques have been developed to select novel polypeptides from extremely large, complex mixtures by virtue of their binding affinity to a target. Since high affinity binding polypeptides are predicted to be present at a very low frequency within the population, these selection methods rely on maintaining a physical link between the polypeptide and the genetic material (generally a nucleic acid such as DNA or RNA) encoding the polypeptide so that selection of the polypeptide automatically includes selection of a nucleic acid encoding it. The nucleic acid encoding the selected polypeptide can be amplified and sequenced to reveal the sequence of both the nucleic acid and the polypeptide. In one approach, phage display (see Cwirla, S. E. et al. (1990). Proc. Natl. Acad. Sci. U.S.A. 87:6378-6382; Dower, W. J. and Cwirla, S. E. U.S. Pat. Nos. 5,427,908 and 5,580,717), each random polypeptide member of the library is displayed on the surface of a bacteriophage particle as part of a fusion protein between the polypeptide and one of the phage coat proteins. The phage particle provides the link between the polypeptide and the encoding DNA by co-localizing them within the same physical entity, and the encoding DNA can be subsequently amplified by infecting bacteria with the selected phage. In another approach, ribosome display (see Kawasaki, G. H. U.S. Pat. Nos. 5,658,754 and 5,643,768), a mixture of messenger RNA (mRNA) molecules is translated in vitro in a manner that produces, for each mRNA in the mixture, a stabilized complex of ribosome, mRNA, and newly synthesized polypeptide protruding from the ribosome. Stabilizing the complex permits it to be held together while the polypeptides are screened for binding to a target of interest. The mRNAs encoding the selected polypeptides can be amplified using polymerase chain reaction (PCR), and then characterized, e.g., by sequencing.

In yet another approach, mRNA display (see Szostak, J. W. and Roberts, R. W., U.S. Pat. No. 6,258,558, the contents of which are incorporated herein by reference in their entirety), each mRNA molecule in the library is modified by the covalent addition of a puromycin-like moiety at its 3' terminus. The puromycin-like moiety is an aminoacyl-tRNA acceptor stem analog that functions as a peptidyl acceptor, and can be added to a growing polypeptide chain by the peptidyl transferase activity of a ribosome translating the mRNA. During in vitro translation, the mRNA and the encoded polypeptide become covalently linked through the puromycin-like moiety, creating an RNA-peptide fusion. After selecting a fusion molecule by binding of its polypeptide component to a target, the RNA component of the selected fusion molecule can be amplified using PCR, and then characterized. Several other methods have been developed to produce a physical linkage between a polypeptide and its encoding nucleic acid to facilitate selection and amplification (see Yanagawa, H., Nemoto, N., Miyamoto, E., and Husimi, Y., U.S. Pat. No. 6,361,943; Nemoto, H., Miyamoto-Sato, E., Husimi, H., and Yanagawa, H. (1997). FEBS Lett. 414:405-408; Gold, L., Tuerk, C., Pribnow, D., and Smith, J. D., U.S. Pat. Nos. 5,843,701 and 6,194,550; Williams, R. B., U.S. Pat. No. 6,962,781; Baskerville, S. and Bartel, D. P. (2002). Proc. Natl. Acad. Sci. USA 99:9154-9159; Baskerville, D. S. and Bartel, D. P., U.S. Pat. No. 6,716,973; Sergeeva, A. et al. (2006). Adv. Drug Deliv. Rev. 58:1622-1654; the contents of each of which are incorporated herein by reference in their entirety).

mRNA display is a particularly useful method for creating large libraries of polypeptides. Accordingly, provided herein are methods of selecting for a polypeptide (or an mRNA encoding a polypeptide) that interacts with complement protein C5. A library will generally contain at least $10^2$ members, more preferably at least $10^6$ members, and more preferably at least 10⁹ members (e.g., any of the mRNA-polypeptide complexes). In some embodiments, the library will include at least 10¹² members or at least 10¹⁴ members. In general, the members will differ from each other; however, it is expected there will be some degree of redundancy in any library. The library can exist as a single mixture of all members, or can be divided into several pools held in separate containers or wells, each containing a subset of the library, or the library can be a collection of containers or wells on a plate, each container or well containing just one or a few members of the library.

Each mRNA in the library preferably comprises a translation initiation sequence, a start codon, and a variable polypeptide (e.g., protein or short peptide) coding region that is generated by, for example, a random or semi-random assembly of nucleotides, and varies from mRNA to mRNA in the library (though there will likely be some degree of redundancy within the library). The translation initiation sequence, start codon, and variable polypeptide coding region can be flanked by known, fixed sequences that can be used for PCR amplification of the mRNA, e.g., after selection. Other fixed sequences that can be present include those corresponding to sequences that encode amino acids that can participate in chemical or enzymatic cross-linking reactions, such that the polypeptide produced can be modified or derivatized after translation, or that encode a fixed C-terminal extension such as a polypeptide tag that can facilitate purification of the peptide-mRNA fusions.

Once a library of mRNA derivatized with puromycin is generated, the library can be translated. The resulting polypeptides (e.g., displayed polypeptides) will be linked to their corresponding mRNAs as described herein (e.g., as an mRNA-polypeptide complex).

Numerous in vitro translation systems have been described in the literature. The most common systems utilize rabbit reticulocyte lysates, wheat germ extracts, or *E. coli* extracts, which are available from a number of commercial sources in kit form (e.g., Ambion, Austin, TX; Promega, Madison, WI; Novagen/EMD Chemicals, Gibbstown, NJ; Qiagen, Valencia, CA).

Unlike phage display or other systems that rely on translation within cells, mRNA display can be adapted to directly produce libraries of peptidomimetics by performing in vitro translation with unnatural or non-standard amino acids. The 20 natural proteinogenic amino acids are identified and referred to herein by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N). Naturally occurring amino acids exist in their levorotary (L) stereoisomeric forms. Amino acids referred to herein are L-stereoisomers except where otherwise indicated Unnatural amino acids have side chains or other features not present in the 20 naturally-occurring amino acids listed above and include, but are not limited to: N-methyl amino acids, N-alkyl amino acids, alpha, alpha substituted amino acids, beta-amino acids, alpha-hydroxy amino acids, D-amino acids, and other unnatural amino acids known in the art (See, e.g., Josephson et al., (2005) J. Am. Chem. Soc. 127: 11727-11735; Forster, A. C. et al. (2003) Proc. Natl. Acad. Sci. USA 100: 6353-6357; Subtelny et al., (2008) J. Am. Chem. Soc. 130: 6131-6136; Hartman, M. C. T. et al. (2007) PLoS ONE 2:e972; and Hartman et al., (2006) Proc. Natl. Acad. Sci. USA 103:4356-4361).

Essentially any amino acid that, when attached to an appropriate tRNA, can be assembled into a polymer by natural or mutant ribosomes can be used (see Sando, S. et al., (2007) J. Am. Chem. Soc. 129:6180-6186; Dedkova, L. et al. (2003) J. Am. Chem. Soc. 125: 6616-6617; Josephson, K., Hartman, M. C. T., and Szostak, J. W. (2005) J. Am. Chem. Soc. 127:11727-11735; Forster, A. C. et al. (2003) Proc. Natl. Acad. Sci. USA 100:6353-6357; Subtelny, A. O., Hartman, M. C. T., and Szostak, J. W. (2008) J. Am. Chem. Soc. 130:6131-6136; and Hartman, M C. T. et al. (2007) PLoS ONE 2:e972).

When unnatural amino acids are desired, it may be advantageous to use a purified translation system that lacks endogenous aminoacylated tRNAs (Shimizu, Y. et al. (2001) Nat. Biotech. 19:751-755; Josephson, K., Hartman, M. C. T., and Szostak, J. W. (2005) J. Am. Chem. Soc. 127: 11727-11735; Forster, A. C. et al. (2003) Proc. Natl. Acad. Sci. USA 100: 6353-6357). If unnatural amino acids are used with an in vitro translation system based on a lysate or extract, it may be desirable to deplete the extract of endogenous tRNAs, as previously described (see Jackson, R. J., Napthine, S., and Brierley, 1. (2001) RNA 7:765-773). A system based on purified *E. coli* translation factors is commercially available (PUREXPRESS™; New England Biolabs, Ipswich, MA). These systems are particularly useful for translation with unnatural amino acids to produce peptidomimetics.

When using natural amino acids with an in vitro translation system based on a lysate or extract, translation is dependent on the enzymatic charging of amino acids onto tRNAs by tRNA synthetases, all of which are components of the extracts. Alternatively, in vitro translation systems that use purified translation factors and ribosomes, or tRNA-depleted extracts, require that aminoacylated tRNAs be provided. In these instances, purified or in vitro synthesized tRNAs can be charged with amino acids using chemical (see Frankel, A., Millward, S. W., and Roberts, R. W. (2003) Chem. Biol. 10:1043-1050) or enzymatic procedures (Josephson, K., Hartman, M. C. T., and Szostak, J. W. (2005) J. Am. Chem. Soc. 127: 11727-11735; Murakami, H. et al. (2006) Nat. Methods 3:357-359).

Numerous publications describe the recovery of mRNA-displayed polypeptides from translation complexes, and these are suitable for use with the methods described herein (Liu, R. et al. (2000). Methods Enzymol. 318:268-293; Baggio, R. et al. (2002). J. Mol. Recognit. 15:126-134, U.S. Pat. No. 6,261,804). The recovery of mRNA-displayed polypeptides may be facilitated by the use of various "tags" that are included in the polypeptide by translation of fixed sequences of the polypeptide coding sequence and which bind to specific substrates or molecules. Numerous reagents for capturing such tags are commercially available, including reagents for capturing the His-tag, FLAG-tag, glutathione-S-transferase (GST) tag, strep-tag, HSV-tag, T7-tag, S-tag, DsbA-tag, DsbC-tag, Nus-tag, myc-tag, hemagglutinin (HA)-tag, or Trx-tag (Novagen, Gibbstown, NJ; Pierce, Rockford, IL). mRNA-displayed polypeptides can also be isolated by binding of a polyA tail on the mRNA to polydT resin, or a combination of a polyA tail and a His-tag.

After the in vitro translation reaction has been performed, and prior to the selection step, the mRNA portion of the functionalized RNA is typically reversed-transcribed to produce a RNA-DNA hybrid molecule. This serves to protect the RNA from degradation, and also prevents the RNA from folding into a secondary structure that could bind to the selection target, which would lead to selection of inappropriate products (e.g., the selection of RNA aptamers rather than polypeptide aptamers).

After in vitro translation and isolation of polypeptide-mRNA fusions, the polypeptide moiety may be modified by intramolecular or intermolecular cross-linking, chemical conjugation, enzymatic cleavage, truncation, or extension with additional amino acid monomers. One way to accomplish this is by incorporating unnatural amino acids with reactive side chains into the polypeptides that make up the library. After translation, the newly formed polypeptides can be reacted with molecules that react specifically with the reactive side chain of the incorporated amino acid. For example, an amino acid with a terminal alkyne side chain can be incorporated into the polypeptide library and subsequently reacted with an azido sugar, creating a library of displayed polypeptides with sugars attached at the positions of the alkynyl side chains (Josephson, K., Hartman, M. C. T., and Szostak, J. W. (2005) J. Am. Chem. Soc. 127: 11727-11735). A variety of reactive side chains can be used for such post-translational conjugation, including amines, carboxyl groups, azides, terminal alkynes, alkenes, and thiols.

One particularly useful modification is based on the cross-linking of amino acids to produce cyclic structures. Cyclic regions in a polypeptide contain a rigid domain, which reduces conformational flexibility and degrees of rotational freedom, leading to very high affinity binding to target proteins. A number of methods for cyclizing a polypeptide are available to those skilled in the art and are incorporated herein by reference. Typically, the chemical reactivity of specific amino acid side chains and/or the carboxyl or amino termini of the polypeptide are exploited to crosslink two sites of the polypeptide to produce a cyclic molecule. In one method, the thiol group of a cysteine residue is cross-linked with another cysteine residue to form a disulfide bond. In some embodiments, thiol groups of cysteine residues react with bromomethyl groups of poly(bromomethyl)benzene molecules to form stable linkages (see Timmerman, P. et al., (2005) ChemBioChem 6:821-824, the contents of which are herein incorporated by reference in their entirety). Poly(bromomethyl)benzene molecules of the present invention may include, but are not limited to 1,2-bis(bromomethyl)benzene, 1,3-bis(bromomethyl)benzene and 1,4-bis(bromomethyl)benzene. Bis-, tris- and tetrakis(bromomethyl)benzene molecules, for example, can be used to generate bridging moieties to produce polypeptides with one, two or three loops, respectively. Bromomethyl groups of a poly(bromomethyl)benzene molecule may be arranged on the benzene ring on adjacent ring carbons (ortho- or o-), with a ring carbon separating the two groups (meta- or m-) or on opposite ring carbons (para- or p-). In some embodiments, m-bis(bromomethyl)benzene (also referred to herein as m-dibromoxylene) is utilized in the formation of cyclic polypeptides. In some embodiments, o-bis(bromomethyl)benzene (also referred to herein as o-dibromoxylene) or p-bis(bromomethyl)benzene (also referred to herein as p-dibromoxylene) are utilized in the formation of cyclic polypeptides. In some embodiments, thiol groups of cysteine residues react with other reagents comprising one or more bromo functional groups to form stable linkages. Such reagents may include, but are not limited to poly(bromomethyl)pyridines (including, but not limited to 2,6-bis(bromomethyl)pyridine), poly(bromomethyl)alkylbenzenes (including, but not limited to 1,2-bis(bromomethyl)-4-alkylbenzene) and/or (E)-1,4-dibromobut-2-ene.

In another exemplary method, a side chain amino group and a terminal amino group are cross-linked with disuccinimidyl glutarate (see Millward, S. W. et al., J. Am. Chem. Soc. 127:14142-14143, 2005). In other approaches, cyclization is accomplished by forming a thioether bond between two sites on the polypeptide (see Timmerman, P. et al., (2005) ChemBioChem 6:821-824; incorporated by reference herein in its entirety). An enzymatic method relies on the reaction between (1) a cysteine and (2) a dehydroalanine or dehydrobutyrine group, catalyzed by a lantibiotic synthetase, to create the thioether bond (see Levengood, M. R. and Van der Donk, W. A., Bioorg. and Med. Chem. Lett. 18:3025-3028, 2008). The dehydro functional group can also be generated chemically by the oxidation of selenium containing amino acid side chains incorporated during translation (see Seebeck, F. P. and Szostak, J. W. J. Am. Chem. Soc. 2006).

A library of mRNA-polypeptide fusions (also referred to herein as an mRNA display library) generated using the methods described above, and which may or not have been subjected to a post-translational modification (such as cyclization of the polypeptide, as described above), can be subjected to a batch selection step to isolate those complexes displaying desirable polypeptides.

Typically, C5 is conjugated to a solid substrate, such as an agarose or synthetic polymer bead. Numerous methods are available for immobilizing C5 to a solid support. In one particularly useful method, C5 is conjugated to biotin and streptavidin beads are used to immobilize the protein. The beads comprising the immobilized C5 are mixed with the mRNA display library and incubated under conditions (e.g., temperature, ionic strength, divalent cations, and competing binding molecules) that permit specific members of the library to bind the target. Alternatively, the biotinylated enzyme can be free in solution and, after binding to an appropriate polypeptide, the mRNA-polypeptide fusions bound to C5 are captured by appropriately modified beads.

The binding conditions can be varied in order to change the stringency of the selection. For example, low concentrations of a competitive binding agent can be added to ensure that the selected polypeptides have a relatively higher affinity. Alternatively, the incubation period can be chosen to be very brief, such that only polypeptides with high km rates (rate of association) will be isolated. In this manner, the incubation conditions play an important role in determining the properties of the selected polypeptides. Negative selections can also be employed. In this case, a selection to remove polypeptides with affinity to the substrate to which the target is bound (e.g., Sepharose) is carried out by applying the displayed library to substrate beads lacking the target protein. This step can remove mRNAs and their encoded polypeptides that are not specific for the target protein. Numerous references describing how to conduct selection experiments are available. (See, e.g., U.S. Pat. No. 6,258,558, Smith, G. P. and Petrenko, V. A., (1997) Chem. Rev. 97:391-410; Keefe, A. D. and Szostak, J. W. (2001) Nature 15:715-718; Baggio, R. et al. (2002) J. Mol. Recog. 15:126-134 and Sergeeva, A. et al. (2006) Adv. Drug Deliv. Rev. 58:1622-1654; the contents of each of which are herein incorporated by reference in their entirety).

The frequency at which binding molecules are present in a library of random sequences is expected to be very low. Thus, in the initial selection step, very few polypeptides meeting the selection criteria (and their associated mRNAs) should be recovered. Typically, the selection is repeated with mRNAs selected from the first round of selection. This is accomplished by using PCR to amplify the mRNAs or corresponding cDNAs selected in the first round, followed by in vitro transcription to produce a new library of mRNAs.

PCR primers corresponding to the 5' and 3' ends of the mRNAs in the library are used. Typically, the 5' primer will extend in the 5' direction beyond the end of the mRNA so that a bacterial promoter, such as a T7 promoter, is added to the 5' end of each amplified molecule. Once amplified, the double-stranded DNA can be used in an in vitro transcription reaction to generate the mRNA for a subsequent round of selection.

The selection process typically involves a number of rounds or cycles, in which the pool of selected molecules is incrementally enriched in a specific set of sequences at the end of each round. The selection conditions may be the same for each round, or the conditions may change, for example, in order to increase the stringency of selection in later rounds. The progress of selection may be monitored by the use of isotopically-labeled amino acids, such as $^{35}$S methionine. The amount of radiolabeled polypeptide bound to the target at each round is measured, and a progressive increase in recovered radiolabel is indicative of a progressive enrichment in RNA molecules encoding polypeptides with binding affinity to the target. After any round, the PCR products may be cloned and sequenced. Generally, cloning and sequencing is performed after a round in which appreciable (e.g. >2% over background to beads lacking immobilized C5) amounts of radiolabeled polypeptide are recovered in the target-bound pool. Sequences that are found in multiple isolates are candidates for encoding polypeptides that bind specifically to the target. Alternatively, high throughput sequencing of thousands of clones can be performed after the first or subsequent rounds. Sequences that increase in frequency between, for example, the third and fourth rounds are candidates for encoding polypeptides that bind specifically to the target. The polypeptide encoded by any sequence may be translated or synthesized and tested for binding affinity to the original target protein used in the selection.

The libraries and methods of the present invention may be used to optimize the function or properties of a polypeptide. In one approach, mutagenic PCR (Keefe, A. D. and Szostak, J. W. (2001). Nature 15:715-718) is used to introduce sequence variation in the library once the population is enriched in polypeptides with a certain level of binding affinity. Alternatively, a single RNA sequence encoding a polypeptide with defined binding properties can be replicated but with a defined level of mutations, or mutagenic PCR can be performed to produce a pool of mutant molecules. Upon in vitro translation the resulting mixture of mRNA molecules produced from such a pool is expected to encode polypeptides with a range of improved, similar, or reduced affinities as compared to the starting sequence, and a selection performed on mRNAs from such a pool may be expected to identify polypeptides with improved affinity if an appropriate stringency regimen is used during the selection.

In a second approach, optimization is performed in a directed manner. A sequence encoding a polypeptide with established binding or functional properties is subjected to site-directed mutagenesis, whereby a series of sequences is produced, with each sequence having one codon replaced with, for example, an alanine codon. The number of sequences in the set is equal to the number of amino acid residues that are to be mutated. After in vitro translation, the polypeptide product of each "alanine scanning" mutant is tested for binding or functional properties. Sites at which an alanine substitution affects the binding or function of the polypeptide are considered critical residues. Similarly, an N-methyl scan may be performed, such that each residue is replaced with the N-methyl derivative, and positions in the polypeptide backbone that can tolerate N-methyl substitutions can be identified.

Alternatively, the sequences can be pooled, subjected to one or more rounds of a high stringency selection, and a pool of sequences representing high affinity binding polypeptides is isolated. Critical residues are identified after DNA sequencing of the recovered DNA as those that cannot be substituted by an alanine residue without loss of activity. Once the critical residues are identified, a pool of mRNA molecules encoding a wide variety of natural (or unnatural) amino acids at each critical position is produced. The resulting pool is subjected to one or more rounds of a high stringency selection (with the appropriate mixture of tRNAs charged with natural or unnatural amino acids), and sequences representing high affinity binding polypeptides are isolated after in vitro translation. In this manner, an optimal polypeptide can be identified. Since the optimal sequence may not necessarily be identified by combining optimal residues at individual sites, it is useful to test mutations at multiple sites in combination.

Both alanine and N-methyl scanning can also be performed using chemical synthesis approaches, such as solid phase polypeptide synthesis (see e.g., Coin, I et al. (2007); Nature Protocols 2(12):3247-56, the contents of which are herein incorporated by reference in their entirety).

Once a pool, population or subset of polypeptides is identified, they may be evaluated for therapeutic or diagnostic applications, including improved pharmacokinetic and/or pharmacodynamic properties.

In one embodiment, polypeptides are evaluated for one or more of target binding affinity, activity in biochemical or cell based assays, protease resistance, in vitro or in vivo permeability, properties related to suitability for use as a pharmaceutical agent such as plasma protein binding, metabolism (in microsomes, hepatocytes, or plasma), P-glycoprotein (Pgp) inhibition and Cytochrome P450 inhibition. Polypeptides of the present invention may also undergo testing for oral bioavailability, toxicity, human ether-α-go-go related gene product (hERG) inhibition, circulating half-life, other pharmacokinetic and pharmacodynamic parameters, and efficacy in animal models of disease.

Polypeptides of the Invention

According to the present invention, once a single polypeptide or a pool of candidate polypeptide molecules is identified, they may undergo one or more rounds of structure-activity relationship (SAR) optimization using standard chemical and polypeptide synthesis techniques. Such optimization may include considerations such as avoiding charged polar side chains (Asp, Glu, Arg, Lys) that may inhibit cell penetration, avoidance of side chains that pose metabolic liabilities (Tyr, Met, Trp, Cys), improving solubility, avoidance of unnecessary molecular weight, avoidance of rotatable bonds, and altering lipophilicity.

In one embodiment, it is a goal of the present invention to provide cyclic peptidomimetics designed to be metabolically stable, cell permeable, and/or orally available.

According to some embodiments, polypeptides of the invention comprise from about 10 to about 18 amino acids or amino acid variants. In some cases, such polypeptides comprise a cyclic loop.

Amino Acid Variants

As used herein, the term "amino acid" includes the residues of the natural amino acids as well as unnatural amino acids. The term also includes amino acids bearing a conventional amino protecting group (e.g. acetyl or benzyloxycarbonyl), as well as natural and unnatural amino acids protected at the carboxy terminus (e.g., as a (C1-C6) alkyl, phenyl or benzyl ester or amide; or as an alpha-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc., and documents cited therein). Polypeptides and/or polypeptide compositions of the present invention may also include modified amino acids.

Unnatural amino acids useful for the optimization of polypeptides and/or polypeptide compositions of the present invention include, but are not limited to 1,2,3,4-tetrahydroisoquinoline-1-carboxylic acid, 1-amino-2,3-hydro-1H-indene-1-carboxylic acid, homolysine, homoarginine, homoserine, 2-aminoadipic acid, 3-aminoadipic acid, beta-alanine, aminopropionic acid, 2-aminobutyric acid, 4-aminobutyric acid, 5-aminopentanoic acid, 5-aminohexanoic acid, 6-aminocaproic acid, 2-aminoheptanoic acid, 2-aminoisobutyric acid, 3-aminoisobutyric acid, 2-aminopimelic acid, desmosine, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylpentylglycine, naphthylalanine, ornithine, pentylglycine, thioproline, norvaline, tert-butylglycine, phenylglycine, azatryptophan, 5-azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, 4-isopropyl-phenylglycine, (S)-2-amino-5-azidopentanoic acid (also referred to herein as "X02"), (S)-2-aminohept-6-enoic acid (also referred to herein as "X30"), (S)-2-aminopent-4-ynoic acid (also referred to herein as "X31"), (S)-2-aminopent-4-enoic acid (also referred to herein as "X12"), (S)-2-amino-5-(3-methylguanidino) pentanoic acid, (S)-2-amino-3-(4-(aminomethyl) phenyl)propanoic acid, (S)-2-amino-3-(3-(aminomethyl) phenyl)propanoic acid, (S)-2-amino-4-(2-aminobenzo[d] oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl) propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid, (S)-2-amino-3-(oxazol-2-yl)butanoic acid, (S)-2-amino-3-(oxazol-5-yl) butanoic acid, (S)-2-amino-3-(1,3,4-oxadiazol-2-yl) butanoic acid, (S)-2-amino-3-(1,2,4-oxadiazol-3-yl) butanoic acid, (S)-2-amino-3-(5-fluoro-1H-indazol-3-yl) butanoic acid, and (S)-2-amino-3-(1H-indazol-3-yl) butanoic acid, 2-(2'MeOphenyl)-2-amino acetic acid, tetrahydro 3-isoquinolinecarboxylic acid and stereoisomers thereof (including, but not limited, to D and L isomers).

Additional unnatural amino acids that are useful in the optimization of polypeptides or polypeptide compositions of the invention include but are not limited to fluorinated amino acids wherein one or more carbon bound hydrogen atoms are replaced by fluorine. The number of fluorine atoms included can range from 1 up to and including all of the hydrogen atoms. Examples of such amino acids include but are not limited to 3-fluoroproline, 3,3-difluoroproline, 4-fluoroproline, 4,4-difluoroproline, 3,4-difluoroproline, 3,3,4,4-tetrafluoroproline, 4-fluorotryptophan, 5-flurotryptophan, 6-fluorotryptophan, 7-fluorotryptophan, and stereoisomers thereof.

Further unnatural amino acids that are useful in the optimization of polypeptides or polypeptide compositions of the invention include but are not limited to those that are disubstituted at the α-carbon. These include amino acids in which the two substituents on the α-carbon are the same, for example α-amino isobutyric acid, and 2-amino-2-ethyl butanoic acid, as well as those where the substituents are different, for example α-methylphenylglycine and α-methylproline. Further the substituents on the α-carbon may be taken together to form a ring, for example 1-aminocyclopentanecarboxylic acid, 1-aminocyclobutanecarboxylic acid, 1-aminocyclohexanecarboxylic acid, 3-aminotetrahydrofuran-3-carboxylic acid, 3-aminotetrahydropyran-3-carboxylic acid, 4-aminotetrahydropyran-4-carboxylic acid, 3-aminopyrrolidine-3-carboxylic acid, 3-aminopiperidine-3-carboxylic acid, 4-aminopiperidine-4-carboxylic acid, and stereoisomers thereof.

Additional unnatural amino acids that are useful in the optimization of polypeptides or polypeptide compositions of the invention include but are not limited to analogs of tryptophan in which the indole ring system is replaced by another 9 or 10 membered bicyclic ring system comprising 0, 1, 2, 3 or 4 heteroatoms independently selected from N, O, or S. Each ring system may be saturated, partially unsaturated or fully unsaturated. The ring system may be substituted by 0, 1, 2, 3, or 4 substituents at any substitutable atom. Each substituent is independently selected from H, F, Cl, Br, CN, COOR, CONRR', oxo, OR, NRR'. Each R and R' is independently selected from H, C1-C20 alkyl, C1-C20 alkyl-O-C1-20 alkyl.

In some embodiments, analogs of tryptophan (also referred to herein as "tryptophan analogs") that are useful in the optimization of polypeptides or polypeptide compositions of the invention include, but are not limited to 5-fluorotryptophan [(5-F)W], 5-methyl-O-tryptophan [(5-MeO) W], 1-methyltryptophan [(1-Me-W) or (1-Me)W], D-tryptophan (D-Trp), azatryptophan (including, but not limited to 4-azatryptophan, 7-azatryptophan and 5-azatryptophan,) 5-chlorotryptophan, 4-fluorotryptophan, 6-fluorotryptophan, 7-fluorotryptophan, and stereoisomers thereof. Except where indicated to the contrary, the term "azatryptophan" and its abbreviation, "azaTrp," as used herein, refer to 7-azatryptophan.

Modified amino acid residues useful for the optimization of polypeptides and/or polypeptide compositions of the present invention include, but are not limited to those which are chemically blocked, reversibly or irreversibly, or chemically modified on their N-terminal amino group or their side chain groups, or chemically modified in the amide backbone, as for example, N-methylated, D (unnatural amino acids) and L (natural amino acids) stereoisomers or residues wherein the side chain functional groups are chemically modified to another functional group. For example, modified amino acids include without limitation, methionine sulfoxide; methionine sulfone; aspartic acid-(beta-methyl ester); a modified amino acid of aspartic acid; N-ethylglycine, a modified amino acid of glycine; or alanine carboxamide, and a modified amino acid of alanine. Unnatural amino acids may be purchased from Sigma-Aldrich (St. Louis, MO), Bachem (Torrance, CA) or other suppliers. Unnatural amino acids may further include any of those listed in Table 2 of US patent publication US 2011/0172126, the contents of which are incorporated herein by reference in their entirety.

In some embodiments, the amino acid sequences of polypeptides and/or polypeptide compositions of the present invention may comprise only naturally occurring amino acids. While it is known in the art that the terms peptides, polypeptides, and/or fragments thereof imply relative size, these terms as used herein should not be considered limiting with respect to the size of the various polypeptide based molecules referred to herein and which are encompassed within this invention, unless otherwise noted. In some embodiments of the present invention, polypeptides may comprise both naturally and non-naturally occurring and/or modified amino acids or be exclusively comprised of non-naturally occurring amino acids.

Polypeptide Variants

According to the present invention, any amino acid based molecule (natural or unnatural) may be termed a "polypeptide" and this term embraces "peptides", "peptidomimetics" and "proteins." Polypeptides are also a category of protein and are traditionally considered to range in size from about 4 to about 50 amino acids. Dipeptides, those having two amino acid residues, are a category of polypeptide as are tripeptides (polypeptides comprising three amino acids). Polypeptides larger than about 50 amino acids are generally termed "proteins." Polypeptide sequences may be linear or cyclic. For example, a cyclic polypeptide can be prepared or may result from the formation of disulfide bonds between two cysteine residues in a sequence. A polypeptide can be cyclized through the carboxy terminus, the amino terminus, or through any other convenient point of attachment, such as, for example, through the sulfur of a cysteine or any side-chain of an amino acid residue or other linkage including, but not limited to, a maleimide linkage, an amide linkage, an ester linkage, an ether linkage, a thiol ether linkage, a hydrazone linkage, or an acetamide linkage. In some embodiments, cyclic polypeptides are formed when a molecule acts as a bridging moiety to link two or more regions of the polypeptide.

The term "amino acid sequence variant" refers to polypeptides with some differences in their amino acid sequences as compared to a starting, reference, or native sequence. The amino acid sequence variants may possess substitutions, deletions, and/or insertions at certain positions within the amino acid sequence. Ordinarily, variants will possess at least about 70% homology to a native or starting sequence, and preferably, they will be at least about 80%, more preferably at least about 90% homologous to a native or starting sequence.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include amino acid sequence variants which differ by one or more amino acid alterations, e.g., substitutions, additions or deletions of amino acid residues that still maintain one or more of the properties of the parent or starting polypeptide.

The present invention contemplates several types of compositions that include polypeptides including variants and derivatives. These include substitutional, insertional, deletion and covalent variants and derivatives. The term "derivative" is used synonymously with the term "variant" and refers to a molecule that has been modified or changed in any way relative to a reference molecule or starting molecule.

As such, included within the scope of this invention are polypeptides containing substitutions, insertions and/or additions, deletions and covalent modifications. For example, sequence tags or amino acids, such as one or more lysines, can be added to the polypeptide sequences of the invention (e.g., at the N-terminal or C-terminal ends). Sequence tags can be used for polypeptide purification or localization. Lysines can be used to increase polypeptide solubility or to allow for site specific modifications, such as, but not limited to, biotinylation or PEGylation. In some cases, polypeptides may be desthiobiotinylated. As used herein, a polypeptide that is desthiobiotinylated may comprise a desthiobiotin (Dtb) moiety conjugated to the epsilon-amino group of a lysine residue. Such lysine residues may be C-terminal residues in some instances. Alternatively, amino acid residues located at the carboxy and amino terminal regions of the amino acid sequence of a polypeptide may optionally be deleted, providing for truncated sequences. Certain amino acids (e.g., C-terminal or N-terminal residues) may alternatively be deleted depending on the use of the sequence, as for example, expression of the sequence as part of a larger sequence, which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic)

residue such as cysteine, glutamine, glutamic acid or lysine and/or a polar residue for a non-polar residue.

"Isosteres" are one of two or more molecules that exhibit some similarity of biological properties as a result of having the same number of total or valence electrons in the same arrangement and that consist of different atoms, not necessarily the same number of atoms. There are two classes of isosteres, classical and non-classical. Classical isosteres have the same number of atoms and/or the same number of valence electrons whereas non-classical isosteres are molecules that produce a similar biological effect in vivo but do not have the same number of atoms and/or valence electrons.

According to the present invention, "peptide bond isosteres" are defined as isosteres having properties resembling peptide bonds. Peptide bond isosteres may be of a linear type comprising at least one peptide bond replacement or may be cyclic and comprise an amine and a carboxylic acid function. Such replacement may be with any moiety which improves the physicochemical, structural or functional properties of the molecule. Replacement of the peptide bond may increase the metabolic stability of the polypeptides and reduce or increase the flexibility. Peptide bond isosteres described herein may be mono-, di-, tri-, tetra-, penta-, sexta-, septa-, octa-, nona-, or deca-peptide bond isosteres, meaning that at least 1, 2, 3, 4, 5, 6, 7, 8, 9 or 10 peptidic bonds may be replaced. Non-limiting examples of linear dipeptide bond isosteres for amide (peptidic) bonds include thioamide, sulfonamide, sulfonate, phosphonamide, phosphonate phosphothioate, phosphinate, alkane, 1 or 2 hydroxyethylene, dihydroxylethylene, C—C single bond (alkane), C—C double bond (alkene), C—C triple bond (alkyne), C—O bond (methyleneoxy), O—N or N—O bond, (methylenemino), triazole, hydrazide, urea, ketone, urethane bond, (di)haloalkene, methylenemercapto, methyleneamino, trifluoroethylamino, hydrazide, amideoxy, and others known to those of skill in the art.

Peptide bond isosteres may also be cyclic molecules that are decorated with an amine and a carboxylic acid function. Non-limiting examples of cyclic peptide bond isosteres with varying ring sizes include carbacycles, azacycles and oxacycles. Azacycles may be based on an alkaloid core which forms a bicyclic structure isostere. An example of an azacyclic isostere includes an isostere based on a triazole ring formed by a copper catalyzed azide-alkyne cycloaddition. Cyclic peptide bond isosteres described herein may be bi-, tri-, tetra-, penta-sexta-, septa-, octa- nona- deca-peptide cyclic isosteres "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Truncated variants" when referring to polypeptides are those with one or more amino acids in the native or starting amino acid sequence removed from either terminus of the polypeptide.

According to the present invention, polypeptides may be modified by the addition of one or more conjugate groups. In some embodiments, polypeptides may be administered in combination with one or more additional molecules.

As used herein, a "conjugate" refers to any molecule or moiety appended to another molecule. In the present invention, conjugates may be polypeptide (amino acid) based or not. Conjugates may comprise lipids, small molecules, RNA, DNA, polypeptides, polymers, or combinations thereof. Functionally, conjugates may serve as targeting molecules or may serve as payload to be delivered to a cell, organ or tissue. Conjugates are typically covalent modifications introduced by reacting targeted amino acid residues or the termini of the polypeptide with an organic derivatizing agent that is capable of reacting with selected side-chains or terminal residues. Such modifications are within the ordinary skill in the art and are performed without undue experimentation.

The conjugation process may involve PEGylation, lipidation, albumination, biotinylation, desthiobiotinylation, the addition of other polypeptide tails, or grafting onto antibody Fc domains, CDR regions of intact antibodies, or antibody domains produced by any number of means. The conjugate may include anchors including cholesterol oleate moiety, cholesteryl laurate moiety, an α-tocopherol moiety, a phytol moiety, an oleate moiety, or an unsaturated cholesterol-ester moiety or a lipophilic compound selected from acetanilides, anilides, aminoquinolines, benzhydryl compounds, benzodiazepines, benzofurans, cannabinoids, cyclic polypeptides, dibenzazepines, digitalis glycosides, ergot alkaloids, flavonoids, imidazoles, quinolines, macrolides, naphthalenes, opiates (such as, but not limited to, morphinans or other psychoactive drugs), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and vinca alkaloids. Lipidated polypeptides of the invention may include C-terminally lipidated polypeptides. In some cases, polypeptides are lipidated with saturated or unsaturated C12, C14, C16, C18, or C20.

As used herein, the term "covalent derivative" when referring to a polypeptide includes modification of a native or starting polypeptide with an organic proteinaceous or non-proteinaceous derivatizing agent, and/or post-translational modification. Covalent modifications are traditionally introduced by reacting targeted amino acid residues of the polypeptide with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant protein. Such modifications are within the ordinary skill in the art and are performed without undue experimentation.

Certain post-translational modifications are the result of the action of recombinant host cells on an expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of tyrosinyl, seryl or threonyl residues, methylation of the alpha-amino groups of lysine, arginine, and histidine side chains (Creighton, T. E., Proteins: Structure and Molecular Properties, W.H. Freeman & Co., San Francisco, 1983, pp. 79-86).

Covalent modifications specifically include the bonding of non-proteinaceous polymers to polypeptides of the invention. Non-proteinaceous polymers may include a hydrophilic synthetic polymer, i.e., a polymer not otherwise found in nature. However, polymers that exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. The polypeptides may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

"Features" when referring to polypeptides are defined as distinct amino acid sequence-based components of a molecule. Features of the polypeptide of the present invention include surface manifestations, local conformational shape, folds, loops, half-loops, domains, half-domains, sites, termini or any combination thereof.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of physicochemically distinct regions. Regions formed in this way include hydrophobic and hydrophilic pockets, and the like.

As used herein the term "turn" as it relates to protein conformation means a bend which alters the direction of the backbone of a polypeptide and may involve one, two, three or more amino acid residues.

As used herein when referring to polypeptides the term "loop" refers to a structural feature of a polypeptide which may serve to reverse the direction of the backbone of a polypeptide. Where the loop is found in a polypeptide and only alters the direction of the backbone, it may comprise four or more amino acid residues. Oliva et al. have identified at least 5 classes of protein loops (Oliva, B. et al., J Mol Biol. 1997 Mar. 7; 266(4):814-30; the contents of which are herein incorporated by reference in their entirety). Loops may be open or closed. Closed loops or "cyclic" loops may be formed when two amino acids are connected by a bridging moiety. The cyclic loop comprises the amino acids along the polypeptide present between the bridged amino acids. Cyclic loops may comprise 2, 3, 4, 5, 6, 7, 8, 9, 10 or more amino acids.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins, the term "region" refers to a zone or general area. In some embodiments, when referring to a protein, a region may comprise a linear sequence of amino acids along the protein or may comprise a specific secondary or tertiary structure and/or one or more features or protein domains.

As used herein, the term "domain," when referring to proteins, refers to a motif of a polypeptide having one or more identifiable structural (such as secondary or tertiary structures) or functional characteristics or properties (e.g., binding capacity, serving as a site for protein-protein interactions.)

As used herein, the term "half-domain," when referring to proteins, refers to a portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the term "site" as it pertains to amino acid based embodiments is used synonymously with "amino acid residue" and "amino acid side chain." A site represents a position within a polypeptide that may be modified, manipulated, altered, derivatized or varied within the polypeptide based molecules of the present invention.

As used herein the terms "termini" or "terminus" when referring to polypeptides refers to an extremity of a polypeptide. Such extremity is not limited only to the first or final site of the polypeptide but may include additional amino acids in the terminal regions. The polypeptide based molecules of the present invention may be characterized as having both an N-terminus and a C-terminus. Polypeptides and/or polypeptide compositions of the present invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

In one embodiment, polypeptides of the present invention may include a terminal region. As used herein, "terminal region" is a terminal region of amino acids that may include a cysteine. The terminal region may be an N- and/or a C-terminal region. In some embodiments, terminal regions may be connected to the parent polypeptides using a bridging moiety. As used herein, "parent polypeptide" refers to the part of the polypeptide that does not include the terminal region. The terminal region may be separated from the parent polypeptide by 1, 2, 3, 4, 5, 6, 7, 8, 9, 10 or more residues. The residues added may be selected from, but are not limited to, any natural or unnatural amino acid, the N-methylated form of any natural or unnatural amino acid, the D-stereoisomer of any natural or unnatural amino acid, norvaline, tert-butylglycine, phenylglycine, azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobutyric acid, (S-2-amino-3-(1H-tetrazol-5-yl)propanoic acid, cyclopentylglycine, cyclohexylglycine, cyclopropylglycine, it-w-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, 4-isopropyl-phenylglycine, (S)-2-amino-5-(3-methylguanidino) pentanoic acid, (S)-2-amino-3-(4-(aminomethyl)phenyl) propanoic acid, (S)-2-amino-3-(3-(aminomethyl)phenyl) propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid.

Additional unnatural amino acids that are useful in the optimization of polypeptides of the invention include but are not limited to fluorinated aminoacids wherein one or more carbon bound hydrogen atoms are replaced by fluorine. The number of fluorine atoms included can range from 1 up to and including all of the hydrogen atoms. Examples of such amino acids include but are not limited to 3-fluoroproline, 3,3-difluoroproline, 4-fluoroproline, 4,4-difluoroproline, 3,4-difluroproline, 3,3,4,4-tetrafluoroproline, 4-fluorotryptophan, 6-fluorotryptophan, 7-fluorotryptophan, and stereoisomers thereof.

Further unnatural amino acids that are useful in the optimization of polypeptides of the invention include but are not limited to those that are disubstituted at the α-carbon. These include amino acids in which the two substituents on the α-carbon are the same, for example α-amino isobutyric acid, and 2-amino-2-ethyl butanoic acid, as well as those where the substituents are different, for example α-methylphenylglycine and α-methylproline. Further the substituents on the α-carbon may be taken together to form a ring, for example 1-aminocyclopentanecarboxylic acid, 1-aminocyclobutanecarboxylic acid, 1-aminocyclohexanecarboxylic acid, 3-aminotetrahydrofuran-3-carboxylic acid, 3-amino-tetrahydropyran-3-carboxylic acid, 4-aminotetrahydropyran-4-carboxylic acid, 3-aminopyrrolidine-3-carboxylic acid, 3-aminopiperidine-3-carboxylic acid, 4-aminopiperidine-4-carboxylic acid, and stereoisomers thereof.

Additional unnatural amino acids that are useful in the optimization of polypeptides of the invention include but are not limited to analogs of tryptophan in which the indole ring system is replaced by another 9 or 10 membered bicyclic ring system comprising 0, 1, 2, 3, or 4 heteroatoms independently selected from N, O, or S. Each ring system may be saturated, partially unsaturated or fully unsaturated. The ring system may be substituted by 0, 1, 2, 3, or 4 substituents at any substitutable atom. Each substituent is independently selected from H, F, Cl, Br, CN, oxo, COOR, CONRR', OR, NRR'. Each R and R' is independently selected from H, C1-C20 alkyl, C1-C20 alkyl-O—C1-20 alkyl.

In some embodiments, analogs of tryptophan (also referred to herein as "tryptophan analogs") that are useful in the optimization of polypeptides of the invention include, but are not limited to 5-fluorotryptophan [(5-F)W], 5-methyl-O-tryptophan [(5-MeO)W], 1-methyltryptophan [(1-Me-W) or (1-Me)W], D-tryptophan (D-Trp), 7-azatryptophan (including, but not limited to 4-azatryptophan, 7-azatryptophan and 5-azatryptophan,) 5-chlorotryptophan, 4-fluorotryptophan, 6-fluorotryptophan, 7-fluorotryptophan, and stereoisomers thereof. Except where indicated to the contrary, the term "azatryptophan" and its abbreviation, "azaTrp," as used herein, refer to 7-azatryptophan.

In one embodiment, polypeptides of the present invention may include a terminal modification at the N- or C-termini with the addition of 1, 2, 3, 4, 5, 6, 7, 8, 9, 10 or more residues and/or a cysteine in the terminal region. The residues added may be selected from, but are not limited to, any natural or unnatural amino acid, the N-methylated form of any natural or unnatural amino acid, the D-stereoisomer of any amino acid, norvaline, tert-butylglycine, phenylglycine, azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobuteric acid, (S)-2-amino-3-(1H-tetrazol-5-yl)propanoic acid, cyclopentylglycine, cyclohexylglycine, cyclopropylglycine, η-α-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, 4-isopropyl-phenylglycine, (S)-2-amino-5-(3-methylguanidino) pentanoic acid, (S)-2-amino-3-(4-(aminomethyl)phenyl) propanoic acid, (S)-2-amino-3-(3-(aminomethyl)phenyl) propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-I-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid.

Polypeptides of the present invention may be conjugated to a polypeptide that increases or decreases plasma protein binding including but not limited to those described in Dennis, M. S. et al., Albumin binding as a general strategy for improving the pharmacokinetics of proteins. J Biol Chem. 2002 Sep. 20; 277(38):35035-43; Nguyen, A. et al., The pharmacokinetics of an albumin-binding Fab (AB Fab) can be modulated as a function of affinity for albumin. Protein Eng Des Sel. 2006 July; 19(7):291-7 and Langerheim, J. F. et al., Improving the pharmacokinetics/pharmacodynamics of prolactin, GH, and their antagonists by fusion to a synthetic albumin-binding polypeptide. J Endocrinol. 2009 December; 203(3):375-87. In some embodiments, such polypeptides bind serum albumin (referred to herein as "albumin-binding polypeptides"). In some embodiments, albumin-binding polypeptides are cyclized by disulfide bond formation between cysteine residues present in their polypeptide sequences. In some embodiments, albumin-binding polypeptides are conjugated by either their N or C-terminal ends. In some embodiments, conjugation to an albumin-binding polypeptide modulates the amount of time that a polypeptide of the present invention remains intact in a subject. In a preferred embodiment, conjugation to an albumin-binding polypeptide increases the amount of time that a polypeptide of the present invention remains in the blood of a subject. Polypeptides of the present invention may be conjugated to polypeptides that have cell penetrating properties (referred to herein as "cell penetrating polypeptides") including but not limited those disclosed in Milletti, F., Cell-penetrating peptides: classes, origin, and current landscape. Drug Discov Today. 2012 August; 17(15-16):850-60. Additional cell penetrating polypeptides are known to those skilled in the art. Polypeptides of the present invention may be conjugated to any of the polypeptide conjugates taught, for example, in US patent publications US20110172126 or US20030040472 the contents of which are incorporated herein by reference in their entirety. Polypeptides of the present invention may be conjugated to a lipophilic molecule that increases plasma protein binding such as the liphophilic substituents taught, for example, in U.S. Pat. No. 6,268,343 or US Publication No. US2013/0053311, the contents of each of which are herein incorporated by reference in their entirety.

Once any of the features have been identified or defined as a desired component of a polypeptide, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of experimentation. As used herein a "consensus" sequence is a single sequence which represents a collective population of sequences allowing for variability at one or more sites.

The term "identity" as known in the art, refers to a relationship between the sequences of two or more polypeptides, as determined by comparing the sequences. In the art, identity also means the degree of sequence relatedness between polypeptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described previously by others (Lesk, A. M., ed., Computational Molecular Biology, Oxford University Press, New York, 1988; Smith, D. W., ed., Biocomputing: Informatics and Genome Projects, Academic Press, New York, 1993; Griffin, A. M. et al., ed., Computer Analysis of Sequence Data, Part 1, Humana Press, New Jersey, 1994; von Heinje, G., Sequence Analysis in Molecular Biology, Academic Press, 1987; Gribskov, M. et al., ed., Sequence Analysis Primer, M. Stockton Press, New York, 1991; and Carillo et al., Applied Math, SIAM J, 1988, 48, 1073).

In some embodiments, a polypeptide variant may have the same or a similar activity as the reference polypeptide. Alternatively, a variant may have an altered activity (e.g., increased or decreased) relative to a reference polypeptide. Generally, variants of a particular polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that of a particular reference polypeptide as determined by sequence alignment programs and parameters described herein and known to those skilled in the art. Such tools for alignment include those of the BLAST suite (Altschul, S. F. et al., Gapped BLAST and PSI-BLAST: a new generation of protein database search programs, Nucleic Acids Res. 1997, 25:3389-3402) Other tools are described herein, specifically in the definition of "identity."

Default parameters in the BLAST algorithm include, for example, an expected threshold of 10, Word size of 28, Match/Mismatch Scores 1, -2, Gap costs Linear. Any filter can be applied as well as a selection for species specific repeats, e.g., *Homo sapiens*.

Abbreviations Used in Polypeptides

As used herein, abbreviations have the following meaning: "Ac" and "NH2" indicate acetyl and amidated termini, respectively; "Nvl" stands for norvaline; "Phg" stands for phenylglycine; "Tbg" stands for tert-butylglycine; "Chg" stands for cyclohexylglycine; "(N-Me)X" stands for the N-methylated form of the amino acid indicated by the letter or three letter amino acid code in place of variable "X" written as N-methyl-X [e.g. (N-Me)A or (N-Me)Ala stand for the N-methylated form of alanine or N-methyl-alanine]; "azaTrp" stands for azatryptophan; "(4-F)Phe" stands for 4-fluorophenylalanine; "Tyr(OMe)" stands for O-methyl tyrosine, "Aib" stands for amino isobutyric acid; "(homo)F" or "(homo)Phe" stands for homophenylalanine; "(2-OMe) Phg" refers to 2-O-methylphenylglycine; "(5-F)W" refers to 5-fluorotryptophan; "D-X" refers to the D-stereoisomer of the given amino acid "X" [e.g. (D-Chg) stands for D-cyclohexylglycine]; "(5-MeO)W" refers to 5-methyl-O-tryptophan; "homoC" refers to homocysteine; "(1-Me-W)" or "(1-Me)W" refers to 1-methyltryptophan; "Ne" refers to norleucine; "Tiq" refers to a tetrahydroisoquinoline residue; "Asp(T)" refers to (S)-2-amino-3-(1H-tetrazol-5-yl)propanoic acid; "(3-Cl-Phe)" refers to 3-chlorophenylalanine; "[(N-Me-4-F)Phe]" or "(N-Me-4-F)Phe" refers to N-methyl-4-fluorophenylalanine; "(m-Cl-homo)Phe" refers to meta-chloro homophenylalanine; "(des-amino)C" refers to 3-thiopropionic acid; "(alpha-methyl)D" refers to alpha-methyl L-aspartic acid; "2Nal" refers to 2-naphthylalanine; "(3-aminomethyl)Phe" refers to 3-aminomethyl-L-phenyalanine; "Cle" refers to cycloleucine; "Ac-Pyran" refers to 4-amino-tetrahydro-pyran-4-carboxylic acid; "(Lys-C16)" refers to N-ε-palmitoyl lysine; "(Lys-C12)" refers to N-α-lauryl lysine; "(Lys-C10)" refers to N-ε-capryl lysine; "(Lys-C8)" refers to N-ε-caprylic lysine; "[xXylyl(y, z)]" refers to the xylyl bridging moiety between two thiol containing amino acids where x may be m, p or o to indicate the use of meta-, para- or ortho-dibromoxylenes (respectively) to generate bridging moieties and the numerical identifiers, y and z, place the amino acid position within the polypeptide of the amino acids participating in the cyclization; "[cyclo(y,z)]" refers to the formation of a bond between two amino acid residues where the numerical identifiers, y and z, place the position of the residues participating in the bond; "[cyclo-olefinyl(y,z)]" refers to the formation of a bond between two amino acid residues by olefin metathesis where the numerical identifiers, y and z, place the position of the residues participating in the bond; "[cyclo-thioalkyl(y,z)]" refers to the formation of a thioether bond between two amino acid residues where the numerical identifiers, y and z, place the position of the residues participating in the bond; "[cyclo-triazolyl(y,z)]" refers to the formation of a triazole ring between two amino acid residues where the numerical identifiers, y and z, place the position of the residues participating in the bond. "B20" refers to N-ε-(PEG2-γ-glutamic acid-N-α-octadecanedioic acid) lysine [also known as (1S,28S)-1-amino-7,16,25,30-tetraoxo-9,12,18,21-tetraoxa-6,15,24,29-tetraazahexatetracontane-1,28,46-tricarboxylic acid.]

ily amino-acid based molecules but may also comprise one or more modifications (including, but not limited to the addition of sugar moieties, fluorescent moieties, chemical tags, etc.)

As used herein the term, "antibody fragment" refers to any portion of an intact antibody. In some embodiments, antibody fragments comprise antigen binding regions from intact antibodies. Examples of antibody fragments may include, but are not limited to Fab, Fab', F(ab')$_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Compounds and/or compositions of the present invention may comprise one or more of these fragments. For the purposes herein, an "antibody" may comprise a heavy and light variable domain as well as an Fc region.

As used herein, the term "native antibody" refers to a usually heterotetrameric glycoprotein of about 150,000 daltons, composed of two identical light (L) chains and two identical heavy (H) chains. Each light chain is linked to a

B20

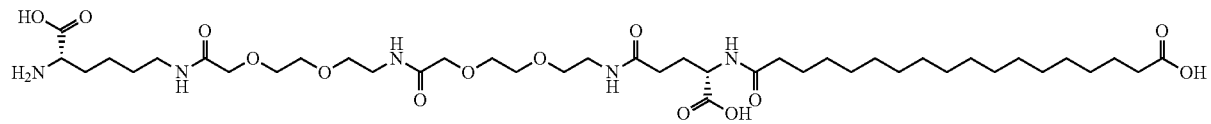

"B28" refers to N-ε-(PEG24-γ-glutamic acid-N-α-hexadecanoyl)lysine.

B28

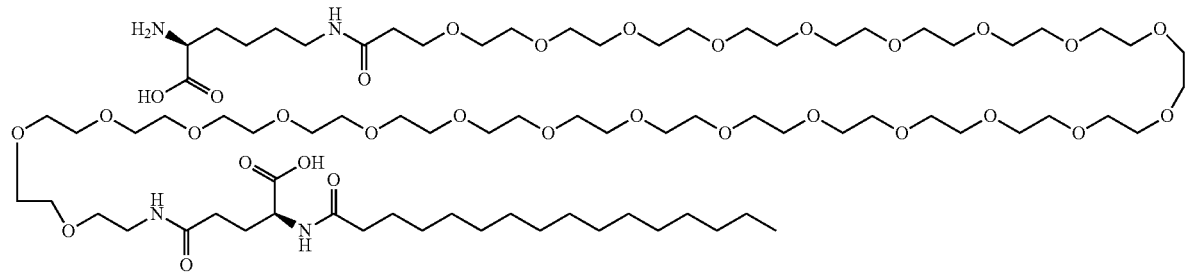

"K14" refers to N-ε-1-(4,4-dimethyl-2,6-dioxocyclohex-1-ylidene)-3-methylbutyl-L-lysine. All other symbols refer to the standard one-letter amino acid code.

Antibodies

In some embodiments, compounds and/or compositions of the present invention may comprise antibodies or fragments thereof. As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies of the present invention may also comprise human antibodies or humanized antibodies. Antibodies are primarheavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains that differ extensively in sequence among antibodies and are used in the binding and specificity of each particular antibody for its particular antigen.

As used herein, the term "Fv" refers to antibody fragments comprising complete antigen-recognition and antigen-binding sites. These regions consist of a dimer of one heavy chain and one light chain variable domain in tight, non-covalent association.

As used herein, the term "light chain" refers to a component of an antibody from any vertebrate species assigned to one of two clearly distinct types, called kappa and lambda based on amino acid sequences of constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "Single-chain Fv" or "scFv" refers to a fusion protein of $V_H$ and $V_L$ antibody domains, wherein these domains are linked together into a single polypeptide chain. In some embodiments, the Fv polypeptide linker enables the scFv to form the desired structure for antigen binding.

As used herein, the term "diabody" refers to a small antibody fragment with two antigen-binding sites. Diabodies comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (Hollinger, P. et al., "Diabodies": Small bivalent and bispecific antibody fragments. PNAS. 1993. 90:6444-8) the contents of each of which are incorporated herein by reference in their entirety.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity.

As used herein, the term "hypervariable region" refers to regions within the antigen binding domain of an antibody comprising amino acid residues responsible for antigen binding. The amino acids present within the hypervariable regions determine the structure of the complementarity determining region (CDR). As used herein, the term "CDR" refers to regions of antibodies comprising a structure that is complimentary to its target antigen or epitope.

In some embodiments, compounds and/or compositions of the present invention may be or comprise antibody mimetics. As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901 and 6,348,584, the contents of each of which are herein incorporated by reference in their entirety). In some embodiments, antibody mimetics may include those known in the art including, but not limited to affibody molecules, affilins, affitins, anticalins, avimers, Centyrins, DARPINS™, Fynomers, Adnectins, and Kunitz domain peptides. In other embodiments, antibody mimetics may include one or more non-peptide region.

As used herein, the term "antibody variant" refers to a biomolecule resembling an antibody in structure and/or function comprising some differences in their amino acid sequence, composition or structure as compared to a native antibody.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

In some embodiments, polypeptide sequences provided herein may be utilized in the production of one or more antibodies. In some cases, such polypeptide sequences may be incorporated into antibody variable domains. Such variable domains may be incorporated into antibodies, antibody mimetics or antibody variants.

Small Molecules

In some embodiments, compounds of the present invention may be small molecules. Such compounds may comprise a size from about 100 to about 2000 Daltons (e.g. from about 100 to about 200, to about 300, to about 400, to about 500, to about 600, to about 700, to about 800, to about 900, to about 1000, to about 1100, to about 1200, to about 1300, to about 1400, to about 1500, to about 1600, to about 1700, to about 1800, to about 1900 or to about 2000 Daltons.) Small molecules may be non-peptidic or share some or many characteristics of polypeptides and cyclic polypeptides, including amide bonds, cyclic structures, and amino acid-like substituents.

Aptamers

In some embodiments, compounds of the present invention may comprise aptamers (Keefe, A. D., Pai, S. and Ellington, A. (2010). Nat. Rev. Drug Discovery 9:537-550). As used herein, the term "aptamer" refers to oligonucleic or polypeptide molecules that are capable of binding specific target molecules. Some aptamers may adopt a three-dimensional conformation capable of binding such target molecules with high affinity and specificity.

Isotopic Variations

Polypeptides of the present invention may comprise one or more atoms that are isotopes. As used herein, the term "isotope" refers to a chemical element that has one or more additional neutrons. In one embodiment, polypeptides of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. Compounds and pharmaceutical compositions of the present invention may be deuterated in order to change a physical property, such as stability, or to allow them to be used in diagnostic and experimental applications.

Formulation and Delivery

The term "pharmaceutical composition" refers to a composition comprising at least one active ingredient (e.g., such as a polypeptide) in a form and amount that permits the active ingredient to be therapeutically effective.

Polypeptide formulations of the present invention include controlled duodenal release formulations, time release formulations, osmotic-controlled release delivery systems, microemulsions, microspheres, liposomes, nanoparticles, patches, pumps, drug depots, and the like. Specifically included in the present invention are solid oral dosage forms, such as powders, softgels, gelcaps, capsules, pills, and tablets.

The pharmaceutical compositions of the present invention may be administered by any route that results in a therapeutically effective outcome. These include, but are not limited to enteral, gastroenteral, epidural, oral, peridural, intracerebral (into the cerebrum), intratracheal (into the airways for delivery to the lung), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (into the posterior chamber of the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), buccal, sublingual, sublabial, enema, eye drops (onto the conjunctiva), or in ear drops.

In some embodiments, polypeptides of the present invention are formulated in a sterile aqueous solution. In some embodiments, polypeptides of the present invention are formulated in a lipid or non-lipid formulation. In another embodiment, polypeptides of the present invention are formulated in a cationic or non-cationic lipid formulation. In either embodiment, the sterile aqueous solution may contain additional active or inactive components. Inactive components, also referred to herein as "excipients," can include, but are not limited to, physiologically compatible salts, sugars, bulking agents, surfactants, or buffers.

Polypeptides and/or polypeptide compositions of the present invention may comprise or be formulated or delivered in conjunction with one or more carrier agents. As used herein, the term "carrier" refers to a substance that aids in the delivery or improves the effectiveness of the polypeptides and/or polypeptide compositions of the present invention. The carrier agent can be a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, or hyaluronic acid); or lipid. The carrier molecule can also be a recombinant or synthetic molecule, such as a synthetic polymer, e.g., a synthetic polyamino acid. Examples of polyamino acids include poly-L-lysine (PLL), poly-L-aspartic acid and, poly-L-glutamic acid, as well as polymers comprising the D-stereoisomers of these amino acids. Other carriers include poly(L-lactide-co-glycolide) copolymer, polyethylene glycol (PEG), polyvinyl alcohol (PVA), poly(2-ethylacrylic acid), and N-isopropylacrylamide polymers. Other useful carrier molecules can be identified by routine methods.

In some embodiments, compounds of the present invention may be combined with one or more pharmaceutically acceptable excipient to form a pharmaceutical composition. As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable excipient," as used herein, refers any ingredient other than the inventive compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol. In some embodiments, pharmaceutical compositions comprise one or more active polypeptide ingredients together with ethanol, corn oil-mono-di-triglycerides, hydrogenated castor oil, DL-tocopherol, propylene glycol, gelatin, glycerol, colorants, flavors and sweeteners.

In other embodiments, pharmaceutical compositions comprise one or more active polypeptide ingredients together with a delivery agent such as 4-(2-hydroxy-4-methoxybenzamido)butanoic acid (or any of the delivery agents described in U.S. Pat. No. 7,744,910B2, the contents of which are incorporated herein by reference in their entirety), a pharmaceutically acceptable buffer, a disintegrant, a detergent, hydroxypropylmethylcellulose, colorants, flavors and sweeteners.

In other embodiments, pharmaceutical compositions comprise one or more active polypeptide ingredients together with ethanol, soy phosphatidyl choline, glycerol diolate which is injected into an excess of saline solution as described in US patent application 2008/0146490A1, the contents of which are incorporated herein by reference in their entirety.

The delivery of one or more polypeptides to a subject in need thereof can be achieved in a number of different ways. In vivo delivery can be performed directly by administering a composition comprising one or more polypeptides, to a subject. Alternatively, delivery can be performed indirectly by administering one or more vectors that encode and direct the expression of the polypeptides.

Local delivery avoids gut permeability and systemic exposure. For example, polypeptides and/or polypeptide compositions of the present invention may be used in the eye as a drop or in the posterior section of the eye by direct injection. They may be applied in the gut to target enzymes. They may be used topically in dermatologic applications (e.g., creams, ointments, transdermal patches).

Polypeptides and/or polypeptide compositions of the present invention may comprise or be formulated with one or more fusogenic agents. As used herein, the term "fusogenic agent" refers to an agent that is responsive to changes, such as pH changes in the environment for example. Upon encountering the pH of an endosome, a fusogenic agent can cause a physical change, e.g., a change in osmotic properties that disrupts or increases the permeability of the endosome membrane. Preferably, the fusogenic agent changes charge, e.g., becomes protonated, at pH lower than physiological range. For example, the fusogenic agent can become protonated at pH 4.5-6.5. A fusogenic agent may serve to release a polypeptide into the cytoplasm of a cell after a composition is taken up, e.g., via endocytosis, by the cell, thereby increasing the cellular concentration of the polypeptide in the cell.

In some embodiments, fusogenic agents may have a moiety, e.g., an amino group, which, when exposed to a specified pH range, will undergo a change, e.g., in charge, e.g., protonation. Changes in charge of fusogenic agents can trigger changes, e.g., osmotic changes, in vesicles, e.g., endocytic vesicles, e.g., endosomes. For example, the fusogenic agent, upon being exposed to the pH environment of an endosome, will cause a solubility or osmotic change substantial enough to increase the porosity of (preferably, to rupture) the endosomal membrane.

Fusogenic agents may be polymers, preferably polyamino chains, e.g., polyethyleneimine (PEI). PEI may be linear, branched, synthetic or natural. PEI may be, e.g., alkyl substituted PEI, or lipid substituted PEI.

In other embodiments, fusogenic agents may be polyhistidine, polyimidazole, polypyridine, polypropyleneimine, mellitin, or polyacetal substances, e.g., cationic polyacetals. In some embodiments, fusogenic agents may have an alpha helical structure. Fusogenic agents may be membrane disruptive agents, e.g., mellittin. Other suitable fusogenic agents can be tested and identified by a skilled artisan.

Polypeptides and/or polypeptide compositions of the present invention may comprise or be formulated with one or more condensing agents. Condensing agents of compositions described herein may interact with (e.g., attract, hold, or bind to) polypeptides and act to (a) condense, e.g., reduce the size or charge of polypeptides and/or (b) protect polypeptides, e.g., protect polypeptides against degradation. Condensing agents may include a moiety, e.g., a charged moiety, which can interact with polypeptides by ionic interactions. Condensing agents would preferably be charged polymers, e.g., polycationic chains. Condensing agents can be polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, polypeptides of the present invention may be bicyclic polypeptides. As used herein, the term "bicyclic polypeptide" refers to a polypeptide with two loops. As a non-limiting example, bicyclic polypeptide inhibitors of C5 may be produced in combinatorial libraries. The bicyclic polypeptides may have 2, 3, 4, 5, 6 or more amino acids per loop.

In some embodiments, polypeptides and/or polypeptide compositions of the present invention may be provided as prodrugs. As used herein, the term "prodrug" refers to a drug that is provided in an inactive form that becomes active at some point after administration. In some embodiments wherein polypeptides are administered in the form of a prodrug, amino acids critical to polypeptide inhibitory activity are unavailable to interact with the target due to a reversible chemical bond, e.g., an ester bond. Upon administration, such prodrugs may be subject to cleavage of the reversible chemical bond, e.g., through enzymatic or acid hydrolysis in the stomach, blood and/or cells of a given target tissue.

C5 Inhibitors

Some polypeptides and/or polypeptide compositions of the present invention inhibit complement activation at the level of complement component C5, referred to herein as "C5 inhibitors." Some C5 inhibitors function by preventing the cleavage of C5 to the cleavage products C5a and C5b, such inhibitors are referred to herein as "C5 cleavage inhibitors." In some embodiments, methods of the present invention may comprise inhibiting C5 cleavage in a system. As used herein, a "system" refers to a group of related parts that function together. Such systems include those comprising C5, referred to here as "C5 systems." C5 systems may include, but are not limited to solutions, matrices, cells, tissues, organs, and bodily fluids (including, but not limited to blood.) In some cases, C5 systems may be cellular systems. As used herein the term "cellular system" refers to a system that comprises one or more cells or one or more components or products of a cell. In some cases, C5 systems may include in vivo systems, in vitro systems and ex vivo systems. In vivo C5 systems may comprise or be comprised in a subject.

In some cases, C5 inhibitors of the invention may include any of the polypeptides listed in Table 1.

TABLE 1

Compounds of the invention

| Compound Number | Sequence | SEQ ID NO. |
|---|---|---|
| R3000 | Ac-Nvl-C-Y-K-N-Y-H-azaTrp-E-Y-P-Tbg-Y-NH2 | 1 |
| R3001 | Ac-Nvl-C-Y-E-N-Tbg-Y-azaTrp-E-Y-(N-Me)G-Nvl-(N-Me)S-NH2 | 2 |
| R3002 | Ac-Nvl-C-Y-E-N-Tbg-Y-azaTrp-E-Y-P-Phg-Nvl-NH2 | 3 |
| R3003 | Ac-Nvl-C-Y-E-N-Tbg-Y-azaTrp-E-Y-P-Phg-P-NH2 | 4 |

TABLE 1 -continued

Compounds of the invention

| Compound Number | Sequence | SEQ ID NO. |
|---|---|---|
| R3004 | Ac-Nvl-C-Y-N-N-Tbg-E-azaTrp-E-Y-P-Phg-Tbg-NH2 | 5 |
| R3005 | Ac-Nvl-C-Y-azaTrp-(N-Me)G-Tbg-Nvl-azaTrp-E-Y-P-Phg-P-NH2 | 6 |
| R3006 | Ac-Y-E-N-Tbg-Y-azaTrp-E-Y-(N-Me)G-Nvl-(N-Me)S-NH2 | 7 |
| R3007 | [mXylyl(2,7)]Ac-Nvl-C-K-E-Phg-Y-C-(N-Me)S-Tbg-K-azaTrp-E-Y-NH2 | 8 |
| R3008 | [mXylyl(2,10)]Ac-Nvl-C-Phg-T-azaTrp-E-Y-(N-Me)S-H-C-Nvl-P-Nvl-NH2 | 9 |
| R3020 | [mXylyl(2,7)]M-C-S-E-R-Y-C-E-V-R-W-E-Y-NH2 | 10 |
| R3021 | [mXylyl(2,7)]M-C-V-E-R-F-C-D-V-Y-W-E-F-NH2 | 11 |
| R3079 | Nvl-Nvl-Y-E-N-Tbg-Y-azaTrp-E-Y-P-Phg-Nvl-NH2 | 12 |
| R3055 | Ac-Nvl-S-Y-E-N-Tbg-Y-azaTrp-E-Y-P-Phg-Nvl-NH2 | 13 |
| R3120 | Ac-Nvl-Nvl-Y-E-(N-Me)N-Tbg-Y-azaTrp-E-Y-P-Chg-Nvl-NH2 | 14 |
| R3057 | [mXylyl(2,7)]M-C-V-E-R-F-C-D-Tbg-Y-azaTrp-E-Y-P-Phg-Nvl-NH2 | 15 |
| R3056 | Ac-Nvl-Nvl-Y-E-N-Tbg-Y-azaTrp-E-Y-P-Phg-Nvl-NH2 | 16 |
| R3054 | Ac-Nvl-C-Y-E-N-Tbg-Y-azaTrp-E-Y-P-Chg-Nvl-NH2 | 17 |
| R3029 | Ac-Nvl-C-Y-E-N-Tbg-Y-azaTrp-E-Y-P-Phg-NH2 | 18 |
| R3048 | [mXylyl(1,6)]Ac-C-V-E-R-F-C-D-V-Y-W-E-F-NH2 | 19 |
| R3072 | Ac-Nvl-Nvl-Y-E-N-Tbg-Y-azaTrp-E-Y-P-Chg-Nvl-K-NH2 | 20 |
| R3024 | Ac-C-Y-E-N-Tbg-Y-azaTrp-E-Y-P-Phg-Nvl-NH2 | 21 |
| R3114 | Ac-Nvl-Nvl-(N-Me)Y-E-N-Tbg-Y-azaTrp-E-Y-P-Chg-Nvl-NH2 | 22 |
| R3050 | [pXylyl(2,10)]Ac-Nvl-C-Phg-T-azaTrp-E-Y-(N-Me)S-H-C-Nvl-NH2 | 23 |
| R3025 | Ac-Y-E-N-Tbg-Y-azaTrp-E-Y-P-Phg-Nvl-NH2 | 24 |
| R3061 | Ac-Nvl-S-Y-E-A-Tbg-Y-azaTrp-E-Y-P-Chg-Nvl-NH2 | 25 |
| R3041 | Ac-Y-E-N-Tbg-Y-W-E-Y-P-Phg-Nvl-NH2 | 26 |
| R3077 | Ac-Nvl-Nvl-Y-E-N-Tbg-Y-azaTrp-E-Y-P-Chg-Nvl-K-(PEG2000)NH2 | 27 |
| R3030 | Ac-Nvl-C-Y-E-N-Tbg-Y-azaTrp-E-Y-P-NH2 | 28 |
| R3062 | Ac-Nvl-S-Y-E-N-A-Y-azaTrp-E-Y-P-Chg-Nvl-NH2 | 29 |
| R3066 | Ac-Nvl-S-Y-E-N-Tbg-A-azaTrp-E-Y-P-Chg-Nvl-NH2 | 30 |
| R3011 | [mXylyl(2,10)]Ac-Nvl-C-Phg-T-azaTrp-E-Y-(N-Me)S-H-C-Nvl-P-NH2 | 31 |
| R3070 | Ac-Nvl-S-Y-E-N-Tbg-Y-azaTrp-E-Y-A-Chg-Nvl-NH2 | 32 |
| R3071 | Ac-Nvl-S-Y-E-N-Tbg-Y-azaTrp-E-Y-P-A-Nvl-NH2 | 33 |
| R3033 | [mXylyl(2,10)]Ac-Nvl-C-Phg-A-azaTrp-E-Y-(N-Me)S-H-C-Nvl-NH2 | 34 |
| R3038 | [mXylyl(2,10)]Ac-Nvl-C-Phg-T-azaTrp-E-Y-(N-Me)S-A-C-Nvl-NH2 | 35 |
| R3012 | [mXylyl(2,10)]Ac-Nvl-C-Phg-T-azaTrp-E-Y-(N-Me)S-H-C-Nvl-NH2 | 36 |
| R3060 | Ac-Nvl-S-Y-A-N-Tbg-Y-azaTrp-E-Y-P-Chg-Nvl-NH2 | 37 |
| R3039 | [mXylyl(2,10)]Ac-Nvl-C-Phg-T-azaTrp-E-Y-(N-Me)S-H-C-A-NH2 | 38 |

TABLE 1 -continued

Compounds of the invention

| Compound Number | Sequence | SEQ ID NO. |
|---|---|---|
| R3037 | [mXylyl(2,10)]Ac-Nvl-C-Phg-T-azaTrp-E-Y-(N-Me)A-H-C-Nvl-NH2 | 39 |
| R3076 | Ac-Nvl-Nvl-Y-E-N-Tbg-Y-azaTrp-E-Y-P-Chg-Nvl-K-(BODIPY-TMR-X)NH2 | 40 |
| R3074 | [mXylyl(2,10)]Ac-Nvl-C-Phg-T-azaTrp-E-Tyr(OMe)-(N-Me)S-H-C-Nvl-NH2 | 41 |
| R3013 | [mXylyl(2,10)]Ac-Nvl-C-Phg-T-azaTrp-E-Y-(N-Me)S-H-C-NH2 | 42 |
| R3065 | [pXylyl(2,10)]Ac-Nvl-C-Phg-T-azaTrp-E-Y-P-H-C-Nvl-NH2 | 43 |
| R3073 | [mXylyl(2,10)]Ac-Nvl-C-Phg-T-azaTrp-E-Phe(4-F)-(N-Me)S-H-C-Nvl-NH2 | 44 |
| R3116 | Ac-Nvl-Nvl-Y-E-N-Tbg-Y-(N-Me)W-E-Y-P-Chg-Nvl-NH2 | 45 |
| R3091 | [mXylyl(2,10)]Ac-Nvl-C-Phg-T-W-E-Y-(N-Me)S-A-C-Nvl-NH2 | 46 |
| R3078 | PEG2000-Nvl-Nvl-Y-E-N-Tbg-Y-azaTrp-E-Y-P-Phg-Nvl-NH2 | 47 |
| R3100 | [mXylyl(2,10)]Ac-Nvl-C-Phg-T-azaTrp-E-F-(N-Me)S-A-C-Nvl-NH2 | 48 |
| R3121 | Ac-Nvl-Nvl-Y-E-N-Tbg-Y-azaTrp-E-Y-P-(N-Me)Phg-Nvl-NH2 | 49 |
| R3043 | [mXylyl(2,7)]M-C-V-E-R-F-C-D-V-Y-W-E-NH2 | 50 |
| R3102 | [mXylyl(2,10)]Ac-Nvl-C-Phg-T-azaTrp-E-Y-P-H-C-Nvl-NH2 | 51 |
| R3026 | Ac-E-N-Tbg-Y-azaTrp-E-Y-P-Phg-Nvl-NH2 | 52 |
| R3031 | [mXylyl(2,10)]Ac-A-C-Phg-T-azaTrp-E-Y-(N-Me)S-H-C-Nvl-NH2 | 53 |
| R3019 | [mXylyl(2,14)]Ac-Nvl-C-Y-E-N-Tbg-Y-azaTrp-E-Y-P-Phg-Nvl-C-NH2 | 54 |
| R3014 | [mXylyl(1,9)]Ac-C-Phg-T-azaTrp-E-Y-(N-Me)S-H-C-Nvl-P-Nvl-NH2 | 55 |
| R3104 | [pXylyl(2,10)]Ac-Nvl-homoC-Phg-T-azaTrp-E-Y-(N-Me)S-H-C-Nvl-NH2 | 56 |
| R3059 | Ac-Nvl-S-A-E-N-Tbg-Y-azaTrp-E-Y-P-Chg-Nvl-NH2 | 57 |
| R3115 | Ac-Nvl-Nvl-Y-(N-Me)E-N-Tbg-Y-azaTrp-E-Y-P-Chg-Nvl-NH2 | 58 |
| R3110 | Ac-Y-E-N-Tbg-Y-(1-Me)W-E-Y-P-Phg-Nvl-NH2 | 59 |
| R3126 | Ac-Nvl-C-Y-N-N-Tbg-E-azaTrp-E-C-P-Phg-Tbg-NH2 | 60 |
| R3049 | [oXylyl(2,10)]Ac-Nvl-C-Phg-T-azaTrp-E-Y-(N-Me)S-H-C-Nvl-NH2 | 61 |
| R3069 | Ac-Nvl-S-Y-E-N-Tbg-Y-azaTrp-E-A-P-Chg-Nvl-NH2 | 62 |
| R3015 | [mXylyl(1,9)]Ac-C-Phg-T-azaTrp-E-Y-(N-Me)S-H-C-NH2 | 63 |
| R3068 | Ac-Nvl-S-Y-E-N-Tbg-Y-azaTrp-A-Y-P-Chg-Nvl-NH2 | 64 |
| R3105 | [mXylyl(2,10)]Ac-Nvl-C-Phg-T-azaTrp-E-Y-(N-Me)S-H-homo C-Nvl-NH2 | 65 |
| R3106 | [pXylyl(2,10)]Ac-Nvl-C-Phg-T-azaTrp-E-Y-(N-Me)S-H-homoC-Nvl-NH2 | 66 |
| R3111 | [mXylyl(4,10)]Ac-Nvl-T-Phg-C-azaTrp-E-Y-(N-Me)S-A-C-Nvl-NH2 | 67 |
| R3112 | [mXylyl(2,10)]Ac-Nle-C-Phg-T-azaTrp-E-Y-(N-Me)S-H-C-Nvl-NH2 | 68 |
| R3113 | [mXylyl(3,11)]Ac-Y-Nvl-C-Phg-T-azaTrp-E-Y-(N-Me)S-H-C-Nvl-NH2 | 69 |
| R3134 | [mXylyl(2,10)]Ac-Nvl-C-Phg-T-azaTrp-E-(3-Cl-Phe)-(N-Me)S-A-C-Nvl-NH2 | 70 |

TABLE 1 -continued

Compounds of the invention

| Compound Number | Sequence | SEQ ID NO. |
|---|---|---|
| R3018 | [mXylyl(2,10)]Ac-Nvl-C-Y-E-N-Tbg-Y-azaTrp-E-C-P-Phg-Nvl-NH2 | 71 |
| R3027 | Ac-N-Tbg-Y-azaTrp-E-Y-P-Phg-Nvl-NH2 | 72 |
| R3028 | Ac-Tbg-Y-azaTrp-E-Y-P-Phg-Nvl-NH2 | 73 |
| R3032 | [mXylyl(2,10)]Ac-Nvl-C-A-T-azaTrp-E-Y-(N-Me)S-H-C-Nvl-NH2 | 74 |
| R3058 | [pXylyl(2,10)]Ac-Nvl-C-Chg-T-azaTrp-E-Y-(N-Me)S-H-C-Nvl-NH2 | 75 |
| R3067 | Ac-Nvl-S-Y-E-N-Tbg-Y-A-E-Y-P-Chg-Nvl-NH2 | 76 |
| R3117 | Ac-Nvl-Nvl-Y-E-N-Tbg-Y-azaTrp-E-(N-Me)Y-P-Chg-Nvl-NH2 | 77 |
| R3022 | Ac-Nvl-C-Phg-T-azaTrp-E-Y-(N-Me)S-H-C-Nvl-P-Nvl-NH2 | 78 |
| R3016 | [mXylyl(1,9)]Ac-C-Tbg-Y-azaTrp-E-Y-(N-Me)S-H-C-NH2 | 79 |
| R3089 | [mXylyl(2,10)]Ac-Chg-C-Phg-T-azaTrp-E-Y-(N-Me)S-A-C-Nvl-NH2 | 80 |
| R3083 | [mXylyl(2,10)]Ac-V-C-Phg-T-azaTrp-E-Y-(N-Me)S-A-C-Nvl-NH2 | 81 |
| R3087 | [mXylyl(2,10)]Ac-Nvl-C-(2-OMe)Phg-T-azaTrp-E-Y-(N-Me)S-H-C-Nvl-NH2 | 82 |
| R3103 | [mXylyl(2,10)]Ac-Nvl-homoC-Phg-T-azaTrp-E-Y-(N-Me)S-H-C-Nvl-NH2 | 83 |
| R3135 | [mXylyl(2,10)]Ac-Nvl-C-Phg-T-azaTrp-E-Y-(N-Me)S-(D-Ala)-C-Nvl-NH2 | 84 |
| R3034 | [mXylyl(2,10)]Ac-Nvl-C-Phg-T-A-E-Y-(N-Me)S-H-C-Nvl-NH2 | 85 |
| R3035 | [mXylyl(2,10)]Ac-Nvl-C-Phg-T-azaTrp-A-Y-(N-Me)S-H-C-Nvl-NH2 | 86 |
| R3036 | [mXylyl(2,10)]Ac-Nvl-C-Phg-T-azaTrp-E-A-(N-Me)S-H-C-Nvl-NH2 | 87 |
| R3044 | [mXylyl(2,7)]M-C-V-E-R-F-C-D-V-Y-W-NH2 | 88 |
| R3080 | [mXylyl(2,9)]Ac-Nvl-C-Phg-T-azaTrp-E-Y-(N-Me)S-C-Nvl-NH2 | 89 |
| R3085 | [mXylyl(2,10)]heptanoyl-Nvl-C-Phg-T-azaTrp-E-Y-(N-Me)S-A-C-Nvl-NH2 | 90 |
| R3086 | [mXylyl(5,13)]Ac-Nvl-S-Y-E-C-Tbg-Y-azaTrp-E-Y-P-Chg-C-Nvl-NH2 | 91 |
| R3092 | [mXylyl(2,10)]Ac-Nvl-C-Phg-T-F-E-Y-(N-Me)S-A-C-Nvl-NH2 | 92 |
| R3095 | [mXylyl(2,10)]Ac-Nvl-C-Phg-T-azaTrp-E-(homo)F-(N-Me)S-A-C-Nvl-NH2 | 93 |
| R3096 | [mXylyl(2,10)]Ac-Nvl-C-Phg-Aib-azaTrp-E-Y-(N-Me)S-H-C-Nvl-NH2 | 94 |
| R3122 | [mXylyl(2,10)]Ac-Nvl-C-Tiq-T-azaTrp-E-Y-(N-Me)S-H-C-Nvl-NH2 | 95 |
| R3075 | [mXylyl(2,11)]Nvl-C-Y-(N-Me)S-Phg-(N-Me-4-F)Phe-(N-Me)S-H-(N-Me-4-F)Phe-G-C-NH2 | 96 |
| R3107 | [mXylyl(2,10)]Ac-Nvl-homoC-Phg-T-azaTrp-E-Y-(N-Me)S-H-homoC-Nvl-NH2 | 97 |
| R3108 | [pXylyl(2,10)]Ac-Nvl-homo C-Phg-T-azaTrp-E-Y-(N-Me)S-H-homoC-Nvl-NH2 | 98 |
| R3127 | [mXylyl(2,10)]Ac-Nvl-C-Y-N-N-Tbg-E-azaTrp-E-C-P-Phg-Tbg-NH2 | 99 |
| R3133 | [mXylyl(2,10)]Ac-Nvl-C-Phg-(D-Ala)-azaTrp-E-Y-(N-Me)S-H-C-Nvl-NH2 | 100 |
| R3009 | [mXylyl(2,10)]Ac-Nvl-C-Y-E-(N-Me)G-Tbg-Y-azaTrp-E-C-Nvl-P-Nvl-NH2 | 101 |

TABLE 1 -continued

Compounds of the invention

| Compound Number | Sequence | SEQ ID NO. |
|---|---|---|
| R3010 | [mXylyl(2,13)]Ac-Nvl-C-Y-E-(N-Me)G-Tbg-Y-azaTrp-E-Nvl-Nvl-P-C-NH2 | 102 |
| R3017 | [mXylyl(2,8)]Ac-Nvl-C-Y-E-N-Tbg-Y-C-E-Y-P-Phg-Nvl-NH2 | 103 |
| R3023 | Ac-Y-P-Y-C-Phg-azaTrp-Tbg-E-Nvl-N-Y-Nvl-E-NH2 | 104 |
| R3040 | [cyclo(2,10)]Ac-Nvl-C-Phg-T-azaTrp-E-Y-(N-Me)S-H-C-Nvl-P-Nvl | 105 |
| R3042 | [cyclo(2,10)]Ac-Nvl-C-Phg-T-azaTrp-E-Y-(N-Me)S-H-C-Nvl-NH2 | 106 |
| R3045 | [mXylyl(2,7)]M-C-V-E-R-F-C-D-V-Y-NH2 | 107 |
| R3046 | [mXylyl(2,7)]M-C-V-E-R-F-C-D-V-NH2 | 108 |
| R3047 | [mXylyl(2,7)]M-C-V-E-R-F-C-NH2 | 109 |
| R3051 | [mXylyl(2,11)]Nvl-C-Y-(N-Me)S-Phg-(N-Me-4-F)Phe-(N-Me)S-H-(N-Me-4-F)Phe-(N-Me)G-C-NH2 | 110 |
| R3052 | [mXylyl(2,9)]Nvl-C-Y-Tbg-Phg-N-(N-Me)G-L-C-Phg-(N-Me)A-NH2 | 111 |
| R3053 | [mXylyl-bicyclo]Nvl-C-C-N-Tbg-Phg-C-Tbg-(N-Me)S-C-Tbg-NH2 | 112 |
| R3063 | Ac-Tbg-Y-azaTrp-E-Y-NH2 | 113 |
| R3064 | Ac-Y-azaTrp-E-Y-P-NH2 | 114 |
| R3081 | Ac-Y-E-N-Tbg-Y-azaTrp-(N-Me)E-Y-P-Phg-Nvl-NH2 | 115 |
| R3082 | [mXylyl(1,9)]heptanoyl-C-Phg-T-azaTrp-E-Y-(N-Me)S-A-C-Nvl-NH2 | 116 |
| R3084 | [mXylyl(2,10)]Ac-Nvl-C-Phg-T-azaTrp-E-Y-S-A-C-Nvl-NH2 | 117 |
| R3088 | [mXylyl(2,10)]Ac-Nvl-C-Phg-T-(5-F)W-E-Y-(N-Me)S-A-C-Nvl-NH2 | 118 |
| R3090 | [mXylyl(2,10)]Ac-Nvl-C-F-T-azaTrp-E-Y-(N-Me)S-A-C-Nvl-NH2 | 119 |
| R3093 | [mXylyl(2,10)]Ac-Nvl-C-(D-Chg)-T-azaTrp-E-Y-(N-Me)S-A-C-Nvl-NH2 | 120 |
| R3094 | Ac-Y-E-N-Tbg-Y-(5-Me 0)W-E-Y-P-Phg-Nvl-NH2 | 121 |
| R3097 | [mXylyl(2,10)]Ac-Nvl-C-Phg-T-azaTrp-D-Y-(N-Me)S-A-C-Nvl-NH2 | 122 |
| R3098 | [mXylyl(2,10)]Ac-Nvl-C-Phg-T-azaTrp-Q-Y-(N-Me)S-A-C-Nvl-NH2 | 123 |
| R3099 | [mXylyl(2,10)]Ac-Nvl-C-Phg-T-azaTrp-N-Y-(N-Me)S-A-C-Nvl-NH2 | 124 |
| R3101 | [mXylyl(2,10)]Ac-Nvl-C-Phg-T-azaTrp-E-Y-(N-Me)S-H-G-C-Nvl-NH2 | 125 |
| R3109 | [mXylyl(2,10)]Ac-Nvl-C-Phg-T-(1-Me-W)-E-Y-(N-Me)S-A-C-Nvl-NH2 | 126 |
| R3118 | Ac-Y-E-N-Tbg-Y-(D-Trp)-E-Y-P-Phg-Nvl-NH2 | 127 |
| R3119 | Ac-Y-E-N-Y-(D-Trp)-E-Y-P-Phg-Nvl-NH2 | 128 |
| R3123 | Ac-Y-E-N-Tbg-Y-azaTrp-(D-Glu)-Y-P-Phg-Nvl-NH2 | 129 |
| R3124 | [mXylyl(1,6)]Ac-C-V-E-R-F-C-V-Y-W-E-F-NH2 | 130 |
| R3125 | [mXylyl(1,6)]Ac-C-V-E-R-F-C-W-E-F-NH2 | 131 |
| R3128 | Ac-Nvl-C-Y-N-N-Tbg-E-C-E-Y-P-Phg-Tbg-NH2 | 132 |
| R3129 | [mXylyl(2,8)]Ac-Nvl-C-Y-N-N-Tbg-E-C-E-Y-P-Phg-Tbg-NH2 | 133 |
| R3130 | Ac-Nvl-Nvl-Y-E-N-Tbg-(N-Me)Y-azaTrp-E-Y-P-Chg-Nvl-NH2 | 134 |

TABLE 1 -continued

Compounds of the invention

| Compound Number | Sequence | SEQ ID NO. |
|---|---|---|
| R3131 | [mXylyl(2,10)]Ac-Nvl-C-Phg-T-W-Asp (T)-Y-(N-Me)S-H-C-Nvl-NH2 | 135 |
| R3132 | [mXylyl(2,10)]Ac-Nyl-C-Phg-T-(D-Trp)-E-Y-(N-Me)S-H-C-Nvl-NH2 | 136 |
| R3136 | [mXylyl(2,10)]heptanoyl-Nyl-C-(D-Phg)-T-azaTrp-E-Y-(N-Me)S-A-C-Nyl-NH2 | 137 |
| R3137 | [mXylyl(1,9)]heptanoyl-C-(D-Phg)-T-azaTrp-E-Y-(N-Me)S-A-C-Nyl-NH2 | 138 |
| R3138 | [mXylyl(1,6)]Ac-C-V-E-R-F-C-D-Tbg-Y-W-E-F-NH2 | 139 |
| R3139 | [mXylyl(1,6)]Ac-C-Tbg-E-R-F-C-D-Tbg-Y-W-E-F-NH2 | 140 |
| R3140 | [mXylyl(1,6)]Ac-C-V-E-R-F-C-D-V-Y-W-E-Y-P-NH2 | 141 |
| R3141 | [mXylyl(1,6)]Ac-C-V-E-R-F-C-D-V-Y-W-E-F-P-NH2 | 142 |
| R3142 | [mXylyl(1,6)]Ac-C-V-E-R-F-C-D-V-Y-azaTrp-E-Y-P-NH2 | 143 |
| R3143 | [mXylyl(1,6)]Ac-C-V-E-R-F-C-D-Tbg-Y-W-E-Y-P-NH2 | 144 |
| R3144 | [mXylyl(1,6)]Ac-C-V-E-R-F-C-D-Tbg-Y-azaTrp-E-Y-P-Phg-Nyl-NH2 | 145 |
| R3145 | [mXylyl(1,6)]Ac-C-V-E-R-F-C-D-Tbg-Y-azaTrp-E-Y-P-(D-Phg)-Nyl-NH2 | 146 |
| R3146 | [mXylyl(1,6)]Ac-C-Tbg-E-R-F-C-D-V-Y-W-E-F-NH2 | 147 |
| R3147 | [mXylyl(1,6)]Ac-C-V-E-R-F-C-D-V-Y-W-E-F-Propargyl-Gly-NH2 | 148 |
| R3148 | [mXylyl(1,6)]Ac-C-A-E-R-F-C-D-Tbg-Y-W-E-Y-P-Phg-Nyl-NH2 | 149 |
| R3149 | [mXylyl(1,6)]Ac-C-A-E-R-F-C-D-Tbg-Y-W-E-Y-P-(D-Phg)-Nyl-NH2 | 150 |
| R3150 | [mXylyl(1,6)]Ac-C-V-A-R-F-C-D-Tbg-Y-azaTrp-E-Y-P-Phg-Nyl-NH2 | 151 |
| R3151 | [mXylyl(1,6)]Ac-C-V-A-R-F-C-D-Tbg-Y-azaTrp-E-Y-P-(D-Phg)-Nyl-NH2 | 152 |
| R3152 | [mXylyl(1,6)]Ac-C-V-E-R-F-C-D-Tbg-Y-azaTrp-E-Y-P-Chg-Nyl-NH2 | 153 |
| R3153 | [mXylyl(1,6)]Ac-C-V-E-A-F-C-D-Tbg-Y-azaTrp-E-Y-P-Phg-Nyl-NH2 | 154 |
| R3154 | [mXylyl(1,6)]Ac-C-V-E-A-F-C-D-Tbg-Y-azaTrp-E-Y-P-(D-Phg)-Nyl-NH2 | 155 |
| R3155 | [mXylyl(1,6)]Ac-C-V-E-R-A-C-D-Tbg-Y-azaTrp-E-Y-P-Phg-Nyl-NH2 | 156 |
| R3156 | [mXylyl(1,6)]Ac-C-V-E-R-A-C-D-Tbg-Y-azaTrp-E-Y-P-(D-Phg)-Nyl-NH2 | 157 |
| R3157 | [mXylyl(1,6)]Ac-C-V-E-R-F-C-A-Tbg-Y-azaTrp-E-Y-P-Phg-Nyl-NH2 | 158 |
| R3158 | [mXylyl(1,6)]Ac-C-V-E-R-F-C-A-Tbg-Y-azaTrp-E-Y-P-(D-Phg)-Nyl-NH2 | 159 |
| R3159 | [mXylyl(1,6)](des-amino)C-V-E-R-F-C-D-Tbg-Y-azaTrp-E-Y-P-Phg-Nyl-NH2 | 160 |
| R3160 | [mXylyl(1,6)](des-amino)C-V-E-R-F-C-D-Tbg-Y-azaTrp-E-Y-P-(D-Phg)-Nyl-NH2 | 161 |

TABLE 1 -continued

Compounds of the invention

| Compound Number | Sequence | SEQ ID NO. |
|---|---|---|
| R3161 | [mXylyl(1,6)]Ac-C-A-E-R-F-C-D-Tbg-Y-azaTrp-E-Y-P-Phg-K-NH2 | 162 |
| R3162 | [mXylyl(1,6)]Ac-C-A-E-R-F-C-D-Tbg-Y-azaTrp-E-Y-P-(D-Phg)-K-NH2 | 163 |
| R3163 | [cyclo(1,6)]Ac-C-V-E-R-F-C-D-Tbg-Y-azaTrp-E-Y-P-Phg-Nvl-NH2 | 164 |
| R3164 | [mXylyl(1,6)]Ac-C-A-E-R-F-C-D-Tbg-Y-azaTrp-E-Y-P-Phg-(Lys-C12)-NH2 | 165 |
| R3165 | [mXylyl(1,6)]Ac-C-A-E-R-F-C-D-Tbg-Y-azaTrp-E-Y-P-Phg-(Lys-C10)-NH2 | 166 |
| R3166 | [mXylyl(1,6)]Ac-C-A-E-R-F-C-D-Tbg-Y-azaTrp-E-Y-P-Phg-(Lys-C8)-NH2 | 167 |
| R3167 | [mXylyl(1,6)]Ac-C-V-E-R-F-C-(alpha-methyl)D-Tbg-Y-azaTrp-E-Y-P-Chg-Nvl-NH2 | 168 |
| R3168 | [mXylyl(1,6)]Ac-C-V-E-R-F-C-Asp(T)-Tbg-Y-azaTrp-E-Y-P-Chg-Nvl-NH2 | 169 |
| R3169 | [cyclo(1,6)]Ac-K-V-E-R-F-D-D-Tbg-Y-azaTrp-E-Y-P-Chg-Nvl-NH2 | 170 |
| R3170 | [mXylyl(1,6)]Ac-C-A-E-R-F-C-D-Tbg-Y-azaTrp-E-Y-P-Phg-K | 171 |
| R3171 | [mXylyl(1,6)]Ac-C-A-E-R-F-C-D-Tbg-Y-azaTrp-E-Y-P-Phg-(Lys-C12) | 172 |
| R3172 | [mXylyl(1,6)]Ac-C-V-E-R-F-C-(N-Me)D-Tbg-Y-azaTrp-E-Y-P-Chg-Nvl-NH2 | 173 |
| R3173 | [cyclo(1,6)]Ac-K-V-E-R-F-D-D-Tbg-Y-azaTrp-E-Y-P-Chg-Nvl | 174 |
| R3174 | [cyclo(1,6)]Ac-K-V-E-R-F-D-Asp(T)-Tbg-Y-azaTrp-E-Y-P-Chg-Nvl | 175 |
| R3175 | [cyclo(1,6)]Ac-K-V-E-R-F-D-D-Tbg-Y-azaTrp-E-Y-P-Chg-B20 | 176 |
| R3176 | [cyclo(1,6)]Ac-K-V-E-R-F-D-(N-Me)D-Tbg-Y-azaTrp-E-Y-P-Chg-Nvl | 177 |
| R3177 | [mXylyl(1,6)]Ac-C-V-E-R-F-C-D-Tbg-Y-azaTrp-E-W-P-Chg-Nvl | 178 |
| R3178 | [mXylyl(1,6)]Ac-C-V-E-R-F-C-D-Tbg-Y-azaTrp-E-(homo)Phe-P-Chg-Nvl | 179 |
| R3179 | [mXylyl(1,6)]Ac-C-V-E-R-F-C-D-Tbg-Y-azaTrp-E-(m-Cl-homo)Phe-P-Chg-Nvl | 180 |
| R3180 | [mXylyl(1,6)]Ac-C-V-E-R-F-C-D-Tbg-Y-azaTrp-E-2Nal-P-Chg-Nvl | 181 |
| R3181 | [mXylyl(1,6)]Ac-C-V-E-R-F-C-D-Tbg-Y-(3-aminomethyl)Phe-E-Y-P-Chg-Nvl | 182 |
| R3182 | [cyc10-triazolyl(1,6)]Ac-X02-V-E-R-F-X31-D-Tbg-Y-azaTrp-E-Y-P-Chg-Nvl | 183 |
| R3183 | [cyclo(1,6)]Ac-K-V-E-R-F-D-(N-Me)D-Tbg-Y-azaTrp-E-Y-P-Chg-(Lys-C16) | 184 |
| R3184 | [cyclo-thioalkyl(1,5)]V-E-R-F-C-D-Tbg-Y-azaTrp-E-Y-P-Chg-Nvl | 185 |
| R3185 | [mXylyl(1,6)]Ac-C-V-E-R-F-C-Cle-Tbg-Y-azaTrp-E-Y-P-Chg-Nvl | 186 |
| R3186 | [mXylyl(1,6)]Ac-C-V-E-R-F-C-(Ac-Pyran)-Tbg-Y-azaTrp-E-Y-P-Chg-Nvl | 187 |
| R3187 | [mXylyl(1,6)]Ac-C-V-E-R-F-C-D-Tbg-Y-azaTrp-E-(3-aminomethyl)Phe-P-Chg-Nvl | 188 |
| R3188 | [cyc10-olefinyl(1,6)]Ac-X30-V-E-R-F-X12-D-Tbg-Y-azaTrp-E-Y-P-Chg-Nvl | 189 |

TABLE 1-continued

Compounds of the invention

| Compound Number | Sequence | SEQ ID NO. |
|---|---|---|
| R3189 | [mXylyl(1,6)]Ac-C-A-E-R-F-C-D-Tbg-Y-azaTrp-E-Y-P-Phg-(Lys-C16) | 190 |
| R3190 | [cyclo(1,6)]Ac-K-V-E-R-F-D-(N-Me)D-Tbg-Y-azaTrp-E-Y-P-Chg-B20 | 191 |
| R3191 | [cyclo(1,6)]Ac-K-V-E-R-F-D-(N-Me)D-Tbg-Y-azaTrp-E-Y-P-Chg-K | 192 |
| R3192 | [cyclo(1,6)]Ac-K-V-E-R-F-D-(N-Me)D-Tbg-Y-azaTrp-E-Y-P-Chg-K-NH2 | 193 |
| R3193 | [cyclo(1,6)]Ac-K-V-E-R-F-D-(N-Me)D-Tbg-Y-azaTrp-E-Y-P-Chg-B28 | 194 |
| R3194 | [cyclo(1,6)]Ac-K-V-E-R-F-D-(N-Me)D-Tbg-Y-azaTrp-E-Y-P-Chg-(Lys-C16)-NH2 | 195 |
| R3195 | [cyclo(1,6)]Ac-K-V-E-R-F-D-(N-Me)D-Tbg-Y-W-E-Y-P-Chg-(Lys-C16) | 196 |
| R3196 | [cyclo(1,6)]Ac-K-V-E-R-F-D-(N-Me)D-Tbg-Y-W-E-Y-P-Chg-K | 197 |
| R3197 | [cyclo(1,6)]Ac-K-V-E-R-F-D-(N-Me)D-Tbg-Y-W-E-Y-P-Chg-K14 | 198 |
| R3198 | [cyclo (1,6)](de samino)C-V-E-R-F-C-(N-Me)D-Tbg-Y-azaTrp-E-Y-P-Chg-(Lys-C16) | 199 |
| R3199 | [cyclo (1,6)](de samino)C-(D-Ala)-E-R-F-C-(N-Me)D-Tbg-Y-azaTrp-E-Y-P-Chg-(Lys-C16) | 200 |
| R3200 | [cyclo(1,6)]Ac-K-V-E-R-F-D-(N-Me)D-Tbg-Y-azaTrp-E-Y-P-Aib-(Lys-C16) | 201 |
| R3201 | [mXylyl(1,6)]Ac-C-V-E-R-F-C-D-Tbg-Y-azaTrp-E-Y-P-Chg-Nvl | 211 |

In C5 systems, C5 and other system components may be in solution or may be fixed, such as in an assay well. C5 systems may further comprise other components of complement, in some cases including all of the components necessary to form the membrane attack complex (MAC.) In some cases, polypeptides and/or polypeptide compositions of the invention may be used to inhibit C5 cleavage in a human subject. Such polypeptides and/or polypeptide compositions may find utility in treating various complement-related disorders and/or diseases as well as accompanying inflammatory conditions. Certain C5 inhibitors are known in the art and are taught in U.S. Pat. Nos. 7,348,401 and 6,355,245; both of which are herein incorporated by reference in their entireties.

Cleavage of C5 yields the proteolytic products C5a and C5b. The cleavage site of C5 that is cleaved to yield these products is referred to herein as the C5a-C5b cleavage site. C5b contributes to the formation of the membrane attack complex (MAC) while C5a stimulates the immune system and the inflammatory response. In some embodiments, polypeptides and/or polypeptide compositions of the present invention prevent the cleavage of C5 and therefore may be useful in the treatment of inflammation through the inhibition of inflammatory events including, but not limited to chemotaxis and activation of inflammatory cells (e.g. macrophages, mast cells, neutrophils and platelets), proliferation of endothelial cells and edema.

Many of the components of the complement system, including but not limited to C3, C4, and C5, are functionally inert in their native state until targeted for cleavage into multiple active components. Cleavage of C3 or C4 causes a conformational change that exposes an internal thioester domain. Within the domain, an internal thioester linkage between cysteine and glutamine residue side chains is a chemically labile bond that confers the ability of C3 and C4 to bind cell surface and/or biological molecules. The cleavage of C3 and C4 also provides the components of the C5 convertase, either C3bC4bC2a or (C3b)$_2$Bb. (Law, S. K., et al. (1997). Protein Science. 6:263-274; van den Elsen, J. M. H., (2002). J. Mol. Biol. 322:1103-1115; the contents of each of which are herein incorporated by reference in their entireties.)

The multiple domain structure of C5 is similar to C3 and C4. The C5 convertase cleaves C5 into the components C5a and C5b. The cleavage of C5 causes a conformational change that exposes the C5b thioester-like domain, which plays a role in C5 binding C6, followed by interactions with C7 and C8 to form the cytolytic MAC. The domain structures of C5 comprise regulatory features that are critical for the processing and downstream activity of complement. (Fredslund, F. et al. (2008). Nature. 9:753-760; Hadders, M. A. et al. (2012). Cell Reports. 1:200-207.)

In some embodiments, compounds of the present invention may bind C5 and prevent cleavage of C5 into C5a and C5b cleavage products.

Recently, a new paradigm for complement activation was proposed, based upon the discovery that thrombin generates previously unidentified C5 products that support the terminal complement activation pathway (Krisinger, et al., (2014). Blood. 120(8):1717-1725).

Thrombin acts in the coagulation cascade, a second circulation-based process by which organisms, in response to injury, are able to limit bleeding, restore vascular integrity, and promote healing. Subsequent to vessel damage, tissue factor is exposed to the circulation, setting off a cascade of proteolytic reactions that leads to the generation of the central coagulation enzyme thrombin, which converts fibrinogen into a fibrin clot.

Historically, the complement activation pathway has been viewed separately from the coagulation cascade; however, the interplay of these two systems is worthy of renewed consideration. Coagulation and complement are coordinately activated in an overlapping spatiotemporal manner in response to common pathophysiologic stimuli to maintain homeostasis, and disease emerges when there is unchecked activation of the innate immune and coagulation responses, as evidenced by, for example, atherosclerosis, stroke, coronary heart disease, diabetes, ischemia-reperfusion injury, trauma, paroxysmal nocturnal hemoglobinuria, age-related macular degeneration, and atypical hemolytic-uremic syndrome. In fact, introduction of complement inhibitors has been found to simultaneously treat the inflammatory and thrombotic disturbances associated with some of these disorders.

As noted above, the complement system is activated via three main pathways, all converging with proteolytic activation of the central complement component C3. Subsequently, the formation of C5 convertases results in cleavage of C5 at arginine 751 (R751) to liberate a chemotactic and anaphylatoxic C5a fragment and generate C5b. C5b is the initiating factor for assembly of the C5b dependent lytic membrane attack complex (MAC; also known as C5b-9), responsible for destroying damaged cells and pathogens.

Several molecular links between complement and coagulation have been identified. Most notably in what was described as a new complement activation pathway, thrombin was found to be capable of directly promoting activation of complement by cleaving C5, presumably at R751, thereby releasing C5a in the absence of C3 (Huber-Lang, et al., 2006. Nature Med. 12(6):682-687). However, these studies did not compare thrombin with the bona fide C5 convertase, and only limited biochemical analyses were performed; thus, the physiologic relevance of the pathway was not evaluable.

Using purified and plasma-based systems, the effects of thrombin and C5 convertase on C5 were assessed by measuring release of the anaphylatoxin C5a and generation of the C5b, component of MAC. It was discovered that, while thrombin cleaved C5 poorly at R751, yielding minimal C5a and C5b, it efficiently cleaved C5 at a newly identified, highly conserved R947 site, generating previously undescribed intermediates $C5_T$ and $C5b_T$. Tissue factor-induced clotting of plasma led to proteolysis of C5 at a thrombin-sensitive site corresponding to this new R947 site and not R751. Combined treatment of C5 with thrombin and C5 convertase yielded C5a and $C5b_T$, the latter forming a $C5b_T$-9 membrane attack complex with significantly more lytic activity than with C5b-9. Thus, a new paradigm has been proposed for complement activation, in which thrombin is an invariant and critical partner with C5 convertase in initiating formation of a more active MAC via formation of previously unidentified C5 products that are generated via cooperative proteolysis by the two enzymes. These discoveries provide new insights into the regulation of innate immunity in the context of coagulation activation occurring in many diseases. (Krisinger, et al., (2014). Blood. 120(8): 1717-1725).

In some embodiments, polypeptides and/or polypeptide compositions of the invention may inhibit thrombin-induced complement activation. Such polypeptides and/or polypeptide compositions may therefore be used to treat hemolysis resulting from thrombin-induced complement activation.

Given the findings of molecular links between the complement and coagulation pathways, it is believed that complement may be activated by additional components of the coagulation and/or inflammation cascades. For example, other serine proteases with slightly different substrate specificity may act in a similar way. Huber-Lang et al. (2006) showed that thrombin not only cleaved C5 but also in vitro-generated C3a when incubated with native C3 (Huber-Lang, et al., 2006. Nature Med. 12(6):682-687; the contents of which are herein incorporated by reference in their entirety). Similarly, other components of the coagulation pathway, such as FXa, FXIa and plasmin, have been found to cleave both C5 and C3.

Specifically, in a mechanism similar to the one observed via thrombin activation, it has been observed that plasmin, FXa, FIXa and FXIa are able to cleave C5 to generate C5a and C5b (Amara, et al., (2010). J. Immunol. 185:5628-5636; Amara, et al., (2008) "Interaction Between the Coagulation and Complement System" in *Current Topics in Complement II*, J. D. Lambris (ed.), pp. 71-79). The anaphylatoxins produced were found to be biologically active as shown by a dose-dependent chemotactic response of neutrophils and HMC-1 cells, respectively. Plasmin-induced cleavage activity could be dose-dependently blocked by the serine protease inhibitor aprotinin and leupeptine. These findings suggest that various serine proteases belonging to the coagulation system are able to activate the complement cascade independently of the established pathways. Moreover, functional C5a and C3a are generated (as detected by immunoblotting and ELISA), both of which are known to be crucially involved in the inflammatory response.

In some embodiments, polypeptides and/or polypeptides compositions of the invention may inhibit activation of C5 by plasmin, FXa, FIXa, FXIa and other proteases of the coagulation pathway.

Human leukocyte elastase (HLE), an enzyme secreted by neutrophils and macrophages during inflammatory processes, has long been known to also release from C5 a chemotactic, C5a-like fragment. However, this C5a-like fragment, is not identical with C5a, as HLE does not cleave peptide bonds at the cleavage site that ordinarily cleaves C5 into C5a and C5b after the exposure to the complement convertases. Rather, cleavage of complement C5 by HLE has also been found to generate a functionally active C5b-like molecule that is able to participate in MAC formation (Vogt, (1999). Immunobiology. 201:470-477).

In some embodiments, polypeptides and/or polypeptides compositions of the invention may inhibit activation of C5 by HLE and other proteases of the inflammation cascade.

In some embodiments, polypeptides and/or polypeptide compositions of the present invention may be useful in the treatment of diseases, disorders and/or conditions where C5 cleavage leads to progression of the disease, disorder and/or condition. Such diseases, disorders and/or conditions may include, but are not limited to immune and autoimmune, neurological, cardiovascular, pulmonary, and ocular diseases, disorders and/or conditions. Immune and autoimmune diseases and/or disorders may include, but are not limited to Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Acute antibody-mediated rejection following organ transplantation, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticaria, Axonal & neuronal neuropathies, Bacterial sepsis and septic shock, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Diabetes Type I, Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia (including atypical hemolytic uremic syndrome and plasma therapy-resistant atypical hemolytic-uremic syndrome), Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type1), Interstitial cystitis, Juvenile arthritis, Juvenile diabetes, Kawasaki syndrome, Lambert-Eaton syndrome, Large vessel vasculopathy, Leukocytoclastic vasculitis, Lichen planus, Lichen sclerosus, Ligneous conjunctivitis, Linear IgA disease (LAD), Lupus (SLE), Lyme disease, Meniere's disease, Microscopic polyangiitis, Mixed connective tissue disease (MCTD), Mooren's ulcer, Mucha-Habermann disease, Multiple endocrine neoplasia syndromes, Multiple sclerosis, Multifocal motor neuropathy, Myositis, Myasthenia gravis, Narcolepsy, Neuromyelitis optica (Devic's), Neutropenia, Ocular cicatricial pemphigoid, Optic neuritis, Osteoarthritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polyendocrinopathies, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic Pulmonary fibrosis, Pyoderma gangrenosum, Pure red cell aplasia, Raynauds phenomenon, Reactive arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Shiga-Toxin producing *Escherichia coli* Hemolytic-Uremic Syndrome (STEC-HUS), Sjogren's syndrome, Small vessel vasculopathy, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Tubular autoimmune disorder, Ulcerative colitis, Undifferentiated connective tissue disease (UCTD), Uveitis, Vesiculobullous dermatosis, Vasculitis, Vitiligo and Wegener's granulomatosis (also known as Granulomatosis with Polyangiitis (GPA)). Neurological diseases, disorders and/or conditions may include, but are not limited to Alzheimer's disease, Parkinson's disease, Lewy body dementia and Multiple sclerosis. Cardiovascular diseases, disorders and/or conditions may include, but are not limited to atherosclerosis, myocardial infarction, stroke, vasculitis, trauma and conditions arising from cardiovascular intervention (including, but not limited to cardiac bypass surgery, arterial grafting and angioplasty). Pulmonary diseases, disorders and/or conditions may include, but are not limited to asthma, pulmonary fibrosis, chronic obstructive pulmonary disease (COPD) and adult respiratory distress syndrome. Ocular related applications include, but are not limited to: Age-related macular degeneration, allergic and giant papillary conjunctivitis, Behcet's disease, choroidal inflammation, complications related to intraocular surgery, corneal transplant rejection, corneal ulcers, cytomegalovirus retinitis, dry eye syndrome, endophthalmitis, Fuch's disease, Glaucoma, immune complex vasculitis, inflammatory conjunctivitis, ischemic retinal disease, keratitis, macular edema, ocular parasitic infestation/migration, retinitis pigmentosa, scleritis, Stargardt disease, subretinal fibrosis, uveitis, vitreo-retinal inflammation, and Vogt-Koyanagi-Harada disease.

Polypeptides and/or polypeptide compositions of the present invention may be particularly useful in the treatment of patients with PNH that show a poor response to monoclonal antibody therapies, such as ECULIZUMAB® therapy, due to mutations in the C5 gene that prevent binding of the antibody to C5 (Nishimura, J-I. (2012). 54$^{th}$ ASH Annual Meeting, Abstract 3197).

Polypeptides and/or polypeptide compositions of the present invention may be useful in the treatment of infectious diseases, disorders and/or conditions, for example, in a subject having an infection. In some preferred embodiments the subject has an infection and is at risk of developing sepsis or a septic syndrome. Polypeptides and/or polypeptide compositions of the present invention are particularly useful in the treatment of sepsis.

Polypeptides and/or polypeptide compositions of the present invention may also be administered to improve the outcome of clinical procedures wherein complement inhibition is desired. Such procedures may include, but are not limited to grafting, transplantation, implantation, catheterization, intubation and the like. In some embodiments, polypeptides and/or polypeptide compositions of the invention are used to coat devices, materials and/or biomaterials used in such procedures. In some embodiments, the inner surface of a tube may be coated with polypeptides and/or polypeptide compositions to prevent complement activation within a bodily fluid that passes through the tube, either in vivo or ex vivo, e.g., extracorporeal shunting, e.g., dialysis and cardiac bypass.

In some embodiments, polypeptides of the invention bind to C5 with 1:1 stoichiometry. In some cases, polypeptides of the invention inhibit through an allosteric mechanism or by blocking binding of convertase.

In some embodiments, polypeptides of the invention inhibit C5 cleavage in PNH patients with ECULIZUMAB®-resistant C5 polymorphisms.

II. Methods of Use

Included herein are methods of using compounds (e.g., any of the compounds listed in Table 1) or compositions of the invention to reduce C5 cleavage and downstream consequences including, but not limited to, complement activation, cell lysis, red blood cell lysis (also referred to herein as "hemolysis"). In some cases, such methods may include reducing cleavage of C5 in vitro or in vivo. In some cases, such methods may be carried out in a biological system, in an assay, or in a subject.

C5 cleavage, complement activation or hemolysis, according to the methods of the invention, may be reduced from about 1% to about 5%, from about 2% to about 10%, from about 5% to about 20%, from about 10% to about 30%, from about 20% to about 50%, from about 25% to about 75%, from about 30% to about 60%, from about 50% to about 75%, from about 50% to about 90%, from about 50% to about 95%, from about 75% to about 100%, from about 80% to about 100%, from about 85% to about 95%, or from about 90% to about 100%. Such reductions may be assessed by examining the levels of one or more C5 cleavage products (e.g., C5a or C5b proteins). In such embodiments, cleavage product levels may be compared to levels in an untreated control sample, subject or system or background measurement and the percent difference may be determined. Such cleavage products may be measured, in some cases, by immunoassay (e.g., EIA or ELISA). Similarly, events downstream of C5 cleavage may be measured and compared to an untreated control sample, subject or system or background measurement. In some cases, such events may include the formation of the membrane attack complex (MAC). MAC formation may be measured by ELISA (e.g., WIESLAB® ELISA, Euro Diagnostica, Malmo, Sweden). In some cases, hemolysis may be measured spectrophotochemically (e.g., observing optical density at about 412 nm wavelength) to detect release of hemoglobin from ruptured blood cells.

In some embodiments, methods of the invention include methods of reducing C5 cleavage in a biological system comprising providing a polypeptide of the invention. In some cases, such reduction is assessed by comparison to an untreated control system. Reduction in C5 cleavage may include reductions of at least 1%, at least 5%, at least 10%, at least 20%, at least 50%, at least 75%, at least 80%, at least 85%, at least 90%, at least 95%, at least 98%, at least 99%, or 100%. According to such methods, polypeptides may be provided at concentrations of from about 0.001 nM to about 5 nM, from about 0.01 nM to about 10 nM, from about 0.1 nM to about 50 nM, from about 1 nM to about 100 nM, from about 20 nM to about 200 nM, or from about 100 nM to about 10,000 nM.

In some embodiments, methods of the invention include methods of reducing hemolysis in a biological system comprising providing a polypeptide of the invention. In some cases, such reduction is assessed by comparison to an untreated control system. Reduction in hemolysis may include reductions of at least 1%, at least 5%, at least 10%, at least 20%, at least 50%, at least 75%, at least 80%, at least 85%, at least 90%, at least 95%, at least 98%, at least 99%, or 100%. According to such methods, polypeptides may be provided at concentrations of from about 0.001 nM to about 5 nM, from about 0.01 nM to about 10 nM, from about 0.1 nM to about 50 nM, from about 1 nM to about 100 nM, from about 20 nM to about 200 nM, or from about 100 nM to about 10,000 nM.

In some embodiments, methods of the invention include methods of reducing hemolysis in a subject relative to hemolysis levels previously observed in the subject. Reduction in hemolysis may include reductions of at least 1%, at least 5%, at least 10%, at least 20%, at least 50%, at least 75%, at least 80%, at least 85%, at least 90%, at least 95%, at least 98%, at least 99%, or 100%. In some cases, reductions in hemolysis may include reductions of from about 1% to about 10%, from about 5% to about 25%, from about 20% to about 60%, from about 40% to about 80%, from about 50% to about 95%, or from about 60% to about 100%. According to such methods, polypeptides may be provided at concentrations that include, but are not limited to from about 0.001 nM to about 5 nM, from about 0.01 nM to about 10 nM, from about 0.1 nM to about 50 nM, from about 1 nM to about 100 nM, from about 20 nM to about 200 nM, or from about 100 nM to about 10,000 nM. In some cases, polypeptides may be administered to human subjects using doses that include, but are not limited to from about 0.001 mg/kg to about 1 mg/kg, from about 0.01 mg/kg to about 2 mg/kg, from about 0.1 mg/kg to about 10 mg/kg, from about 1 mg/kg to about 20 mg/kg, or from about 5 mg/kg to about 50 mg/kg. In some cases, polypeptide concentrations used for administration may be varied to achieve a desired level of the polypeptide in the plasma of the subject receiving the polypeptide. In some cases, desired plasma levels of polypeptides of the invention may include, but are not limited to from about 0.001 µM to about 2 µM, from about 0.01 µM to about 3 µM, from about 0.1 µM to about 20 µM, or from about 1 µM to about 50 µM.

Therapeutic Indications

The invention relates in particular to the use of polypeptide (e.g. peptidomimetics and cyclic polypeptides) and compositions containing at least one polypeptide, for the treatment of a disorder, condition or disease. In some cases, compounds and compositions of the invention may be used to treat subjects suffering from paroxysmal nocturnal hemoglobinuria (PNH). Subjects with PNH are unable to synthesize functional versions of the complement regulatory proteins CD55 and CD59 on hematopoietic stem cells. This results in complement-mediated hemolysis and a variety of downstream complications. Other complement-related disorders and diseases include, but are not limited to autoimmune diseases and disorders, neurological diseases and disorders, blood diseases and disorders and infectious diseases and disorders. Experimental evidence suggests that many complement-related disorders are alleviated through inhibition of complement activity.

Current treatments for PNH include the use of ECULIZUMAB® (Alexion Pharmaceuticals, Cheshire, CT). In some cases, ECULIZUMAB® may be ineffective due to mutation in C5, short half-life, immune reaction, or other reason. In some embodiments, methods of the invention include methods of treating subjects with PNH, wherein such subjects have been treated previously with ECULIZUMAB®. In some cases, ECULIZUMAB® is ineffective in such patients, making treatment with polypeptides of the invention important for therapeutic relief. In some cases, polypeptides of the invention are administered simultaneously or in conjunction with ECULIZUMAB® therapy. In such cases, such subjects may experience one or more beneficial effects of such combined treatment, including, but not limited to more effective relief, faster relief or fewer side effects.

An acquired mutation in the phosphatidylinositol glycan anchor biosynthesis, class A (PIG-A) gene that originates from a multipotent hematopoietic stem cell results in a rare disease known as paroxysmal nocturnal hemoglobinuria (PNH) (Pu, J. J. et al., Paroxysmal nocturnal hemoglobinuria from bench to bedside. Clin Transl Sci. 2011 June; 4(3): 219-24). PNH is characterized by bone marrow disorder, hemolytic anemia and thrombosis. The PIG-A gene product is necessary for the production of a glycolipid anchor, glycosylphosphatidylinositol (GPI), utilized to tether proteins to the plasma membrane. Two complement-regulatory proteins, CD55 and CD59, become nonfunctional in the absence of GPI. This leads to complement-mediated destruction of these cells. Polypeptides and/or polypeptide compositions of the present invention are particularly useful in the treatment of PNH.

In some embodiments, methods of the invention include methods of reducing hemolysis in subjects with PNH. Such methods may include administering polypeptides of the invention to such subjects. According to such methods, polypeptides may be administered at doses that include, but are not limited to from about 0.001 mg/kg to about 1 mg/kg, from about 0.01 mg/kg to about 2 mg/kg, from about 0.1 mg/kg to about 10 mg/kg, from about 1 mg/kg to about 20 mg/kg, or from about 5 mg/kg to about 50 mg/kg. Additional methods may include single or multiple doses. In cases where multiple doses are administered, administration may include, but is not limited to daily, weekly, monthly, or yearly administration.

As used herein the terms "treat," "treatment," and the like, refer to relief from or alleviation of pathological processes. In the context of the present invention insofar as it relates to any of the other conditions recited herein below, the terms "treat," "treatment," and the like mean to relieve or alleviate at least one symptom associated with such condition, or to slow or reverse the progression or anticipated progression of such condition, such as slowing the progression of a malignancy or cancer, or increasing the clearance of an infectious organism to alleviate/reduce the symptoms caused by the infection, e.g., hepatitis caused by infection with a hepatitis virus or reducing the destruction of red blood cells (as measured by reduced transfusion requirements or increased hematocrit or hemoglobin levels) resulting from paroxysmal nocturnal hemoglobinuria.

By "lower" or "reduce" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

By "increase" or "raise" in the context of a disease marker or symptom is meant a statistically significant rise in such level. The increase can be, for example, at least 10%, at least 20%, at least 30%, at least 40% or more, and is preferably up to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes or an overt symptom of one or more pathological processes. The specific amount that is therapeutically effective can be readily determined by an ordinary medical practitioner, and may vary depending on factors known in the art, such as, for example, the type of pathological processes, patient history and age, the stage of pathological processes, and the administration of other agents that inhibit pathological processes.

As used herein, a "pharmaceutical composition" comprises a pharmacologically effective amount of a polypeptide and a pharmaceutically acceptable carrier. As used herein, "pharmacologically effective amount," "therapeutically effective amount" or simply "effective amount" refers to that amount of a polypeptide effective to produce the intended pharmacological, therapeutic or preventive result. For example, if a given clinical treatment is considered effective when there is at least a 10% alteration (increase or decrease) in a measurable parameter associated with a disease or disorder, a therapeutically effective amount of a drug for the treatment of that disease or disorder is the amount necessary to effect at least a 10% alteration in that parameter. For example, a therapeutically effective amount of a polypeptide may be one that alters binding of a target to its natural binding partner by at least 10%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a polypeptide or pharmaceutical composition thereof, "effective against" a disease or disorder indicates that administration in a clinically appropriate manner results in a beneficial effect for at least a fraction of patients, such as an improvement of symptoms, a cure, a reduction in disease load, reduction in tumor mass or cell numbers, extension of life, improvement in quality of life, a reduction in the need for blood transfusions or other effect generally recognized as positive by medical doctors familiar with treating the particular type of disease or disorder.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given polypeptide drug or formulation of that drug can also be judged using an experimental animal model for the given disease as known in the art. When using an experimental animal model, efficacy of treatment is evidenced when a statistically significant modulation in a marker or symptom is observed.

The polypeptide and an additional therapeutic agent can be administered in combination in the same composition, e.g., parenterally, or the additional therapeutic agent can be administered as part of a separate composition or by another method described herein.

Inflammatory Indications

In some embodiments, compounds and compositions of the invention may be used to treat subjects with diseases, disorders and/or conditions related to inflammation. Inflammation may be upregulated during the proteolytic cascade of the complement system. Although inflammation may have beneficial effects, excess inflammation may lead to a variety of pathologies (Markiewski et al. 2007. Am J Pathol. 17: 715-27). Accordingly, compounds and compositions of the present invention may be used to reduce or eliminate inflammation associated with complement activation.

Sterile Inflammation

In some embodiments, compounds and compositions of the present invention may be used to treat, prevent or delay development of sterile inflammation. Sterile inflammation is inflammation that occurs in response to stimuli other than infection. Sterile inflammation may be a common response to stress such as genomic stress, hypoxic stress, nutrient stress or endoplasmic reticulum stress caused by a physical, chemical, or metabolic noxious stimuli. Sterile inflammation may contribute to pathogenesis of many diseases such as, but not limited to, ischemia-induced injuries, rheumatoid arthritis, acute lung injuries, drug-induced liver injuries, inflammatory bowel diseases and/or other diseases, disorders or conditions. Mechanism of sterile inflammation and methods and compositions for treatment, prevention and/or delaying of symptoms of sterile inflammation may include any of those taught by Rubartelli et al. in Frontiers in Immunology, 2013, 4:398-99, Rock et al. in Annu Rev Immunol. 2010, 28:321-342 or in U.S. Pat. No. 8,101,586, the contents of each of which are herein incorporated by reference in their entirety.

Systemic Inflammatory Response (SIRS) and Sepsis

In some embodiments, compounds and compositions of the invention may be used to treat and/or prevent systemic inflammatory response syndrome (SIRS). SIRS is inflammation affecting the whole body. Where SIRS is caused by an infection, it is referred to as sepsis. SIRS may also be caused by non-infectious events such as trauma, injury, burns, ischemia, hemorrhage and/or other conditions. During sepsis and SIRS, complement activation leads to excessive generation of complement activation products which may cause multi organ failure (MOF) in subjects. Compounds and compositions of the invention may be used to control and/or balance complement activation for prevention and treatment of SIRS, sepsis and/or MOF. The methods of applying complement inhibitors to treat SIRS and sepsis may include those taught by Rittirsch et al. in Clin Dev Immunol, 2012, 962927, in U.S. publication No. US2013/0053302 or in U.S. Pat. No. 8,329,169, the contents of each of which are herein incorporated by reference in their entirety.

Acute Respiratory Distress Syndrome (ARDS)

In some embodiments, compounds and compositions of the invention may be used to treat and/or prevent development of acute respiratory distress syndrome (ARDS). ARDS is a widespread inflammation of the lungs and may be caused by trauma, infection (e.g., sepsis), severe pneumonia and/or inhalation of harmful substances. ARDS is typically a severe, life-threatening complication. Studies suggest that neutrophils may contribute to development of ARDS by affecting the accumulation of polymorphonuclear cells in the injured pulmonary alveoli and interstitial tissue of the lungs. Accordingly, compounds and compositions of the invention may be administered to reduce and/or prevent tissue factor production in alveolar neutrophils. Compounds and compositions of the invention may further be used for treatment, prevention and/or delaying of ARDS, in some cases according to any of the methods taught in International publication No. WO2009/014633, the contents of which are herein incorporated by reference in their entirety.

Periodontitis

In some embodiments, compounds and compositions of the invention may be used to treat or prevent development of periodontitis and/or associated conditions. Periodontitis is a widespread, chronic inflammation leading to the destruction of periodontal tissue which is the tissue supporting and surrounding the teeth. The condition also involves alveolar bone loss (bone that holds the teeth). Periodontitis may be caused by a lack of oral hygiene leading to accumulation of bacteria at the gum line, also known as dental plaque. Certain health conditions such as diabetes or malnutrition and/or habits such as smoking may increase the risk of periodontitis. Periodontitis may increase the risk of stroke, myocardial infarction, atherosclerosis, diabetes, osteoporosis, pre-term labor, as well as other health issues. Studies demonstrate a correlation between periodontitis and local complement activity. Periodontal bacteria may either inhibit or activate certain components of the complement cascade. Accordingly, compounds and compositions of the invention may be used to prevent and/or treat periodontitis and associated diseases and conditions. Complement activation inhibitors and treatment methods may include any of those taught by Hajishengallis in Biochem Pharmacol. 2010, 15; 80(12): 1 and Lambris or in US publication No. US2013/0344082, the contents of each of which are herein incorporated by reference in their entirety.

Wounds and Injuries

Compounds and compositions of the invention may be used to treat and/or promote healing of different types of wounds and/or injuries. As used herein, the term "injury" typically refers to physical trauma, but may include localized infection or disease processes. Injuries may be characterized by harm, damage or destruction caused by external events affecting body parts and/or organs. Wounds are associated with cuts, blows, burns and/or other impacts to the skin, leaving the skin broken or damaged. Wounds and injuries are often acute but if not healed properly they may lead to chronic complications and/or inflammation.

Wounds and Burn Wounds

In some embodiments, compounds and compositions of the invention may be used to treat and/or to promote healing of wounds. Healthy skin provides a waterproof, protective barrier against pathogens and other environmental effectors. The skin also controls body temperature and fluid evaporation. When skin is wounded these functions are disrupted making skin healing challenging. Wounding initiates a set of physiological processes related to the immune system that repair and regenerate tissue. Complement activation is one of these processes. Complement activation studies have identified several complement components involved with wound healing as taught by van de Goot et al. in J Burn Care Res 2009, 30:274-280 and Cazander et al. Clin Dev Immunol, 2012, 2012:534291, the contents of each of which are herein incorporated by reference in their entirety. In some cases, complement activation may be excessive, causing cell death and enhanced inflammation (leading to impaired wound healing and chronic wounds). In some cases, compounds and compositions of the present invention may be used to reduce or eliminate such complement activation to promote wound healing. Treatment with compounds and compositions of the invention may be carried out according to any of the methods for treating wounds disclosed in International publication number WO2012/174055, the contents of which are herein incorporated by reference in their entirety.

Head Trauma

In some embodiments, compounds and compositions of the invention may be used to treat and/or promote healing of head trauma. Head traumas include injuries to the scalp, the skull or the brain. Examples of head trauma include, but are not limited to concussions, contusions, skull fracture, traumatic brain injuries and/or other injuries. Head traumas may be minor or severe. In some cases, head trauma may lead to long term physical and/or mental complications or death. Studies indicate that head traumas may induce improper intracranial complement cascade activation, which may lead to local inflammatory responses contributing to secondary brain damage by development of brain edema and/or neuronal death (Stahel et al. in Brain Research Reviews, 1998, 27: 243-56, the contents of which are herein incorporated by reference in their entirety). Compounds and compositions of the invention may be used to treat head trauma and/or to reduce or prevent related secondary complications. Methods of using compounds and compositions of the invention to control complement cascade activation in head trauma may include any of those taught by Holers et al. in U.S. Pat. No. 8,911,733, the contents of which are herein incorporated by reference in their entirety.

Crush Injury

In some embodiments, compounds and compositions of the invention may be used to treat and/or promote healing of crush injuries. Crush injuries are injuries caused by a force or a pressure put on the body causing bleeding, bruising, fractures, nerve injuries, wounds and/or other damages to the body. Compounds and compositions of the invention may be used to reduce complement activation following crush injuries, thereby promoting healing after crush injuries (e.g. by promoting nerve regeneration, promoting fracture healing, preventing or treating inflammation, and/or other related complications). Compounds and compositions of the invention may be used to promote healing according to any of the methods taught in U.S. Pat. No. 8,703,136; International Publication Nos. WO2012/162215; WO2012/174055; or US publication No. US2006/0270590, the contents of each of which are herein incorporated by reference in their entirety.

Autoimmune Disease

The compounds and compositions of the invention may be used to treat subjects with autoimmune diseases and/or disorders. The immune system may be divided into innate and adaptive systems, referring to nonspecific immediate defense mechanisms and more complex antigen-specific systems, respectively. The complement system is part of the innate immune system, recognizing and eliminating pathogens. Additionally, complement proteins may modulate adaptive immunity, connecting innate and adaptive responses. Autoimmune diseases and disorders are immune abnormalities causing the system to target self tissues and substances. Autoimmune disease may involve certain tissues or organs of the body. Compounds and compositions of the invention may be used to modulate complement in the treatment and/or prevention of autoimmune diseases. In some cases, such compounds and compositions may be used according to the methods presented in Ballanti et al. Immunol Res (2013) 56:477-491, the contents of which are herein incorporated by reference in their entirety.

Anti-Phospholipid Syndrome (APS) and Catastrophic Anti-Phospholipid Syndrome (CAPS)

In some embodiments, compounds and compositions of the invention may be used to prevent and/or treat anti-phospholipid syndrome (APS) by complement activation control. APS is an autoimmune condition caused by anti-phospholipid antibodies that cause the blood to clot. APS may lead to recurrent venous or arterial thrombosis in organs, and complications in placental circulations causing pregnancy-related complications such as miscarriage, still birth, preeclampsia, premature birth and/or other complications. Catastrophic anti-phospholipid syndrome (CAPS) is an extreme and acute version of a similar condition leading to occlusion of veins in several organs simultaneously. Studies suggest that complement activation may contribute to APS-related complications including pregnancy-related complications, thrombotic (clotting) complications, and vascular complications. Compound and compositions of the invention may be used to treat APS-related conditions by reducing or eliminating complement activation. In some cases, compounds and compositions of the invention may be used to treat APS and/or APS-related complications according to the methods taught by Salmon et al. Ann Rheum Dis 2002; 61(Suppl II):ii46-ii50 and Mackworth-Young in Clin Exp Immunol 2004, 136:393-401, the contents of which are herein incorporated by reference in their entirety.

Cold Agglutinin Disease

In some embodiments, compounds and compositions of the invention may be used to treat cold agglutinin disease (CAD), also referred to as cold agglutinin-mediated hemolysis. CAD is an autoimmune disease resulting from a high concentration of IgM antibodies interacting with red blood cells at low range body temperatures [Engelhardt et al. Blood, 2002, 100(5):1922-23]. CAD may lead to conditions such as anemia, fatigue, dyspnea, hemoglobinuria and/or acrocyanosis. CAD is related to robust complement activation and studies have shown that CAD may be treated with complement inhibitor therapies. Accordingly, the present invention provides methods of treating CAD using compounds and compositions of the invention. In some cases, compounds and compositions of the invention may be used to treat CAD according to the methods taught by Roth et al in Blood, 2009, 113:3885-86 or in International publication No. WO2012/139081, the contents of each of which are herein incorporated by reference in their entirety.

Vascular Indications

In some embodiments, compounds and compositions of the invention may be used to treat vascular indications affecting blood vessels (e.g., arteries, veins, and capillaries). Such indications may affect blood circulation, blood pressure, blood flow, organ function and/or other bodily functions.

Thrombotic Microangiopathy (TMA)

In some embodiments, compounds and compositions of the invention may be used to treat and/or prevent thrombotic microangiopathy (TMA) and associated diseases. Microangiopathies affect small blood vessels (capillaries) of the body causing capillary walls to become thick, weak, and prone to bleeding and slow blood circulation. TMAs tend to lead to the development of vascular thrombi, endothelial cell damage, thrombocytopenia, and hemolysis. Organs such as the brain, kidney, muscles, gastrointestinal system, skin, and lungs may be affected. TMAs may arise from medical operations and/or conditions that include, but are not limited to, hematopoietic stem cell transplantation (HSCT), renal disorders, diabetes and/or other conditions. TMAs may be caused by underlying complement system dysfunction, as described by Meri et al. in European Journal of Internal Medicine, 2013, 24: 496-502, the contents of which are herein incorporated by reference in their entirety. Generally, TMAs may result from increased levels of certain complement components leading to thrombosis. In some cases, this may be caused by mutations in complement proteins or related enzymes. Resulting complement dysfunction may lead to complement targeting of endothelial cells and platelets leading to increased thrombosis. In some embodiments, TMAs may be prevented and/or treated with compounds and compositions of the invention. In some cases, methods of treating TMAs with compounds and compositions of the invention may be carried out according to those described in US publication Nos. US2012/0225056 or US2013/0246083, the contents of each of which are herein incorporated by reference in their entirety.

Disseminated Intravascular Coagulation (DIC)

In some embodiments, compounds and compositions of the invention may be used to prevent and/or treat disseminated intravascular coagulation (DIC) by controlling complement activation. DIC is a pathological condition where the clotting cascade in blood is widely activated and results in formation of blood clots especially in the capillaries. DIC may lead to an obstructed blood flow of tissues and may eventually damage organs. Additionally, DIC affects the normal process of blood clotting that may lead to severe bleeding. Compounds and compositions of the invention may be used to treat, prevent or reduce the severity of DIC by modulating complement activity. In some cases compounds and compositions of the invention may be used according to any of the methods of DIC treatment taught in U.S. Pat. No. 8,652,477, the contents of which are herein incorporated by reference in their entirety.

Vasculitis

In some embodiments, compounds and compositions of the invention may be used to prevent and/or treat vasculitis. Generally, vasculitis is a disorder related to inflammation of blood vessels, including veins and arteries, characterized by white blood cells attacking tissues and causing swelling of the blood vessels. Vasculitis may be associated with an infection, such as in Rocky Mountain spotted fever, or autoimmunity. An example of autoimmunity associated vasculitis is Anti-Neutrophil Cytoplasmic Autoantibody (ANCA) vasculitis. ANCA vasculitis is caused by abnormal antibodies attacking the body's own cells and tissues. ANCAs attack the cytoplasm of certain white blood cells and neutrophils, causing them to attack the walls of the vessels in certain organs and tissues of the body. ANCA vasculitis may affect skin, lungs, eyes and/or kidney. Studies suggest that ANCA disease activates an alternative complement pathway and generates certain complement components that create an inflammation amplification loop resulting in a vascular injury (Jennette et al. 2013, Semin Nephrol. 33(6): 557-64, the contents of which are herein incorporated by reference in their entirety). In some cases, compounds and compositions of the invention may be used to prevent and/or treat ANCA vasculitis by inhibiting complement activation.

Neurological Indications

The compounds and compositions of the invention may be used to prevent, treat and/or ease the symptoms of neurological indications, including, but not limited to neurodegenerative diseases and related disorders. Neurodegeneration generally relates to a loss of structure or function of neurons, including death of neurons. These disorders may be treated by inhibiting the effect of complement on neuronal cells using compounds and compositions of the invention. Neurodegenerative related disorders include, but are not limited to, Amyelotrophic Lateral Sclerosis (ALS), Multiple Sclerosis (MS), Parkinson's disease and Alzheimer's disease.

Amyotrophic Lateral Sclerosis (ALS)

In some embodiments, compounds and compositions of the invention may be used to prevent, treat and/or ease the symptoms of ALS. ALS is a fatal motor neuron disease characterized by the degeneration of spinal cord neurons, brainstems and motor cortex. ALS causes loss of muscle strength leading eventually to a respiratory failure. Complement dysfunction may contribute to ALS, and therefore ALS may be prevented, treated and/or the symptoms may be reduced by therapy with compounds and compositions of the invention targeting complement activity. In some cases, compounds and compositions of the invention may be used to promote nerve regeneration. In some cases, compounds and compositions of the invention may be used as complement inhibitors according to any of the methods taught in US publication No. US2014/0234275 or US2010/0143344, the contents of each of which are herein incorporated by reference in their entirety.

Alzheimer's Disease

In some embodiments, compounds and compositions of the invention may be used to prevent and/or treat Alzheimer's disease by controlling complement activity. Alzheimer's disease is a chronic neurodegenerative disease with symptoms that may include disorientation, memory loss, mood swings, behavioral problems and eventually loss of bodily functions. Alzheimer's disease is thought to be caused by extracellular brain deposits of amyloid that are associated with inflammation-related proteins such as complement proteins (Sjoberg et al. 2009. Trends in Immunology. 30(2): 83-90, the contents of which are herein incorporated by reference in their entirety). In some cases, compounds and compositions of the invention may be used as complement inhibitors according to any of the Alzheimer's treatment methods taught in US publication No. US2014/0234275, the contents of which are herein incorporated by reference in their entirety.

Kidney-Related Indications

The compounds and compositions of the invention may be used to treat certain diseases, disorders and/or conditions related to kidneys, in some cases by inhibiting complement activity. Kidneys are organs responsible for removing metabolic waste products from the blood stream. Kidneys regulate blood pressure, the urinary system, and homeostatic functions and are therefore essential for a variety of bodily functions. Kidneys may be more seriously affected by inflammation (as compared to other organs) due to unique structural features and exposure to blood. Kidneys also produce their own complement proteins which may be activated upon infection, kidney disease, and renal transplantations. In some cases, compounds and compositions of the invention may be used as complement inhibitors in the treatment of certain diseases, conditions, and/or disorders of the kidney according to the methods taught by Quigg, J Immunol 2003; 171:3319-24, the contents of which are herein incorporated by reference in their entirety.

Lupus Nephritis

In some embodiments, compounds and compositions of the invention may be used to prevent and/or treat lupus nephritis by inhibiting complement activity. Lupus nephritis is a kidney inflammation caused by an autoimmune disease called systemic lupus erythematosus (SLE). Symptoms of lupus nephritis include high blood pressure; foamy urine; swelling of the legs, the feet, the hands, or the face; joint pain; muscle pain; fever; and rash. Lupus nephritis may be treated by inhibitors that control complement activity, including compounds and compositions of the present invention. Methods and compositions for preventing and/or treating Lupus nephritis by complement inhibition may include any of those taught in US publication No. US2013/0345257 or U.S. Pat. No. 8,377,437, the contents of each of which are herein incorporated by reference in their entirety.

Membranous Glomerulonephritis (MGN)

In some embodiments, compounds and compositions of the invention may be used to prevent and/or treat membranous glomerulonephritis (MGN) disorder by inhibiting the activation of certain complement components. MGN is a disorder of the kidney that may lead to inflammation and structural changes. MGN is caused by antibodies binding to a soluble antigen in kidney capillaries (glomerulus). MGN may affect kidney functions, such as filtering fluids and may lead to kidney failure. Compounds and compositions of the invention may be used according to methods of preventing and/or treating MGN by complement inhibition taught in U.S. publication No. US2010/0015139 or in International publication No. WO2000/021559, the contents of each of which are herein incorporated by reference in their entirety.

Hemodialysis Complications

In some embodiments, compounds and compositions of the invention may be used to prevent and/or treat complications associated with hemodialysis by inhibiting complement activation. Hemodialysis is a medical procedure used to maintain kidney function in subjects with kidney failure. In hemodialysis, the removal of waste products such as creatinine, urea, and free water from blood is performed externally. A common complication of hemodialysis treatment is chronic inflammation caused by contact between blood and the dialysis membrane. Another common complication is thrombosis referring to a formation of blood clots that obstructs the blood circulation. Studies have suggested that these complications are related to complement activation. Hemodialysis may be combined with complement inhibitor therapy to provide means of controlling inflammatory responses and pathologies and/or preventing or treating thrombosis in subjects going through hemodialysis due to kidney failure. Methods of using compounds and compositions of the invention for treatment of hemodialysis complications may be carried out according to any of the methods taught by DeAngelis et al in Immunobiology, 2012, 217(11): 1097-1105 or by Kourtzelis et al. Blood, 2010, 116(4):631-639, the contents of each of which are herein incorporated by reference in their entirety.

Ocular Diseases

In some embodiments, compounds and compositions of the invention may be used to prevent and/or treat certain ocular related diseases, disorders and/or conditions. In a healthy eye the complement system is activated at a low level and is continuously regulated by membrane-bound and soluble intraocular proteins that protect against pathogens. Therefore the activation of complement plays an important role in several complications related to the eye and controlling complement activation may be used to treat such diseases. Compounds and compositions of the invention may be used as complement inhibitors in the treatment of ocular disease according to any of the methods taught by Jha et al. in Mol Immunol. 2007; 44(16): 3901-3908 or in U.S. Pat. No. 8,753,625, the contents of each of which are herein incorporated by reference in their entirety.

Age-Related Macular Degeneration (AMD)

In some embodiments, compounds and compositions of the invention may be used to prevent and/or treat age-related macular degeneration (AMD) by inhibiting ocular complement activation. AMD is a chronic ocular disease causing blurred central vision, blind spots in central vision, and/or eventual loss of central vision. Central vision affects ability to read, drive a vehicle and/or recognize faces. AMD is generally divided into two types, non-exudative (dry) and exudative (wet). Dry AMD refers to the deterioration of the macula which is the tissue in the center of the retina. Wet AMD refers to the failure of blood vessels under the retina leading to leaking of blood and fluid. Several human and animal studies have identified complement proteins that are related to AMD and novel therapeutic strategies included controlling complement activation pathways, as discussed by Jha et al. in Mol Immunol. 2007; 44(16): 3901-8. Methods of the invention involving the use of compounds and compositions of the invention for prevention and/or treatment of AMD may include any of those taught in US publication Nos. US2011/0269807 or US2008/0269318, the contents of each of which are herein incorporated by reference in their entirety.

Corneal Disease

In some embodiments, compounds and compositions of the invention may be used to prevent and/or treat corneal diseases by inhibiting ocular complement activation. The complement system plays an important role in protection of the cornea from pathogenic particles and/or inflammatory antigens. The cornea is the outermost front part of the eye covering and protecting the iris, pupil and anterior chamber and is therefore exposed to external factors. Corneal diseases include, but are not limited to, keratoconus, keratitis, ocular herpes and/or other diseases. Corneal complications may cause pain, blurred vision, tearing, redness, light sensitivity and/or corneal scarring. The complement system is critical for corneal protection, but complement activation may cause damage to the corneal tissue after an infection is cleared as certain complement compounds are heavily expressed. Methods of the present invention for modulating complement activity in the treatment of corneal disease may include any of those taught by Jha et al. in Mol Immunol. 2007; 44(16): 3901-8, the contents of which are herein incorporated by reference in their entirety.

Autoimmune Uveitis

In some embodiments, compounds and compositions of the invention may be used to prevent and/or treat uveitis, which is an inflammation of the uveal layer of the eye. Uvea is the pigmented area of the eye comprising the choroids, iris and ciliary body of the eye. Uveitis causes redness, blurred vision, pain, synechia and may eventually cause blindness. Studies have indicated that complement activation products are present in the eyes of patients with autoimmune uveitis and complement plays an important role in disease development. In some cases, compounds and compositions of the invention may be used to treat and/or prevent uveitis according to any of the methods identified in Jha et al. in Mol Immunol. 2007. 44(16): 3901-8, the contents of which are herein incorporated by reference in their entirety.

Diabetic Retinopathy

In some embodiments, compounds and compositions of the invention may be used to prevent and/or treat diabetic retinopathy which is a disease caused by changes in retinal blood vessels in diabetic patients. Retinopathy may cause blood vessel swelling and fluid leaking and/or growth of abnormal blood vessels. Diabetic retinopathy affects vision and may eventually lead to blindness. Studies have suggested that activation of complement has an important role in the development of diabetic retinopathy. In some cases, compounds and compositions of the invention may be used according to methods of diabetic retinopathy treatment described in Jha et al. Mol Immunol. 2007; 44(16): 3901-8, the contents of which are herein incorporated by reference in their entirety.

Pre-Eclampsia and HELLP-Syndrome

In some embodiments, compounds and compositions of the invention may be used to prevent and/or treat pre-eclampsia and/or HELLP (abbreviation standing for syndrome features of 1) hemolysis, 2) elevated liver enzymes and 3) low platelet count) syndrome by complement inhibitor therapy. Pre-eclampsia is a disorder of pregnancy with symptoms including elevated blood pressure, swelling, shortness of breath, kidney dysfunction, impaired liver function and/or low blood platelet count. Pre-eclampsia is typically diagnosed by a high urine protein level and high blood pressure. HELLP syndrome is a combination of hemolysis, elevated liver enzymes and low platelet conditions. Hemolysis is a disease involving rupturing of red blood cells leading to the release of hemoglobin from red blood cells. Elevated liver enzymes may indicate a pregnancy-induced liver condition. Low platelet levels lead to reduced clotting capability, causing danger of excessive bleeding. HELLP is associated with a pre-eclampsia and liver disorder. HELLP syndrome typically occurs during the later stages of pregnancy or after childbirth. It is typically diagnosed by blood tests indicating the presence of the three conditions it involves. Typically HELLP is treated by inducing delivery.

Studies suggest that complement activation occurs during HELLP syndrome and pre-eclampsia and that certain complement components are present at increased levels during HELLP and pre-eclampsia. Complement inhibitors may be used as therapeutic agents to prevent and/or treat these conditions. Compounds and compositions of the invention may be used according to methods of preventing and/or treating HELLP and pre-eclampsia taught by Heager et al. in Obstetrics & Gynecology, 1992, 79(1):19-26 or in International publication No. WO201/078622, the contents of each of which are herein incorporated by reference in their entirety.

Dosage and Administration

For use as treatment of human subjects, polypeptides can be formulated as pharmaceutical compositions. Depending on the subject to be treated, the mode of administration, and the type of treatment desired (e.g., prevention, prophylaxis, or therapy) the polypeptides are formulated in ways consonant with these parameters. A summary of such techniques is found in Remington: The Science and Practice of Pharmacy, 21st Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

Compositions of the present invention are preferably provided in a therapeutically effective amount, which may be, for example, a daily amount of from about 0.1 mg to about 100 mg, from about 0.5 mg to about 200 mg, from about 1 mg to about 300 mg, from about 5 mg to about 500 mg, from about 10 mg to about 750 mg, from about 50 mg to about 1000 mg or at least 1000 mg. In one embodiment, a pharmaceutical composition comprises a capsule, for example in unit dosage form.

According to some methods of the invention, compounds and compositions of the invention are provided at concentrations needed to achieve a desired effect. In some cases, compounds and compositions of the invention are provided at an amount necessary to reduce a given reaction or process by half. The concentration needed to achieve such a reduction is referred to herein as the half maximal inhibitory concentration, or "$IC_{50}$." Alternatively, compounds and compositions of the invention may be provided at an amount necessary to increase a given reaction, activity or process by half. The concentration needed for such an increase is referred to herein as the half maximal effective concentration of "$EC_{50}$."

Unit Dosage Forms

The polypeptides of the invention may be present in amounts totaling 0.1-95% by weight of the total weight of the composition. The composition may be provided in a dosage form that is suitable for oral administration. Thus, the pharmaceutical composition may be in the form of, e.g., hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, minicapsules, lozenges, films, strips, gelcaps, dragees, solutions, emulsions, suspensions, syrups, or sprays.

Subjects may be administered a therapeutic amount of a polypeptide, including, but not limited to doses of 0.01 mg/kg, 1.0 mg/kg, or 15 mg/kg. In some cases, polypeptides of the invention are administered at from about 0.001 mg/kg to about 1.0 mg/kg, from about 0.01 mg/kg to about 2.0 mg/kg, from about 0.05 mg/kg to about 5.0 mg/kg, from about 0.03 mg/kg to about 3.0 mg/kg, from about 0.01 mg/kg to about 10 mg/kg, from about 1.0 mg/kg to about 5.0 mg/kg, from about 2.0 mg/kg to about 4.0 mg/kg, from about 1.5 mg/kg to about 7.5 mg/kg, from about 5.0 mg/kg to about 15 mg/kg, from about 7.5 mg/kg to about 12.5 mg/kg, or from about 10 mg/kg to about 20 mg/kg. Such ranges include ranges suitable for administration to human subjects. In some cases, human subjects may be administered from about 0.01 mg/kg to about 10 mg/kg, from about 0.01 mg/kg to about 15 mg/kg, or from about 3 mg/kg to about 5 mg/kg. Dosage levels may be highly dependent on the nature of the condition; drug efficacy; the condition of the patient; the judgment of the practitioner; and the frequency and mode of administration.

In some cases, polypeptides of the invention are provided at concentrations adjusted to achieve a desired level of such polypeptides in a sample, biological system, or subject (e.g., plasma level in a subject). In some cases, desired concentrations of polypeptides in a sample, biological system or subject may include concentrations of from about 0.001 nM to about 0.01 nM, from about 0.005 nM to about 0.05 nM, from about 0.02 nM to about 0.2 nM, from about 0.03 nM to about 0.3 nM, from about 0.05 nM to about 0.5 nM, from about 0.01 nM to about 2.0 nM, from about 0.1 nM to about 50 nM, from about 0.1 nM to about 10 nM, from about 0.1 nM to about 5 nM, or from about 0.2 nM to about 20 nM. In some cases, desired concentrations of polypeptides in subject plasma may be from about 0.01 mg/L to about 2 mg/L, from about 0.02 mg/L to about 4 mg/L, from about 0.05 mg/L to about 5 mg/L, from about 0.1 mg/L to about 1.0 mg/L, from about 0.2 mg/L to about 2.0 mg/L, from about 0.5 mg/L to about 5 mg/L, from about 1 mg/L to about 5 mg/L, from about 2 mg/L to about 10 mg/L, from about 3 mg/L to about 9 mg/L, or from about 5 mg/L to about 20 mg/L.

In other embodiments, the polypeptides are administered at a frequency of e.g., every 4 hr, every 6 hr, every 12 hr, every 18 hr, every 24 hr, every 36 hr, every 72 hr, every 84 hr, every 96 hr, every 5 days, every 7 days, every 10 days, every 14 days, every 3 weeks, or more. The compositions can be administered once daily or the polypeptide can be administered as two, three, or more sub-doses at appropriate intervals throughout the day or delivery through a controlled release formulation. In that case, the polypeptide contained in each sub-dose must be correspondingly smaller in order to achieve the total daily dosage. The dosage unit can also be compounded for delivery over several days, e.g., using a conventional sustained release formulation, which provides sustained release of the polypeptide over a several-day-period.

Sustained release formulations are well known in the art and are particularly useful for delivery of agents to a particular site, such as could be used with the polypeptide compositions of the present invention. The effect of a single dose can be long-lasting, such that subsequent doses are administered at not more than 3-, 4-, or 5-day intervals, or at not more than 1, 2-, 3-, or 4-week intervals.

The polypeptide can be administered by intravenous infusion over a period of time, such as over a 5 minute, 10 minute, 15 minute, 20 minute, or 25 minute period. The administration may be repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the polypeptide or composition can reduce, lower, increase or alter binding or any physiologically deleterious process, e.g., in a cell, tissue, blood, urine or other compartment of a patient by at least 10%, at least 15%, at least 20%, at least 25%, at least 30%, at least 40%, at least 50%, at least 60%, at least 70%, at least 80% or at least 90% or more.

Before administration of a full dose of the polypeptide and/or polypeptide composition, patients can be administered a smaller dose, such as 5% of a full dose, and monitored for adverse effects, such as an allergic reaction or infusion reaction, or for elevated lipid levels or blood pressure. In another example, the patient can be monitored for unwanted immunostimulatory effects, such as increased cytokine (e.g., TNF-alpha, Il-1, Il-6, or Il-10) levels.

Genetic predisposition plays a role in the development of some diseases or disorders. Therefore, a patient in need of a polypeptide and/or polypeptide composition may be identified by taking a family history, or, for example, screening for one or more genetic markers or variants. A healthcare provider, such as a doctor, nurse, or family member, can take a family history before prescribing or administering a therapeutic composition of the present invention.

III. Kits

Any of the compositions described herein may be comprised in a kit. In a non-limiting example, polypeptides may be included in a kit for treating a disease. The kit may include a vial of sterile, dry polypeptide powder, sterile solution for dissolving the dried powder, and a syringe for infusion set for administering the polypeptide.

When polypeptides are provided as a dried powder it is contemplated that between 10 micrograms and 1000 milligrams of polypeptide, or at least or at most those amounts are provided in kits of the invention The container means will generally include at least one vial, test tube, flask, bottle, syringe and/or other container means, into which the polypeptide formulations are placed, preferably, suitably allocated. The kits may also comprise a second container means for containing a sterile, pharmaceutically acceptable buffer and/or other diluent.

A kit can include instructions for employing the kit components as well the use of any other reagent not included in the kit. Instructions may include variations that can be implemented.

While various embodiments of the invention have been particularly shown and described, it will be understood by those skilled in the art that various changes in form and details may be made therein without departing from the spirit and scope of the invention as defined by the appended claims.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the terms "consisting of" and "or including" are thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Preparation of Biotinylated C5

An effective final molar ratio of 1:4 C5 to biotin was used for large scale biotinylation. A 10 mM solution of EZ-Link Sulfo-NHS-LC Biotin (Thermo Scientific, Billerica, MA) was prepared as per the manufacturer's instructions. To 1 mg of 1 mg/ml C5 (Complement Tech, Tyler TX), 2.1 µl of the 10 mM biotin solution was added and incubated on ice for 2 hours. The reaction was quenched for 30 minutes at 4° C. after the addition of 100 µl of 1 M Tris HCl pH 7.5. The reaction was dialyzed overnight against cold PBST (phosphate buffered saline (PBS)+0.1% Tween 80). The biotinylated-C5 was aliquoted and stored at −80° C. Biotinylated C5 was characterized by SDS-PAGE under reducing and non-reducing conditions and characterized for activity by a red blood cell hemolysis assay. Biotinylated C5 was also checked for recovery on streptavidin beads (Invitrogen, Grand Island, NY). Capture was performed using conditions recommended by the manufacturer. To capture 4 µg of biotinylated-C5 from a 100 nM solution, 40 µl of bead slurry was used and incubated at 4° C. for 1 hour. The concentration of the captured biotinylated C5 was calculated by running a known amount of C5 on a NuPage 4-12% Bis-Tris gel (Invitrogen, Grand Island, NY).

Example 2. Human Hemolysis Assay for OC of Biotinylated C5

A hemolysis assay was performed with C5-depleted sera and biotinylated C5 and non-biotinylated C5 to compare the lysis activities of C5 before and after biotinylation. Antibody-sensitized sheep erythrocytes (Complement Technology, Tyler TX) in solution at $5 \times 10^8$ cell/ml were centrifuged at 2,090×gravity for 3 minutes and resuspended in GVB++ buffer (Complement Technology, Tyler TX). C5-depleted human sera (Complement Technology, Tyler TX) was rapidly thawed at 37° C. and placed on ice until diluted in GVB++. Non-biotinylated C5 protein (Complement Technology, Tyler TX) and biotinylated C5 protein (in-house biotinylation) was rapidly thawed at 37° C. and placed on a wet ice slurry until diluted in GVB++. 100 µl of cells (at a final concentration of $2.5 \times 10^7$ cells/ml) was combined with C5-depleted human sera and 50 µl biotinylated C5 or non-biotinylated C5 (with final concentrations of either 10 µg/ml, 3 µg/ml or 1 µg/ml) in a tissue culture-treated clear 96-well microtitre plate (USA Scientific, Ocala, FL). The plate was incubated for 1 hour at 37° C. After incubation, plates were then centrifuged at 2,090×gravity for 2 minutes before transferring 100 µl of supernatant to a new microtitre plate. Absorbance was read at 412 nm and percent lysis activity of non-biotinylated C5 and biotinylated C5 was compared.

Example 3. Selection of Polypeptides Binding C5

C5 inhibitors were identified through several rounds of mRNA display and selection. mRNA display was performed generally as described (Roberts, R. W., and Szostak, J. W. (1997). Proc. Natl. Acad. Sci. USA 94, 12297-12302; WO2009067191; herein incorporated by reference in its entirety) with modifications as described herein. RNA pools were generated by in vitro transcription from DNA synthesized with fixed N-terminal methionine and cysteine codons, followed by three positions of a sixteen codon phosphoramidite mixture, followed by eight positions of a second codon mixture also containing the cysteine codon. The resulting mRNA library has a fixed initiating methionine followed by a cysteine residue, followed by three positions lacking cysteine, followed by eight positions in which cysteine occurs with a frequency of 12.5%. To conduct the selection, the first round of enrichment comprised a first step in which RNA pools containing a 3' terminal UV cross-linked oligonucleotide containing puromycin were translated in vitro with the purified translation components listed in Table 2. Translation was carried out under two separate conditions to generate two unique libraries based on amino acid variation. The first condition utilized only the 20 natural amino acids while the second condition utilized natural amino acids (0.1 mM of histidine, threonine, proline, lysine, asparagine, tyrosine, glutamic acid and cysteine), unnatural amino acids (2 mM tertbutyl-glycine (Tbg), 0.8 mM 7-azatryptophan (abbreviated by "azaTrp" in this example) and 1 mM norvaline (Nvl), azaleucine and phenyl-glycine (Phg)) and N-methyl amino acids (450 µM mix of N-methylated serine [(N-Me)S], alanine [(N-Me)A], glycine [(N-Me)G] and 4-fluoro-N-methylphenylalanine [(N-Me-4-F)Phe]). $^{35}$S-labeled cysteine residues were included in both conditions to enable monitoring of polypeptide enrichment per round.

TABLE 2

In vitro translation components

| Component | Conc. |
|---|---|
| Creatine phosphate | 20 mM |
| MeTHF, pH 7.6 | 15 µg/ml |
| HEPES-KOH, pH 7.6 | 51 mM |
| KCl | 101 mM |
| Spermidine | 2 mM |
| DTT | 1 mM |
| Creatine kinase | 4 mM |
| Myokinase | 3 mM |
| Nucleotide diphosphate kinase | 1 mM |
| Pyrophosphate | 1 mM |
| ATP + GTP' | 2 mM each |
| EF-Tu | 50 µM |
| Ribosomes | 1 µM |
| MTF | 0.56 µM |
| 1F1 | 0.96 µM |
| IF2 | 0.40 µM |
| IF3 | 0.44 µM |
| EF-G | 0.64 µM |
| EF-Ts | 1.58 µM |
| RF1 | 0.24 µM |
| RF3 | 0.17 µM |
| RRF | 0.46 µM |
| Mg | 17.46 mM |

The tRNAs were enzymatically charged with their respective amino acids using tRNA synthetases. The four N-methyl tRNAs were pre-charged, whereas all other tRNAs were enzymatically charged during the in vitro translation reaction. The tRNA synthetases were added on a volume basis irrespective of their concentrations. 0.1 µl of each tRNA synthetase (except for methionine tRNA synthetase, which was added at 0.4 µl per 25 µl translation reaction) was added for in-situ charging during translation for a 25 µl translation reaction. Cross-linked mRNA was added at a final concentration of 0.75 µM. The translation reaction was kept at 37° C. for 1 hour. After translation, the fusion of the translated polypeptides to their respective mRNAs was carried out by adding high salt to the translation mix and incubating at 37°

C. for 1.5 hours. A library for the selection of natural polypeptides was prepared from eight individual libraries with a fixed cysteine codon in positions 5-11. The random positions in these libraries, with all 20 amino acids possible, were made combinatorially with repeating codon units of NNS (N is A, G, C, or T; S is G or C) (Devlin, J. J., et. al., (1990). Science 249, 404-406.) The translation of these libraries into natural polypeptides was done using a rabbit reticulocyte in vitro translation kit rather than the reconstituted system described above.

Recovery of the mRNA-displayed polypeptides was done using both Oligo dT and Ni-NTA affinity, to isolate fusion molecules containing both polyA mRNA and His tagged polypeptides. Oligo dT bead-bound polypeptides were then cyclized with dibromoxylene as described by others (J. Am. Chem. Soc. 127:1 1727 (2005)).

Direct selection of the polypeptides by target affinity was then performed. mRNA-displayed polypeptides were allowed to bind for 1 hour at 4° C. to biotinylated C5 in a 100 nM solution of biotinylated C5 in PBST. The RNA corresponding to the affinity selected polypeptides was reverse transcribed and PCR amplified to create a double-stranded DNA pool. The DNA pool was in vitro transcribed to generate mRNA, and the mRNA produced was cross-linked as before at its 3' terminus with a puromycin-containing oligonucleotide. The mRNA-puromycin fusions were subjected to in vitro translation to generate the second round of the library, which is now enriched in polypeptides that bind complement component C5. The selection cycle was repeated for six rounds. After the sixth round, the DNA pool representing the selected polypeptides was cloned and sequenced, and the amino acid sequences of candidate C5 inhibitors were determined based on the DNA sequences. The polypeptide sequences identified are listed in Table 3.

As used in all of the following tables as well as in the sequence listing, abbreviations have the following meaning: "Ac" and "NH2" indicate acetyl and amidated termini, respectively; "Nvl" stands for norvaline; "Phg" stands for phenylglycine; "Sar" stands for sarcosine; "Tbg" stands for tert-butylglycine; "Trt" stands for trityl or triphenylmethyl; "Chg" stands for cyclohexylglycine; "(N-Me)X" stands for the N-methylated form of the amino acid indicated by the letter or three letter abbreviation for that amino acid in place of variable "X" written as N-methyl-X [e.g. (N-Me)A and (N-Me)Ala both stand for the N-methylated form of alanine or N-methyl-alanine]; 7-aza-tryptophan is incorporated where "azaTrp" is indicated; "(4-F)Phe" stands for 4-fluorophenylalanine; "Tyr(OMe)" stands for O-methyl tyrosine, "Aib" stands for amino isobutyric acid; "(homo)F" or "(homo)Phe" stands for homophenylalanine; "(2-OMe)Phg" refers to 2-O-methylphenylglycine; "PropargylGly" refers to propargyl-glycine; "(5-F)W" or "(5-F)Trp" refers to 5-fluorotryptophan; "D-X" refers to the D-stereoisomer of the given amino acid "X" wherein the amino acid may be abbreviated using single or three letter code [e.g. (D-Chg) stands for D-cyclohexylglycine and (D-W) stands for D-tryptophan]; "(5-MeO)W" or "(5-MeO)Trp" refers to 5-methyl-O-tryptophan; "homoC" refers to homocysteine; "(1-Me-W)" or "(1-Me)W" or "(1-Me-Trp)" or "(1-Me)Trp" refers to 1-methyltryptophan; "Nle" refers to norleucine; 1,2,3,4-tetrahydroisoquinoline-1-carboxylic acid is incorporated where "Tiq" is indicated; "Asp(T)" refers to (S)-2-amino-3-(1H-tetrazol-5-yl)propanoic acid; "(3-Cl-Phe)" refers to 3-chlorophenylalanine; "[(N-Me-4-F)Phe]" or "(N-Me-4-F)Phe" refers to N-methyl-4-fluorophenylalanine; "Boc" is a tert-Butyloxycarbonyl protecting group; "[xXylyl (y, z)]" refers to the xylyl bridging moiety between two cysteines where x may be m, p or o to indicate the use of meta-, para- or ortho-dibromoxylenes (respectively) to generate bridging moieties and the numerical identifiers, y and z, place the amino acid position within the polypeptide of the cysteines participating in the cyclization; "[cyclo(y,z)]" refers to the formation of a bond between two residues where the numerical identifiers, y and z, place the position of the residues participating in the bond; "[mXylyl-bicyclo]" indicates that the polypeptide comprises two cyclic loops and that the bridging moiety is generated by reaction with a meta-dibromoxylene. All other symbols refer to the standard one-letter amino acid code. Additionally, polypeptides comprising PEG2000 or BODIPY-TMR-X sequence tags are indicated.

TABLE 3

Polypeptide Sequences

| Compound Number | Sequence | SEQ ID NO |
|---|---|---|
| R3000 | Ac-Nvl-C-Y-K-N-Y-H-azaTrp-E-Y-P-Tbg-Y-NH2 | 1 |
| R3001 | Ac-Nvl-C-Y-E-N-Tbg-Y-azaTrp-E-Y-(N-Me)G-Nvl-(N-Me)S-NH2 | 2 |
| R3002 | Ac-Nvl-C-Y-E-N-Tbg-Y-azaTrp-E-Y-P-Phg-Nvl-NH2 | 3 |
| R3003 | Ac-Nvl-C-Y-E-N-Tbg-Y-azaTrp-E-Y-P-Phg-P-NH2 | 4 |
| R3004 | Ac-Nvl-C-Y-N-N-Tbg-E-azaTrp-E-Y-P-Phg-Tbg-NH2 | 5 |
| R3005 | Ac-Nvl-C-Y-azaTrp-(N-Me)G-Tbg-Nvl-azaTrp-E-Y-P-Phg-P-NH2 | 6 |
| R3006 | Ac-Y-E-N-Tbg-Y-azaTrp-E-Y-(N-Me)G-Nvl-(N-Me)S-NH2 | 7 |
| R3007 | [mXylyl(2,7)]Ac-Nvl-C-K-E-Phg-Y-C-(N-Me)S-Tbg-K-azaTrp-E-Y-NH2 | 8 |
| R3008 | [mXylyl(2,10)]Ac-Nvl-C-Phg-T-azaTrp-E-Y-(N-Me)S-H-C-Nvl-P-Nvl-NH2 | 9 |
| R3020 | [mXylyl(2,7)]M-C-S-E-R-Y-C-E-V-R-W-E-Y-NH2 | 10 |
| R3021 | [mXylyl(2,7)]M-C-V-E-R-F-C-D-V-Y-W-E-F-NH2 | 11 |

Example 4. Polypeptide Synthesis

Polypeptides are synthesized using standard solid-phase Fmoc/tBu methods. The synthesis is typically performed on a Liberty automated microwave peptide synthesizer (CEM, Matthews NC) using standard protocols with Rink amide resin, although other automated synthesizers without microwave capability may also be used. All amino acids are obtained from commercial sources unless otherwise noted. The coupling reagent used is 2-(6-chloro-1-H-benzotriazole-1yl)-1,1,3,3,-tetramethylaminium hexafluorophosphate (HCTU) and the base is diisopropylethylamine (DIEA). Polypeptides are cleaved from resin with 95% TFA, 2.5% TIS and 2.5% water for 3 hours and isolated by precipitation with ether. The crude polypeptides are purified on a reverse phase preparative HPLC using a C18 column, with an acetonitrile/water 0.1% TFA gradient from 20/6-50% over 30 min. Fractions containing the pure polypeptide are collected and lyophilized and all polypeptides are analyzed by LC-MS.

Example 5. Formation of Disulfide Cyclized Polypeptides

To produce disulfide cyclized polypeptides, the linear polypeptide is dissolved in a mixture of water and DMSO and the resulting solution is stirred vigorously under an air atmosphere for 12 hrs.

Example 6. Dibromoxylene Polypeptide Cyclization

A 100 mL flask is charged with acetonitrile (12 mL) and water (24 mL) and is degassed with argon for about 5 min. Linear polypeptide (0.01 mmole) and 200 mM ammonium bicarbonate (6 mL) are added followed by 0.012 mmole or 1,3-bis(bromomethyl) benzene, 1,2-bis(bromomethyl)benzene, 1,4-bis(bromomethyl)benzene, 2,6-bis(bromomethyl) pyridine or (E)-1,4-dibromobut-2-ene. The reaction mixture is stirred under argon at room temperature for approximately 2 hours and monitored by LC-MS. After the reaction is complete, the reaction solution is frozen and lyophilized. HPLC purification of the crude lyophilized product followed by lyophilization of fractions containing pure polypeptide yield the final cyclized product as a white powder.

Example 7. Lactam Polypeptide Cyclization

Cyclization of polypeptides using a lactam moiety was performed in the solid phase. A polypeptide was first synthesized on a solid support Wang resin by standard Fmoc chemistry. Fmoc-ASP(allyl)-OH and Fmoc-LYS(alloc)-OH were incorporated in the polypeptide at the indicated positions as the two precursor monomers for the lactam bridge formation. After full elongation the resin was washed with dry dichloromethane (3×) and purged with dry Nitrogen gas for 10 min. To remove the allyl and alloc protecting groups, the resin was treated with a 5 fold molar excess of phenylsilane and purged with Nitrogen for 10 min. A catalytic amount of tetrakis Pd(0) was dissolved in dry dichloromethane and added to the suspension of resin. After one hour the resin was washed sequentially with dichloromethane (3×), dimethylformamide (3×), sodium diethyldithiocarbamate trihydrate (3×), dimethylformamide (3×) and dichloromethane (3×). Lactam cyclization was achieved in dimethylformamide (DMF) by treating the deprotected polypeptide containing resin with PyAOP ((3-Hydroxy-3H-1,2,3-triazolo[4,5-b]pyridinato-O)tri-1-pyrrolidinyl-phosphorus hexafluorophosphate) and diisopropylethylamine and allowed to react overnight. The resin was rinsed with DMF and treated with fresh PyAOP and diisopropylethylamine for additional 60 minutes at 45° C. The resin was rinsed and washed with dimethylformamide five times. The polypeptide was cleaved and purified as described in example 4.

Example 8. Triazole Polypeptide Cyclization

Cyclization of polypeptides containing an azide and an alkyne moiety was performed on the solid phase. Polypeptide containing resin (0.05 mmol) was treated with dichloromethane and allowed to swell for 10 min. The solvent was then exchanged to DMF (3-5 mL) and after 10 min, a solution of Cu-TBTA ligand was added (125 μL of a 20 mM solution). The suspension was purged with Argon gas and then ascorbic acid (5 μmoles) was added. The solution was shaken for 2 h and the excess reagents removed, the resin was washed with a solution of EDTA in DMF to remove excess copper. The polypeptide was cleaved and purified as described in Example 4.

Example 9. Polypeptides of the Current Invention

Polypeptides of the current invention were synthesized. These include the compounds listed in Table 4.

TABLE 4

Compounds of the invention

| Compound Number | Sequence | SEQ ID NO. |
|---|---|---|
| R3000 | Ac-Nvl-C-Y-K-N-Y-H-azaTrp-E-Y-P-Tbg-Y-NH2 | 1 |
| R3001 | Ac-Nvl-C-Y-E-N-Tbg-Y-azaTrp-E-Y-(N-Me)G-Nvl-(N-Me)S-NH2 | 2 |
| R3002 | Ac-Nvl-C-Y-E-N-Tbg-Y-azaTrp-E-Y-P-Phg-Nvl-NH2 | 3 |
| R3003 | Ac-Nvl-C-Y-E-N-Tbg-Y-azaTrp-E-Y-P-Phg-P-NH2 | 4 |
| R3004 | Ac-Nvl-C-Y-N-N-Tbg-E-azaTrp-E-Y-P-Phg-Tbg-NH2 | 5 |
| R3005 | Ac-Nvl-C-Y-azaTrp-(N-Me)G-Tbg-Nvl-azaTrp-E-Y-P-Phg-P-NH2 | 6 |
| R3006 | Ac-Y-E-N-Tbg-Y-azaTrp-E-Y-(N-Me)G-Nvl-(N-Me)S-NH2 | 7 |
| R3007 | [mXylyl(2,7)]Ac-Nvl-C-K-E-Phg-Y-C-(N-Me)S-Tbg-K-azaTrp-E-Y-NH2 | 8 |
| R3008 | [mXylyl(2,10)]Ac-Nvl-C-Phg-T-azaTrp-E-Y-(N-Me)S-H-C-Nvl-P-Nvl-NH2 | 9 |
| R3020 | [mXylyl(2,7)]M-C-S-E-R-Y-C-E-V-R-W-E-Y-NH2 | 10 |
| R3021 | [mXylyl(2,7)]M-C-V-E-R-F-C-D-V-Y-W-E-F-NH2 | 11 |
| R3079 | Nvl-Nvl-Y-E-N-Tbg-Y-azaTrp-E-Y-P-Phg-Nvl-NH2 | 12 |
| R3055 | Ac-Nvl-S-Y-E-N-Tbg-Y-azaTrp-E-Y-P-Phg-Nvl-NH2 | 13 |

TABLE 4-continued

Compounds of the invention

| Compound Number | Sequence | SEQ ID NO. |
|---|---|---|
| R3120 | Ac-Nvl-Nvl-Y-E-(N-Me)N-Tbg-Y-azaTrp-E-Y-P-Chg-Nvl-NH2 | 14 |
| R3057 | [mXylyl(2,7)]M-C-V-E-R-F-C-D-Tbg-Y-azaTrp-E-Y-P-Phg-Nvl-NH2 | 15 |
| R3056 | Ac-Nvl-Nvl-Y-E-N-Tbg-Y-azaTrp-E-Y-P-Phg-Nvl-NH2 | 16 |
| R3054 | Ac-Nvl-C-Y-E-N-Tbg-Y-azaTrp-E-Y-P-Chg-Nvl-NH2 | 17 |
| R3029 | Ac-Nvl-C-Y-E-N-Tbg-Y-azaTrp-E-Y-P-Phg-NH2 | 18 |
| R3048 | [mXylyl(1,6)]Ac-C-V-E-R-F-C-D-V-Y-W-E-F-NH2 | 19 |
| R3072 | Ac-Nvl-Nvl-Y-E-N-Tbg-Y-azaTrp-E-Y-P-Chg-Nvl-K-NH2 | 20 |
| R3024 | Ac-C-Y-E-N-Tbg-Y-azaTrp-E-Y-P-Phg-Nvl-NH2 | 21 |
| R3114 | Ac-Nvl-Nvl-(N-Me)Y-E-N-Tbg-Y-azaTrp-E-Y-P-Chg-Nvl-NH2 | 22 |
| R3050 | [pXylyl(2,10)]Ac-Nvl-C-Phg-T-azaTrp-E-Y-(N-Me)S-H-C-Nvl-NH2 | 23 |
| R3025 | Ac-Y-E-N-Tbg-Y-azaTrp-E-Y-P-Phg-Nvl-NH2 | 24 |
| R3061 | Ac-Nvl-S-Y-E-A-Tbg-Y-azaTrp-E-Y-P-Chg-Nvl-NH2 | 25 |
| R3041 | Ac-Y-E-N-Tbg-Y-W-E-Y-P-Phg-Nvl-NH2 | 26 |
| R3077 | Ac-Nvl-Nvl-Y-E-N-Tbg-Y-azaTrp-E-Y-P-Chg-Nvl-K-(PEG2000)NH2 | 27 |
| R3030 | Ac-Nvl-C-Y-E-N-Tbg-Y-azaTrp-E-Y-P-NH2 | 28 |
| R3062 | Ac-Nvl-S-Y-E-N-A-Y-azaTrp-E-Y-P-Chg-Nvl-NH2 | 29 |
| R3066 | Ac-Nvl-S-Y-E-N-Tbg-A-azaTrp-E-Y-P-Chg-Nvl-NH2 | 30 |
| R3011 | [mXylyl(2,10)]Ac-Nvl-C-Phg-T-azaTrp-E-Y-(N-Me)S-H-C-Nvl-P-NH2 | 31 |
| R3070 | Ac-Nvl-S-Y-E-N-Tbg-Y-azaTrp-E-Y-A-Chg-Nvl-NH2 | 32 |
| R3071 | Ac-Nvl-S-Y-E-N-Tbg-Y-azaTrp-E-Y-P-A-Nvl-NH2 | 33 |
| R3033 | [mXylyl(2,10)]Ac-Nvl-C-Phg-A-azaTrp-E-Y-(N-Me)S-H-C-Nvl-NH2 | 34 |
| R3038 | [mXylyl(2,10)]Ac-Nvl-C-Phg-T-azaTrp-E-Y-(N-Me)S-A-C-Nvl-NH2 | 35 |
| R3012 | [mXylyl(2,10)]Ac-Nvl-C-Phg-T-azaTrp-E-Y-(N-Me)S-H-C-Nvl-NH2 | 36 |
| R3060 | Ac-Nvl-S-Y-A-N-Tbg-Y-azaTrp-E-Y-P-Chg-Nvl-NH2 | 37 |
| R3039 | [mXylyl(2,10)]Ac-Nvl-C-Phg-T-azaTrp-E-Y-(N-Me)S-H-C-A-NH2 | 38 |
| R3037 | [mXylyl(2,10)]Ac-Nvl-C-Phg-T-azaTrp-E-Y-(N-Me)A-H-C-Nvl-NH2 | 39 |
| R3076 | Ac-Nvl-Nvl-Y-E-N-Tbg-Y-azaTrp-E-Y-P-Chg-Nvl-K-(BODIPY-TMR-X)NH2 | 40 |
| R3074 | [mXylyl(2,10)]Ac-Nvl-C-Phg-T-azaTrp-E-Tyr(OMe)-(N-Me)S-H-C-Nvl-NH2 | 41 |
| R3013 | [mXylyl(2,10)]Ac-Nvl-C-Phg-T-azaTrp-E-Y-(N-Me)S-H-C-NH2 | 42 |
| R3065 | [pXylyl(2,10)]Ac-Nvl-C-Phg-T-azaTrp-E-Y-P-H-C-Nvl-NH2 | 43 |
| R3073 | [mXylyl(2,10)]Ac-Nvl-C-Phg-T-azaTrp-E-Phe(4-F)-(N-Me)S-H-C-Nvl-NH2 | 44 |
| R3116 | Ac-Nvl-Nvl-Y-E-N-Tbg-Y-(N-Me)W-E-Y-P-Chg-Nvl-NH2 | 45 |
| R3091 | [mXylyl(2,10)]Ac-Nvl-C-Phg-T-W-E-Y-(N-Me)S-A-C-Nvl-NH2 | 46 |
| R3078 | PEG2000-Nvl-Nvl-Y-E-N-Tbg-Y-azaTrp-E-Y-P-Phg-Nvl-NH2 | 47 |
| R3100 | [mXylyl(2,10)]Ac-Nvl-C-Phg-T-azaTrp-E-F-(N-Me)S-A-C-Nvl-NH2 | 48 |
| R3121 | Ac-Nvl-Nvl-Y-E-N-Tbg-Y-azaTrp-E-Y-P-(N-Me)Phg-Nvl-NH2 | 49 |

TABLE 4 -continued

Compounds of the invention

| Compound Number | Sequence | SEQ ID NO. |
|---|---|---|
| R3043 | [mXylyl(2,7)]M-C-V-E-R-F-C-D-V-Y-W-E-NH2 | 50 |
| R3102 | [mXylyl(2,10)]Ac-Nvl-C-Phg-T-azaTrp-E-Y-P-H-C-Nvl-NH2 | 51 |
| R3026 | Ac-E-N-Tbg-Y-azaTrp-E-Y-P-Phg-Nvl-NH2 | 52 |
| R3031 | [mXylyl(2,10)]Ac-A-C-Phg-T-azaTrp-E-Y-(N-Me)S-H-C-Nvl-NH2 | 53 |
| R3019 | [mXylyl(2,14)]Ac-Nvl-C-Y-E-N-Tbg-Y-azaTrp-E-Y-P-Phg-Nvl-C-NH2 | 54 |
| R3014 | [mXylyl(1,9)]Ac-C-Phg-T-azaTrp-E-Y-(N-Me)S-H-C-Nvl-P-Nvl-NH2 | 55 |
| R3104 | [pXylyl(2,10)]Ac-Nvl-homoC-Phg-T-azaTrp-E-Y-(N-Me)S-H-C-Nvl-NH2 | 56 |
| R3059 | Ac-Nvl-S-A-E-N-Tbg-Y-azaTrp-E-Y-P-Chg-Nvl-NH2 | 57 |
| R3115 | Ac-Nvl-Nvl-Y-(N-Me)E-N-Tbg-Y-azaTrp-E-Y-P-Chg-Nvl-NH2 | 58 |
| R3110 | Ac-Y-E-N-Tbg-Y-(1-Me)W-E-Y-P-Phg-Nvl-NH2 | 59 |
| R3126 | Ac-Nvl-C-Y-N-N-Tbg-E-azaTrp-E-C-P-Phg-Tbg-NH2 | 60 |
| R3049 | [oXylyl(2,10)]Ac-Nvl-C-Phg-T-azaTrp-E-Y-(N-Me)S-H-C-Nvl-NH2 | 61 |
| R3069 | Ac-Nvl-S-Y-E-N-Tbg-Y-azaTrp-E-A-P-Chg-Nvl-NH2 | 62 |
| R3015 | [mXylyl(1,9)]Ac-C-Phg-T-azaTrp-E-Y-(N-Me)S-H-C-NH2 | 63 |
| R3068 | Ac-Nvl-S-Y-E-N-Tbg-Y-azaTrp-A-Y-P-Chg-Nvl-NH2 | 64 |
| R3105 | [mXylyl(2,10)]Ac-Nvl-C-Phg-T-azaTrp-E-Y-(N-Me)S-H-homoC-Nvl-NH2 | 65 |
| R3106 | [pXylyl(2,10)]Ac-Nvl-C-Phg-T-azaTrp-E-Y-(N-Me)S-H-homoC-Nvl-NH2 | 66 |
| R3111 | [mXylyl(4,10)]Ac-Nvl-T-Phg-C-azaTrp-E-Y-(N-Me)S-A-C-Nvl-NH2 | 67 |
| R3112 | [mXylyl(2,10)]Ac-Nle-C-Phg-T-azaTrp-E-Y-(N-Me)S-H-C-Nvl-NH2 | 68 |
| R3113 | [mXylyl(3,11)]Ac-Y-Nvl-C-Phg-T-azaTrp-E-Y-(N-Me)S-H-C-Nvl-NH2 | 69 |
| R3134 | [mXylyl(2,10)]Ac-Nvl-C-Phg-T-azaTrp-E-(3-Cl-Phe)-(N-Me)S-A-C-Nvl-NH2 | 70 |
| R3018 | [mXylyl(2,10)]Ac-Nvl-C-Y-E-N-Tbg-Y-azaTrp-E-C-P-Phg-Nvl-NH2 | 71 |
| R3027 | Ac-N-Tbg-Y-azaTrp-E-Y-P-Phg-Nvl-NH2 | 72 |
| R3028 | Ac-Tbg-Y-azaTrp-E-Y-P-Phg-Nvl-NH2 | 73 |
| R3032 | [mXylyl(2,10)]Ac-Nvl-C-A-T-azaTrp-E-Y-(N-Me)S-H-C-Nvl-NH2 | 74 |
| R3058 | [pXylyl(2,10)]Ac-Nvl-C-Chg-T-azaTrp-E-Y-(N-Me)S-H-C-Nvl-NH2 | 75 |
| R3067 | Ac-Nvl-S-Y-E-N-Tbg-Y-A-E-Y-P-Chg-Nvl-NH2 | 76 |
| R3117 | Ac-Nvl-Nvl-Y-E-N-Tbg-Y-azaTrp-E-(N-Me)Y-P-Chg-Nvl-NH2 | 77 |
| R3022 | Ac-Nvl-C-Phg-T-azaTrp-E-Y-(N-Me)S-H-C-Nvl-P-Nvl-NH2 | 78 |
| R3016 | [mXylyl(1,9)]Ac-C-Tbg-Y-azaTrp-E-Y-(N-Me)S-H-C-NH2 | 79 |
| R3089 | [mXylyl(2,10)]Ac-Chg-C-Phg-T-azaTrp-E-Y-(N-Me)S-A-C-Nvl-NH2 | 80 |
| R3083 | [mXylyl(2,10)]Ac-V-C-Phg-T-azaTrp-E-Y-(N-Me)S-A-C-Nvl-NH2 | 81 |
| R3087 | [mXylyl(2,10)]Ac-Nvl-C-(2-OMe)Phg-T-azaTrp-E-Y-(N-Me)S-H-C-Nvl-NH2 | 82 |
| R3103 | [mXylyl(2,10)]Ac-Nvl-homoC-Phg-T-azaTrp-E-Y-(N-Me)S-H-C-Nvl-NH2 | 83 |
| R3135 | [mXylyl(2,10)]Ac-Nvl-C-Phg-T-azaTrp-E-Y-(N-Me)S-(D-Ala)-C-Nvl-NH2 | 84 |

TABLE 4 -continued

Compounds of the invention

| Compound Number | Sequence | SEQ ID NO. |
|---|---|---|
| R3034 | [mXylyl(2,10)]Ac-Nvl-C-Phg-T-A-E-Y-(N-Me)S-H-C-Nvl-NH2 | 85 |
| R3035 | [mXylyl(2,10)]Ac-Nvl-C-Phg-T-azaTrp-A-Y-(N-Me)S-H-C-Nvl-NH2 | 86 |
| R3036 | [mXylyl(2,10)]Ac-Nvl-C-Phg-T-azaTrp-E-A-(N-Me)S-H-C-Nvl-NH2 | 87 |
| R3044 | [mXylyl(2,7)]M-C-V-E-R-F-C-D-V-Y-W-NH2 | 88 |
| R3080 | [mXylyl(2,9)]Ac-Nvl-C-Phg-T-azaTrp-E-Y-(N-Me)S-C-Nvl-NH2 | 89 |
| R3085 | [mXylyl(2,10)]heptanoyl-Nvl-C-Phg-T-azaTrp-E-Y-(N-Me)S-A-C-Nvl-NH2 | 90 |
| R3086 | [mXylyl(5,13)]Ac-Nvl-S-Y-E-C-Tbg-Y-azaTrp-E-Y-P-Chg-C-Nvl-NH2 | 91 |
| R3092 | [mXylyl(2,10)]Ac-Nvl-C-Phg-T-F-E-Y-(N-Me)S-A-C-Nvl-NH2 | 92 |
| R3095 | [mXylyl(2,10)]Ac-Nvl-C-Phg-T-azaTrp-E-(homo)F-(N-Me)S-A-C-Nvl-NH2 | 93 |
| R3096 | [mXylyl(2,10)]Ac-Nvl-C-Phg-Aib-azaTrp-E-Y-(N-Me)S-H-C-Nvl-NH2 | 94 |
| R3122 | [mXylyl(2,10)]Ac-Nvl-C-Tiq-T-azaTrp-E-Y-(N-Me)S-H-C-Nvl-NH2 | 95 |
| R3075 | [mXylyl(2,11)]Nvl-C-Y-(N-Me)S-Phg-(N-Me-4-F)Phe-(N-Me)S-H-(N-Me-4-F)Phe-G-C-NH2 | 96 |
| R3107 | [mXylyl(2,10)]Ac-Nvl-homoC-Phg-T-azaTrp-E-Y-(N-Me)S-H-homoC-Nvl-NH2 | 97 |
| R3108 | [pXylyl(2,10)]Ac-Nvl-homo C-Phg-T-azaTrp-E-Y-(N-Me)S-H-homoC-Nvl-NH2 | 98 |
| R3127 | [mXylyl(2,10)]Ac-Nvl-C-Y-N-N-Tbg-E-azaTrp-E-C-P-Phg-Tbg-NH2 | 99 |
| R3133 | [mXylyl(2,10)]Ac-Nvl-C-Phg-(D-Ala)-azaTrp-E-Y-(N-Me)S-H-C-Nvl-NH2 | 100 |
| R3009 | [mXylyl(2,10)]Ac-Nvl-C-Y-E-(N-Me)G-Tbg-Y-azaTrp-E-C-Nvl-P-Nvl-NH2 | 101 |
| R3010 | [mXylyl(2,13)]Ac-Nvl-C-Y-E-(N-Me)G-Tbg-Y-azaTrp-E-Nvl-Nvl-P-C-NH2 | 102 |
| R3017 | [mXylyl(2,8)]Ac-Nvl-C-Y-E-N-Tbg-Y-C-E-Y-P-Phg-Nvl-NH2 | 103 |
| R3023 | Ac-Y-P-Y-C-Phg-azaTrp-Tbg-E-Nvl-N-Y-Nvl-E-NH2 | 104 |
| R3040 | [cyclo(2,10)]Ac-Nvl-C-Phg-T-azaTrp-E-Y-(N-Me)S-H-C-Nvl-P-Nvl | 105 |
| R3042 | [cyclo(2,10)]Ac-Nvl-C-Phg-T-azaTrp-E-Y-(N-Me)S-H-C-Nvl-NH2 | 106 |
| R3045 | [mXylyl(2,7)]M-C-V-E-R-F-C-D-V-Y-NH2 | 107 |
| R3046 | [mXylyl(2,7)]M-C-V-E-R-F-C-D-V-NH2 | 108 |
| R3047 | [mXylyl(2,7)]M-C-V-E-R-F-C-NH2 | 109 |
| R3051 | [mXylyl(2,11)]Nvl-C-Y-(N-Me)S-Phg-(N-Me-4-F)Phe-(N-Me)S-H-(N-Me-4-F)Phe-(N-Me)G-C-NH2 | 110 |
| R3052 | [mXylyl(2,9)]Nvl-C-Y-Tbg-Phg-N-(N-Me)G-L-C-Phg-(N-Me)A-NH2 | 111 |
| R3053 | [mXylyl-bicyclo]Nvl-C-C-N-Tbg-Phg-C-Tbg-(N-Me)S-C-Tbg-NH2 | 112 |
| R3063 | Ac-Tbg-Y-azaTrp-E-Y-NH2 | 113 |
| R3064 | Ac-Y-azaTrp-E-Y-P-NH2 | 114 |
| R3081 | Ac-Y-E-N-Tbg-Y-azaTrp-(N-Me)E-Y-P-Phg-Nvl-NH2 | 115 |
| R3082 | [mXylyl(1,9)]heptanoyl-C-Phg-T-azaTrp-E-Y-(N-Me)S-A-C-Nvl-NH2 | 116 |
| R3084 | [mXylyl(2,10)]Ac-Nvl-C-Phg-T-azaTrp-E-Y-S-A-C-Nvl-NH2 | 117 |
| R3088 | [mXylyl(2,10)]Ac-Nvl-C-Phg-T-(5-F)W-E-Y-(N-Me)S-A-C-Nvl-NH2 | 118 |
| R3090 | [mXylyl(2,10)]Ac-Nvl-C-F-T-azaTrp-E-Y-(N-Me)S-A-C-Nvl-NH2 | 119 |

TABLE 4 -continued

Compounds of the invention

| Compound Number | Sequence | SEQ ID NO. |
|---|---|---|
| R3093 | [mXylyl(2,10)]Ac-Nvl-C-(D-Chg)-T-azaTrp-E-Y-(N-Me)S-A-C-Nvl-NH2 | 120 |
| R3094 | Ac-Y-E-N-Tbg-Y-(5-MeO)W-E-Y-P-Phg-Nvl-NH2 | 121 |
| R3097 | [mXylyl(2,10)]Ac-Nvl-C-Phg-T-azaTrp-D-Y-(N-Me)S-A-C-Nvl-NH2 | 122 |
| R3098 | [mXylyl(2,10)]Ac-Nvl-C-Phg-T-azaTrp-Q-Y-(N-Me)S-A-C-Nvl-NH2 | 123 |
| R3099 | [mXylyl(2,10)]Ac-Nvl-C-Phg-T-azaTrp-N-Y-(N-Me)S-A-C-Nvl-NH2 | 124 |
| R3101 | [mXylyl(2,10)]Ac-Nvl-C-Phg-T-azaTrp-E-Y-(N-Me)S-H-G-C-Nvl-NH2 | 125 |
| R3109 | [mXylyl(2,10)]Ac-Nvl-C-Phg-T-(1-Me-W)-E-Y-(N-Me)S-A-C-Nvl-NH2 | 126 |
| R3118 | Ac-Y-E-N-Tbg-Y-(D-Trp)-E-Y-P-Phg-Nvl-NH2 | 127 |
| R3119 | Ac-Y-E-N-Y-(D-Trp)-E-Y-P-Phg-Nvl-NH2 | 128 |
| R3123 | Ac-Y-E-N-Tbg-Y-azaTrp-(D-Glu)-Y-P-Phg-Nvl-NH2 | 129 |
| R3124 | [mXylyl(1,6)]Ac-C-V-E-R-F-C-V-Y-W-E-F-NH2 | 130 |
| R3125 | [mXylyl(1,6)]Ac-C-V-E-R-F-C-W-E-F-NH2 | 131 |
| R3128 | Ac-Nvl-C-Y-N-N-Tbg-E-C-E-Y-P-Phg-Tbg-NH2 | 132 |
| R3129 | [mXylyl(2,8)]Ac-Nvl-C-Y-N-N-Tbg-E-C-E-Y-P-Phg-Tbg-NH2 | 133 |
| R3130 | Ac-Nvl-Nvl-Y-E-N-Tbg-(N-Me)Y-azaTrp-E-Y-P-Chg-Nvl-NH2 | 134 |
| R3131 | [mXylyl(2,10)]Ac-Nvl-C-Phg-T-W-Asp (T)-Y-(N-Me)S-H-C-Nvl-NH2 | 135 |
| R3132 | [mXylyl(2,10)]Ac-Nvl-C-Phg-T-(D-Trp)-E-Y-(N-Me)S-H-C-Nvl-NH2 | 136 |
| R3136 | [mXylyl(2,10)]heptanoyl-Nvl-C-(D-Phg)-T-azaTrp-E-Y-(N-Me)S-A-C-Nvl-NH2 | 137 |
| R3137 | [mXylyl(1,9)]heptanoyl-C-(D-Phg)-T-azaTrp-E-Y-(N-Me)S-A-C-Nvl-NH2 | 138 |
| R3138 | [mXylyl(1,6)]Ac-C-V-E-R-F-C-D-Tbg-Y-W-E-F-NH2 | 139 |
| R3139 | [mXylyl(1,6)]Ac-C-Tbg-E-R-F-C-D-Tbg-Y-W-E-F-NH2 | 140 |
| R3140 | [mXylyl(1,6)]Ac-C-V-E-R-F-C-D-V-Y-W-E-Y-P-NH2 | 141 |
| R3141 | [mXylyl(1,6)]Ac-C-V-E-R-F-C-D-V-Y-W-E-F-P-NH2 | 142 |
| R3142 | [mXylyl(1,6)]Ac-C-V-E-R-F-C-D-V-Y-azaTrp-E-Y-P-NH2 | 143 |
| R3143 | [mXylyl(1,6)]Ac-C-V-E-R-F-C-D-Tbg-Y-W-E-Y-P-NH2 | 144 |
| R3144 | [mXylyl(1,6)]Ac-C-V-E-R-F-C-D-Tbg-Y-azaTrp-E-Y-P-Phg-Nvl-NH2 | 145 |
| R3145 | [mXylyl(1,6)]Ac-C-V-E-R-F-C-D-Tbg-Y-azaTrp-E-Y-P-(D-Phg)-Nvl-NH2 | 146 |
| R3146 | [mXylyl(1,6)]Ac-C-Tbg-E-R-F-C-D-V-Y-W-E-F-NH2 | 147 |
| R3147 | [mXylyl(1,6)]Ac-C-V-E-R-F-C-D-V-Y-W-E-F-Propargyl-Gly-NH2 | 148 |
| R3148 | [mXylyl(1,6)]Ac-C-A-E-R-F-C-D-Tbg-Y-W-E-Y-P-Phg-Nvl-NH2 | 149 |
| R3149 | [mXylyl(1,6)]Ac-C-A-E-R-F-C-D-Tbg-Y-W-E-Y-P-(D-Phg)-Nvl-NH2 | 150 |
| R3150 | [mXylyl(1,6)]Ac-C-V-A-R-F-C-D-Tbg-Y-azaTrp-E-Y-P-Phg-Nvl-NH2 | 151 |
| R3151 | [mXylyl(1,6)]Ac-C-V-A-R-F-C-D-Tbg-Y-azaTrp-E-Y-P-(D-Phg)-Nvl-NH2 | 152 |
| R3152 | [mXylyl(1,6)]Ac-C-V-E-R-F-C-D-Tbg-Y-azaTrp-E-Y-P-Chg-Nvl-NH2 | 153 |
| R3153 | [mXylyl(1,6)]Ac-C-V-E-A-F-C-D-Tbg-Y-azaTrp-E-Y-P-Phg-Nvl-NH2 | 154 |
| R3154 | [mXylyl(1,6)]Ac-C-V-E-A-F-C-D-Tbg-Y-azaTrp-E-Y-P-(D-Phg)-Nvl-NH2 | 155 |

TABLE 4 -continued

Compounds of the invention

| Compound Number | Sequence | SEQ ID NO. |
|---|---|---|
| R3155 | [mXylyl(1,6)]Ac-C-V-E-R-A-C-D-Tbg-Y-azaTrp-E-Y-P-Phg-Nvl-NH2 | 156 |
| R3156 | [mXylyl(1,6)]Ac-C-V-E-R-A-C-D-Tbg-Y-azaTrp-E-Y-P-(D-Phg)-Nvl-NH2 | 157 |
| R3157 | [mXylyl(1,6)]Ac-C-V-E-R-F-C-A-Tbg-Y-azaTrp-E-Y-P-Phg-Nvl-NH2 | 158 |
| R3158 | [mXylyl(1,6)]Ac-C-V-E-R-F-C-A-Tbg-Y- azaTrp-E-Y-P-(D-Phg)-Nvl-NH2 | 159 |
| R3159 | [mXylyl(1,6)](des-amino)C-V-E-R-F-C-D-Tbg-Y-azaTrp-E-Y-P-Phg-Nvl-NH2 | 160 |
| R3160 | [mXylyl(1,6)](des-amino)C-V-E-R-F-C-D-Tbg-Y-azaTrp-E-Y-P-(D-Phg)-Nvl-NH2 | 161 |
| R3161 | [mXylyl(1,6)]Ac-C-A-E-R-F-C-D-Tbg-Y-azaTrp-E-Y-P-Phg-K-NH2 | 162 |
| R3162 | [mXylyl(1,6)]Ac-C-A-E-R-F-C-D-Tbg-Y-azaTrp-E-Y-P-(D-Phg)-K-NH2 | 163 |
| R3163 | [cyclo(1,6)]Ac-C-V-E-R-F-C-D-Tbg-Y-azaTrp-E-Y-P-Phg-Nvl-NH2 | 164 |
| R3164 | [mXylyl(1,6)]Ac-C-A-E-R-F-C-D-Tbg-Y-azaTrp-E-Y-P-Phg-(Lys-C12)-NH2 | 165 |
| R3165 | [mXylyl(1,6)]Ac-C-A-E-R-F-C-D-Tbg-Y-azaTrp-E-Y-P-Phg-(Lys-C10)-NH2 | 166 |
| R3166 | [mXylyl(1,6)]Ac-C-A-E-R-F-C-D-Tbg-Y-azaTrp-E-Y-P-Phg-(Lys-C8)-NH2 | 167 |
| R3167 | [mXylyl(1,6)]Ac-C-V-E-R-F-C-(alpha-methyl)D-Tbg-Y-azaTrp-E-Y-P-Chg-Nvl-NH2 | 168 |
| R3168 | [mXylyl(1,6)]Ac-C-V-E-R-F-C-Asp(T)-Tbg-Y-azaTrp-E-Y-P-Chg-Nvl-NH2 | 169 |
| R3169 | [cyclo(1,6)]Ac-K-V-E-R-F-D-D-Tbg-Y-azaTrp-E-Y-P-Chg-Nvl-NH2 | 170 |
| R3170 | [mXylyl(1,6)]Ac-C-A-E-R-F-C-D-Tbg-Y-azaTrp-E-Y-P-Phg-K | 171 |
| R3171 | [mXylyl(1,6)]Ac-C-A-E-R-F-C-D-Tbg-Y-azaTrp-E-Y-P-Phg-(Lys-C12) | 172 |
| R3172 | [mXylyl(1,6)]Ac-C-V-E-R-F-C-(N-Me)D-Tbg-Y-azaTrp-E-Y-P-Chg-Nvl-NH2 | 173 |
| R3173 | [cyclo(1,6)]Ac-K-V-E-R-F-D-D-Tbg-Y-azaTrp-E-Y-P-Chg-Nvl | 174 |
| R3174 | [cyclo (1,6)]Ac-K-V-E-R-F-D-Asp(T)-Tbg-Y-azaTrp-E-Y-P-Chg-Nvl | 175 |
| R3175 | [cyclo(1,6)]Ac-K-V-E-R-F-D-D-Tbg-Y-azaTrp-E-Y-P-Chg-B20 | 176 |
| R3176 | [cyclo(1,6)]Ac-K-V-E-R-F-D-(N-Me)D-Tbg-Y-azaTrp-E-Y-P-Chg-Nvl | 177 |
| R3177 | [mXylyl(1,6)]Ac-C-V-E-R-F-C-D-Tbg-Y-azaTrp-E-W-P-Chg-Nvl | 178 |
| R3178 | [mXylyl(1,6)]Ac-C-V-E-R-F-C-D-Tbg-Y-azaTrp-E-(homo)Phe-P-Chg-Nvl | 179 |
| R3179 | [mXylyl(1,6)]Ac-C-V-E-R-F-C-D-Tbg-Y-azaTrp-E-(m-Cl-homo)Phe-P-Chg-Nvl | 180 |
| R3180 | [mXylyl(1,6)]Ac-C-V-E-R-F-C-D-Tbg-Y-azaTrp-E-2Nal-P-Chg-Nvl | 181 |
| R3181 | [mXylyl(1,6)]Ac-C-V-E-R-F-C-D-Tbg-Y-(3-aminomethyl)Phe-E-Y-P-Chg-Nvl | 182 |
| R3182 | [cyc10-triazolyl(1,6)]Ac-X02-V-E-R-F-X31-D-Tbg-Y-azaTrp-E-Y-P-Chg-Nvl | 183 |
| R3183 | [cyclo(1,6)]Ac-K-V-E-R-F-D-(N-Me)D-Tbg-Y-azaTrp-E-Y-P-Chg-(Lys-C16) | 184 |
| R3184 | [cyclo-thioalkyl(1,5)]V-E-R-F-C-D-Tbg-Y-azaTrp-E-Y-P-Chg-Nvl | 185 |
| R3185 | [mXylyl(1,6)]Ac-C-V-E-R-F-C-Cle-Tbg-Y-azaTrp-E-Y-P-Chg-Nvl | 186 |
| R3186 | [mXylyl(1,6)]Ac-C-V-E-R-F-C-(Ac-Pyran)-Tbg-Y-azaTrp-E-Y-P-Chg-Nvl | 187 |
| R3187 | [mXylyl(1,6)]Ac-C-V-E-R-F-C-D-Tbg-Y-azaTrp-E-(3-aminomethyl)Phe-P-Chg-Nvl | 188 |

TABLE 4 -continued

Compounds of the invention

| Compound Number | Sequence | SEQ ID NO. |
|---|---|---|
| R3188 | [cyc10-olefinyl(1,6)]Ac-X30-V-E-R-F-X12-D-Tbg-Y-azaTrp-E-Y-P-Chg-Nvl | 189 |
| R3189 | [mXylyl(1,6)]Ac-C-A-E-R-F-C-D-Tbg-Y-azaTrp-E-Y-P-Phg-(Lys-C16) | 190 |
| R3190 | [cyclo(1,6)]Ac-K-V-E-R-F-D-(N-Me)D-Tbg-Y-azaTrp-E-Y-P-Chg-B20 | 191 |
| R3191 | [cyclo(1,6)]Ac-K-V-E-R-F-D-(N-Me)D-Tbg-Y-azaTrp-E-Y-P-Chg-K | 192 |
| R3192 | [cyclo(1,6)]Ac-K-V-E-R-F-D-(N-Me)D-Tbg-Y-azaTrp-E-Y-P-Chg-K-NH2 | 193 |
| R3193 | [cyclo(1,6)]Ac-K-V-E-R-F-D-(N-Me)D-Tbg-Y-azaTrp-E-Y-P-Chg-B28 | 194 |
| R3194 | [cyclo(1,6)]Ac-K-V-E-R-F-D-(N-Me)D-Tbg-Y-azaTrp-E-Y-P-Chg-(Lys-C16)-NH2 | 195 |
| R3195 | [cyclo(1,6)]Ac-K-V-E-R-F-D-(N-Me)D-Tbg-Y-W-E-Y-P-Chg-(Lys-C16) | 196 |
| R3196 | [cyclo(1,6)]Ac-K-V-E-R-F-D-(N-Me)D-Tbg-Y-W-E-Y-P-Chg-K | 197 |
| R3197 | [cyclo(1,6)]Ac-K-V-E-R-F-D-(N-Me)D-Tbg-Y-W-E-Y-P-Chg-K14 | 198 |
| R3198 | [cyclo(1,6)](desamino)C-V-E-R-F-C-(N-Me)D-Tbg-Y-azaTrp-E-Y-P-Chg-(Lys-C16) | 199 |
| R3199 | [cyclo (1,6)](desamino)C-(D-Ala)-E-R-F-C-(N-Me)D-Tbg-Y-azaTrp-E-Y-P-Chg-(Lys-C16) | 200 |
| R3200 | [cyclo(1,6)]Ac-K-V-E-R-F-D-(N-Me)D-Tbg-Y-azaTrp-E-Y-P-Aib-(Lys-C16) | 201 |

Polypeptides R3183 (SEQ ID NO: 184) and R3193 (SEQ ID NO: 194) were synthesized according to the amino acid sequences of R3176 (SEQ ID NO: 177) with the exception of the replacement of Nvl-NH$_2$ with Lys. The side chain amine group of the Lys residue was modified with the different lipophilic moieties resulting in lipidated polypeptides.

Example 10. Optimization and Testing of C5 Inhibitors

Polypeptides selected according to Example 3 and listed in Table 3 were tested for their ability to inhibit complement-mediated cell lysis. Additionally, a variety of optimized polypeptides were synthesized according to the methods of Examples 4-8 and tested as well (see Table 4). Optimized polypeptide sequences include those obtained by making a variety of truncations, deletions, additions and/or substitutions to compounds R3002 (SEQ ID NO: 3), R3008 (SEQ ID NO: 9) and R3021 (SEQ ID NO: 11) or through the formation of hybrid polypeptides comprising combinations of regions selected from any of the three.

Human Hemolysis Assay (RBC Lysis Assay Using Complete Human Sera)

Polypeptides listed in Table 3, as well as their optimized derivatives (see Table 4) were assessed for inhibitor activity using a red blood cell hemolysis assay. Antibody-sensitized sheep erythrocytes (Complement Technology, Tyler, TX) were plated at $2.5 \times 10^7$ cells/well with complete human sera (Complement Technology, Tyler TX) and polypeptides to determine the inhibitory effect of the polypeptides on the lysis of red blood cells. Cells were centrifuged for 3 minutes at 2,090×gravity and resuspended in fresh GVB++ buffer (Complement Technology, Tyler TX). Human sera was rapidly thawed at 37° C. and then stored on ice until diluted into GVB++. Ten 6-fold serial dilutions of polypeptides (10 mM stock, DMSO) were performed in DMSO and then added to buffer. 50 µl of each polypeptide dilution was combined with sera and 100 µl of cells in individual wells of a 96-well tissue culture-treated clear microtitre plate (USA Scientific, Ocala, FL) and resuspended by pipetting. Samples were incubated at 37° C. for one hour. Following incubation, plates were centrifuged at 2,090×gravity for 2 minutes. 100 µl of supernatant was transferred to a new plate and the absorbance was read at 412 nm. Data was fit with a log-logit formula producing a dose-response curve and IC$_{50}$. As used herein, the term "IC$_{50}$" refers to the half maximal inhibitory concentration, a value used to indicate the amount of the inhibitor needed to reduce a given reaction or process by half. Compounds tested are listed in Table 5.

TABLE 5

Compounds analyzed

| Compound Number | Avg. IC$_{50}$ (nM) | SEQ ID NO. |
|---|---|---|
| R3000 | >10,000 | 1 |
| R3001 | 67.2 | 2 |
| R3002 | 11.9 | 3 |
| R3003 | 13.9 | 4 |
| R3004 | 53.5 | 5 |
| R3005 | 66.7 | 6 |
| R3006 | 267 | 7 |
| R3007 | 314 | 8 |
| R3008 | 97 | 9 |
| R3009 | >100,000 | 101 |
| R3010 | >100,000 | 102 |
| R3011 | 112 | 31 |

TABLE 5-continued

Compounds analyzed

| Compound Number | Avg. IC$_{50}$ (nM) | SEQ ID NO. |
|---|---|---|
| R3012 | 148.5 | 36 |
| R3013 | 344 | 42 |
| R3014 | 1420 | 55 |
| R3015 | >3,960 | 63 |
| R3016 | >13,000 | 79 |
| R3017 | >100,000 | 103 |
| R3018 | >5,730 | 71 |
| R3019 | 1320 | 54 |
| R3020 | 24.6 | 10 |
| R3021 | 27.5 | 11 |
| R3022 | >10,200 | 78 |
| R3023 | >100,000 | 104 |
| R3024 | 32.5 | 21 |
| R3025 | 47.5 | 24 |
| R3026 | 1020 | 52 |
| R3027 | >10,000 | 72 |
| R3028 | >10,000 | 73 |
| R3029 | 18.5 | 18 |
| R3030 | 83.6 | 28 |
| R3031 | 1090 | 53 |
| R3032 | >10,000 | 74 |
| R3033 | 131 | 34 |
| R3034 | >50,000 | 85 |
| R3035 | >50,000 | 86 |
| R3036 | >50,000 | 87 |
| R3037 | 276 | 39 |
| R3038 | 140 | 35 |
| R3039 | 240 | 38 |
| R3040 | >100,000 | 105 |
| R3041 | 71.3 | 26 |
| R3042 | >100,000 | 106 |
| R3043 | 934 | 50 |
| R3044 | >50,000 | 88 |
| R3045 | >100,000 | 107 |
| R3046 | >100,000 | 108 |
| R3047 | >100,000 | 109 |
| R3048 | 19.3 | 19 |
| R3049 | >3,100 | 61 |
| R3050 | 42.9 | 23 |
| R3051 | >100,000 | 110 |
| R3052 | >100,000 | 111 |
| R3053 | >100,000 | 112 |
| R3054 | 14.1 | 17 |
| R3055 | 10.4 | 13 |
| R3056 | 13.8 | 16 |
| R3057 | 12.4 | 15 |
| R3058 | >10,000 | 75 |
| R3059 | 2160 | 57 |
| R3060 | 161 | 37 |
| R3061 | 53.9 | 25 |
| R3062 | 89.9 | 29 |
| R3063 | >100,000 | 113 |
| R3064 | >100,000 | 114 |
| R3065 | 394 | 43 |
| R3066 | 104 | 30 |
| R3067 | >10,000 | 76 |
| R3068 | >4,500 | 64 |
| R3069 | >3,670 | 62 |
| R3070 | 123 | 32 |
| R3071 | 128 | 33 |
| R3072 | 26.9 | 20 |
| R3073 | 403 | 44 |
| R3074 | 308 | 41 |
| R3075 | >75,000 | 96 |
| R3076 | 297 | 40 |
| R3077 | 81.7 | 27 |
| R3078 | 568 | 47 |
| R3079 | 7.3 | 12 |
| R3080 | >50,000 | 89 |
| R3081 | >100,000 | 115 |
| R3083 | >25,000 | 81 |
| R3084 | >100,000 | 117 |
| R3086 | >50,000 | 91 |
| R3087 | >25,000 | 82 |
| R3088 | >100,000 | 118 |
| R3089 | >15,000 | 80 |
| R3090 | >100,000 | 119 |
| R3091 | 483 | 46 |
| R3092 | >50,000 | 92 |
| R3093 | >100,000 | 120 |
| R3094 | >100,000 | 121 |
| R3095 | >50,000 | 93 |
| R3096 | >50,000 | 94 |
| R3097 | >100,000 | 122 |
| R3098 | >100,000 | 123 |
| R3099 | >100,000 | 124 |
| R3100 | 626 | 48 |
| R3101 | >100,000 | 125 |
| R3102 | 978 | 51 |
| R3103 | >25,000 | 83 |
| R3104 | >2,000 | 56 |
| R3105 | >5,000 | 65 |
| R3106 | >5,000 | 66 |
| R3107 | >75,000 | 97 |
| R3108 | >75,000 | 98 |
| R3109 | >100,000 | 126 |
| R3110 | 2940 | 59 |
| R3111 | >5,000 | 67 |
| R3112 | >5,000 | 68 |
| R3113 | >5,000 | 69 |
| R3114 | 36.6 | 22 |
| R3115 | 2780 | 58 |
| R3116 | 441 | 45 |
| R3117 | >10,000 | 77 |
| R3118 | >100,000 | 127 |
| R3119 | >100,000 | 128 |
| R3120 | 12.2 | 14 |
| R3121 | 804 | 49 |
| R3122 | >50,000 | 95 |
| R3123 | >100,000 | 129 |
| R3124 | >100,000 | 130 |
| R3125 | >100,000 | 131 |
| R3126 | >3000 | 60 |
| R3127 | >75,000 | 99 |
| R3128 | >100,000 | 132 |
| R3129 | >100,000 | 133 |
| R3130 | >100,000 | 134 |
| R3131 | >100,000 | 135 |
| R3132 | >100,000 | 136 |
| R3133 | >75,000 | 100 |
| R3134 | >5,000 | 70 |
| R3135 | >25,000 | 84 |
| R3136 | >50,000 | 137 |
| R3137 | >100,000 | 138 |
| R3138 | 87.2 | 139 |
| R3139 | 97.2 | 140 |
| R3140 | 17.9 | 141 |
| R3141 | 24.5 | 142 |
| R3142 | 44.6 | 143 |
| R3143 | 18.6 | 144 |
| R3144 | 6.7 | 145 |
| R3145 | 39 | 146 |
| R3146 | 107 | 147 |
| R3147 | 138 | 148 |
| R3148 | 8.5 | 149 |
| R3149 | 13.6 | 150 |
| R3150 | 32 | 151 |
| R3151 | 165 | 152 |
| R3152 | 11 | 153 |
| R3153 | 175 | 154 |
| R3154 | 592 | 155 |
| R3155 | 1530 | 156 |
| R3156 | >10,000 | 157 |
| R3157 | 84.5 | 158 |
| R3158 | 327 | 159 |
| R3159 | 7.6 | 160 |
| R3160 | 37.1 | 161 |
| R3161 | 7 | 162 |

TABLE 5-continued

Compounds analyzed

| Compound Number | Avg. IC$_{50}$ (nM) | SEQ ID NO. |
|---|---|---|
| R3162 | 16.5 | 163 |
| R3163 | 17 | 164 |
| R3164 | 36 | 165 |
| R3165 | 18.5 | 166 |
| R3166 | 17.5 | 167 |
| R3167 | 11 | 168 |
| R3168 | 7.5 | 169 |
| R3169 | 5 | 170 |
| R3170 | 4.5 | 171 |
| R3172 | 12 | 173 |

Example 11. Alternative Human Hemolysis Assay Using C5 Depleted Sera

Polypeptides listed in Table 6 were tested for functional activity in a red blood cell hemolysis assay using human C5 depleted sera and purified human C5 rather than complete human sera. To assess activity, antibody-sensitized sheep erythrocytes (Complement Technology, Tyler, TX) were plated 2.5×10$^7$ cells/well with 1.5% human C5 depleted sera (Complement Technology, Tyler, TX) and 0.5 nM purified human C5 (Complement Technology, Tyler, TX). The antibody-sensitized sheep erythrocytes were centrifuges at 2,090×gravity for 3 minutes and then resuspended in fresh GVB++(Complement Technology, Tyler, TX). The human C5 depleted sera and purified human C5 were rapidly thawed at 37° C. and then stored on ice or wet ice, respectively. The polypeptide stock (10 mM, DMSO) was serially diluted in DMSO in order to obtain 10$^6$-fold dilutions and then GVB++ was added to them. 50 µl of each polypeptide dilution was combined with 25 µl C5 depleted sera, 25 µl purified human C5 and 100 µl cells in individual wells of a 96-well tissue culture-treated clear microtitre plate (USA Scientific, Ocala, FL) and resuspended by pipetting. The samples were incubated at 37° C. for one hour. At the completion of the incubation, the plates were centrifuged at 2,090×gravity for 2 minutes. 100 µl of supernatant was transferred to a new plate and the absorbance was read at 412 nm. Data was fit with a log-logit formula producing a dose-response curve and IC$_{50}$.

TABLE 6

Compounds analyzed

| Compound Number | Avg. IC$_{50}$ (nM) | SEQ ID NO. |
|---|---|---|
| R3171 | 5.67 | 172 |
| R3173 | 2.5 | 174 |
| R3174 | 2.3 | 175 |
| R3176 | 1.1 | 177 |
| R3177 | 12 | 178 |
| R3179 | 83 | 180 |
| R3180 | 29 | 181 |
| R3181 | 1496 | 182 |
| R3182 | 13 | 183 |
| R3183 | 13.25 | 184 |
| R3184 | 4 | 185 |
| R3185 | 12.5 | 189 |
| R3186 | 18 | 187 |
| R3189 | 81.5 | 190 |
| R3190 | 35.33 | 191 |

TABLE 6-continued

Compounds analyzed

| Compound Number | Avg. IC$_{50}$ (nM) | SEQ ID NO. |
|---|---|---|
| R3191 | 2.5 | 192 |
| R3192 | 1.5 | 193 |
| R3193 | 24 | 194 |
| R3194 | 15.5 | 195 |
| R3195 | 62.5 | 196 |
| R3196 | 3 | 197 |
| R3197 | 4 | 198 |
| R3198 | 142 | 199 |
| R3199 | 112 | 200 |
| R3200 | 88.5 | 201 |

Example 12. Enzyme Immunoassay to Assess C5 Inhibition

C5 inhibitory activity was assessed by enzyme immunoassay (EIA). Inhibition of the production of C5a and the membrane attack complex (MAC) were measured by MicroVue EIA kits (Quidel Corporation, San Diego, CA).

C5a EA

Figure 1:
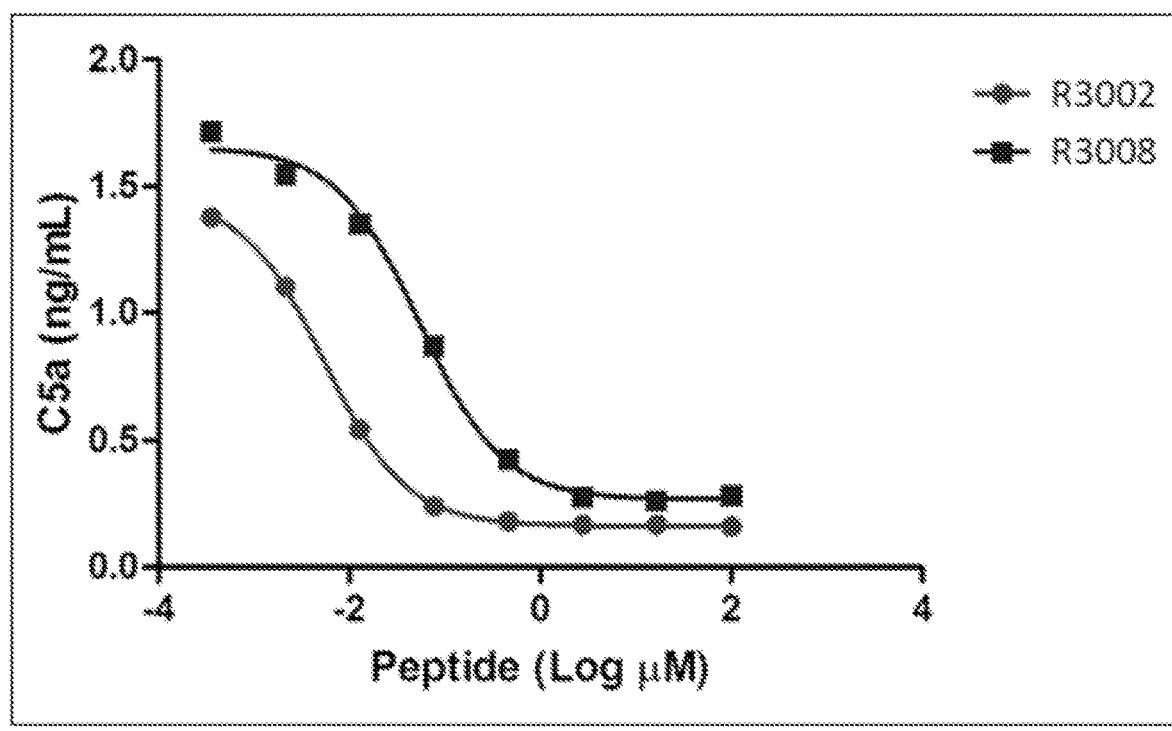
FIG. 1 is a line graph displaying the results of an enzyme immunoassay (EIA) for the detection of C5a in supernatant from a human red blood cell (RBC) hemolysis assay with increasing concentrations of inhibitors R3002 (SEQ ID NO: 3) and R3008 (SEQ ID NO: 9). Levels of C5a correlate with complement activity and are therefore an indicator of the ability of the compounds tested to inhibit complement activity. Supernatant from the hemolysis assay was diluted 1:50 and assayed for C5a levels. C5a levels decreased in human hemolysis assay supernatant samples with increasing levels of either inhibitor assayed. R3002 (SEQ ID NO: 3) had an $IC_{50}$ of 5.4 nM while R3008 (SEQ ID NO: 9) had an $IC_{50}$ of 54.5 nM. As used herein, the term "$IC_{50}$" refers to the half maximal inhibitory concentration, a value used to indicate the amount of the inhibitor needed to reduce a given reaction or process by half.

Supernatant from a human RBC hemolysis assay of R3002 (SEQ ID NO: 3) and R3008 (SEQ ID NO: 9) was diluted 1:50 and assayed by C5a EIA (FIG. 1). Both polypeptides inhibited the formation of C5a. R3002 (SEQ ID NO: 3) had an IC$_{50}$ of 5.4 nM, R3008 (SEQ ID NO: 9) had an IC$_{50}$ of 54.5 nM.

Membrane Attack Complex (MAC) EIA

Figure 2:
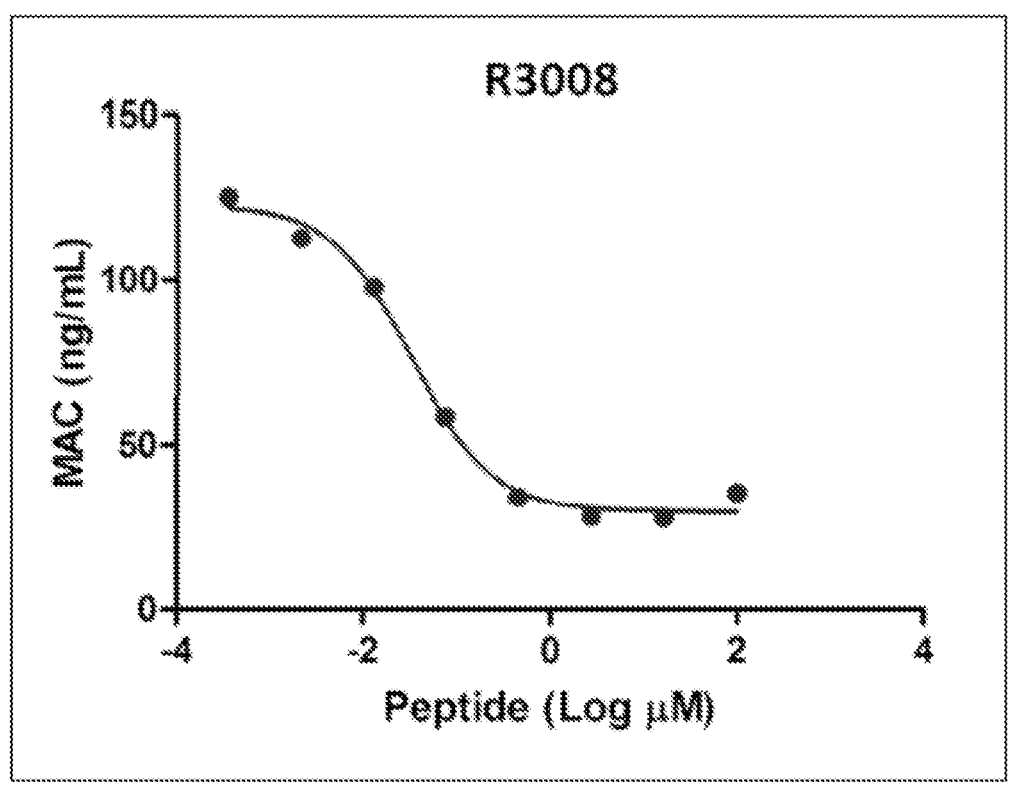
FIG. 2 is a line graph displaying the results of an EIA for the detection of the membrane attack complex (MAC) in supernatant from a human RBC hemolysis assay with increasing concentrations of R3008 (SEQ ID NO: 9). Levels of the MAC correlate with complement activity and are therefore an indicator of the ability of R3008 (SEQ ID NO: 9) to inhibit complement activity. Supernatant from the hemolysis assay was diluted 1:5 and assayed for MAC levels. MAC levels decreased in hemolysis assay supernatant samples with increasing levels of the inhibitor assayed with an $IC_{50}$ of 33 nM.

The MAC EIA was performed on the diluted supernatant (1:5) of R3008 (SEQ ID NO: 9) from a human RBC hemolysis assay (FIG. 2). This polypeptide was shown to inhibit the formation of the MAC with an IC$_{50}$ of 33 nM.

Example 13. Characterization of Peptidomimetic Binding by Fluorescence Polarization Fluorescence polarization (FP) allows binding events to be measured in a homogenous solution (Banks, P. et al., Impact of a red-shifted dye label for high throughput fluorescence polarization assays of G protein-coupled receptors. J Biomol Screen. 2000 October; 5(5):329-34 and Parker, G. J. et al., Development of high throughput screening assays using fluorescence polarization: nuclear receptor-ligand-binding and kinase/phosphatase assays. J Biomol Screen. 2000 April; 5(2):77-88). The key concept of FP is that the degree by which a fluorophore polarizes light is inversely related to its molecular rotation (Lea, W. A. et al., Fluorescence polarization assays in small molecule screening. Expert Opin Drug Discov. 2011 January; 6(1):17-32), and a fluorophore bound to a much larger target protein rotates more slowly than an unbound fluorophore, resulting in an increase in polarization that can be quantified. FP has been used increasingly in high throughput campaigns as a method to measure ligand-target binding (Parker, G. J. et al., Development of high throughput screening assays using fluorescence polarization: nuclear receptor-ligand-binding and kinase/phosphatase assays. J Biomol Screen. 2000 April; 5(2):77-88), for equilibrium dissociation constant (K$_D$) determination (Prystay, L. et al., Determination of equilibrium dissociation constants in fluorescence polarization. J Biomol Screen. 2001 June: 6(3):141-50), and lead discovery through competitive binding assays (Tian, W. et al., Development of novel fluorescence polarization-based assay for studying the β-catenin/Tcf4 interaction. J Biomol Screen. 2012 April; 17(4):530-4).

Materials and Methods

FP was used for screening competitive polypeptide inhibitors of the C5 protein. Probe R3076 (SEQ ID NO: 40) was generated by incubating the parent polypeptide, R3072 (SEQ ID NO: 20) with BODIPY-TMR-X, SE (Life Technologies, Grand Island, NY) in DMF (Sigma, Saint Louis, MO) for 4 hours. The BODIPY-TMR dye attached to the C-terminal lysine of the protein and the subsequent labeled probe was purified by HPLC.

The equilibrium dissociation constant ($K_D$) for binding of R3076 (SEQ ID NO: 40) to human C5 protein (Complement Technology, Tyler, TX) was determined by incubating a solution of 25 nM R3076 (SEQ ID NO: 40) with increasing concentrations of C5 protein. Polarization was measured over time, until binding reached equilibrium. $K_D$ was determined using Graphpad Prism (using "Saturating Binding Curves, One Site—Specific Binding With Hill Slope" as the curve fit to determine $K_D$). Equilibrium was reached after 10 minutes, with values for K), hill slope and maximal binding remaining stable over 60 minutes. A final $K_D$ value of 8.07 nM (0.53 standard deviation) was determined by averaging $K_D$ values from 10 to 60 minutes. Based on this information, 25 nM and 50 nM concentrations for R3076 (SEQ ID NO: 40) and C5 protein, respectively, were chosen for use in the competition assay. These concentrations represented the approximate level of protein necessary for 95% probe binding to C5 protein. R3023 (SEQ ID NO: 104) is a scrambled polypeptide variant of R3002 (SEQ ID NO: 3) and was included in all assays as a negative control.

Human C5 protein was diluted to 200 nM in assay buffer, composed of TBS (EMD Millipore, Billerica, MA)+0.005% Triton-X (Sigma, Saint Louis, MO). 10 µl of assay buffer was added to all wells of a black, non-binding, 384-well assay plate (Greiner, Monroe, NC) and 10 µl of diluted C5 protein stock was added to experimental and designated control wells.

Probe R3076 (SEQ ID NO: 40) was diluted 1 to 10 in DMSO (Life Technologies, Grand Island, NY) and 30 µl of that stock was diluted in 3 ml of assay buffer to yield a 100 nM stock. 10 µl of this working stock was then added to each well in the assay plate. The assay plate was incubated at room temperature, protected from light, for 20 minutes to allow binding to reach equilibrium.

Test articles listed in Table 7 were subsequently diluted in DMSO then assay buffer, comprising $10^2$-fold dilutions and were then added to the assay plate in triplicate, rapidly. The assay plate was then incubated in the Paradigm (Molecular Devices, Sunnyvale, CA) plate reader for 60 minutes at 25° C.

After incubation for 60 minutes, the plate was read using the Paradigm FP protocol (Molecular Devices, Sunnyvale, CA) and raw polarization values were imported into Graphpad Prism. $K_i$ (using the One Site $K_i$ Curve fitting model, probe concentration=25 nM, $K_D$=8.07 nM, with baseline constrained to the average of the 0% binding control) and $IC_{50}$ (log inhibitor vs response, 4 parameter curve fit) were determined in Graphpad.

Results

Figure 3:
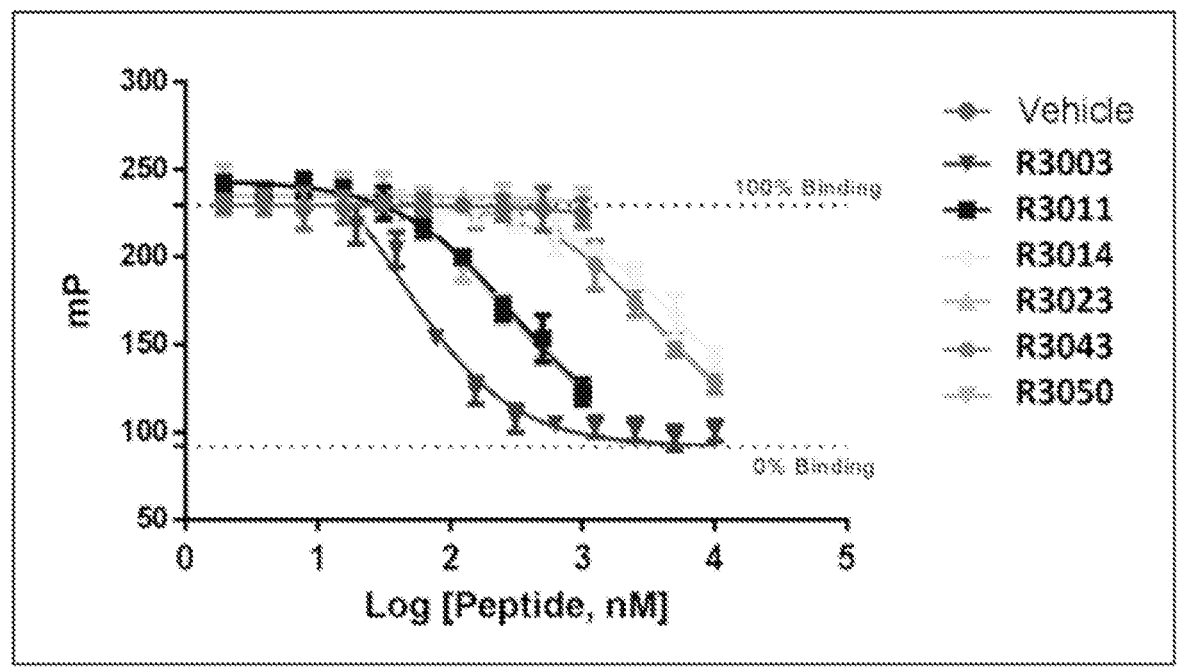
FIG. 3 is a line graph displaying competitive fluorescence polarization (FP) data for test articles R3003 (SEQ ID NO: 4), R3011 (SEQ ID NO: 31), R3014 (SEQ ID NO: 55), R3023 (SEQ ID NO: 104), R3043 (SEQ ID NO: 50) and R3050 (SEQ ID NO: 23). FP allows binding events to be measured in a homogenous solution. A competitive binding assay was conducted wherein a 25 nM solution of compound R3076 (SEQ ID NO: 40), which has a fluorescent tag, was combined with increasing amounts of the test articles and measured for changes in FP (in milli-polarization units; mP). Decreasing mP levels correlate with successful competition for C5 by the test articles. The averages of two independent experiments conducted in triplicate (+/−standard deviation) are shown. Of the articles tested, R3003 (SEQ ID NO: 4) was the most potent while R3023 (SEQ ID NO: 104), a control polypeptide, showed no activity at the highest concentration tested.

All test articles were able to compete with the labeled probe for binding to human C5 protein (FIG. 3, Table 7). R3003 (SEQ ID NO: 4) was the most potent polypeptide tested, with a K, value of 9.54 nM. R3023 (SEQ ID NO: 104) binding was not detected at the highest concentration tested.

TABLE 7

Competitive fluorescence polarization data

| Compound Number | SEQ ID NO | $K_i$ nM, Exp 1 | $K_i$ nM, Exp 2 | $IC_{50}$ nM, Exp 1 | $IC_{50}$ nM, Exp 2 | Avg, nM $K_i$ | Std. Dev. $K_i$ | Avg, nM $IC_{50}$ | Std. Dev. $IC_{50}$ |
|---|---|---|---|---|---|---|---|---|---|
| R3003 | 4 | 10.39 | 8.69 | 72.65 | 64.06 | 9.54 | 1.20 | 68.36 | 6.07 |
| R3011 | 31 | 73.17 | 86.91 | 294.8 | 261.3 | 80.04 | 9.72 | 278.1 | 23.69 |
| R3014 | 55 | 1405 | 1585 | 6064 | 7579 | 1495 | 127.3 | 6822 | 1071 |
| R3023 | 104 | >1000 | >1000 | >1000 | >1000 | >1000 | — | >1000 | — |
| R3043 | 50 | 866.1 | 882.1 | 4332 | 4122 | 874.1 | 11.31 | 4227 | 148.5 |
| R3050 | 23 | 71.08 | 57.6 | 266.9 | 292.7 | 64.34 | 9.53 | 279.8 | 18.24 |

Data shown in Table 7 were obtained from curve fitting analysis performed by Graphpad Prism software as described above. Triplicate values were averaged to yield the data points presented in each experiment. Of the polypeptides tested, R3003 (SEQ ID NO: 4) was identified originally by mRNA display selection. The affinity of R3003 (SEQ ID NO: 4) for C5 was verified by the results of FP analysis displaying low K, as well as $IC_{50}$ values. Inhibitors R3011 (SEQ ID NO: 31) and R3050 (SEQ ID NO: 23) also displayed relatively strong affinity for C5. A control polypeptide, R3023 (SEQ ID NO: 104), displayed no affinity for C5, while inhibitors R3014 (SEQ ID NO: 55) and R3043 (SEQ ID NO: 50) displayed weak affinity.

Example 14. Analysis of Compound Stability in Plasma

Compounds were assayed for stability in human plasma under the following conditions. Human plasma was obtained from Bioreclamation (Westbury, NY) and collected in sodium heparin. Plasma was adjusted to pH 7.4. DMSO stocks at 10 mM concentration were prepared for the test compounds. Aliquots of the DMSO solutions were dosed into I mL of plasma, which had been pre-warmed to 37° C., at a final test compound concentration of 10 µM. The vials were kept in a benchtop THERMOMIXER® (Eppendorf, Hauppauge, NY) for the duration of the experiment. Aliquots (100 µL) were taken at each timepoint and added to a 96-well plate that had been pre-filled with 300 µL of an acetonitrile solution containing mixture of the internal standards (metoprolol, propranolol and warfarin each at 500 ng/mL). Samples were stored at 4° C. until the end of the experiment. After the final timepoint was sampled, the plate was mixed and then centrifuged at 3,000 rpm for 10 minutes. Aliquots of the supernatant were removed and analyzed by LC-HRAMS. Liquid chromatography settings are listed in Table 8 and mass spectrometry settings are listed in Table 9.

TABLE 8

Liquid chromatography settings

| | |
|---|---|
| Column: | Luna C18 (Luna, Torrance, CA) 50 mm × 2.0 mm, 3 µm |
| M.P. Buffer: | Aqueous Reservoir (A): 0.1% Acetic acid in water Organic Reservoir (B): 0.1% Acetic acid in MeOH:MeCN = 1:1 Gradient Program: |

| Time (Min) | Flow rate (mL/min) | % A | % B |
|---|---|---|---|
| 0.0 | 0.3 | 100 | 0 |
| 5 | 0.3 | 0 | 100 |
| 7.5 | 0.3 | 0 | 100 |
| 7.6 | 0.45 | 100 | 0 |
| 10.5 | 0.3 | 100 | 0 |

| | |
|---|---|
| Total Run Time: | 10.5 minutes |
| Autosampler: | Agilent 1100 Bin (Agilent, Santa Clara, CA) |
| Injection loop volume: | 20 µL |
| Injection volume: | 10 µL |
| Autosampler Wash 1: | Methanol/water 1:1; with 0.2% formic acid |
| Autosampler Wash 2: | Methanol/2-propanol:1/1; with 0.2% formic acid |

TABLE 9

Mass spectrometry settings

| | |
|---|---|
| Instrument: | LTQ Orbitrap XL (Thermo Scientific, St. Louis, MO) |
| Positive Mode: | Electrospray, positive mode (+5000 V) |
| Interface: | High Resolution Mass Spectroscopy |
| Mode: | Capillary Temperature: 275° C. |
| Ion Source Settings: | Capillary Voltage: 47 Sheath gas: 45 Auxiliary gas: 15 Sweep gas: 10 |
| Orbitrap Settings: | Scan Range 200-2000, Resolution = 30000 (Full width at half maximum) Setting for MS/MS Data Dependent Acquisition Isolation Width: 2 Normalized Collision Energy: 35 |

The concentration of test compound R3050 (SEQ ID NO: 23) was determined by comparison to a previously determined calibration curve (Table 10).

TABLE 10

Stability profile

| Percent remaining at time (hrs) | | | | | Half-Life |
|---|---|---|---|---|---|
| 0 hrs | 2 hrs | 4 hrs | 12 hrs | 24 hrs | (min.) |
| 100 | 108.9 | 100.4 | 88 | 98.1 | >1440 |

Under these conditions, R3050 (SEQ ID NO: 23) was shown to be highly stable.

Example 15. Polypeptide Variants Comprising Tryptophan Analogs

In some embodiments, polypeptides of the present invention comprise 7-azatryptophan. To determine the importance of this residue in C5 inhibition, amino acid substitution analysis was carried out wherein 7-azatryptophan was replaced by natural tryptophan as well as various other tryptophan analogs including 5-fluorotryptophan [(5-F)W], 1-methyl-tryptophan [(1-Me)W], D-tryptophan and 5-methyl-N-tryptophan [(5-MeO)W]. Similar polypeptides with non-tryptophan substitutions were analyzed as well.

Polypeptide variants of R3002 (SEQ ID NO: 3) and R3008 (SEQ ID NO: 9) were synthesized and tested for their ability to inhibit red blood cell lysis as described in Example 10 (see Tables 11 and 12). Of the variants tested, all with substitution of the 7-azatryptophan residue demonstrated a decreased ability to inhibit red blood cell lysis as indicated by increasing average $IC_{50}$ values (a measure of the half maximal inhibitory concentration, a value used to indicate the amount of the inhibitor needed to reduce a given reaction or process by half).

TABLE 11

7-azatryptophan variant polypeptides of R3002 (SEQ ID NO: 3) analyzed by human hemolysis assay

| Compound Number | Sequence | Avg. $IC_{50}$ (nM) | SEQ ID NO |
|---|---|---|---|
| R3002 | Ac-Nvl-C-Y-E-N-Tbg-Y-azaTrp-E-Y-P-Phg-Nvl-NH2 | 11.9 | 3 |
| R3041 | Ac-Y-E-N-Tbg-Y-W-E-Y-P-Phg-Nvl-NH2 | 71.3 | 26 |
| R3094 | Ac-Y-E-N-Tbg-Y-(5-MeO)W-E-Y-P-Phg-Nvl-NH2 | >100,000 | 121 |
| R3110 | Ac-Y-E-N-Tbg-Y-(1-Me)W-E-Y-P-Phg-Nvl-NH2 | 2,940 | 59 |
| R3118 | Ac-Y-E-N-Tbg-Y-(D-Trp)-E-Y-P-Phg-Nvl-NH2 | >100,000 | 127 |
| R3119 | Ac-Y-E-N-Y-(D-Trp)-E-Y-P-Phg-Nvl-NH2 | >100,000 | 128 |
| R3128 | Ac-Nvl-C-Y-N-N-Tbg-E-C-E-Y-P-Phg-Tbg-NH2 | >100,000 | 132 |
| R3067 | Ac-Nvl-S-Y-E-N-Tbg-Y-A-E-Y-P-Chg-Nvl-NH2 | >10,000 | 76 |
| R3116 | Ac-Nvl-Nvl-Y-E-N-Tbg-Y-(N-Me)W-E-Y-P-Chg-Nvl-NH2 | 441 | 45 |
| R3017 | [mXylyl(2,8)]Ac-Nvl-C-Y-E-N-Tbg-Y-C-E-Y-P-Phg-Nvl-NH2 | >100,000 | 103 |
| R3129 | [mXylyl(2,8)]Ac-Nvl-C-Y-N-N-Tbg-E-C-E-Y-P-Phg-Tbg-NH2 | >100,000 | 133 |

TABLE 12

7-azatryptophan variant polypeptides of R3008 (SEQ ID NO: 9) analyzed by human hemolysis assay

| Compound Number | Sequence | Avg. $IC_{50}$ (nM) | SEQ ID NO |
|---|---|---|---|
| R3008 | [mXylyl(2,10)]Ac-Nvl-C-Phg-T-azaTrp-E-Y-(N-Me)S-H-C-Nvl-P-Nvl-NH2 | 97 | 9 |
| R3088 | [mXylyl(2,10)]Ac-Nvl-C-Phg-T-(5-F)W-E-Y-(N-Me)S-A-C-Nvl-NH2 | >100,000 | 118 |
| R3091 | [mXylyl(2,10)]Ac-Nvl-C-Phg-T-W-E-Y-(N-Me)S-A-C-Nvl-NH2 | 483 | 46 |

TABLE 12 -continued 7-azatryptophan variant polypeptides of R3008
(SEQ ID NO: 9) analyzed by human hemolysis assay

| Compound Number | Sequence | Avg. IC$_{50}$ (nM) | SEQ ID NO |
|---|---|---|---|
| R3092 | [mXylyl(2,10)]Ac-Nvl-C-Phg-T-F-E-Y-(N-Me)S-A-C-Nvl-NH2 | >50,000 | 92 |
| R3109 | [mXylyl(2,10)]Ac-Nvl-C-Phg-T-(1-Me)W-E-Y-(N-Me)S-A-C-Nvl-NH2 | >100,000 | 126 |
| R3131 | [mXylyl(2,10)]Ac-Nvl-C-Phg-T-W-Asp(T)-Y-(N-Me)S-H-C-Nvl-NH2 | >100,000 | 135 |
| R3034 | [mXylyl(2,10)]Ac-Nvl-C-Phg-T-A-E-Y-(N-Me)S-H-C-Nvl-NH2 | >50,000 | 85 |
| R3132 | [mXylyl(2,10)]Ac-Nvl-C-Phg-T-(D-Trp)-E-Y-(N-Me)S-H-C-Nvl-NH2 | >100,000 | 136 |

Example 16. Effect of Polypeptide Truncation and Amino Acid Deletion Analyzed by Human Hemolysis Assay C-terminally truncated polypeptide variants of R3021 (SEQ ID NO: 11) were synthesized and assayed by the human hemolysis assay described in Example 10 for their ability to inhibit C5-dependent red blood cell lysis. Average IC$_{50}$ values (a measure of the half maximal inhibitory concentration, a value used to indicate the amount of the inhibitor needed to reduce a given reaction or process by half) for each polypeptide tested are listed in Table 13. Truncated polypeptides demonstrated decreased ability (as indicated by an increase in the IC$_{50}$ value) to inhibit red blood cell lysis with those variants lacking tryptophan having the largest IC$_{50}$ values.

Additionally, polypeptide variants of R3021 (SEQ ID NO. 11) with internal amino acid deletions were synthesized and assayed (see Table 14) for their ability to inhibit C5-dependent red blood cell lysis according to the method described in Example 10. Additionally, the N-terminal methionine in these variants was replaced by an acetyl group. Average IC$_{50}$ values for each polypeptide tested are listed in Table 14. Interestingly, acetyl group replacement of the N-terminal methionine alone [R3048 (SEQ ID NO: 19)] increased the ability of the polypeptide to inhibit red blood cell lysis. Removal of internal residue D [R3124 (SEQ ID NO: 130)] or internal residues DVY [R3125 (SEQ ID NO: 131), corresponding to residues 8, 9 and 10 from R3021 (SEQ ID NO: 11)] led to a decrease in the ability of the polypeptide to inhibit red blood cell lysis.

TABLE 13

C-terminally truncated polypeptide variants of R3021 (SEQ ID NO: 11) analyzed by human hemolysis assay

| Compound Number | Sequence | Avg. IC$_{50}$ (nM) | SEQ ID NO |
|---|---|---|---|
| R3021 | [mXylyl(2,7)]M-C-V-E-R-F-C-D-V-Y-W-E-F-NH2 | 27.5 | 11 |
| R3043 | [mXylyl(2,7)]M-C-V-E-R-F-C-D-V-Y-W-E-NH2 | 934 | 50 |
| R3044 | [mXylyl(2,7)]M-C-V-E-R-F-C-D-V-Y-W-NH2 | >50,000 | 88 |
| R3045 | [mXylyl(2,7)]M-C-V-E-R-F-C-D-V-Y-NH2 | >100,000 | 107 |
| R3046 | [mXylyl(2,7)]M-C-V-E-R-F-C-D-V-NH2 | >100,000 | 108 |
| R3047 | [mXylyl(2,7)]M-C-V-E-R-F-C-NH2 | >100,000 | 109 |

TABLE 14

Polypeptide variants of R3021 (SEQ ID NO: 11) with internal amino acid deletions analyzed by human hemolysis assay

| Compound Number | Sequence | Avg. IC$_{50}$ (nM) | SEQ ID NO |
|---|---|---|---|
| R3021 | [mXylyl(2,7)]M-C-V-E-R-F-C-D-V-Y-W-E-F-NH2 | 27.5 | 11 |
| R3048 | [mXylyl(1,6)]Ac-C-V-E-R-F-C-D-V-Y-W-E-F-NH2 | 19.3 | 19 |
| R3124 | [mXylyl(1,6)]Ac-C-V-E-R-F-C-V-Y-W-E-F-NH2 | >100,000 | 130 |
| R3125 | [mXylyl(1,6)]Ac-C-V-E-R-F-C-W-E-F-NH2 | >100,000 | 131 |

Example 17. Incorporation of Albumin-Binding Polypeptides

Polypeptides are conjugated to one or more polypeptides that modulate plasma protein binding. These polypeptides, referred to herein as "albumin-binding polypeptides" are listed in Table 15.

TABLE 15

Albumin-binding polypeptides

| Albumin-binding polypeptide sequence | SEQ ID NO |
|---|---|
| Ac-R-L-I-E-D-I-C-L-I-P-R-W-G-C-L-W-E-D-D-NH2 | 202 |
| Q-R-L-M-E-D-I-C-L-P-R-W-G-C-L-W-E-D-D-F-NH2 | 203 |
| Ac-Q-R-L-I-E-D-I-C-L-P-R-W-G-C-L-W-E-D-D-F-NH2 | 204 |

Albumin-binding polypeptides are cyclized by disulfide bond formation at cysteine residues. In some embodiments, albumin-binding polypeptides are conjugated by either their N or C-terminal ends, thus having slightly different structures (e.g. no acetyl group).

Example 18. Incorporation of Cell Penetrating Polypeptides

Polypeptides are conjugated to a polypeptide that has cell penetrating properties. These polypeptides are listed in Table 16 and are described in Milletti, F., Cell-penetrating polypeptides: classes, origin, and current landscape. Drug Discov Today. 2012 August; 17(15-16):850-60.

TABLE 16

Cell penetrating polypeptides

| Cell penetrating polypeptide | SEQ ID NO |
|---|---|
| R-K-K-R-R-E-S-R-K-K-R-R-R-E-S | 205 |
| R-K-K-R-R-Q-R-R-R | 206 |
| R-Q-I-K-I-W-F-Q-N-R-R-M-K-W-K-K | 207 |
| A-A-V-L-L-P-V-L-L-A-A-P | 208 |
| V-P-T-L-K | 209 |
| P-L-I-L-R-L-L-R-G-Q-F | 210 |

Example 19. Analysis of Polypeptide Mixtures Comprising Amino Acid Stereoisomers Polypeptides R3136 (SEQ ID NO: 137) and R3137 (SEQ ID NO: 138) were synthesized according to the amino acid sequences of R3085 (SEQ ID NO: 90) and R3082 (SEQ ID NO: 116), respectively with the exception of the replacement of Phg in each with D-Phg (see Table 17). Compositions comprising either R3136 (SEQ ID NO: 137) and R3085 (SEQ ID NO: 90) or R3137 (SEQ ID NO: 138) and R3082 (SEQ ID NO: 116) were analyzed for their ability to inhibit red blood cell lysis according to the human hemolysis assay described in Example 10. The composition comprising R3136 (SEQ ID NO: 137) and R3085 (SEQ ID NO: 90) yielded an average $IC_{50}$ (nM) of >50,000, while the composition comprising R3137 (SEQ ID NO: 138) and R3082 (SEQ ID NO: 116) yielded an average $IC_{50}$ (nM) of >100,000.

TABLE 17

Compounds used in amino acid stereoisomer polypeptide mixtures

| Compound Number | Sequence | SEQ ID NO. |
|---|---|---|
| R3136 | [mXylyl(2,10)]heptanoyl-Nvl-C-(D-Phg)-T-azaTrp-E-Y-(N-Me)S-A-C-Nvl-NH2 | 137 |
| R3137 | [mXylyl(1,9)]heptanoyl-C-(D-Phg)-T-azaTrp-E-Y-(N-Me)S-A-C-Nvl-NH2 | 138 |
| R3085 | [mXylyl(2,10)]heptanoyl-Nvl-C-Phg-T-azaTrp-E-Y-(N-Me)S-A-C-Nvl-NH2 | 90 |
| R3082 | [mXylyl(1,9)]heptanoyl-C-Phg-T-azaTrp-E-Y-(N-Me)S-A-C-Nvl-NH2 | 116 |

Example 20. Pharmacokinetic Studies in Non-Human Primates

Pharmacokinetic studies were carried out in non-human primates using the compounds listed in Table 18. In the table, "Cmpd" refers to compound and "Avg" refers to average.

TABLE 18

Compounds tested in in vivo studies

| Cmpd No. | Sequence | Avg $IC_{50}$ | SEQ ID NO. |
|---|---|---|---|
| R3152 | [mXylyl(1,6)]Ac-C-V-E-R-F-C-D-Tbg-Y-azaTrp-E-Y-P-Chg-Nvl-NH2 | 16.4 | 153 |
| R3201 | [mXylyl(1,6)]Ac-C-V-E-R-F-C-D-Tbg-Y-azaTrp-E-Y-P-Chg-Nvl | 7.7 | 211 |

Figure 4:
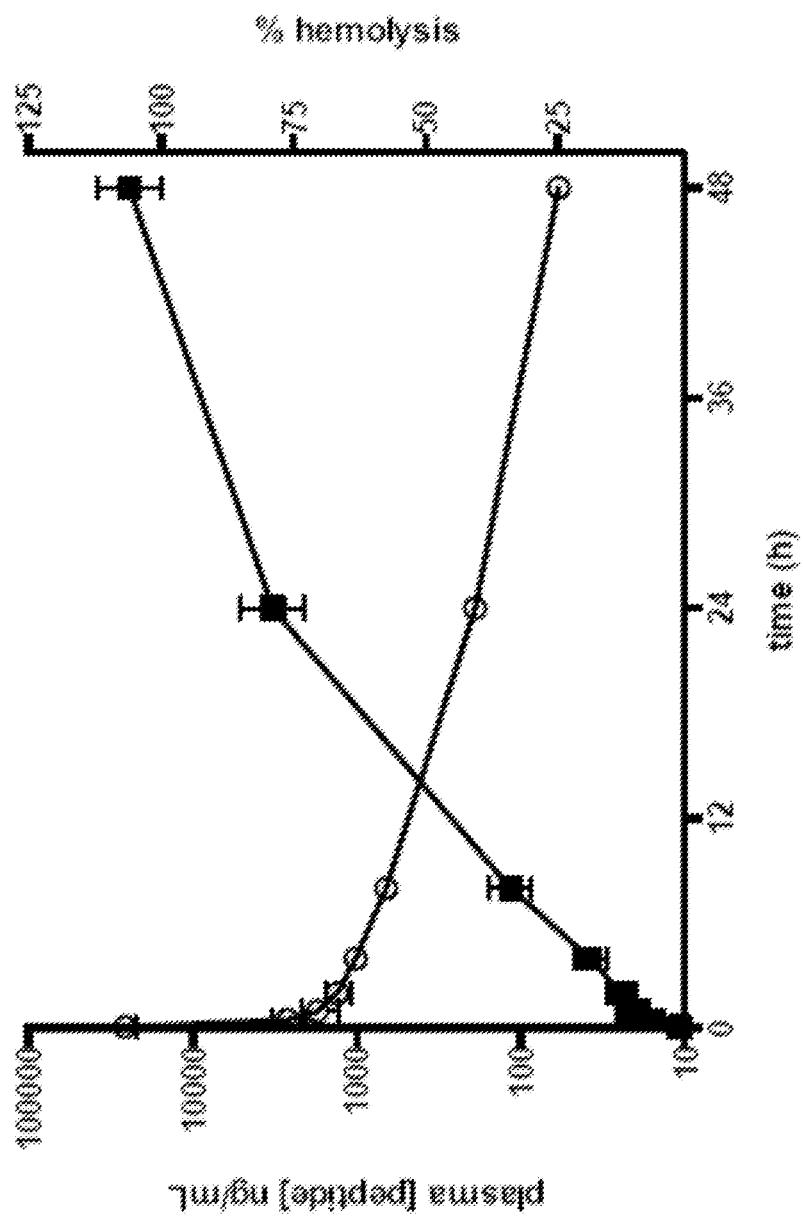
FIG. 4 is a line graph showing results from a study in cynomolgus monkey. Changes in R3152 (SEQ ID NO: 153) plasma concentration (circles) following a single 3 mg/kg IV dose in cynomolgus monkey are shown. Also shown are changes in hemolytic activity (squares) at the same time points.

The plasma concentration of polypeptide R3152 (SEQ ID NO: 153) was determined in cynomolgus monkeys following a single intravenous (IV) dose. Three male animals received 3 mg/kg polypeptide and plasma concentrations of polypeptide were determined using LC/MS-MS following acetonitrile precipitation and extraction on Sirocco Protein Precipitation plate (Waters Corporation, Milford, MA.) Pharmacokinetic (PK) parameters were calculated from the time course (see FIG. 4) of the combined plasma concentrations of R3152 (SEQ ID NO: 153,) determined immediately post-dose to up to 48 h post-dose. Plasma drug levels fell rapidly during an initial distribution phase (<1 hour) and then plateaued and were detectable for up to 48 hours. R3152 (SEQ ID NO: 153) had a mean terminal half-life of 10.9 f 0.8 hours. The mean clearance rate was 0.129±0.0122 L/hr/kg which is approximately 5% of the liver blood flow of a typical monkey (2.6 L/hr/kg). The mean volume of distribution was 1.49±0.152 L/kg which is approximately double the total body water for a typical monkey (0.7 L/kg). The average $AUC_\infty$ was 23319±2120 hr*ng/mL.

R3152 (SEQ ID NO: 153) binds with high affinity to primate C5 protein and blocks the complement pathway by preventing the generation of the C5a and C5b products and the production of a multimeric Membrane Attack Complex (MAC). The inhibition of complement-mediated MAC formation in plasma samples from the above PK study was examined using an established ex vivo assay (see the human hemolysis assay described in Example 10), in which plasma was diluted 1:100 and incubated with activated sheep red blood cells (Complement Technology, Tyler, TX). At each time-point, the hemolytic activity was determined as an indicator of active serum complement (see FIG. 4). In plasma containing >200 ng/mL R3152 (SEQ ID NO: 153) there was a clear inhibition of complement-mediated hemolysis, indicating a blockade of MAC formation. Exogenous R3152 (SEQ ID NO: 153) added to normal cynomolgus plasma has an $IC_{50}$=2-20 ng/mL. Hemolytic activity returned to normal levels 48 hours after dosing as plasma levels of R3152 (SEQ ID NO: 153) fell below 100 ng/ml.

Example 21. Pharmacokinetic Studies in Rat

Figure 5:
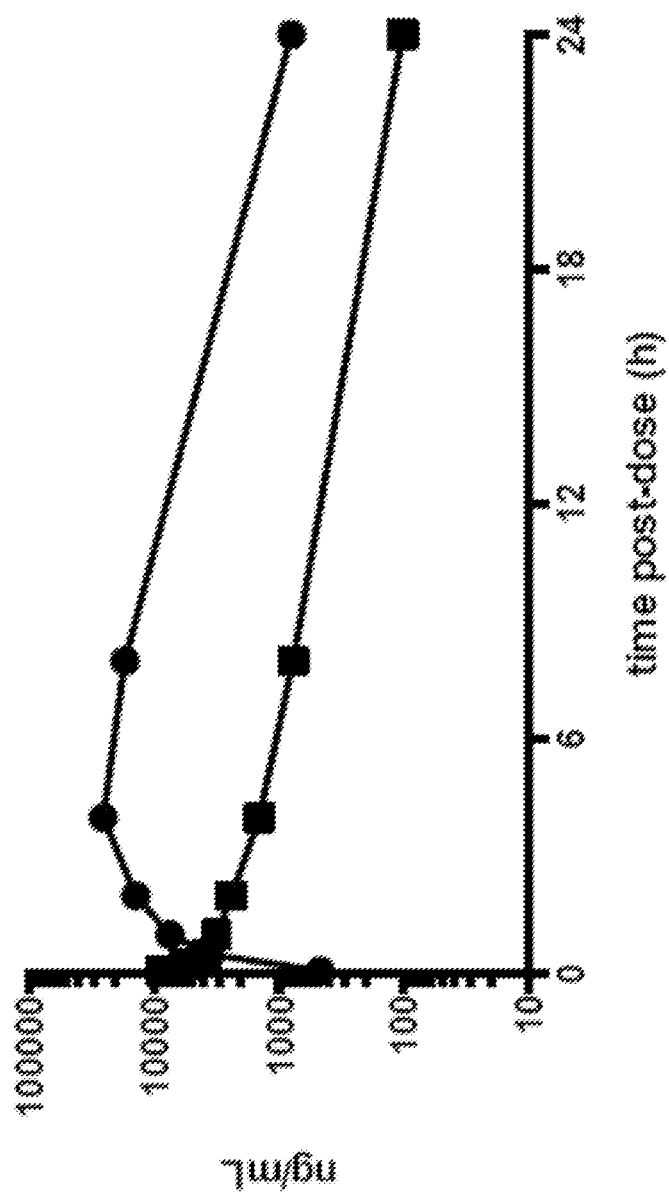
FIG. 5 is a line graph showing results of compound monitoring in plasma following intravenous (IV; squares) or subcutaneous (SC; circles) administration of 2 mg/kg of R3152 (SEQ ID NO: 153) in male Sprague-Dawley rats. Monitoring comprised determination of combined plasma concentrations of R3152 (SEQ ID NO: 153) as well as its equipotent C-terminally deamidated metabolite, R3201 (SEQ ID NO: 211.)

R3152 (SEQ ID NO: 153) was delivered as an intravenous (IV) or subcutaneous (SC) dose to male rats at 2 and 30 mg/kg, respectively. Following IV dosing, R3152 (SEQ ID NO: 153) was monitored by using LC/MS-MS following acetonitrile precipitation and extraction on Sirocco Protein Precipitation plate (Waters Corporation, Milford, MA) as described above. Pharmacokinetic (PK) parameters were calculated from the time course of the combined plasma concentrations of R3152 (SEQ ID NO: 153) and its equipotent C-terminally deamidated metabolite, R3201 (SEQ ID NO: 211). Results are presented in FIG. 5. In the figure, circles represent concentrations obtained after SC dose and squares represent concentrations obtained after IV dose.

R3152 (SEQ ID NO: 153)/R3201 (SEQ ID NO: 211) exhibited a fast distribution phase, followed by a slow elimination with a $t_{1/2}$=5.3 hrs. A similar elimination rate was observed after SC dosing of 30 mg/kg, with approximately 65% bioavailability of dose, based on AUC. The $T_{max}$ of 4 hrs and prolonged drug exposure seen in SC doses allowed for extended coverage of the therapeutic concentration in plasma. As R3152 (SEQ ID NO: 153) and R3201 (SEQ ID NO: 211) do not bind to rat C5, very little inhibitory activity was observed in ex vivo hemolysis assays.

Figure 6A:
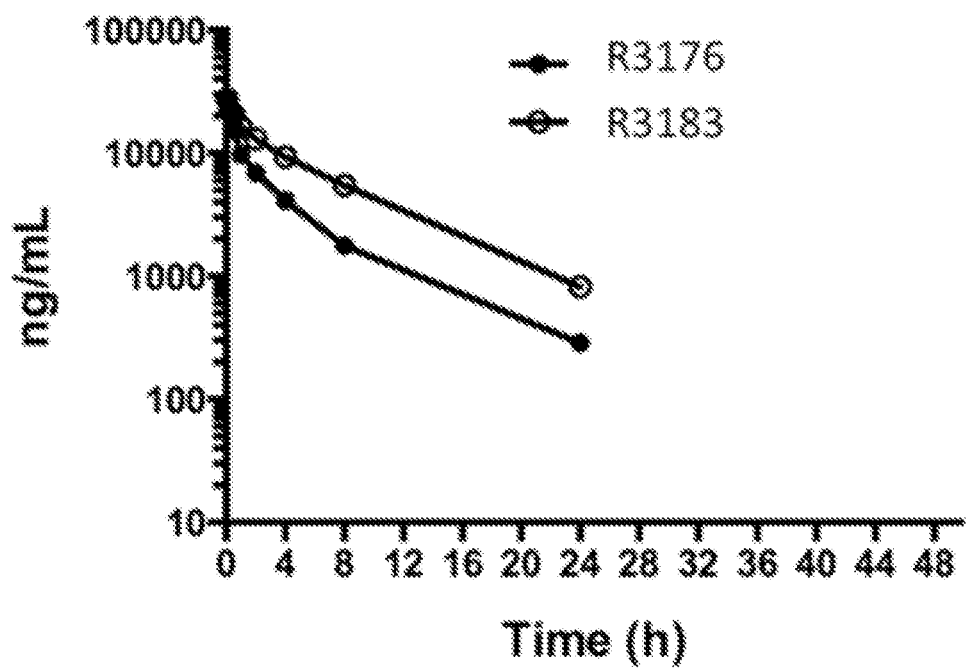
FIGS. 6A and 6B are line graphs depicting the pharmacokinetics of compounds of the present invention in rats. Male Sprague-Dawley rats (n=3) were injected intravenously at a single 2 mg/kg dose. Blood samples were collected at indicated time points, processed into plasma, and analyzed for the indicated compound by LC-MS (FIG. 6A). Black circles indicate results with R3176 (SEQ ID NO: 177) (unlipidated compound) and open circles indicate results with R3183 (SEQ ID NO: 184) (C16 lipidated compound). Male Sprague-Dawley rats (n=3) were also injected subcutaneously at a single 15 mg/kg dose. Blood samples were collected at indicated time points, processed into plasma, and analyzed for the indicated compound by LC-MS (FIG. 6B). Black circles indicate results with R3176 (SEQ ID NO: 177) (unlipidated compound) and open circles indicate results with R3183 (SEQ ID NO: 184) (C16 lipidated compound).
Figure 6B:
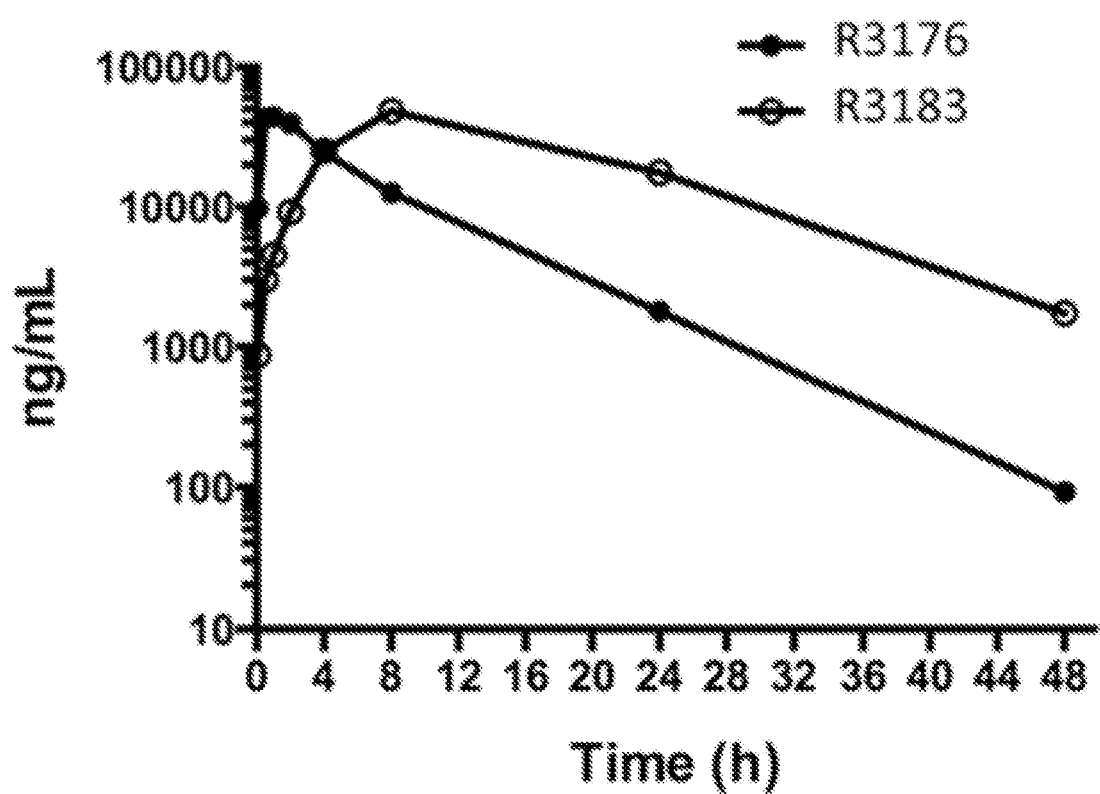

Lipidated and non-lipidated compounds R3183 (SEQ ID NO: 184) and R3176 (SEQ ID NO: 177), respectively, were evaluated for pharmacokinetic properties in Male Sprague-Dawley Rats following intravenous or subcutaneous administration. FIGS. 6A and 6B show the results. FIG. 6A shows Male Sprague-Dawley rats (n=3) injected intravenously with a single 2 mg/kg dose. Blood samples were collected at indicated time points, processed into plasma, and analyzed for the indicated compound by LC-MS. Black circles: R3176 (SEQ ID NO: 177) (unlipidated compound); Open circles: R3183 (SEQ ID NO: 184) (C16 lipidated compound). FIG. 6B shows Male Sprague-Dawley rats (n=3) injected subcutaneously with a single 15 mg/kg dose. Blood samples were collected at indicated time points, processed into plasma, and analyzed for the indicated compound by LC-MS. Black circles: R3176 (SEQ ID NO: 177) (unlipidated compound); Open circles: R3183 (SEQ ID NO: 184) (C16 lipidated compound). Lipidation resulted in an increase in exposure as assessed by determination of the Area under the curve (AUC) by 2.1-fold by the intravenous route and 2.7-fold by the subcutaneous route.

Example 22. Inhibition of Hemolysis in the Thrombin-Induced Complement Pathway

Thrombin can induce complement activity by cleaving C5 into C5-r which will then be cleaved into C5a and C5b$_T$. C5b$_T$, like C5b, will associate with C6 and the remaining terminal components of the complement pathway, C7, C8 and C9, which will lead to formation of the Membrane Attack Complex (MAC) causing lysis of red blood cells (Krisinger, et al., (2014). Blood. 120(8):1717-1725). Thus, R3183 and an anti-C5 monoclonal antibody similar to ECULIZUMAB® were tested for their ability to inhibit hemolysis through the thrombin-induced complement pathway.

Figure 7:
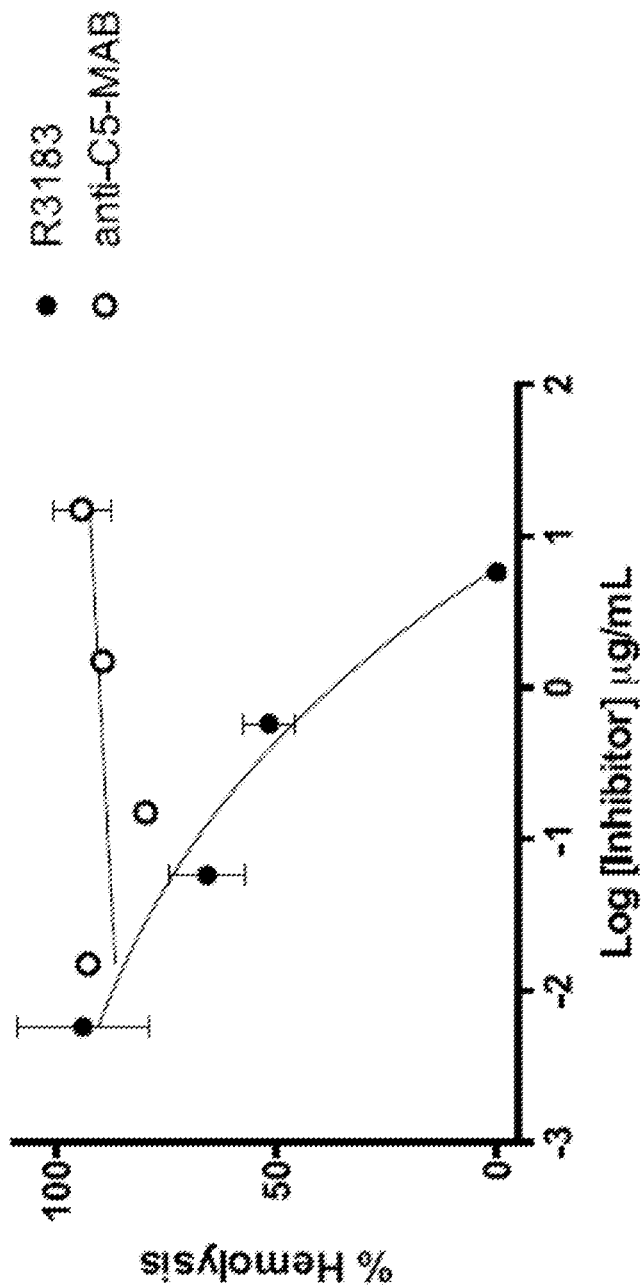
FIG. 7 is a scatter plot presenting the effects of R3183 (SEQ ID NO: 184) (C16 lipidated compound) or an anti-C5 monoclonal antibody similar to ECULIZUMAB® on inhibition of hemolysis via the thrombin-induced complement pathway.

To assess inhibitor activity, C5 (Complement Technology, Tyler, TX) was added to achieve a concentration of 400 nM, and the sample was incubated with C6 at a final concentration of 600 nM (Complement Technology, Tyler, TX) and thrombin at a concentration of 50 nM (Enzyme Research Laborites, South Bend, IN) at 37° C. for 30 minutes, in the presence of either R3183 or the anti-C5 monoclonal antibody similar to ECULIZUMAB®, or no inhibitor. The reaction was stopped with the addition of hirudin to 150 nM (Cell Sciences, Canton, MA) in the buffer GVB+EDTA (Complement Technology, Tyler, TX) and incubated 5 minute at room temperature. These diluted samples were mixed with antibody-sensitized sheep erythrocytes (Complement Technology, Tyler, TX) in a 96-well microtitre plate (USA Scientific, Ocala, FL) and incubated at 37° C. for 5 minutes. C7 (Complement Technology, Tyler, TX) was then added to the wells to achieve a concentration of 15 nM and the plate was returned to 37° C. for 15 minutes. A complex of C8 (10 nM; Complement Technology, Tyler, TX) and C9 (25 nM; Complement Technology, Tyler, TX) was then added to the assay mixture and the samples were incubated for 30 minutes at 37° C. Following incubation, the plate was centrifuged at 1000×g and 100 µL of supernatant was transferred to a new microtitre plate and the absorbance was read at 412 nm. The resulting data are shown in FIG. 7. R3183 was found to inhibit hemolysis by the thrombin-induced complement pathway at concentrations higher than 6 ng/mL, while the anti-C5 monoclonal antibody did not.

Example 23. Surface Plasmon Resonance Analysis of R3183 Binding

Surface Plasmon Resonance (SPR) experiments were conducted at 25° C. using the ProteOn XPR36 system from BioRad Laboratories, Inc. (Hercules, CA). C5 protein [or human serum albumin (HSA) control] was immobilized by direct amine coupling on a ProteOn GLH sensor chip designed for maximal binding capacity using pH 5 acetate buffer. Kinetic characterization of R3183 binding was performed in binding buffer containing 10 mM HEPES, pH 7.4, 150 mM NaCl, 0.5 mM MgCl$_2$, 0.15 mM CaCl$_2$), 0.005% Tween-20, and 1% DMSO to determine $k_{on}$, $k_{off}$, and $K_D$. Data analysis was performed using BioRad ProteOn Manager software. Sensograms were fit to the heterogeneous ligand model (see FIG. 8). The concentrations of R3183 evaluated in this experiment were 3.3, 1.1, 0.37 and 0.12 µM as indicated in the figure.

R3183 was found to have a $k_a$ (1/Ms) of 1.18×10$^5$ for C5, as well as a $k_d$ (1/s) of 3.04×10$^{-4}$ and a $K_D$ (M) of 2.58×10$^{-9}$. Values for HSA binding were: $k_a$(1/Ms) of 3.01×10$^4$, $k_d$ (1/s) of 1.76×10$^{-1}$ and a $K_D$ (M) of 5.86×10$^{-6}$.

Example 24. Structural Studies

Crystallography studies were carried out to compare C5 binding sites between a close chemical analog of R3183 and ECULIZUMAB® (Alexion Pharmaceuticals, Cheshire, CT). An induced fit model revealed that the analog binds to a site distinct from that reported for ECULIZUMAB®.

Example 25. Immunoassay Analysis of R3183 Inhibitory Activity

C5 inhibitory activity for R3183 was assessed by enzyme immunoassay (EIA). Inhibition of the production of C5a and the membrane attack complex (MAC) were measured by MicroVue EIA kits (Quidel Corporation, San Diego, CA).

Supernatant from a human red blood cell (RBC) hemolysis assay of R3183 was diluted 1:50 and assayed by C5a EIA (FIG. 9). R3183 inhibited the formation of C5a with an IC$_{50}$ of 11 nM.

The MAC EIA was performed with R3183 on the same supernatant, diluted 1:5 (see FIG. 10). This compound was shown to inhibit the formation of the MAC with an IC$_{50}$ of 6.9 nM. Serum samples containing different concentrations of R3183 were also analyzed for inhibition of the alternative pathway of complement activation using the WIESLAB® complement system screening kit (Euro Diagnostica, Malmo, Sweden). Results indicated an $IC_{50}$ of 12.5 nM for R3183.

Example 26. Human Hemolysis Assay

R3183 inhibitor activity was compared to an ECULIZUMAB®-like antibody (mAb-C5) using a red blood cell hemolysis assay. A DNA expression vector for a IgG monoclonal antibody inhibitor of C5 (mAb-C5) was constructed from the published sequence for the variable heavy and light chain sequences of h5G1.1, h5G1.1VHC+F and h5G1.1VLC+F, respectively (Thomas et al. 1996. Molecular Immunology. 33(17-18):1389-401). The human constant light chain kappa and IgG2 constant heavy chain sequences were used for the constants regions of the antibody. This antibody was expressed from human embryonic kidney cells (HEK293) and purified by Protein A affinity chromatography. Antibody-sensitized sheep erythrocytes (Complement Technology, Tyler, TX) were plated at $2.5 \times 10^7$ cells/well with complete human sera (Complement Technology, Tyler TX) with or without inhibitors to determine the inhibitory effect of the compounds on the lysis of red blood cells. Cells were centrifuged for 3 minutes at 2,090x gravity and resuspended in fresh GVB++ buffer (Complement Technology, Tyler TX). Human sera was rapidly thawed at 37° C. and then stored on ice until diluted into GVB++. Ten 6-fold serial dilutions of each compound (10 mM stock, DMSO) were performed in DMSO and then added to buffer. 50 µl of each compound dilution was combined with sera and 100 µl of cells in individual wells of a 96-well tissue culture-treated clear microtitre plate (USA Scientific, Ocala, FL) and resuspended by pipetting. Samples were incubated at 37° C. for one hour. Following incubation, plates were centrifuged at 2,090xgravity for 2 minutes. 100 µl of supernatant was transferred to a new plate and the absorbance was read at 412 nm. Data was fit with a log-logit formula producing a dose-response curve and $IC_{50}$ (see FIG. 11A). The $IC_{50}$ for R3183 was 8.1 nM as compared to 0.2 nM for mAb-C5. Interestingly, the molecular weight for R3183 is 2 kDa, while the molecular weight for mAb-C5 is 140 kDa, indicating a much lower overall amount needed for therapeutic applications.

Similar studies indicated that R3183 is also active in serum from cynomolgus monkeys and pigs, but less active in the serum of rodents and dogs. When 1% human serum was compared to 1% cynomolgus monkey serum in the assay, R3183 had an $IC_{50}$ of 1.9 nM and an $IC_{90}$ of 5.2 nM with human serum as compared to an $IC_{50}$ of 4.2 nM and an $IC_{90}$ of 13.2 nM with cynomolgus monkey serum (see FIG. 11B).

Example 27. Pharmacodynamic and Pharmacokinetic Studies

Studies were carried out in non-human primates to determine the dose and regimen of R3183 needed to achieve sustained complement inhibition, as well to determine the pharmacokinetic profile of R3183 during the administration period and over time after administration of the final dose. A low dose (Dose A) group of three male animals received 0.3 mg/kg of R3183 daily for seven days and were monitored for 10 days thereafter. A second, high dose group of three male animals received a single low dose (Dose A; 0.3 mg/kg) of R3183 on day 1 and received higher daily doses (Dose B; 3.0 mg/kg) of R3183 for 6 days thereafter. This group was also monitored for 10 days after receiving the final dose. Plasma samples were obtained prior to each dose, immediately post-dose and twice thereafter each day until daily dosing was completed. Samples were taken periodically thereafter for 10 days. Concentrations of R3183 were determined in each plasma sample using LC/MS-MS following acetonitrile precipitation and extraction on Sirocco Protein Precipitation plates (Waters Corporation, Milford, MA).

R3183 binds with high affinity to primate C5 protein and blocks the complement pathway by preventing the generation of the C5a and C5b products and the production of a multimeric Membrane Attack Complex (MAC). The inhibition of complement-mediated MAC formation in the same plasma samples was examined using an established ex vivo assay in which plasma was diluted 1:100 and incubated with activated sheep red blood cells (Complement Technology, Tyler, TX). At each time-point, the hemolytic activity was determined as an indicator of active serum complement (see FIGS. 12A and 12B). In the low dose group, 90% inhibition was observed with some R3183 plasma concentrations between 2000 and 4000 ng/ml, with greater than 90% inhibition with most concentrations above 4000 ng/ml (FIG. 12A). R3183 inhibition of hemolytic activity was detected up to 10 days after final treatments. A combined graphical representation of the data from low and high dose groups is presented in FIG. 13.

Example 28. Inhibition of Lysis with Addition of Terminal Components

C5 was incubated with C6 and thrombin at 37° C. for 30 minutes with and without R3183. The reaction was stopped with the addition of hirudin. The diluted samples were mixed with antibody-sensitized sheep erythrocytes and then incubated for 5 minutes at 37° C. Purified C7 was added and incubated for 15 minutes at 37° C. A complex of purified C8 and C9 was then added and the mixture was incubated for 30 minutes at 37° C. The plate was centrifuged and the supernatant transferred and read at 412 nm. Results demonstrate strong inhibition in the presence of R3183 (see FIG. 14).

Example 29. Hemolysis Analysis in PNH Patient Samples

Activation and inhibition of the alternative complement pathway in blood cells obtained from patients with paroxysmal nocturnal hemoglobinuria (PNH) was monitored in the presence or absence of complement inhibitors by flow cytometry as described in Risitano et al., 2012. Blood. 119(6): 6307-16, the contents of which are herein incorporated by reference in their entirety. Complement activation may be increased when serum is acidified. Here, red blood cells from patients having PNH were incubated in serum in the presence or absence of R3144 (SEQ ID NO: 145) or ECULIZUMAB®. Heat inactivated serum was used as a negative control (i.e., no red blood lysis takes place). The pH in samples was lowered by addition of hydrochloric acid (1:20 dilution of 0.1 N HCl) to initiate complement activation. Samples were incubated for 24 hours at 37° C. before analysis. Red blood cells were pelleted, and 1 µl was resuspended in 1 ml saline. Samples were then incubated with anti-CD59 antibodies with phycoerythrin labels as well as fluorescein isothiocyanate (FITC)-labeled anti-C3 antibodies for 1 hour prior to fluorescence-associated cell sorting (FACS) analysis. Results indicated similar levels of inhibition above baseline levels for both R3144 and ECULIZUMAB®.

What is claimed is:

1. A method of treating a C5-complement-related disorder in a subject, the method comprising administering a polypeptide of SEQ ID NO: 194 or SEQ ID NO: 184 to the subject, wherein hemolysis in the subject is reduced by at least 50% relative to hemolysis levels previously observed in the subject.

2. The method of claim 1, wherein the polypeptide is administered to the subject at a dose of from about 0.1 mg/kg to about 10 mg/kg.

3. The method of claim 2, wherein the polypeptide is administered to the subject at a dose of from about 0.3 mg/kg to about 3 mg/kg.

4. The method of claim 2, wherein the polypeptide is administered to the subject at a dose of about 0.3 mg/kg.

5. The method of claim 1, wherein the polypeptide is administered to the subject daily.

6. The method of claim 1, wherein the polypeptide is administered to the subject for seven days.

7. The method of claim 1, wherein the polypeptide is of SEQ ID NO: 184.

8. The method of claim 1, wherein the polypeptide is of SEQ ID NO: 194.

9. The method of claim 1, wherein the C5-complement-related disorder is paroxysmal nocturnal hemoglobinuria (PNH).

10. The method of claim 1, wherein the subject has previously been treated with eculizumab.

11. The method of claim 1, wherein the subject is also receiving treatment with eculizumab.

12. The method of claim 1, wherein treatment with eculizumab is ineffective.

13. The method of claim 1, wherein hemolysis in the subject is reduced by at least 90% relative to hemolysis levels previously observed in the subject.

* * * * *